US006329508B1

(12) United States Patent
Friden

(10) Patent No.: US 6,329,508 B1
(45) Date of Patent: Dec. 11, 2001

(54) TRANSFERRIN RECEPTOR REACTIVE CHIMERIC ANTIBODIES

(75) Inventor: Phillip M. Friden, Bedford, MA (US)

(73) Assignee: Alkermes, Inc., Cambridge, MA (US)

( * ) Notice: Subject to any disclaimer, the term of this patent is extended or adjusted under 35 U.S.C. 154(b) by 0 days.

(21) Appl. No.: 08/232,246

(22) PCT Filed: Nov. 24, 1992

(86) PCT No.: PCT/US92/10206

§ 371 Date: Jul. 5, 1994

§ 102(e) Date: Jul. 5, 1994

(87) PCT Pub. No.: WO93/10819

PCT Pub. Date: Jun. 10, 1993

Related U.S. Application Data

(63) Continuation-in-part of application No. 07/800,458, filed on Nov. 26, 1991, now abandoned, which is a continuation-in-part of application No. PCT/US90/05077, filed on Sep. 7, 1990, which is a continuation-in-part of application No. 07/404,089, filed on Sep. 7, 1989, now Pat. No. 5,154,924.

(51) Int. Cl.[7] .......... C12P 21/08
(52) U.S. Cl. .......... 530/387.3; 530/388.15
(58) Field of Search .......... 530/387.3, 388.15, 530/388.22, 388.2, 394, 839; 424/134.1, 143.1, 152

(56) References Cited

U.S. PATENT DOCUMENTS

| | | | |
|---|---|---|---|
| 4,292,425 | 9/1981 | Buckler et al. | 536/4 |
| 4,434,156 | 2/1984 | Trowbridge | 424/85 |
| 4,444,744 | 4/1984 | Goldenberg | 424/1.1 |
| 4,545,985 | 10/1985 | Pastan et al. | 424/85 |
| 4,569,789 | 2/1986 | Blattler et al. | 260/112 R |
| 4,626,507 | 12/1986 | Trowbridge et al. | 435/240 |
| 4,631,190 | 12/1986 | Shen et al. | 424/85.8 |
| 4,801,575 | 1/1989 | Pardridge | 514/4 |
| 4,816,567 | 3/1989 | Cabilly et al. | 530/387 |
| 4,892,827 | 1/1990 | Pastan et al. | 435/193 |
| 4,902,505 | 2/1990 | Pardridge et al. | 424/85.7 |
| 4,992,255 | 2/1991 | Pardridge | 424/1.1 |
| 5,004,697 | 4/1991 | Pardridge | 436/547 |
| 5,028,697 | 7/1991 | Johnson et al. | 530/388 |
| 5,087,616 | 2/1992 | Myers et al. | 514/21 |
| 5,091,513 | 2/1992 | Huston et al. | 530/387 |
| 5,130,129 | 7/1992 | Pardridge | 424/85.8 |
| 5,132,405 | 7/1992 | Huston et al. | 530/387.3 |
| 5,141,736 | 8/1992 | Iwasa et al. | 530/387.3 |
| 5,154,924 | 10/1992 | Friden | 424/85.91 |
| 5,182,107 | 1/1993 | Friden | 424/85.91 |

FOREIGN PATENT DOCUMENTS

| | | | |
|---|---|---|---|
| 0094844 | 11/1983 | (EP) | A61K/47/00 |
| 0175560 | 3/1986 | (EP) | G01N/33/535 |
| 0253202 | 1/1988 | (EP) | A61K/39/395 |
| 0286418 | 10/1988 | (EP) | A61K/9/50 |
| 0286441 | 10/1988 | (EP) | A61K/35/78 |
| 0324625 | 7/1989 | (EP) | A61K/39/385 |
| 0327169 | 8/1989 | (EP) | A61K/47/00 |
| 0328147 | 8/1989 | (EP) | A61K/47/00 |
| 0336383 | 10/1989 | (EP) | A61K/37/00 |
| 0449769 | 10/1991 | (EP) | C07K/15/28 |
| 1564666 | 9/1980 | (GB) | A61K/35/14 |
| 86/01409 | 3/1986 | (WO) | A61K/39/00 |
| 88/07365 | 10/1988 | (WO) | A61K/9/16 |
| 91/03259 | 3/1991 | (WO) | A61K/47/48 |
| 91/04753 | 4/1991 | (WO) | A61K/47/48 |
| 91/09965 | 7/1991 | (WO) | C12P/21/00 |
| 91/14438 | 10/1991 | (WO) | A61K/35/14 |

OTHER PUBLICATIONS

Hoogenboom, H.R. et al., "Construction and Expression of Antibody–Tumor Necrosis Factor Fusion Proteins," *Molecular Immunology,* 28(9): 1027–1037 (Sep. 1991).

Trowbridge, I.S. et al., "Anti–transferrin Receptor Monoclonal Antibody and Toxin–antibody Conjugates Affect Growth of Human Tumour Cells," *Nature,* 294: 171–173 (Nov. 1981).

Zovickian, J. et al., "Potent and Specific Killing of Human Malignant Brain Tumor Cells by an Anti–Transferrin Receptor Antibody–Ricin Immunotaxin," *J. Neurosurg.,* 66: 850–861 (1987).

Raso, V. et al., "Monensin is Obligatory for the Cytotoxic Action of a Disulfide Linked Methotrexate–Anti–Transferrin Receptor Conjugate," *Biochem. Biophy. Res. Comm.,* 150(1): 104–110 (Jan. 15, 1988).

Alkan, S.S. et al., "Antiviral and Antiproliferative Effects of Interferons Delivered via Monoclonal Antibodies," *J. Interferon Res.,* 4(3): 355–363 (1984).

Capon, D.J. et al., "Designing CD4 Immunoadhesins for AIDS Therapy," *Nature,* 337: 525–531 (Feb. 9, 1989).

Pietersz, G.A. et al., "Novel Synthesis and in Vitro Characterization of Disulfide–Linked Ricin–Monoclonal Antibody Conjugates Devoid of Galactose Binding Activity," *Cancer Res.,* 48: 4469–4476 (Aug. 15, 1988).

Pietersz, G.A. et al., "The Use of Monoclonal Antibody Conjugates for the Diagnosis and Treatment of Cancer," *Immunol. and Cell. Biol.,* 65(pt. 2): 111–125 (1987).

(List continued on next page.)

* cited by examiner

*Primary Examiner*—Sheela Huff
(74) *Attorney, Agent, or Firm*—Hamilton Brook Smith & Reynolds, P.C.

(57) ABSTRACT

The present invention pertains to chimeric antibodies that are reactive with transferrin receptors on brain capillary endothelial cells. These antibodies are composed of a variable region, immunologically reactive with the transferrin receptors, that is obtained from one animal source, and a constant region that is derived from an animal source other than the one that provided the variable region. These chimeric antibodies can exist either as isolated entities or as conjugates with a neuropharmaceutical agent for transferal across the blood brain barrier.

4 Claims, 77 Drawing Sheets

OTHER PUBLICATIONS

Gascoigne, N.R.J. et al., "Secretion of a Chimeric T–Cell Receptor–Immunoglobulin Protein," *Proc. Nat'l Acad. Sci. USA 84:* 2936–2940 (May 1987).

Baldwin, R.W. et al., "Monoclonal Antibodies for Radioimmunodetection of Tumours and for Targeting," *Bull. Cancer* (Paris) 70(2): 132–136 (1983).

Bryn, R.A. et al., "Biological Properties of a CD4 Immunoadhesin," *Nature,* 344: 667–670 (Apr. 12, 1990).

Dautry–Varsat, A. et al., "pH and the Recycling of Transferrin During Receptor Mediated Endocytosis," *Proc. Nat'l. Acad. Sci. USA 80:* 2258–2262 (Apr. 1983).

Shen, W.–C. et al., "Cis–Aconityl Spacer between Daunomycin and Macromolecular Carriers: A Model of pH–Sensitive Linkage Releasing Drug from a Lysosomotropic Conjugate," *Biochem. & Biophy. Res. Comm. 102*(3): 1048–1054, (Oct. 15, 1981).

Fishman, J.B. et al., "Receptor–Mediated Transcytosis of Transferrin Across the Blood–Brain Barrier," *J. Neur. Res., 18:* 299–304 (1987).

Pardridge, W.M. et al., "Selective Transport of an Anti––Transferrin Receptor Antibody through the Blood–Brain Barrier in Vivo," *J. Pharmacol. and Exp. Therapeutics,* 259(1): 66–70 (1991).

Sutherland, R. et al., "Ubiquitous Cell–Surface Glycoprotein on Tumor Cells is Proliferation–Associated Receptor for Transferrin," *Proc. Nat'l Acd. Sci. USA,* 78(7): 4514–4519 (Jul. 1981).

Friden, P.M. et al., "Anti–Transferrin Receptor Antibody and Antibody–Drug Conjugates Cross the Blood–Brain Barrier," *Proc. Nat'l Acad. Sci. USA,* 88(11): 4771–4775 (Jun. 1, 1991).

Batra, J.K. et al., "Antitumor Activity in Mice of an Immunotoxin made with Anti–Transferrin Receptor and a Recombinant Form of *Pseudomonas* Exotoxin," *Proc. Nat'l Acad. Sci. USA,* 86: 8545–8549 (Nov. 1989).

Batra, J.K. et al., "Single–Chain Immunotoxins Directed at the Human Transferrin Receptor Containing *Pseudomonas* Exotoxin A or Diphtheria Toxin: Anti–TFR (Fv) –PE40 and DT388–Anti–TFR (Fv)," *Mol. and Cell. Biol. 11*(4): 2200–2205 (Apr. 1991).

Friden, P.M. et al., "Blood–Brain Barrier Penetration and in Vivo Activity of an NGF Conjugate," *Science 259:* 373–377 (Jan. 15, 1993).

Cazzola, M. et al., "Cytotoxic Activity of an Anti–Transferrin Receptor Immunotoxin on Normal and Leukemic Human Hematopoietic Progenitors," *Cancer Res. 51:* 536–541 (Jan. 15, 1991).

Bjorn, M. et al., "Immunotoxins to the Murine Transferrin Receptor: Intracavitary Therapy of Mice Bearing Syngeneic Paritoneal Tumors," *Cancer Res. 47:* 6639–6645 (Dec. 15, 1987).

Smyth, M.J. et al., "The Mode of Action of Methotrexate––Monoclonal Antibody Conjugates," *Immun. and Cell Biol. 65*(Pt. 2): 189–200 (1987).

Griffin, T.W. et al., "In Vitro Cytotoxicity of Recombinant Ricin A Chain–Antitransferrin Receptor Immunotoxin Against Human Adenocarcinomas of the Colon and Pancreas," *J. of Biological Response Modifiers 7*(6): 559–567 (1988).

Pirker, R. et al., "Anti–Transferrin Receptor Antibody Linked to *Pseudomonas* Exotoxin as a Model Immunotoxin in Human Ovarian Carcinoma Cell Lines," *Cancer Res. 45:* 751–757 (Feb. 1985).

Morrison, S.L. et al., "Genetically Engineered Antibody Molecules: New Tools for Cancer Therapy," *Cancer Investigation 6*(2): 185–192 (1988).

Roitt (1991) "Essential Immunology" Blackwell Scientific Publications, pp. 65–68 & 74.*

Boch et al. (1993) Immunology Today 14: 421–425.*

Gregoriadis et al (1993) Trends in Biotech. 11: 440–442.*

Thorpe (1993) Trends in Biotech 11: 40–42.*

Jeffries et al (1984) Nature 312: 162–163.*

Jeffries et al (1985) Immunology 54: 333–341.*

Domingo et al (1985) Meth. Engynot. 112: 238–247.*

Pardridge et al (1986) Endocrine Re. 7(3): 314–329.*

Huston et al (1988) Proc. Nat'l. Acad. Sci. 85: 5879–5883.*

Riechmann et al. (1988) Nature 332: 323–327.*

Morrison et al (1984) Proc. Nat'l. Acad. Sci. 81: 6851–6855.*

Boulianne et al (1984) Nature 312: 643–646.*

Hoogenboom, H.R. et al., "Cloning and Expression of a Chimeric Antibody Directed Against the Human Transferrin Receptor," *J. Immunology, 144*(8): 3211–3217, (Apr. 15, 1990).

Domingo, D.L. et al., "Transferrin Receptor as a Target for Antibody–Drug Conjugates," *Methods in Enzymology, 112:* 238–247 (1985).

Jeffries, W.A., et al., "Transferrin Receptor on Endothelium of Brain Capillaries," *Nature,* 312: 162–163 (Nov. 8, 1984).

Pardridge, W.M., "Receptor–Mediated Peptide Transport through the Blood–Brain Barrier," *Endocrine Reviews,* 7(3): 314–330 (Aug. 1986).

Friden, P.M. et al., "Anti–Transferrin Receptor Antibody and Antibody–Drug Conjugates Cross the Blood–Brain Barrier," *Proc. Nat'l Acad. Sci. USA,* 88(11): 4771–4775 (Jun. 1, 1991).

CGTTGTCAGAAGTAAGTTGGCCGCAGTGTTATCACTCATGGTTATGGCAGCACTGCATAATTCTCTTACTGTCATGCCAT
CCGTAAGATGCTTTTCTGTGACTGGTGAGTACTCAACCAAGTCATTCTGAGAATAGTGTATGCGGCGACCGAGTTGCTCT
TGCCCGGCGTCAACACGGGATAATACCGCGCCACATAGCAGAACTTTAAAAGTGCTCATCATTGGAAAACGTTCTTCGGG
GCGAAAACTCTCAAGGATCTTACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAAAAGGGAATAAGGGCGACACGG
AAATGTTGAATACTCATACTCTTCCTTTTTCAATATTATTGAAGCATTTATCAGGGTTATTGTCTCATGAGCGGATACAT
ATTTGAATGTATTTAGAAAAATAAACAAATAGGGGTTCCGCGCACATTTCCCCGAAAAGTGCCACCTGACGTCTAAGAAA
CCATTATTATCATGACATTAACCTAT

EcoRI

AAAAATAGGCGTATCACGAGGCCCTTTCGTCTTCAAGAATTCAGAGAGGTCTGGTGGAGCCTGCAAAAGTCCAGCTTTCA
AAGGAACACAGAAGTATGTGTATGGAATATTAGAAGATGTTGCTTTTACTCTTAAGTTGGTTCCTAGGAAAAATAGTTAA
ATACTGTGACTTTAAAATGTGAGAGGGTTTTCAAGTACTCATTTTTTTAAATGTCCAAAATTTTTGTCAATCAATTTGAG
GTCTTGTTTGTGTAGAACTGACATTACTTAAAGTTTAACCGAGGAATGGGAGTGAGGCTCTCTCATACCCTATTCAGAAC
TGACTTTTAACAATAATAAATTAAGTTTAAAATATTTTTAAATGAATTGAGCAATGTTGAGTTGAGTCAAG

PvuII

ATGGCCGATCAGAACCGGAACACCTGCAGCAGCTGGCAGGAAGCAGGTCATGTGGCAAGGCTATTTGGGGAAGGGAAAAT
AAAACCACTAGGTAAACTTGTAGCTGTGGTTTGAAGAAGTGGTTTTGAAACACTCTGTCCAGCCCCACCAAACCGAAAGT
CCAGGCTGAGCAAAACACCACCTGGGTAATTTGCATTTCTAAAATAAGTTGAGGATTCAGCCGAAACTGGAGAGGTCCTC
TTTTAACTTATTGAGTTCAACCTTTTAATTTTAGCTTGAGTAGTTCTAGTTTCCCCAAACTTAAGTTTATCGACTTCTAA
AATGT

EcoRI

ATTTAGAATTCCTTTGCCTAATATTAATGAGGACTTAACCTGTGGAAATATTTTGATGTGGGAAGCTGTTACTGTTAAAA
CTGAGGTTATTGGGGTAACTGCTATGTTAAACTTGCATTCAGGGACACAAAAAACTCATGAAAATGGTGCTGGAAAACCC
ATTCAAGGGTCAAATTTTCATTTTTTTGCTGTTGGTGGGGAACCTTTGGAGCTGCAGGGTGTGTTAGCAAACTACAGGAC
CAAATATCCTGCTCAAACTGTAACCCCAAAAAATGCTACAGTTGACAGTCAGCAGATGAACACTGACCACAAGGCTGTTT
TGGATAAGGATAATGCTTATCCAGTGGAGTGCTGGGTTCCTGATCCAAGTAAAAATGAAAACACTAGATATTTTGGAACC
TACACAGGTGGGGAAAATGTGCCTCCTGTTTTGCACATTACTAACACAGCAACCACAGTGCTGCTTGATGAGCAGGGTGT
TGGGCCCTTGTGCAAAGCTGACAGCTTGTATGTTTCTGCTGTTGACATTTGTGGGCTGTTTACCAACACTTCTGGAACAC
AGCAGTGGAAGGGACTTCCCAGATATTTTAAAATTACCCTTAGAAAGCGGTCTGTGAAAAACCCCTACCCAATTTCCTTT
TTGTTAAGTGACCTAATTAACAGGAGGACACAGAGGGTGGATGGCAGCCTATGATTGGAATGTCCTCTCAAGT

FIG. 11A

BamHI

AGAGGAGGTTAGGGTTTATGAGGACACAGAGGAGCTTCCTGGGGATCCGATCCNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNATATAGC
ACAAAGACATGCAA

FIG. 11B

```
                                           HindIII
ATAATATTTCCCTATGCTCATAAAAACAGCCCTGACCATGAAGCTTTGACAGACGCACAACCCTG
                                            EcoRV
GACTCCCAAGTCTTTCTCTTCAGTGACAAACACAGACATAGGATATCCACCATGGAATGGAGCTG
                                                   PvuII
GGTAATGCTCTTCCTCCTGTCAGGAACTGCAGGTGTCCGCTCTGAGGTCCAGCTGCAACAGTCTGGACCTGAACTGGTGA
AGCCTGGAGCTTCAATGAAGATTTCCTGCAAGGCTTCTGGTTACTCATTCACTGGCTACACCATGAACTGGGTGAAGCAG
AGCCATGGAGAGAACCTTGAGTGGATTGGACGTATTAATCCTCACAATGGTGGTACTGACTACAACCAGAAGTTCAAGGA
CAAGGCCCCTTTAACTGTAGACAAGTCATCCAACACAGCCTACATGGAGCTCCTCAGTCTGACATCTGAGGACTCTGCAG
TCTATTACTGTGCAAGAGGCTACTATTACTATTCTTTGGACTACTGGGGTCAAGGAACCTCAGTCACCGT
     NheI
CTCCTCAGCTAGCACCAAGGGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAAAGTTGGTGAGAGGCCAGCACAGG
GAGGGAGGGTGTCTGCTGGAAGCAGGCTCAGCGCTCCTGCCTGGACGCATCCCGGCTATGCAGCCCCAGTCCAGGGCAGC
AAGGCAGGCCCCGTCTGCCTCTTCACCCGGAGCCTCTGCCCGCCCCACTCATGCTCAGGGAGAGGGTCTTCTGGCTTTTT
CCCAGGCTCTGGGCAGGCACAGGCTAGGTGCCCCTAACCCAGGCCCTGCACACAAAGGGGCAGGTGCTGGGCTCAGACCT
GCCAAGAGCCATATCCGGGAGGACCCTGCCCCTGACCTAAGCCCACCCCAAAGGCCAAACTCTCCACTCCCTCAGCTCGG
ACACCTTCTCTCCTCCCAGATTCCAGTAACTCCCAATCTTCTCTCTGCAGAGCCCAAATCTTGTGACAAAACTCACACAT
GCCCACCGTGCCCAGGTAAGCCAGCCCAGGCCTCGCCCTCCAGCTCAAGGCGGGACAGGTGCCCTAGAGTAGCCTGCATC
CAGGGACAGGCCCCAGCCGGGTGCTGACACGTCCACCTCCATCTCTTCCTCAGCACCTGAACTCCTGGGGGGACCGTCAG
TCTTCCTCTTCCCCCCAAAACCCAAGGACACCCTCATGATCTCCCGGACCCCTGAGGTCACATGCGTGGTGGTGGACGTG
AGCCACGAAGACCCTGAGGTCAAGTTCAACTGGTACGTGGACGGCGTGGAGGTGCATAATGCCAAGACAAAGCCGCGGGA
GGAGCAGTACAACAGCACGTACCGGGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGTGGGACCCGTGGGGTG
CGAGGGCCACATGGACAGAGGCCGGCTCGGCCCACCCTCTGCCCTGAGAGTGACCGCTGTACCAACCTCTGTCCTACAGG
```

FIG. 11C

```
GCAGCCCCGAGAACCACAGGTGTACACCCTGCCCCCATCCCGGGATGAGCTGACCAAGAACCAGGTCAGCCTGACCTGCC
TGGTCAAAGGCTTCTATCCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTCCGGGTAAAT
GAGTGCGACGGCCGGCAAGCCCCGCTCCCCGGGCTCTCGCGGTCGCACGAGGATGCTTGGCACGTACCCCCTGTACATAC
TTCCCGGGCGCCCAGCATGGAAATAAAGCACCCAGCGCTGCCCTGGGCCCCTGCGAGACTGTGATGGTTCTTTCCACGGG
TCAGGCCGAGTCTGAGGCCTGAGTGGCATGAGGGAGGCAGAGCGGGTCNAANNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNN
   MboI
  BamHI
NNGGATCCAGACATGATAAGATACATTGATGAGTTTGGACAAACCACAACTAGAATGCAGTGAAAAAAATGCTTTATTTG
TGAAATTTGTGATGCTATTGCTTTATTTGTAACCATTATAAGCTGCAATA
```

FIG. 11D

```
    HpaI
AACAAGTTAACAACAACAATTGCATTCATTTTATGTTTCAGGTTCAGGGGGAGGTGTGGGAGGTT
                                                         MboI
TTTTAAAGCAAGTAAAACCTCTACAAATGTGGTATGGCTGATTATGATCTCTAGTCAAGGCACTATACATCAAATATTCC
TTATTAACCCCTTTACAAATTAAAAAGCTAAAGGTACACAATTTTTGAGCATAGTTATTAATAGCAGACACTCTATGCCT
GTGTGGAGTAAGAAAAAACAGTATGTTATGATTATAACTGTTATGCCTACTTATAAAGGTTACAGAATATTTTTCCATAA
TTTTCTTGTATAGCAGTGCAGCTTTTTCCTTTGTGGTGTAAATAGCAAAGCAAGCAAGAGTTCTATTACTAAACACAGCA
TGACTCAAAAAACTTAGCAATTCTGAAGGAAAGTCCTTGGGGTCTTCTACCTTTCTCTTCTTTTTGGAGGAGTAGAATG
TTGAGAGTCAGCAGTAGCCTCATCATCACTAGATGGCATTTCTTCTGAGCAAAACAGGTTTTCCTCATTAAAGGCATTCC
ACCACTGCTCCCATTCATCAGTTCCATAGGTTGGAATCTAAAATACACAAACAATTAGAATCAGTAGTTTAACACATTAT
ACACTTAAAAATTTTATATTTACCTTATAGCTTTAAATCTCTGTAGGTAGTTTGTCCAATTATGTCACACCACAGAAGTA
AGGTTCCTTC
    MboI                                                              HpaI
ACAAAGATCCGGNNNNNNNNNNNNNNNNNNNNNNNNNNTCATGCTTGCTCCTTGAGGGCGTTAACGCGCAAGGTAACGGCA
TTTTTATGGGCGGTCAGACGTTCGGCGGCGGCCAGTGTTTCTATGGTTGAAGCCACCGCGGAGAACCCCTCTTTCGACAG
TTCCTGTACGGTCATACGCTTCTGGAAATCTGCCAGCCCGAGGCTGGAACAGGTGGCGGTGTAACCGTAAGTCGGTAGAA
CGTGGTTGGTTCCGGAGGCGTAATCACCTGCCGATTCCGGTGACCAGTCACCAAGAAATACCGAACCGGCGCTGGTGATG
CTATCGACCAGTTCACGGGCGTTGCGGGTCTGAATGATCAGGTGCTCCGGGCCGTACTGATTAGAGATCTCCACGCACTG
CGCTGAATCTTTAGTCACGATCAGGCGGCTGGCGTTCAGTGCCTGGCGGGCGGTTTCGGCACGCGGCAGTTCCGCCAGTT
GGCGTTCGACGGCCTCGGCAACGCGACGCGCCATATCAGCAGCGGGCGTCAGTAAAATCACCTGTGAGTCCGGGCCGTGT
TCAGCCTGAGAGAGCAAATCAGAAG
                                                                      ClaI
CCACGAAATCCGGCGTTGCGCCGCTGTCAGCAATCACCAGCACTTCCGACGGGCCTGCGGGCATATCGATCTCCGCACCG
TCCAGACGCTGGCTCACCTGACGTTTCGCTTCGGTGACAAAGGCGTTACCCGGCCCGAAGATTTGTCCACTTTTGGCAC
GGATTCCGTACCAAACGCCAGTGCGGCAAT
```

FIG. 11E

PvuII
GGCCTGTGCGCCGCCGACGTTGAACACGTCCTGCACACCGCACAGCTGCGCCGCATAAAGGATCTCATCGGCAATCGGCG
GCGGTGAGCACAGCACCACTTTTTTACAGCCCGCAATACGCGCCGGAGTCGCCAGCATTAATACCGTTGAGAAGAGCGGG
GCGGAGCCGCCAGGAATATACAACCCAACTGAAGCTACCGGACGCGTGACCTGCTGGCAACGCACGCCTGGCTGCGTTTC
TACATCTACCGGCGGCAGTTTTTGCGCAGTGTGGAAGGTTTCAATATTCTTTACTGCCACCGCCATCGCCTGTTTTAGCT
CGTCGCTCAGGCGTTCGCTGGCGGCGGCGATCTCCTCTGCAGACACCTTCAGCGCGGTAACCGTGGTTTTATCAAACTTC
GCGCTGTATTCCCGCAGGGCCTCATCGCCGCGTGCTTTCACGTTATCGAGAATATCGTTAACAGTGCGGGTAATGCTTT
PvuII
CAGAGGCGGAAATCGCCGGGCGCGTTAACAGCTGGCGTTGTTGCACCGCAGTACAGCTATTCCAGTCAATGATTGTGTTA
AAGCTCATNNNNCCGGATCAGCTTTTTGCAAAAGCCTAGGCCTCCAAAAAAGCCTCCTCACTACTTCTGGAATAGCTCAG
AGGCCGAGGCGCCTCGGCCTCTGCATAAATAAAAAAAATTAGTCAGCCATGGGGCGGAGAATGGGCGGAACTGGGCGGAG
TTAGGGGCGGGATGGGCGGAGTTAGGGGCGGGACTATGGTTGCTGACTAATTGAGATGCATGCTTTGCATACTTCTGCCT
GCTGGGGAGCCTGGGGACTTTCCACACCTGGTTGCTGACTAATTGAGATGCATGCTTTGCATACTTCTGCCTGCTGGGGA
GCCTGGGGACTTTCCACACCCTAACTGACACACATTCCACAGCTGCCTCGCGCGTTTCGGTGATGACGGTGAAAACCTCT
GACACATGCAGCTCCCGGAGACGGTCACAGCTTGTCTGTAAGCGGATGCCGGGAGCAGACAAGCCCGTCAGGGCGCGTCA
GCGGGTGTTGGCGGGTGTCGGGGCGCAGCCATGACCCAGTCACGTAGCGATAGCGGAGTGTATACTGGCTTAACTATGCG
GCATCAGAGCAGATTGTACTGAGAGTGCACCATATGCGGTGTGAAATACCGCACAGATGCGTAAGGAGAAAATACCGCAT
CAGGCGCTCTTCCGCTTCCTCGCTCACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCAATGCTCACGCTGTAGG
TATCTCAGTTCGGTGTAGGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGAAGATCCTTTGATCTTTTCTA

FIG. 11F

```
CGGGGTCTGACGCTCAGTGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCTGACTCCCCGTCGTGTAGATAACTA
CGATACGGGAGGGCTTACCATCTGGCCCCAGTGCTGCAATGATACCGCGAGACCCACGCTCACCGGCTCCAGATTTATCA
GCAATAAACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCC
                                  PstI
AGTTAATAGTTTGCGCAACGTTGTTGCCATTGCTGCAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAGCGGTTAGCTCCT
          PvuI
TCGGTCCTCCG
```

FIG. 11G

| | | | | | | | | | | | | | | | |
|---|---|---|---|---|---|---|---|---|---|---|---|---|---|---|---|
| | | | | | | | | | | | | | ATG | GAA | TGG |
| | | | | | | | | | | | | | Met | Glu | Trp |
| | | | | | | | | | | | | | 1 | | |
| AGC | TGG | GTA | ATG | CTC | TTC | CTC | CTG | TCA | GGA | ACT | GCA | GGT | GTC | CGC | TCT |
| Ser | Trp | Val | Met | Leu | Phe | Leu | Leu | Ser | Gly | Thr | Ala | Gly | Val | Arg | Ser |
| | 5 | | | | | 10 | | | | | 15 | | | | |
| GAG | GTC | CAG | CTG | CAA | CAG | TCT | GGA | CCT | GAA | CTG | GTG | AAG | CCT | GGA | GCT |
| Glu | Val | Gln | Leu | Gln | Gln | Ser | Gly | Pro | Glu | Leu | Val | Lys | Pro | Gly | Ala |
| 20 | | | | | 25 | | | | | 30 | | | | | 35 |
| TCA | ATG | AAG | ATT | TCC | TGC | AAG | GCT | TCT | GGT | TAC | TCA | TTC | ACT | GGC | TAC |
| Ser | Met | Lys | Ile | Ser | Cys | Lys | Ala | Ser | Gly | Tyr | Ser | Phe | Thr | Gly | Tyr |
| | | | | 40 | | | | | 45 | | | | | 50 | |
| ACC | ATG | AAC | TGG | GTG | AAG | CAG | AGC | CAT | GGA | GAG | AAC | CTT | GAG | TGG | ATT |
| Thr | Met | Asn | Trp | Val | Lys | Gln | Ser | His | Gly | Glu | Asn | Leu | Glu | Trp | Ile |
| | | | 55 | | | | | 60 | | | | | 65 | | |
| GGA | CGT | ATT | AAT | CCT | CAC | AAT | GGT | GGT | ACT | GAC | TAC | AAC | CAG | AAG | TTC |
| Gly | Arg | Ile | Asn | Pro | His | Asn | Gly | Gly | Thr | Asp | Tyr | Asn | Gln | Lys | Phe |
| | | 70 | | | | | 75 | | | | | 80 | | | |
| AAG | GAC | AAG | GCC | CCT | TTA | ACT | GTA | GAC | AAG | TCA | TCC | AAC | ACA | GCC | TAC |
| Lys | Asp | Lys | Ala | Pro | Leu | Thr | Val | Asp | Lys | Ser | Ser | Asn | Thr | Ala | Tyr |
| | 85 | | | | | 90 | | | | | 95 | | | | |
| ATG | GAG | CTC | CTC | AGT | CTG | ACA | TCT | GAG | GAC | TCT | GCA | GTC | TAT | TAC | TGT |
| Met | Glu | Leu | Leu | Ser | Leu | Thr | Ser | Glu | Asp | Ser | Ala | Val | Tyr | Tyr | Cys |
| 100 | | | | | 105 | | | | | 110 | | | | | 115 |
| GCA | AGA | GGC | TAC | TAT | TAC | TAT | TCT | TTG | GAC | TAC | TGG | GGT | CAA | GGA | ACC |
| Ala | Arg | Gly | Tyr | Tyr | Tyr | Tyr | Ser | Leu | Asp | Tyr | Trp | Gly | Gln | Gly | Thr |
| | | | | 120 | | | | | 125 | | | | | 130 | |
| TCA | GTC | ACC | GTC | TCC | TCA | GCT | AGC | ACC | AAG | GGC | CCA | TCG | GTC | TTC | CCC |
| Ser | Val | Thr | Val | Ser | Ser | Ala | Ser | Thr | Lys | Gly | Pro | Ser | Val | Phe | Pro |
| | | | 135 | | | | | 140 | | | | | 145 | | |
| CTG | GCA | CCC | TCC | TCC | AAG | AGC | ACC | TCT | GGG | GGC | ACA | GCG | GCC | CTG | GGC |
| Leu | Ala | Pro | Ser | Ser | Lys | Ser | Thr | Ser | Gly | Gly | Thr | Ala | Ala | Leu | Gly |
| | | 150 | | | | | 155 | | | | | 160 | | | |
| TGC | CTG | GTC | AAG | GAC | TAC | TTC | CCC | GAA | CCG | GTG | ACG | GTG | TCG | TGG | AAC |
| Cys | Leu | Val | Lys | Asp | Tyr | Phe | Pro | Glu | Pro | Val | Thr | Val | Ser | Trp | Asn |
| | 165 | | | | | 170 | | | | | 175 | | | | |
| TCA | GGC | GCC | CTG | ACC | AGC | GGC | GTG | CAC | ACC | TTC | CCG | GCT | GTC | CTA | CAG |
| Ser | Gly | Ala | Leu | Thr | Ser | Gly | Val | His | Thr | Phe | Pro | Ala | Val | Leu | Gln |
| 180 | | | | | 185 | | | | | 190 | | | | | 195 |

FIG. 11H

```
TCC TCA GGA CTC TAC TCC CTC AGC AGC GTG GTG ACC GTG CCC TCC AGC
Ser Ser Gly Leu Tyr Ser Leu Ser Ser Val Val Thr Val Pro Ser Ser
                200                 205                 210

AGC TTG GGC ACC CAG ACC TAC ATC TGC AAC GTG AAT CAC AAG CCC AGC
Ser Leu Gly Thr Gln Thr Tyr Ile Cys Asn Val Asn His Lys Pro Ser
            215                 220                 225

AAC ACC AAG GTG GAC AAG AAA GTT
Asn Thr Lys Val Asp Lys Lys Val
        230                 235
```

FIG. 11I

| | | | | | | | | | | | | | | |
|---|---|---|---|---|---|---|---|---|---|---|---|---|---|---|
| GAG | CCC | AAA | TCT | TGT | GAC | AAA | ACT | CAC | ACA | TGC | CCA | CCG | TGC | CCA |
| Glu | Pro | Lys | Ser | Cys | Asp | Lys | Thr | His | Thr | Cys | Pro | Pro | Cys | Pro |
| 1 | | | | 5 | | | | | 10 | | | | | 15 |

FIG. 11J

```
GCA CCT GAA CTC CTG GGG GGA CCG TCA GTC TTC CTC TTC CCC CCA AAA
Ala Pro Glu Leu Leu Gly Gly Pro Ser Val Phe Leu Phe Pro Pro Lys
  1               5                  10                  15

CCC AAG GAC ACC CTC ATG ATC TCC CGG ACC CCT GAG GTC ACA TGC GTG
Pro Lys Asp Thr Leu Met Ile Ser Arg Thr Pro Glu Val Thr Cys Val
             20                  25                  30

GTG GTG GAC GTG AGC CAC GAA GAC CCT GAG GTC AAG TTC AAC TGG TAC
Val Val Asp Val Ser His Glu Asp Pro Glu Val Lys Phe Asn Trp Tyr
         35                  40                  45

GTG GAC GGC GTG GAG GTG CAT AAT GCC AAG ACA AAG CCG CGG GAG GAG
Val Asp Gly Val Glu Val His Asn Ala Lys Thr Lys Pro Arg Glu Glu
     50                  55                  60

CAG TAC AAC AGC ACG TAC CGG GTG GTC AGC GTC CTC ACC GTC CTG CAC
Gln Tyr Asn Ser Thr Tyr Arg Val Val Ser Val Leu Thr Val Leu His
 65                  70                  75                  80

CAG GAC TGG CTG AAT GGC AAG GAG TAC AAG TGC AAG GTC TCC AAC AAA
Gln Asp Trp Leu Asn Gly Lys Glu Tyr Lys Cys Lys Val Ser Asn Lys
                 85                  90                  95

GCC CTC CCA GCC CCC ATC GAG AAA ACC ATC TCC AAA GCC AAA
Ala Leu Pro Ala Pro Ile Glu Lys Thr Ile Ser Lys Ala Lys
            100                 105                 110
```

FIG. 11K

```
                                        GGG CAG CCC CGA GAA CCA
                                        Gly Gln Pro Arg Glu Pro
                                         1               5

CAG GTG TAC ACC CTG CCC CCA TCC CGG GAT GAG CTG ACC AAG AAC CAG
Gln Val Tyr Thr Leu Pro Pro Ser Arg Asp Glu Leu Thr Lys Asn Gln
             10                  15                  20

GTC AGC CTG ACC TGC CTG GTC AAA GGC TTC TAT CCC AGC GAC ATC GCC
Val Ser Leu Thr Cys Leu Val Lys Gly Phe Tyr Pro Ser Asp Ile Ala
         25                  30                  35

GTG GAG TGG GAG AGC AAT GGG CAG CCG GAG AAC AAC TAC AAG ACC ACG
Val Glu Trp Glu Ser Asn Gly Gln Pro Glu Asn Asn Tyr Lys Thr Thr
     40                  45                  50

CCT CCC GTG CTG GAC TCC GAC GGC TCC TTC TTC CTC TAC AGC AAG CTC
Pro Pro Val Leu Asp Ser Asp Gly Ser Phe Phe Leu Tyr Ser Lys Leu
 55                  60                  65                  70

ACC GTG GAC AAG AGC AGG TGG CAG CAG GGG AAC GTC TTC TCA TGC TCC
Thr Val Asp Lys Ser Arg Trp Gln Gln Gly Asn Val Phe Ser Cys Ser
                 75                  80                  85

GTG ATG CAT GAG GCT CTG CAC AAC CAC TAC ACG CAG AAG AGC CTC TCC
Val Met His Glu Ala Leu His Asn His Tyr Thr Gln Lys Ser Leu Ser
             90                  95                 100

CTG TCT CCG GGT AAA
Leu Ser Pro Gly Lys
        105
```

FIG. 11L

```
Met Ser Phe Asn Thr Ile Ile Asp Trp Asn Ser Cys Thr Ala Val Gln
 1               5                  10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270
```

FIG. 11M

Pro Ala Ala Asp Met Ala Arg Arg Val Ala Glu Ala Val Glu Arg Gln
275 280 285

Leu Ala Glu Leu Pro Arg Ala Glu Thr Ala Arg Gln Ala Leu Asn Ala
290 295 300

Ser Arg Leu Ile Val Thr Lys Asp Ser Ala Gln Cys Val Glu Ile Ser
305 310 315 320

Asn Gln Tyr Gly Pro Glu His Leu Ile Ile Gln Thr Arg Asn Ala Arg
325 330 335

Glu Leu Val Asp Ser Ile Thr Ser Ala Gly Ser Val Phe Leu Gly Asp
340 345 350

Trp Ser Pro Glu Ser Ala Gly Asp Tyr Ala Ser Gly Thr Asn His Val
355 360 365

Leu Pro Thr Tyr Gly Tyr Thr Ala Thr Cys Ser Ser Leu Gly Leu Ala
370 375 380

Asp Phe Gln Lys Arg Met Thr Val Gln Glu Leu Ser Lys Glu Gly Phe
385 390 395 400

Ser Ala Val Ala Ser Thr Ile Glu Thr Leu Ala Ala Ala Glu Arg Leu
405 410 415

Thr Ala His Lys Asn Ala Val Thr Leu Arg Val Asn Ala Leu Lys Glu
420 425 430

Gln Ala

FIG. 11N

HindIII
TTGCAAGCTTTTTGCAAAAGCCTAGGCCTCCAAAAAAGCCTCCTCACTACTTCTGGAATAGCTCAGAGGCCGAGGCGCCT
CGGCCTCTGCATAAATAAAAAAAATTAGTCAGCCATGGGGCGGAGAATGGGCGGAACTGGGCGGAGTTAGGGGCGGGATG
GGCGGAGTTAGGGGCGGGACTATGGTTGCTGACTAATTGAGATGCATGCTTTGCATACTTCTGCCTGCTGGGGAGCCTGG
GGACTTTCCACACCTGGTTGCTGACTAATTGAGATGCATGCTTTGCATACTTCTGCCTGCTGGGGAGCCTGGGGACTTTC
CACAC PvuII
CCTAACTGACACACATTCCACAGCTGCCTCGCGCGTTTCGGTGATGACGGTGAAAACCTCTGACACATGCAGCTCCCGGA
GACGGTCACAGCTTGTCTGTAAGCGGATGCCGGGAGCAGACAAGCCCGTCAGGGCGCGTCAGCGGGTGTTGGCGGGTGTC
GGGGCGCAGCCATGACCCAGTCACGTAGCGATAGCGGAGTGTATACTGGCTTAACTATGCGGCATCAGAGCAGATTGTAC
TGAGAGTGCACCATATGCGGTGTGAAATACCGCACAGATGCGTAAGGAGAAAATACCGCATCAGGCGCTCTTCCGCTTCC
TCGCTCACTGACTCGCTGCGCTCGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCAATGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGGACAGTATTTGGTATCTGCGCTCTGCTGA
AGCCAGTTACCTTCGGAAAAAGAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGATCCTTTTAAATTAAAAAT
GAAGTTTTAAATCAATCTAAAGTATATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGTTGCCGGGAAGCTAGAGTA
AGTAGTTCGCCAGTTAATAGTTTGCGCAACGTTGTTGCCATTGCTGCAGGCATCGTGGTGTCACGCTCGTCGTTTGGTAT
GGCTTCATTCAGCTCCGGTTCCCAA PvuI
CGATCAAGGCGAGTTACATGATCCCCCATGTTGTGCAAAAAAGCGGTTAGCTCCTTCGGTCCTCGATCGTTGTCAGAAGT
AAGTTGGCCGCAGTGTTATCACTCATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGACCGAGTTGCTCTTGCCCGGCGTCAA

FIG. 13A

```
CACGGGATAATACCGCGCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGACGTCTAAGAAACCATTATTATCAT
GACATTAACC

                                      EcoRI
TATAAAAATAGGCGTATCACGAGGCCCTTTCGTCTTCAAGAATTCCTTTGCCTAATATTAATGAGGACTTAACCTGTGGA
AATATTTTGATGTGGGAAGCTGTTACTGTTAAAACTGAGGTTATTGGGGTAACTGCTATGTTAAACTTGCATTCAGGGAC
ACAAAAAACTCATGAAAATGGTGCTGGAAAACCCATTCAAGGGTCAAATTTTCATTTTTTTGCTGTTGGTGGGGAACCTT
TGGAGCTGCAGGGTGTGTTAGCAAACTACAGGACCAAATATCCTGCTCAAACTGTAACCCCAAAAAATGCTACAGTTGAC
AGTCAGCAGATGAACACTGACCACAAGGCTGTTTTGGATAAGGATAATGCTTATCCAGTGGAGTGCTGGGTTCCTGATCC
AAGTAAAAATGAAAACACTAGATATTTTGGAACCTACACAGGTGGGGAAAATGTGCCTCCTGTTTTGCACATTACTAACA
CAGCAACCACAGTGCTGCTTGATGAGCAGGGTGTTGGGCCCTTGTGCAAAGCTGACAGCTTGTATGTTTCTGCTGTTGAC
ATTTGTGGGCTGTTTACCAACACTTCTGGAACACAGCAGTGGAAGGGACTTCCCAGATATTTTAAAATTACCCTTAGAAA
GCGGTCTGTGAAAAACCCCTACCCAATTTCCTTTTTGTTAAGTGACCTAATTAACAGGAGGACACAGAGGGTGGATGGGC
AGCCTATGATTGGAA

                                                  BamHI
TGTCCTCTCAAGTAGAGGAGGTTAGGGTTTATGAGGACACAGAGGAGCTTCCTGGATCCNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
```

FIG. 13B

NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
ATATAGCACAAAGACATGCAAATAATATTTCCCTATGCTCATAAAAACAGCCCTGACCATGAAGCTTTGACAGACGCACA
ACCCTGGACTCCCAAGTCTTTCTCTTCAGTGACAAACACAGACAT

EcoRV
AGGATATCCACCATGGATTTTCAAGTGCAGATTTTCAGCTTCCTGCTAATCAGTGCCTCAGTCATACTGTCCAGAGGACA
AATTGTTCTCACCCAGTCTCCAGCAATCATGTCTGCATCTCCAGGGGAGAAGGTCACCATGACCTGCAGTGCCAGCTCAA
GTATAGATTACATTCACTGGTACCAGCAGAAGTCAGGCACCTCCCCCAAAAGATGGATTTATGACACATCCAAACTGGCT
TCTGGAGTCCCTGCTCGCTTCAGTGGCAGTGGGTCTGGGACCTCTTATTCTCTCACAATCAGCAGCATGGAGCCTGAAGA
TGCTG CCACTTATTACTGCCATCAGCGGAATAGTTACCCATGGACGTTCGGTGGAGGGACCAGGCTGGAA

SalI
ATCAGACGTAAGTCGACTTTCTCATCTTTTTTTATGTGTAAGACACAGGTTTTCATGTTAGGAGTTAAAGTCAGTTCAGA
AAATCTTGAGAAAATGGAGAGGGCTCATTATCAGTTGACGTGGCATACAGTGTCAGATTTTCTGTTTATCAAGCTAGTGA
GATTAGGGGCAAAAAGAGGCTTTAGTTGAGAGGAAAGTAATTAATACTATGGTCACCATCCAAGAGATTGGATCGGAGAA
TAAGCATGAGTAGTTATTGA

XbaI
GATCTGGGTCTGACTGCAGGTAGCGTGGTCTTCTAGACGTTTAAGTGGGAGATTTGGAGGGGATGAGGAATGAAGGAACT
TCAGGATAGAAAAGGGCTGAAGTCAAGTTCAGCTCCTAAAATGGATGTGGGAGCAAACTTTGAAGATAAACTGAATGACC
CAGAGGATGAAACAGCGCAGATCAAAGAGGGGCCTAGAGCTCTGAGAAGAGAAGGAGACTCATCCGTGTTGAGTTTCCAC
AAGTACTGTCTTGAGTTTTGCAATAAAAGTGGGATAGCAGAGTTGAGTGTNAGCCGTANAGTATACTCTCTTTTGTCTCC
TAAGATTTTTATGACTACAAAAATCAGTAGTATGTCCTGAAATAATCATTAAGCTGTTTGAAAGTATGACTGCTTGCCAT
GTAGATACCATGGCTTGCTGAATGATCAGAAGAGGTGTGACTCTTATTCTAAAATTTGTCACAAAATGTCAAAA

PvuII
TGAGAGACTCTGTAGGAACGAGTCCCTTGACAGACAGCTGCAAGGGGTTTTTTTCCTTTGTCTCATTTCTACATGAAAGT
AAATTTGAAATGATCNTTTTTTATTATAAGAGTAGAAATACAGTTGGGTTTGAACTATATGTTTTAATNGGCCNCACGGT
TTTGTAAGACATTTGGTCCTTTGTTTTCCCAGTTATTACTCGATTGTAATTTTATATCGCCAGCANTGGTCTGAAACGGT
NNNNNNCGCAACCTCTTCGTTTACTAACTGGGTGACCTTCGGCTGTGCCAGCCATTTGGCGTTCACCCTGCCGCNGGCCN
ATGAGAACCCCCGCGGTAGNNCCCTTGCTCCGCGTGGACCACTTTCCTGAGGACACAGTGATAGGAACAGAGCCACTAAT
CTGAAGAGAACAGAGATGTGACAGACTACACTAATGTGAGAAAAACAAGGAAAGGGTGACTTATTGGAGATTTCAGAAAT
AAAATGCATTTATTATTATATTCCCTTATTTTAATTTTCT

FIG. 13C

HindIII

ATTAGGGAATTAGAAAGGGCATAAACTGCTTTATCCAGTGTTATATTAAAAGCTTNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNAATCATTTCAAAATGATTTTAGAGAGCCTTTTGAAAACTCTTTTAA
ACACTTTTTAAACTCTATTAAAACTAATAAGATAACTTGAAATAATTTTCATGTCAAATACATTAACTGTTTAATGTTTA
AATGCCAGATGAAAAATGTAAAGCTATCAAGAATTCACCCAGATAGGAGTATCTTCATAGCATGTTTTTCCCTGCTTATT
TTCCAGTGATCACATTATTTTGCTACCATGGTTATTTTATACAATTATCTGAAAAAAATTAGTTATGAAGATTAAAAGAG
AAGAAAATATTAAACATAAGAGATTCAGTCTTTCATGTTGAACTGCTTGGTTAACAGTGAAGTTAGTTTTAAAAA

PvuII

AAAAAAAAACTATTTCTGTTATCAGCTGACTTCTCCCTATCTGTTGACTTCTCCCAGCAAAAGATTCTTACTTATTTTAC
ATTTTAACCTACTGCTCTCCCACCCAACGGGTGGAATCCCCCAGAGGGGGATTTCCAAGAGGCCACCTGGCAGTTGCTGA
GGGTCAGAAGTGAAGCTAGCCACTTCCTCTTAGGCAGGTGGCCAAGATTACAGTTGACCTCTCCTGGTATGGCTGAAAAT
TGCTGCATATGGTTACAGGCCTTGAGGCTTTGGGAGGGCTTAGAGAGAGTTGCTGGAACAGTCAGAAGGTGGAGGGGCTG
ACACCACCCAGGCGCAGAGGCAGGGCTCAGGGCCTGCTCTGCAGGGAGGTTTTAGCCCAGCCCAGCCAAAGTAACCCCCG
GGAGCCTGTTATCCCAGCACAGTCCTGGAAGAGGCACAGGGGAAATAAAAGCGGACGGAGGCTTTCCTTGACTCAGCCGC
TGCCTGGTCTTCTTCAGACCTGTTCTGAATTCTAAACTCTGAGGGGGTCGGATGACGTGGCCATTCTTTGCCTAAAGCAT
TGAGTTTACTGCAAGGTCAGAAAAGCATGCAAAGCCCTCAGAATGGCTGCAAAGAGCTCCAACAAAACAATTTAGAACTT
TATTAAGGAATAGGGGGAAGCTAGGAAGAAACTCAAAACATCAAGATTTTAAATACGCTTCTTGGTCTCCTTGCTATAAT
TATCTGGGATAAGCATGCTGTTTTCTGTCTGTCCCTAACATGCCCTGTGATTATCCGCAAACAACACACCCAAGGGCAGA
ACTTTGTTACTTAAACACCATCCTGTTTGCTTCTTTCCTCAGGAACTGTGGCTGCACCATCTGTCTTCATCTTCCCGCCA
TCTGATGAGCAGTTGAAATCTGGAACTGCCTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGAGCAGGACAGCAAGGACAGCACCTACA
GCCTCAGCAGCACCCTGACGCTGAGCAAAGCAGACTACGAGAAACACAAAGTCTACGCCTGCGAAGTCACCCATCAGGGC
CTGAGCTCGCCCGTCACAAAGAGCTTCAACAGGGGAGAGTGTTAGAGGGAGAAGTGCCCCCACCTGCTCCTCAGTTCCAG
CCTGACCCCCTCCCATCCTTTGGCCTCTGACCCTTTTTCCACAGGGGACCTACCCCTATTGCGGTCCTCCAGCTCATCTT
TCACCTCACCCCCCTCCTCCTCCTTGGCTTTAATTATGCTAATGTTGGAGGAGAATGAATAAATAAAGTGAATCTTTGCA
CCTGTGGTTTCTCTCTTTCCTCAATTTAATAATTATTATCTGTTGTTTACCAACTACTCAATTTCTCTTATAAGGGACTA
AATATGTAGTCATCCTAAGGCGCATAACCATTTATAAAAATCATCCTTCATTCTATTTTACCCTATCATCCTCTGCAAGA
CAGTCCTCCCTCAAACCCACAAGCCTTCTGTCCTCACAGTCCCCTGGGCCGTGGTAGGAGAGACTTGCTTCCTTGTTTTC
CCCTCCTCAGCAAGCCCTCATAGTCCTTTTTAAGGGTGACAGGTCTTACGGTCATATATCCTTTGATTCAATTCCCTGGG
AATCAACCAAGGCAAATTTTTCAAAAGAAGAAACCTGCNANNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN

FIG. 13D

NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNGATTCNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN

FIG. 13E

BamHI

NNNNNNNNNNNNNNNNNNNNNNNNNNNNNNNNNNNNNNNNNNNNNNNNNNNNGGATCCAGACATGATAAGATACATT
GATGAGTTTGGACAAACCACAACTAGAATGCAGTGAAAAAAATGCTTTATTTGTGAAATTTGTGATGCTATTGCTTTATT
TGTAACCATTATAAGCTGCAATAAACAAGTTAACAACAACAATTGCATTCATTTTATGTTTCAGGTTCAGGGGGAGGTGT
GGGAGGTTTTTTAAAGCAAGTAAAACCTCTACAAATGTGGTATGGCTGATTATGATCTCTAGTCAAGGCACTATACATCA
AATATTCCTTATTAACCCCTTTACAAATTAAAAAGCTAAAGGTACACAATTTTTGAGCATAGTTATTAATAGCAGACACT
CTATGCCTGTGTGGAGTAAGAAAAAACAGTATGTTATGATTATAACTGTTATGCCTACTTATAAAGGTTACAGAATATTT
TTCCATAATTTCTTGTATAGCAGTGCAGCTTTTTCCTTTGTGGTGTAAATAGCAAAGCAAGCAAGAGTTCTATTACTAA
ACACAGCATGACTCAAAAAACTTAGCAATTCTGAAGGAAAGTCCTTGGGGTCTTCTACCTTTCTCTTCTTTTTGGAGGA
GTAGAATGTTGAGAGTCAGCAGTAGCCTCATCATCACTAGATGGCATTTCTTCTGAGCAAAACAGGTTTTCCTCATTAAA
GGCATTCCACCACTGCTCCCATTCATCAGTTCCATAGGTTGGAATCTAAAATACACAAACAATTAGAATCAGTAGTTTAA
CACATTATACACTTAAAAATTTATATTTACCTTATAGCTTTAAATCTCTGTAGGTAGTTTGTCCAATTATGTCACACCA
CAGAAGTAAGGTTCCTTCACAAAGATCGATCCGGGGCCCACTCATAAATCCAGTTGCCGCCACGGTAGCCAATCACCGTA
TCGTATAAATCATCGCGGTACGTTCGGCATCGCTCATCACAATACGTGCCTGGACGTCGAGGATTTCGCGTGGGTCAAT
GCCGCGCCAGATCCACATCAGACGGTTAATCATGCGATACCAGTGAGGGATGGTTTTACCATCAAGGGCCGACTGCACAG
GCGGTTGTGCGCCGTGATTAAAGCGGCGGACTAGCGTCGAGGTTTCAGGATGTTTAAAGCGGGGTTTGAACAGGGTTTCG
CTCAGGTTTGCCTGTGTCATGGATGCAGCCTCCAGAATACTTACTGGAAACTATTGTAACCCGCCTGAAGTTAAAAAGAA
CAACGCCCGGCAGTGCCAGGCGTTGAAAAGATTAGCGACCGGAGATTGGCGGGACGAATACGACGCCCATATCCCACGGC
TGTTC

EcoRV

AATCCAGGTATCTTGCGGGATATCAACAACATAGTCATCAACCAGCGGACGACCAGCCGGTTTTGCGAAGATGGTGACAA
AGTGCGCTTTTGGATACATTTCACGAATCGCAACCGCAGTACCACCGGTATCCACCAGGTCATCAATAACGATGAAGCCT
TCGCCATCGCCTTCTGCGCGTTTCAGCACTTTAAGCTCGCGCTGGTTGTCGTGATCGTAGCTGGAAATACAAACGGTATC
GACATGACGAATACCCAGTTCACGCGCCAGTAACGCACCCGGTACCAGACCGCCACGGCTTACGGCAATAATGCCTTTCC
ATTGTTCAGAAGGCATCAGTCGGCTTGCGAGTTTACGTGCATGGATCTGCAACATGTCCCAGGTGACGATGTATTTTTCG
CTCATGTGAAGTGTCCCAGCCTGTTTATCTACGGCTTAAAAAGTGTTCGAGGGGAAAATAGGTTGCGCGAGATTATAGAG
ATCTGGCGCACTAAAAACCAGTATTTCACATGAGTCCGCGTCTTTTTACGCACTGCCTCTCCCTGACGCGGATAAAGTG
GTATTCTCAAACATATCTCGCAAGCCTGTCTTGTGTCC

FIG. 13F

| | | | | | | | | | | | | | | | |
|---|---|---|---|---|---|---|---|---|---|---|---|---|---|---|---|
| ATG | | | | | | | | | | | | | | | |
| Met | | | | | | | | | | | | | | | |
| 1 | | | | | | | | | | | | | | | |
| GAT | TTT | CAA | GTG | CAG | ATT | TTC | AGC | TTC | CTG | CTA | ATC | AGT | GCC | TCA | GTC |
| Asp | Phe | Gln | Val | Gln | Ile | Phe | Ser | Phe | Leu | Leu | Ile | Ser | Ala | Ser | Val |
| | | | 5 | | | | | 10 | | | | | 15 | | |
| ATA | CTG | TCC | AGA | GGA | CAA | ATT | GTT | CTC | ACC | CAG | TCT | CCA | GCA | ATC | ATG |
| Ile | Leu | Ser | Arg | Gly | Gln | Ile | Val | Leu | Thr | Gln | Ser | Pro | Ala | Ile | Met |
| | | 20 | | | | | 25 | | | | | 30 | | | |
| TCT | GCA | TCT | CCA | GGG | GAG | AAG | GTC | ACC | ATG | ACC | TGC | AGT | GCC | AGC | TCA |
| Ser | Ala | Ser | Pro | Gly | Glu | Lys | Val | Thr | Met | Thr | Cys | Ser | Ala | Ser | Ser |
| | 35 | | | | | 40 | | | | | 45 | | | | |
| AGT | ATA | GAT | TAC | ATT | CAC | TGG | TAC | CAG | CAG | AAG | TCA | GGC | ACC | TCC | CCC |
| Ser | Ile | Asp | Tyr | Ile | His | Trp | Tyr | Gln | Gln | Lys | Ser | Gly | Thr | Ser | Pro |
| 50 | | | | | 55 | | | | | 60 | | | | | 65 |
| AAA | AGA | TGG | ATT | TAT | GAC | ACA | TCC | AAA | CTG | GCT | TCT | GGA | GTC | CCT | GCT |
| Lys | Arg | Trp | Ile | Tyr | Asp | Thr | Ser | Lys | Leu | Ala | Ser | Gly | Val | Pro | Ala |
| | | | | 70 | | | | | 75 | | | | | 80 | |
| CGC | TTC | AGT | GGC | AGT | GGG | TCT | GGG | ACC | TCT | TAT | TCT | CTC | ACA | ATC | AGC |
| Arg | Phe | Ser | Gly | Ser | Gly | Ser | Gly | Thr | Ser | Tyr | Ser | Leu | Thr | Ile | Ser |
| | | | 85 | | | | | 90 | | | | | 95 | | |
| AGC | ATG | GAG | CCT | GAA | GAT | GCT | GCC | ACT | TAT | TAC | TGC | CAT | CAG | CGG | AAT |
| Ser | Met | Glu | Pro | Glu | Asp | Ala | Ala | Thr | Tyr | Tyr | Cys | His | Gln | Arg | Asn |
| | | 100 | | | | | 105 | | | | | 110 | | | |
| AGT | TAC | CCA | TGG | ACG | TTC | GGT | GGA | GGG | ACC | AGG | CTG | GAA | ATC | AGA | |
| Ser | Tyr | Pro | Trp | Thr | Phe | Gly | Gly | Gly | Thr | Arg | Leu | Glu | Ile | Arg | |
| | 115 | | | | | 120 | | | | | 125 | | | | |

FIG. 13G

ACT GTG GCT GCA CCA TCT GTC
Thr Val Ala Ala Pro Ser Val
1 5

TTC ATC TTC CCG CCA TCT GAT GAG CAG TTG AAA TCT GGA ACT GCC TCT
Phe Ile Phe Pro Pro Ser Asp Glu Gln Leu Lys Ser Gly Thr Ala Ser
10 15 20

GTT GTG TGC CTG CTG AAT AAC TTC TAT CCC AGA GAG GCC AAA GTA CAG
Val Val Cys Leu Leu Asn Asn Phe Tyr Pro Arg Glu Ala Lys Val Gln
25 30 35

TGG AAG GTG GAT AAC GCC CTC CAA TCG GGT AAC TCC CAG GAG AGT GTC
Trp Lys Val Asp Asn Ala Leu Gln Ser Gly Asn Ser Gln Glu Ser Val
40 45 50 55

ACA GAG CAG GAC AGC AAG GAC AGC ACC TAC AGC CTC AGC AGC ACC CTG
Thr Glu Gln Asp Ser Lys Asp Ser Thr Tyr Ser Leu Ser Ser Thr Leu
60 65 70

ACG CTG AGC AAA GCA GAC TAC GAG AAA CAC AAA GTC TAC GCC TGC GAA
Thr Leu Ser Lys Ala Asp Tyr Glu Lys His Lys Val Tyr Ala Cys Glu
75 80 85

GTC ACC CAT CAG GGC CTG AGC TCG CCC GTC ACA AAG AGC TTC AAC AGG
Val Thr His Gln Gly Leu Ser Ser Pro Val Thr Lys Ser Phe Asn Arg
90 95 100

GGA GAG TGT
Gly Glu Cys
105

FIG. 13H

GATCCGATCCNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNATATAGCACAAAGACATGCAAATAATATTTCCCTATGCTCATAAAAACAG
CCCTGACCATGAAGCTTTGACAGACGCACAACCCTGGACTCCCAAGTCTTTCTCTTCAGTGA

EcoRV

CAAACACAGACATAGGATATCCACCATGGAATGGAGCTGGGTAATGCTCTTCCTCCTGTCAGGAA

PvuII

CTGCAGGTGTCCGCTCTGAGGTCCAGCTGCAACAGTCTGGACCTGAACTGGTGAAGCCTGGAGCTTCAATGAAGATTTCC
TGCAAGGCTTCTGGTTACTCATTCACTGGCTACACCATGAACTGGGTGAAGCAGAGCCATGGAGAGAACCTTGAGTGGAT
TGGACGTATTAATCCTCACAATGGTGGTACTGACTACAACCAGAAGTTCAAGGACAAGGCCCCTTTAACTGTAGACAAGT
CATCCAACACAGCCTACATGGAGCTCCTCAGTCTGACATCTGAGGACTCTGCAGTCTATTACTGTGCAAGAGGCTACTAT
TACTA

FIG. 17A

```
                                                    NheI
TTCTTTGGACTACTGGGGTCAAGGAACCTCAGTCACCGTCTCCTCAGCTAGCACCAAGGGCCCATCGGTCTTCCCCCTGG
CGCCCTGCTCCAGGAGCACCTCCGAGAGCACAGCGGCCCTGGGCTGCCTGGTCAAGGACTACTTCCCCGAACCGGTGACG
GTGTCGTGGAACTCAGGCGCTCTGACCAGCGGCGT
          PvuII
GCACACCTTCCCAGCTGTCCTACAGTCCTCAGGACTCTACTCCCTCAGCAGCGTGGTGACCGTGCCCTCCAGCAACTTCG
GCACCCAGACCTACACCTGCAACGTAGATCACAAGCCCAGCAACACCAAGGTGGACAAGACAGTTGGTGAGAGGCCAGCT
CAGGGAGGGAGGGTGTCTGCTGGAAGCCAGGCTCAGCCCTCCTGCCTGGACGCACCCCGGCTGTGCAGCCCCAGCCCAGG
GCAGCAAGGCAGGCCCCATC
              StuI
TGTCTCCTCACCCGGAGGCCTCTGCCCGCCCCACTCATGCTCAGGGAGAGGGTCTTCTGGCTTTTTCCACCAGGCTCCAG
GCAGGCACAGGCTGGGTGCCCCTACCCCAGGCCCTTCACACACAGGGGCAGGTGCTTGGCTCAGACCTGCCAAAAGCCAT
ATCCGGGAGGACCCTGCCCCTGACCTAAGCCGACCCCAAAGGCCAAACTGTCCACTCCCTCAGCTCGGACACCTTCTCTC
CTCCCAGATCCGAGTAACTC
                                                                        StuI
CCAATCTTCTCTCTGCAGAGCGCAAATGTTGTGTCGAGTGCCCACCGTGCCCAGGTAAGCCAGCCCAGGCCTCGCCCTCC
AGC
                                                         PvuII
TCAAGGCGGGACAGGTGCCCTAGAGTAGCCTGCATCCAGGGACAGGCCCCAGCTGGGTGCTGACACGTCCACCTCCATCT
CTTCCTCAGCACCACCTGTGGCAGGACCGTCAGTCTTCCTCTTCCCCCCAAAACCCAAGGACACCCTCATGATCTCCCGG
ACCCCTGAGGTCACGTGCGTGGTGGTGGACGTGAGCCACGAAGACCCCGAGGTCCAGTTCAACTGGTACGTGGACGGCGT
GGAGGTGCATAATGCCAAGACAAAGCCACGGGAGGAGCAGTTCAACAGCACGTTCCGTGTGGTCAGCGTCCTCACCGTTG
TGCAC
                                                       StuI
CAGGACTGGCTGAACGGCAAGGAGTACAAGTGCAAGGTCTCCAACAAAGGCCTCCCAGCCCCCAT
                                                                      BglI
CGAGAAAACCATCTCCAAAACCAAAGGTGGGACCCGCGGGGTATGAGGGCCACATGGACAGAGGCCGGCTCGGCCCACCC
TCTGCCCTGGGAGTGACCGCTGTGCCAACCTCTGTCCCTACAGGGAGGAGATGACCAAGAACCAGGTCAGCCTGACCTGC
CTGGTCAAAGGCTTCTACCCCAGCGACATCGCCGTGGAGTGGGAGAGCAATGGGCAGCCGGAGAACAACTACAAGACCAC
ACCTCCCATGCTGGACTCCGACGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTCTCCCTGTCTCCGGGTAAA
TGAGTGCCACGGCCGGCAAGCCCCCGCTCCCCAGGCTCTCGGGGTCGCGTGAGGATGCTTGGCACGTACCCCGTGTACAT
ACTTCCCAGGCACCCAGCATGGAAATAAAGCACCCAGCGC
```

FIG. 17B

```
                                                          BglI
                                                        StuI
TGCCCTGGGCCCCTGCGAGACTGTGATGGTTCTTTCCGTGGGTCAGGCCGAGTCTGAGGCCTGAGTGGCATGAGGGAGGC
AGAGTGGGTCANNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
 PvuII
NCAGCTGNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNN
            BamHI
NNNNNNNNNNNNGGATCCAGACATGATAAGATACATTGATGAGTTTGGACAAACCACAACTAGAATGCAGTGAAAAAAAT
GCTTTATTTGTGAAATTTGTGATGCTATTGCTTTATTTGTAACCATTATA
               HpaI
AGCTGCAATAAACAAGTTAACAACAACAATTGCATTCATTTTATGTTTCAGGTTCAGGGGGAGGTGTGGGAGGTTTTTTA
AAGCAAGTAAAACCTCTACAAATGTGGTATGGCTGATTATGATCTCTAGTCAAGGCACTATACATCAAATATTCCTTATT
AACCCCTTTACAAATTAAAAAGCTAAAGGTACACAATTTTTGAGCATAGTTATTAATAGCAGACACTCTATGCCTGTGTG
GAGTAAGAAAAAACAGTATGTTATGATTATAACTGTTATGCCTACTTATAAAGGTTACAGAATATTTTTCCATAATTTTC
TTGTATAGCAGTGCAGCTTTTTCCTTTGTGGTGTAAATAGCAAAGCAAGCAAGAGTTCTATTACTAAACACAGCATGACT
CAAAAAACTTAGCAATTCTGAAGGAAAGTCCTTGGGGTCTTCTACCTTTCTCTTCTTTTTTGGAGGAGTAGAATGTTGAG
AGTCAGCAGTAGCCTCATCATCACTAGATGGCATTTCTTCTGAGCAAAACAGGTTTTCCTCATTAAAGGCATTCCACCAC
TGCTCCCATTCATCAGTTCCATAGGTTGGAATCTAAAATACACAAACAATTAGAATCAGTAGTTTAACACATTATACACT
TAAAAATTTTATATTTACCTTATAGCTTTAAATCTCTGTAGGTAGTTTGTCCAATTATGTCACACCACAGAAGTAAGGTT
CCTTCACAAAGATCCGGNNNNNNNNNNNNNNNNNNNNNNNNNTCATGCTTGCTCCTTGAG
  HpaI
GGCGTTAACGCGCAAGGTAACGGCATTTTTATGGGCGGTCAGACGTTCGGCGGCGGCCAGTGTTTCTATGGTTGAAGCCA
CCGCGGAGAACCCCTCTTTCGACAGTTCCTGTACGGTCATACGCTTCTGGAAATCTGCCAGCCCGAGGCTGGAACAGGTG
GCGGTGTAACCGTAAGTCGGTAGAACGTGGTTGGTTCCGGAGGCGTAATCACCTGCCGATTCCGGTGACCAGTCACCAAG
AAATACCGAACCGGCGCTGGTGATGCTATCGACCAGTTCACGGGCGTTGCGGGTCTGAATGATCAGGTGCTCCGGGCCGT
ACTGATTAGAGATCTCCACGCACTGCGCTGAATCTTTAGTCACGATCAGGCGGCTGGCGTTCAGTGCCTGGCGGGCGGTT
TCGGCACGCGGCAGTTCCGCCAGTTGGCGTTCGACGGCCTCGGCAACGCGACGCGCCATATCAGCAGCGGGCGTCAGTAA
AATCACCTGTGAGTCCGGGCCGTGTTCAGCCTGAGAGAGCAAATCAGAAGCCACGAAAT
```

FIG. 17C

ClaI
CCGGCGTTGCGCCGCTGTCAGCAATCACCAGCACTTCCGACGGGCCTGCGGGCATATCGATCTCCGCACCGTCCAGACGC
TGGCTCACCTGACGTTTCGCTTCGGTGACAAAGGCGTTACCCGGCCCGAAGATTTTGTCCACTTTTGGCACGGATTCCGT
ACCAAACGCCAGTGCGGCAATGGCCTGTGCGCCGC
PvuII
CGACGTTGAACACGTCCTGCACACCGCACAGCTGCGCCGCATAAAGGATCTCATCGGCAATCGGCGGCGGTGAGCACAGC
ACCACTTTTTTACAGCCCGCAATACGCGCCGGAGTCGCCAGCATTAATACCGTTGAGAAGAGCGGGGCGGAGCCGCCAGG
AATATACAACCCAACTGAAGCTACCGGACGCGTGACCTGCTGGCAACGCACGCCTGGCTGCGTTTCTACATCTACCGGCG
GCAGTTTTTGCGCAGTGTGGAAGGTTTCAATATTCTTTACTGCCACCGCCATCGCCTGTTTTAGCTCGTCGCTCAGGCGT
TCGCTGGCGGCGGCGATCTCCTCTGCAGACACCTTCAGCGCGGTAACCGTGGTTTTATCAAACTTCGCGCTGTATTCCCG
CAGGGCCTCATCGCCGCGTGCTTTCACGTTATCGAGAATATCGTTAACAGTGCGGGTAATGCTTTCAGAGGCGGAAATCG
CCGGGCGCGTTAA
PvuII
CAGCTGGCGTTGTTGCACCGCAGTACAGCTATTCCAGTCAATGATTGTGTTAAAGCTCATNNNNCCGGATCAGCTTTTTG
CAAAAGCCTAGGCCTCCAAAAAAGCCTCCTCACTACTTCTGGAATAGCTCAGAGGCCGAGGCGCCTCGGCCTCTGCATAA
ATAAAAAAAATTAGTCAGCCATGGGGCGGAGAATGGGCGGAACTGGGCGGAGTTAGGGGCGGGATGGGCGGAGTTAGGGG
CGGGACTATGGTTGCTGACTAATTGAGATGCATGCTTTGCATACTTCTGCCTGCTGGGGAGCCTGGGGACTTTCCACACC
TGGTTGCTGACTAATTGAGATGCATGCTTTGC
PvuII
ATACTTCTGCCTGCTGGGGAGCCTGGGGACTTTCCACACCCTAACTGACACACATTCCACAGCTGCCTCGCGCGTTTCGG
TGATGACGGTGAAAACCTCTGACACATGCAGCTCCCGGAGACGGTCACAGCTTGTCTGTAAGCGGATGCCGGGAGCAGAC
AAGCCCGTCAGGGCGCGTCAGCGGGTGTTGGCGGGTGTCGGGGCGCAGCCATGACCCAGTCACGTAGCGATAGCGGAGTG
TATACTGGCTTAACTATGCGGCATCAGAGCAGATTGTACTGAGAGTGCACCATATGCGGTGTGAAATACCGCACAGATGC
GTAAGGAGAAAATACCGCATCAGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCGCTTT
CTCAATGCTCACGCTGTAGGTATCTCAGTTCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTCATGAGATTAT

FIG. 17D

TCTGACAGTTACCAATGCTTAATCAGTGAGGCACCTATCTCAGCGATCTGTCTATTTCGTTCATCCATAGTTGCCTGACT
CCCCGTCGTGTAGATAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAA

PstI

GTAGTTCGCCAGTTAATAGTTTGCGCAACGTTGTTGCCATTGCTGCAGGCATCGTGGTGTCACGCTCGTCGTTTGGTATG
GCTTCATTCAGCTCCGGTTCCCAACGATCAAGGCGAGTTACATGATCCCC

PvuI

CATGTTGTGCAAAAAAGCGGTTAGCTCCTTCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAACACGGGATAATACCGCGCCACATAG
CAGAACTTTAAAAGTGCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATACTCTTCCTTTTTCAATATTA
TTGAAGCATTTATCAGGGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACC

EcoRI

ATTATTATCATGACATTAACCTATAAAAATAGGCGTATCACGAGGCCCTTTCGTCTTCAAGAATTCAGAGAGGTCTGGTG
GAGCCTGCAAAAGTCCAGCTTTCAAAGGAACACAGAAGTATGTGTATGGAATATTAGAAGATGTTGCTTTTACTCTTAAG
TTGGTTCCTAGGAAAAATAGTTAAATACTGTGACTTTAAAATGTGAGAGGGTTTTCAAGTACTCATTTTTTTAAATGTCC
AAAATTTTTGTCAATCAATTTGAGGTCTTGTTTGTGTAGAACTGACATTACTTAAAGTTTAACCGAGGAATGGGAGTGAG
GCTCTCTCATACCCTATTCAGAACTGACTTTTAACAATAATAAATTAAGTTTAAAATATTTTTAAATGAA

PvuII

TTGAGCAATGTTGAGTTGAGTCAAGATGGCCGATCAGAACCGGAACACCTGCAGCAGCTGGCAGGAAGCAGGTCATGTGG
CAAGGCTATTTGGGGAAGGGAAAATAAAACCACTAGGTAAACTTGTAGCTGTGGTTTGAAGAAGTGGTTTTGAAACACTC
TGTCCAGCCCCACCAAACCGAAAGTCCAGGCTGAGCAAAACACCACCTGGGTAATTTGCATTTCTAAAATAAGTTGAGGA
TTCAGCCGAAACTGGAGAGGTCCTCTTTTAACTTATTGAGTTCAACCTTTTAATTTTAGCTTGAGTAGTTCTAGTTTCCC
CAAAC

EcoRI

TTAAGTTTATCGACTTCTAAAATGTATTTAGAATTCCTTTGCCTAATATTAATGAGGACTTAACCTGTGGAAATATTTTG
ATGTGGGAAGCTGTTACTGTTAAAACTGAGGTTATTGGGGTAACTGCTATGTTAAACTTGCATTCAGGGACACAAAAAAC
TCATGAAAATGGTGCTGGAAAACCCATTCAAGGGTCAAATTTTCATTTTTTTGCTGTTGGTGGGGAACCTTTGGAGCTGC
AGGGTGTGTTAGCAAACTACAGGACCAAATATCCTGCTCAAACTGTAACCCCAAAAAATGCTACAGTTGACAGTCAGCAG
ATGAACACTGACCACAAGGCTGTTTTGGATAAGGATAATGCTTATCCAGTGGAGTGCTGGGTTCCTGATCCAAGTAAAAA

FIG. 17E

```
TGAAAACACTAGATATTTTGGAACCTACACAGGTGGGGAAAATGTGCCTCCTGTTTTGCACATTACTAACACAGCAACCA
CAGTGCTGCTTGATGAGCAGGGTGTTGGGCCCTTGTGCAAAGCTGACAGCTTGTATGTTTCTGCTGTTGACATTTGTGGG
CTGTTTACCAACACTTCTGGAACACAGCAGTGGAAGGGACTTCCCAGATATTTTAAAATTACCCTTAGAAAGCGGTCTGT
GAAAAACCCCTACCCAATTTCCTTTTTGTTAAGTGACCTAATTAACAGGAGGACACAGAGGGTGGATGGGCAGCC
                                                                   BamHI
TATGATTGGAATGTCCTCTCAAGTAGAGGAGGTTAGGGTTTATGAGGACACAGAGGAGCTTCCTGGG
```

FIG. 17F

```
                                                ATG GAA TGG AGC TGG GTA ATG CTC
                                                Met Glu Trp Ser Trp Val Met Leu
                                                 1               5

TTC CTC CTG TCA GGA ACT GCA GGT GTC CGC TCT GAG GTC CAG CTG CAA
Phe Leu Leu Ser Gly Thr Ala Gly Val Arg Ser Glu Val Gln Leu Gln
     10                  15                  20

CAG TCT GGA CCT GAA CTG GTG AAG CCT GGA GCT TCA ATG AAG ATT TCC
Gln Ser Gly Pro Glu Leu Val Lys Pro Gly Ala Ser Met Lys Ile Ser
 25                  30                  35                  40

TGC AAG GCT TCT GGT TAC TCA TTC ACT GGC TAC ACC ATG AAC TGG GTG
Cys Lys Ala Ser Gly Tyr Ser Phe Thr Gly Tyr Thr Met Asn Trp Val
                 45                  50                  55

AAG CAG AGC CAT GGA GAG AAC CTT GAG TGG ATT GGA CGT ATT AAT CCT
Lys Gln Ser His Gly Glu Asn Leu Glu Trp Ile Gly Arg Ile Asn Pro
             60                  65                  70

CAC AAT GGT GGT ACT GAC TAC AAC CAG AAG TTC AAG GAC AAG GCC CCT
His Asn Gly Gly Thr Asp Tyr Asn Gln Lys Phe Lys Asp Lys Ala Pro
         75                  80                  85

TTA ACT GTA GAC AAG TCA TCC AAC ACA GCC TAC ATG GAG CTC CTC AGT
Leu Thr Val Asp Lys Ser Ser Asn Thr Ala Tyr Met Glu Leu Leu Ser
     90                  95                 100

CTG ACA TCT GAG GAC TCT GCA GTC TAT TAC TGT GCA AGA GGC TAC TAT
Leu Thr Ser Glu Asp Ser Ala Val Tyr Tyr Cys Ala Arg Gly Tyr Tyr
105                 110                 115                 120

TAC TAT TCT TTG GAC TAC TGG GGT CAA GGA ACC TCA GTC ACC GTC TCC
Tyr Tyr Ser Leu Asp Tyr Trp Gly Gln Gly Thr Ser Val Thr Val Ser
                125                 130                 135

TCA GCT AGC ACC AAG GGC CCA TCG GTC TTC CCC CTG GCG CCC TGC TCC
Ser Ala Ser Thr Lys Gly Pro Ser Val Phe Pro Leu Ala Pro Cys Ser
            140                 145                 150

AGG AGC ACC TCC GAG AGC ACA GCG GCC CTG GGC TGC CTG GTC AAG GAC
Arg Ser Thr Ser Glu Ser Thr Ala Ala Leu Gly Cys Leu Val Lys Asp
        155                 160                 165

TAC TTC CCC GAA CCG GTG ACG GTG TCG TGG AAC TCA GGC GCT CTG ACC
Tyr Phe Pro Glu Pro Val Thr Val Ser Trp Asn Ser Gly Ala Leu Thr
    170                 175                 180

AGC GGC GTG CAC ACC TTC CCA GCT GTC CTA CAG TCC TCA GGA CTC TAC
Ser Gly Val His Thr Phe Pro Ala Val Leu Gln Ser Ser Gly Leu Tyr
185                 190                 195                 200
```

FIG. 17G

| | | | | | | | | | | | | | | | |
|---|---|---|---|---|---|---|---|---|---|---|---|---|---|---|---|
| TCC | CTC | AGC | AGC | GTG | GTG | ACC | GTG | CCC | TCC | AGC | AAC | TTC | GGC | ACC | CAG |
| Ser | Leu | Ser | Ser | Val | Val | Thr | Val | Pro | Ser | Ser | Asn | Phe | Gly | Thr | Gln |
| | | | | 205 | | | | | 210 | | | | | 215 | |

| | | | | | | | | | | | | | | | |
|---|---|---|---|---|---|---|---|---|---|---|---|---|---|---|---|
| ACC | TAC | ACC | TGC | AAC | GTA | GAT | CAC | AAG | CCC | AGC | AAC | ACC | AAG | GTG | GAC |
| Thr | Tyr | Thr | Cys | Asn | Val | Asp | His | Lys | Pro | Ser | Asn | Thr | Lys | Val | Asp |
| | | | 220 | | | | | 225 | | | | | 230 | | |

| | | |
|---|---|---|
| AAG | ACA | GTT |
| Lys | Thr | Val |
| | | 235 |

FIG. 17H

| | | | | | | | | | | | |
|---|---|---|---|---|---|---|---|---|---|---|---|
| GAG | CGC | AAA | TGT | TGT | GTC | GAG | TGC | CCA | CCG | TGC | CCA |
| Glu | Arg | Lys | Cys | Cys | Val | Glu | Cys | Pro | Pro | Cys | Pro |
| 1 | | | | 5 | | | | | 10 | | |

FIG. 17I

GCA CCA CCT GTG GCA
Ala Pro Pro Val Ala
1 5

GGA CCG TCA GTC TTC CTC TTC CCC CCA AAA CCC AAG GAC ACC CTC ATG
Gly Pro Ser Val Phe Leu Phe Pro Pro Lys Pro Lys Asp Thr Leu Met
10 15 20

ATC TCC CGG ACC CCT GAG GTC ACG TGC GTG GTG GTG GAC GTG AGC CAC
Ile Ser Arg Thr Pro Glu Val Thr Cys Val Val Val Asp Val Ser His
25 30 35

GAA GAC CCC GAG GTC CAG TTC AAC TGG TAC GTG GAC GGC GTG GAG GTG
Glu Asp Pro Glu Val Gln Phe Asn Trp Tyr Val Asp Gly Val Glu Val
40 45 50

CAT AAT GCC AAG ACA AAG CCA CGG GAG GAG CAG TTC AAC AGC ACG TTC
His Asn Ala Lys Thr Lys Pro Arg Glu Glu Gln Phe Asn Ser Thr Phe
55 60 65

CGT GTG GTC AGC GTC CTC ACC GTT GTG CAC CAG GAC TGG CTG AAC GGC
Arg Val Val Ser Val Leu Thr Val Val His Gln Asp Trp Leu Asn Gly
70 75 80 85

AAG GAG TAC AAG TGC AAG GTC TCC AAC AAA GGC CTC CCA GCC CCC ATC
Lys Glu Tyr Lys Cys Lys Val Ser Asn Lys Gly Leu Pro Ala Pro Ile
90 95 100

GAG AAA ACC ATC TCC AAA ACC AAA
Glu Lys Thr Ile Ser Lys Thr Lys
105

FIG. 17J

Met Ser Phe Asn Thr Ile Ile Asp Trp Asn Ser Cys Thr Ala Val Gln
1 5 10 15

Gln Arg Gln Leu Leu Thr Arg Pro Ala Ile Ser Ala Ser Glu Ser Ile
20 25 30

Thr Arg Thr Val Asn Asp Ile Leu Asp Asn Val Lys Ala Arg Gly Asp
35 40 45

Glu Ala Leu Arg Glu Tyr Ser Ala Lys Phe Asp Lys Thr Thr Val Thr
50 55 60

Ala Leu Lys Val Ser Ala Glu Glu Ile Ala Ala Ala Ser Glu Arg Leu
65 70 75 80

Ser Asp Glu Leu Lys Gln Ala Met Ala Val Ala Val Lys Asn Ile Glu
85 90 95

Thr Phe His Thr Ala Gln Lys Leu Pro Pro Val Asp Val Glu Thr Gln
100 105 110

Pro Gly Val Arg Cys Gln Gln Val Thr Arg Pro Val Ala Ser Val Gly
115 120 125

Leu Tyr Ile Pro Gly Gly Ser Ala Pro Leu Phe Ser Thr Val Leu Met
130 135 140

Leu Ala Thr Pro Ala Arg Ile Ala Gly Cys Lys Lys Val Val Leu Cys
145 150 155 160

Ser Pro Pro Pro Ile Ala Asp Glu Ile Leu Tyr Ala Ala Gln Leu Cys
165 170 175

Gly Val Gln Asp Val Phe Asn Val Gly Gly Ala Gln Ala Ile Ala Ala
180 185 190

Leu Ala Phe Gly Thr Glu Ser Val Pro Lys Val Asp Lys Ile Phe Gly
195 200 205

Pro Gly Asn Ala Phe Val Thr Glu Ala Lys Arg Gln Val Ser Gln Arg
210 215 220

Leu Asp Gly Ala Glu Ile Asp Met Pro Ala Gly Pro Ser Glu Val Leu
225 230 235 240

Val Ile Ala Asp Ser Gly Ala Thr Pro Asp Phe Val Ala Ser Asp Leu
245 250 255

Leu Ser Gln Ala Glu His Gly Pro Asp Ser Gln Val Ile Leu Leu Thr
260 265 270

FIG. 17K

```
Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```

FIG. 17L

GATCCGATCCNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNATATAGCACAAAGACATGCAAATAATATTTCCCTATGCTCATAAAAACAG
CCCTGACCATGAAGCTTTGACAGACGCACAACCCTGGACTCCCAAGTCTTTCTCTTCAGTGA

EcoRV

CAAACACAGACATAGGATATCCACCATGGAATGGAGCTGGGTAATGCTCTTCCTCCTGTCAGGAACTGCAGGTGTCCGCT
CTGAGGTCCAGCTGCAACAGTCTGGACCTGAACTGGTGAAGCCTGGAGCTTCAATGAAGATTTCCTGCAAGGCTTCTGGT
TACTCATTCACTGGCTACACCATGAACTGGGTGAAGCAGAGCCATGGAGAGAACCTTGAGTGGATTGGACGTATTAATCC
TCACAATGGTGGTACTGACTACAACCAGAAGTTCAAGGACAAGGCCCCTTTAACTGTAGACAAGTCATCCAACACAGCCT
ACATGGAGCTCCTCAGTCTGACATCTGAGGACTCTGCAGTCTATTACTGTGCAAGAGGCTACTATTACTATTCTTTGGAC
TACTGGGGTCAAGGAACCTCAGTCACCGTCTCCTCAACCAAGGGCCCATCGGTCTTCCCCCTGGCGCCCTGCTCCAGGAG
CACCTCTGGGGGCACAGCGGCCCTGGGCTGCCTGGTCAAGGACTACTTCCCCGAACCGGTGACGGTGTCGTGGAACTCAG
GCGCCCTGACCAGCGGCGTGCACAC

FIG. 18A

BstEII

CTTCCCGGCTGTCCTACAGTCCTCAGGACTCTACTCCCTCAGCAGCGTGGTGACCGTGCCCTCCAGCAGCTTGGGCACCC
AGACCTACACCTGCAACGTGAATCACAAGCCCAGCAACACCAAGGTGGACAAGAGAGTTGGTGAGAGGCCAGCGCAGGGA
GGGAGGGTGTCTGCTGGAAGCCAGGCTCAGCCCTCCTGCCTGGACGCATCCCGGCTGTGCAGTCCCAGCCCAGGGCACCA
AGGCAGGCCCCGTCTGACTCCTCACCCGGAGGCCTCTGCCCGCCCCACTCATGCTCAGGGAGAGGGTCTTCTGGCTTTTT
CCACCAGGCTCCGGGCAGGCACAGGCTGGATGCCCCTACCCCAGGCCCTTCACACACAGGGGCAGGTGCTGCGCTCAGAG
CTGCCAAGAGCCATATCCAGGAGGACCCTGCCCCTGACCTAAGCCCACCCCAAAG

BglII

GCCAAACTCTCTACTCACTCAGCTCAGACACCTTCTCTCTTCCCAGATCTGAGTAACTCCCAATCTTCTCTCTGCAGAGC
TCAAAACCCCACTTGGTGACACAACTCACACATGCCCACGGTGCCCAGGTAAGCCAGCCCAGGCCTCGCCCTCCAGCTCA
AGGCGGGACAAGAGCCCTAGAGTGGCCTGAGTCCAGGGACAGGCCCCAGCAGGGTGCTGACGCATCCACCTCCATCCCAG
ATCCCCGTAACTCCCAATCTTCTCTCTGCAGAGCCCAAATCTTGTGACACACCTCCCCCGTGCCCAAGGTGCCCAGGTAA
GCCAGCCCAGGCCTCGCCCTCCAGCTCAAGGCAGGACAGGTGCCCTAGAGTGGCCTGAGTCCAGGGACAGGCCCCAGCAG
GGTGCTGACGCATCCACCTCCATCCCAGATCCCCGTAACTCCCAATCTTCTCTCTGCAGAGCCCAAATCTTGTGACACAC
CTCCCCCGTGCCCAAGGTGCCCAGGTAAGCCAGCCCAGGCCTCGCCCTCCAGCTCAAGGCAGGACAGGTGCCCTAGAGTG
GCCTGAGTCCAGGGACAGGCCCCAGCAGGGTGCTGACGCATCCACCTCCATCCCAGATCCCCGTAACTCCCAATCTTCTC
TCTGCAGAGCCCAAATCTTGTGACACACCTCCCCCGTGCCCAAGGTGCCCAGGTAAGCCAGCCCAGGCCTCGCCCTCCAG
CTCAAGGCAGGACAGGTGCCCTAGAGTGGCCTGCATCCAGGGACAGGTCCCAGTCGGGTGCTGACACATCTGCCTCCATC
TCTTCCTCAGCACCTGAACTCCTGGGAGGACCGTCAGTCTTCCTCTTCCCCCCAAAACCCAAGGATACCCTTATGATTTC
CCGGACCCCTGAGGTCACGTGCGTGGTGGTGGACGTGAGCCACGAAGACCCCGAGGTCCAGTTCAAGTGGTACGTGGACG
GCGTGGAGGTGCATAATGCCAAGACAAAGCTGCGGGAGGAGCAGTACAACAGCACGTTCCGTGTGGTCAGCGTCCTCACC
GTCCTGCACCAGGACTGGCTGAACGGCAAGGAGTACAAGTGCAAGGTCTCCAACAAAGCCCTCCCAGCCCCCATCGAGAA
AAC

SacII

CATCTCCAAAGCCAAAGGTGGGACCCGCGGGGTATGAGGGCCACGTGGACAGAGGCCAGCTTGACCCACCCTCTGCCCTG
GGAGTGACCGCTGTGCCAACCTCTGTCCCTACAGGACAGCCCCGAGAACCACAGGTGTACACCCTGCCCCCATCCCGGGA
GGAGATGACCAAGAACCAGGTCAGCCTGACCTGCCTGGTCAAAGGCTTCTACCCCAGCGACATCGCCGTGGAGTGGGAGA
GCAATGGGCAGCCGGAGAACAACTACAACACCACGCCTCCCATGCTGGACTCCGACGGCTCCTTCTTCCTCTACAGCAAG
CTCAC

NsiI

CGTGGACAAGAGCAGGTGGCAGCAGGGGAACATCTTCTCATGCTCCGTGATGCATGAGGCTCTGCACAACCGCTACACCC
AGAAGAGCCTCTCCCTGTCTCCGGGTAAATGAGTGCGACAGCCGGCAAGCCCCCGCTCCCCGGGCTCTCGGGGTCGCGCG
AGGATGCTTGGCACGTACCCCGTGTACATACTTCCCGGGCACCCAGCATGGAAATAAAGCACCCAGCGCTGCCCTGGGCC
CCTGTGAGACTGTGATGGTTCTTTCCACGGGTCAGGCCGAGTCTGAGGCCTGAGTGACATGAGGGAGGCAGAGCGGGTCN

FIG. 18B

```
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNCAGCTGNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNN
                                                      BamHI
NNNNNNNNNNNNNNNNNNNNNNNNNNNNNNNNNNNNNNNNNNNNNNNNNNNNNNGGATCCAGACATGATAAGATACATTG
ATGAGTTTGGACAAACCACAACTAGAATGCAGTGAAAAAAATGCTTTATTTGTGAAATTTGTGATGCTA
                                         HpaI
TTGCTTTATTTGTAACCATTATAAGCTGCAATAAACAAGTTAACAACAACAATTGCATTCATTTTATGTTTCAGGTTCAG
GGGGAGGTGTGGGAGGTTTTTTAAAGCAAGTAAAACCTCTACAAATGTGGTATGGCTGATTATGATCTCTAGTCAAGGCA
CTATACATCAAATATTCCTTATTAACCCCTTTACAAATTAAAAAGCTAAAGGTACACAATTTTTGAGCATAGTTATTAAT
AGCAGACACTCTATGCCTGTGTGGAGTAAGAAAAAACAGTATGTTATGATTATAACTGTTATGCCTACTTATAAAGGTTA
CAGAATATTTTTCCATAATTTTCTTGTATAGCAGTGCAGCTTTTTCCTTTGTGGTGTAAATAGCAAAGCAAGCAAGAGTT
CTATTACTAAACACAGCATGACTCAAAAAACTTAGCAATTCTGAAGGAAAGTCCTTGGGGTCTTCTACCTTTCTCTTCTT
TTTTGGAGGAGTAGAATGTTGAGAGTCAGCAGTAGCCTCATCATCACTAGATGGCATTTCTTCTGAGCAAAACAGGTTTT
CCTCATTAAAGGCATTCCACCACTGCTCCCATTCATCAGTTCCATAGGTTGGAATCTAAAATACACAAACAATTAGAATC
AGTAGTTTAACACATTATACACTTAAAAATTTTATATTTACCTTATAGCTTTAAATCTCTGTAGGTAGTTTGTCCAATTA
TGTCACACCACAGAAGTAAGGTTCCTTCACAAAGATCCGGNNNNNNNNNNNNNNNNNNNN
                         HpaI
NNNNNTCATGCTTGCTCCTTGAGGGCGTTAACGCGCAAGGTAACGGCATTTTTATGGGCGGTCAGACGTTCGGCGGCGGC
CAGTGTTTCTATGGTTGAAGCCACCGCGGAGAACCCCTCTTTCGACAGTTCCTGTACGGTCATACGCTTCTGGAAATCTG
CCAGCCCGAGGCTGGAACAGGTGGCGGTGTAACCGTAAGTCGGTAGAACGTGGTTGGTTCCGGAGGCGTAATCACCTGCC
GATTCCGGTGACCAGTCACCAAGAAATACCGAACCGGCGCTGGTGATGCTATCGACCAGTTCACGGGCGTTGCGGGTCTG
```

FIG. 18C

AATGATCAGGTGCTCCGGGCCGTACTGATTAGAGATCTCCACGCACTGCGCTGAATCTTTAGTCACGATCAGGCGGCTGG
CGTTCAGTGCCTGGCGGGCGGTTTCGGCACGCGGCAGTTCCGCCAGTTGGCGTTCGACGGCCTCGGCAACGCGACGCGCC
ATATCAGCAGCGGGCGTCAGTAAAATCACCTGTGAGTCCGGGCCGTGTTCAGCCTGAGAGAGCAAATCAGAAGCCACGAA
ATCCGGCGTTGCGCCGCTGTCAGCA

ClaI

ATCACCAGCACTTCCGACGGGCCTGCGGGCATATCGATCTCCGCACCGTCCAGACGCTGGCTCACCTGACGTTTCGCTTC
GGTGACAAAGGCGTTACCCGGCCCGAAGATTTTGTCCACTTTTGGCACGGATTCCGTACCAAACGCCAGTGCGGCAATGG
CCTGTGCGCCGCCGACGTTGAACACGTCCTGCACA

PvuII

CCGCACAGCTGCGCCGCATAAAGGATCTCATCGGCAATCGGCGGCGGTGAGCACAGCACCACTTTTTTACAGCCCGCAAT
ACGCGCCGGAGTCGCCAGCATTAATACCGTTGAGAAGAGCGGGGCGGAGCCGCCAGGAATATACAACCCAACTGAAGCTA
CCGGACGCGTGACCTGCTGGCAACGCACGCCTGGCTGCGTTTCTACATCTACCGGCGGCAGTTTTTGCGCAGTGTGGAAG
GTTTCAATATTCTTTACTGCCACCGCCATCGCCTGTTTTAGCTCGTCGCTCAGGCGTTCGCTGGCGGCGGCGATCTCCTC
TGCAGACACCTTCAGCGCGGTAACCGTGGTTTTATCAAACTTCGCGCTGTATTCCCGCAGGGCCTCATCGCCGCGTGCTT
TCACGTTATCGAGAATATCGTTAACAGTGCGGGTAATGCTTTCAGAGGCGGAAAT

PvuII

CGCCGGGCGCGTTAACAGCTGGCGTTGTTGCACCGCAGTACAGCTATTCCAGTCAATGATTGTGTTAAAGCTCATNNNNC
CGGATCAGCTTTTTGCAAAAGCCTAGGCCTCCAAAAAAGCCTCCTCACTACTTCTGGAATAGCTCAGAGGCCGAGGCGCC
TCGGCCTCTGCATAAATAAAAAAAATTAGTCAGCCATGGGGCGGAGAATGGGCGGAACTGGGCGGAGTTAGGGGCGGGAT
GGGCGGAGTTAGGGGCGGGACTATGGTTGCTGACTAATTGAGATGCATGCTTTGCATACTTCTGCCTGCTGGGGAGCCTG
GGGACTTTCCACACCTGGTTGCTGACTAATTGAGATGCATGCTTTGCATACTTCTGCCTGCTGGGGAGCC

PvuII

TGGGGACTTTCCACACCCTAACTGACACACATTCCACAGCTGCCTCGCGCGTTTCGGTGATGACGGTGAAAACCTCTGAC
ACATGCAGCTCCCGGAGACGGTCACAGCTTGTCTGTAAGCGGATGCCGGGAGCAGACAAGCCCGTCAGGGCGCGTCAGCG
GGTGTTGGCGGGTGTCGGGGCGCAGCCATGACCCAGTCACGTAGCGATAGCGGAGTGTATACTGGCTTAACTATGCGGCA
TCAGAGCAGATTGTACTGAGAGTGCACCATATGCGGTGTGAAATACCGCACAGATGCGTAAGGAGAAAATACCGCATCAG
GCGCTCTTCCGCTTCCTCGCTCACTGACTCGCTGCGCTCGGTCGTTCGGCTGCGGCGAGCGGTATCAGCTCACTCAAAGG
CGGTAATACGGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAATGCTCACGCTGTAGGTAT
CTCAGTTCGGTGTAGGTCGTTCGCTCCAAGCTGGGCTGTGTGCACGAACCCCCCGTTCAGCCCGACCGCTGCGCCTTATC
CGGTAACTATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGGACAGTATTTGGT

FIG. 18D

ATCTGCGCTCTGCTGAAGCCAGTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGAAGATCCTTTGATCTTTTCTACGG
GGTCTGACGCTCAGTGGAACGAAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTCTGACAGTTACCAATGCTTAAT
CAGTGAGGCACCTATCTCAGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTG
PstI
CTGCAGGCATCGTGGTGTCACGCTCGTCGTTTGGTATGGCTTCATTCAGCTCCGGTTCCCAACGA
PvuI
TCAAGGCGAGTTACATGATCCCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGCTCTTGCCCGGCGTCAACA
CGGGATAATACCGCGCCACATAGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATCTTCAGCATCTTTTACTTTCACCA
GCGTTTCTGGGTGAGCAAAAACAGGAAGGCAAAATGCCGCAAAAAAGGGAATAAGGGCGACACGGAAATGTTGAATACTC
ATACTCTTCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTATTATCATGA
CATTAACCTA
EcoRI
TAAAAATAGGCGTATCACGAGGCCCTTTCGTCTTCAAGAATTCAGAGAGGTCTGGTGGAGCCTGCAAAAGTCCAGCTTTC
AAAGGAACACAGAAGTATGTGTATGGAATATTAGAAGATGTTGCTTTTACTCTTAAGTTGGTTCCTAGGAAAAATAGTTA
AATACTGTGACTTTAAAATGTGAGAGGGTTTTCAAGTACTCATTTTTTTAAATGTCCAAAATTTTTGTCAATCAATTTGA
GGTCTTGTTTGTGTAGAACTGACATTACTTAAAGTTTAACCGAGGAATGGGAGTGAGGCTCTCTCATACCCTATTCAGAA
CTGACTTTTAACAATAATAAATTAAGTTTAAAATATTTTTAAATGAATTGAGCAATGTTGAGTTGAGTCA
PvuII
AGATGGCCGATCAGAACCGGAACACCTGCAGCAGCTGGCAGGAAGCAGGTCATGTGGCAAGGCTATTTGGGGAAGGGAAA
ATAAAACCACTAGGTAAACTTGTAGCTGTGGTTTGAAGAAGTGGTTTTGAAACACTCTGTCCAGCCCCACCAAACCGAAA
GTCCAGGCTGAGCAAAACACCACCTGGGTAATTTGCATTTCTAAAATAAGTTGAGGATTCAGCCGAAACTGGAGAGGTCC
TCTTTTAACTTATTGAGTTCAACCTTTTAATTTTAGCTTGAGTAGTTCTAGTTTCCCCAAACTTAAGTTTATCGACTTCT
AAAAT

FIG. 18E

```
        EcoRI
GTATTTAGAATTCCTTTGCCTAATATTAATGAGGACTTAACCTGTGGAAATATTTTGATGTGGGAAGCTGTTACTGTTAA
AACTGAGGTTATTGGGGTAACTGCTATGTTAAACTTGCATTCAGGGACACAAAAAACTCATGAAAATGGTGCTGGAAAAC
CCATTCAAGGGTCAAATTTTCATTTTTTTGCTGTTGGTGGGGAACCTTTGGAGCTGCAGGGTGTGTTAGCAAACTACAGG
ACCAAATATCCTGCTCAAACTGTAACCCCAAAAAATGCTACAGTTGACAGTCAGCAGATGAACACTGACCACAAGGCTGT
TTTGGATAAGGATAATGCTTATCCAGTGGAGTGCTGGGTTCCTGATCCAAGTAAAAATGAAAACACTAGATATTTTGGAA
CCTACACAGGTGGGGAAAATGTGCCTCCTGTTTTGCACATTACTAACACAGCAACCACAGTGCTGCTTGATGAGCAGGGT
GTTGGGCCCTTGTGCAAAGCTGACAGCTTGTATGTTTCTGCTGTTGACATTTGTGGGCTGTTTACCAACACTTCTGGAAC
ACAGCAGTGGAAGGGACTTCCCAGATATTTTAAAATTACCCTTAGAAAGCGGTCTGTGAAAAACCCCTACCCAATTTCCT
TTTTGTTAAGTGACCTAATTAACAGGAGGACACAGAGGGTGGATGGGCAGCCTATGATTGGAATGTCCTCTCAAGTAGAG
                                                 BamHI
GAGGTTAGGGTTTATGAGGACACAGAGGAGCTTCCTGGG
```

FIG. 18F

```
                                                ATG GAA TGG AGC TGG GTA ATG CTC
                                                Met Glu Trp Ser Trp Val Met Leu
                                                 1               5

TTC CTC CTG TCA GGA ACT GCA GGT GTC CGC TCT GAG GTC CAG CTG CAA
Phe Leu Leu Ser Gly Thr Ala Gly Val Arg Ser Glu Val Gln Leu Gln
     10                  15                  20

CAG TCT GGA CCT GAA CTG GTG AAG CCT GGA GCT TCA ATG AAG ATT TCC
Gln Ser Gly Pro Glu Leu Val Lys Pro Gly Ala Ser Met Lys Ile Ser
 25                  30                  35                  40

TGC AAG GCT TCT GGT TAC TCA TTC ACT GGC TAC ACC ATG AAC TGG GTG
Cys Lys Ala Ser Gly Tyr Ser Phe Thr Gly Tyr Thr Met Asn Trp Val
                 45                  50                  55

AAG CAG AGC CAT GGA GAG AAC CTT GAG TGG ATT GGA CGT ATT AAT CCT
Lys Gln Ser His Gly Glu Asn Leu Glu Trp Ile Gly Arg Ile Asn Pro
             60                  65                  70

CAC AAT GGT GGT ACT GAC TAC AAC CAG AAG TTC AAG GAC AAG GCC CCT
His Asn Gly Gly Thr Asp Tyr Asn Gln Lys Phe Lys Asp Lys Ala Pro
         75                  80                  85

TTA ACT GTA GAC AAG TCA TCC AAC ACA GCC TAC ATG GAG CTC CTC AGT
Leu Thr Val Asp Lys Ser Ser Asn Thr Ala Tyr Met Glu Leu Leu Ser
     90                  95                 100

CTG ACA TCT GAG GAC TCT GCA GTC TAT TAC TGT GCA AGA GGC TAC TAT
Leu Thr Ser Glu Asp Ser Ala Val Tyr Tyr Cys Ala Arg Gly Tyr Tyr
105                 110                 115                 120

TAC TAT TCT TTG GAC TAC TGG GGT CAA GGA ACC TCA GTC ACC GTC TCC
Tyr Tyr Ser Leu Asp Tyr Trp Gly Gln Gly Thr Ser Val Thr Val Ser
                125                 130                 135

TCA ACC AAG GGC CCA TCG GTC TTC CCC CTG GCG CCC TGC TCC AGG AGC
Ser Thr Lys Gly Pro Ser Val Phe Pro Leu Ala Pro Cys Ser Arg Ser
            140                 145                 150

ACC TCT GGG GGC ACA GCG GCC CTG GGC TGC CTG GTC AAG GAC TAC TTC
Thr Ser Gly Gly Thr Ala Ala Leu Gly Cys Leu Val Lys Asp Tyr Phe
        155                 160                 165

CCC GAA CCG GTG ACG GTG TCG TGG AAC TCA GGC GCC CTG ACC AGC GGC
Pro Glu Pro Val Thr Val Ser Trp Asn Ser Gly Ala Leu Thr Ser Gly
    170                 175                 180
```

FIG. 18G

```
GTG CAC ACC TTC CCG GCT GTC CTA CAG TCC TCA GGA CTC TAC TCC CTC
Val His Thr Phe Pro Ala Val Leu Gln Ser Ser Gly Leu Tyr Ser Leu
185                 190                 195                 200

AGC AGC GTG GTG ACC GTG CCC TCC AGC AGC TTG GGC ACC CAG ACC TAC
Ser Ser Val Val Thr Val Pro Ser Ser Ser Leu Gly Thr Gln Thr Tyr
                205                 210                 215

ACC TGC AAC GTG AAT CAC AAG CCC AGC AAC ACC AAG GTG GAC AAG AGA
Thr Cys Asn Val Asn His Lys Pro Ser Asn Thr Lys Val Asp Lys Arg
            220                 225                 230

GTT
Val
```

FIG. 18H

```
                                                  GAG CTC AAA ACC
                                                  Glu Leu Lys Thr
                                                   1

CCA CTT GGT GAC ACA ACT CAC ACA TGC CCA CGG TGC CCA
Pro Leu Gly Asp Thr Thr His Thr Cys Pro Arg Cys Pro
 5                  10                  15
```

FIG. 18I

```
GAG CCC AAA TCT TGT GAC ACA CCT CCC CCG TGC CCA
Glu Pro Lys Ser Cys Asp Thr Pro Pro Pro Cys Pro
 1              5                   10

AGG TGC CCA
Arg Cys Pro
         15
```

FIG. 18J

```
                                                GAG CCC AAA TCT
                                                Glu Pro Lys Ser
                                                  1

TGT GAC ACA CCT CCC CCG TGC CCA AGG TGC CCA
Cys Asp Thr Pro Pro Pro Cys Pro Arg Cys Pro
  5                  10                  15
```

FIG. 18K

```
GAG CCC AAA TCT TGT GAC ACA CCT CCC CCG TGC CCA AGG TGC CCA
Glu Pro Lys Ser Cys Asp Thr Pro Pro Pro Cys Pro Arg Cys Pro
  1               5                  10                  15
```

FIG. 18L

```
GCA CCT GAA CTC CTG GGA GGA CCG TCA GTC TTC CTC TTC CCC CCA AAA
Ala Pro Glu Leu Leu Gly Gly Pro Ser Val Phe Leu Phe Pro Pro Lys
 1               5                  10                  15

CCC AAG GAT ACC CTT ATG ATT TCC CGG ACC CCT GAG GTC ACG TGC GTG
Pro Lys Asp Thr Leu Met Ile Ser Arg Thr Pro Glu Val Thr Cys Val
            20                  25                  30

GTG GTG GAC GTG AGC CAC GAA GAC CCC GAG GTC CAG TTC AAG TGG TAC
Val Val Asp Val Ser His Glu Asp Pro Glu Val Gln Phe Lys Trp Tyr
        35                  40                  45

GTG GAC GGC GTG GAG GTG CAT AAT GCC AAG ACA AAG CTG CGG GAG GAG
Val Asp Gly Val Glu Val His Asn Ala Lys Thr Lys Leu Arg Glu Glu
    50                  55                  60

CAG TAC AAC AGC ACG TTC CGT GTG GTC AGC GTC CTC ACC GTC CTG CAC
Gln Tyr Asn Ser Thr Phe Arg Val Val Ser Val Leu Thr Val Leu His
65                  70                  75                  80

CAG GAC TGG CTG AAC GGC AAG GAG TAC AAG TGC AAG GTC TCC AAC AAA
Gln Asp Trp Leu Asn Gly Lys Glu Tyr Lys Cys Lys Val Ser Asn Lys
                85                  90                  95

GCC CTC CCA GCC CCC ATC GAG AAA ACC ATC TCC AAA GCC AAA
Ala Leu Pro Ala Pro Ile Glu Lys Thr Ile Ser Lys Ala Lys
            100                 105                 110
```

FIG. 18M

GGA CAG CCC CGA GAA CCA
Gly Gln Pro Arg Glu Pro
1 5

CAG GTG TAC ACC CTG CCC CCA TCC CGG GAG GAG ATG ACC AAG AAC CAG
Gln Val Tyr Thr Leu Pro Pro Ser Arg Glu Glu Met Thr Lys Asn Gln
10 15 20

GTC AGC CTG ACC TGC CTG GTC AAA GGC TTC TAC CCC AGC GAC ATC GCC
Val Ser Leu Thr Cys Leu Val Lys Gly Phe Tyr Pro Ser Asp Ile Ala
25 30 35

GTG GAG TGG GAG AGC AAT GGG CAG CCG GAG AAC AAC TAC AAC ACC ACG
Val Glu Trp Glu Ser Asn Gly Gln Pro Glu Asn Asn Tyr Asn Thr Thr
40 45 50

CCT CCC ATG CTG GAC TCC GAC GGC TCC TTC TTC CTC TAC AGC AAG CTC
Pro Pro Met Leu Asp Ser Asp Gly Ser Phe Phe Leu Tyr Ser Lys Leu
55 60 65 70

ACC GTG GAC AAG AGC AGG TGG CAG CAG GGG AAC ATC TTC TCA TGC TCC
Thr Val Asp Lys Ser Arg Trp Gln Gln Gly Asn Ile Phe Ser Cys Ser
75 80 85

GTG ATG CAT GAG GCT CTG CAC AAC CGC TAC ACC CAG AAG AGC CTC TCC
Val Met His Glu Ala Leu His Asn Arg Tyr Thr Gln Lys Ser Leu Ser
90 95 100

CTG TCT CCG GGT AAA
Leu Ser Pro Gly Lys
105

FIG. 18N

```
Met Ser Phe Asn Thr Ile Ile Asp Trp Asn Ser Cys Thr Ala Val Gln
 1               5                  10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270
```

FIG. 18O

Pro Ala Ala Asp Met Ala Arg Arg Val Ala Glu Ala Val Glu Arg Gln
275 280 285

Leu Ala Glu Leu Pro Arg Ala Glu Thr Ala Arg Gln Ala Leu Asn Ala
290 295 300

Ser Arg Leu Ile Val Thr Lys Asp Ser Ala Gln Cys Val Glu Ile Ser
305 310 315 320

Asn Gln Tyr Gly Pro Glu His Leu Ile Ile Gln Thr Arg Asn Ala Arg
325 330 335

Glu Leu Val Asp Ser Ile Thr Ser Ala Gly Ser Val Phe Leu Gly Asp
340 345 350

Trp Ser Pro Glu Ser Ala Gly Asp Tyr Ala Ser Gly Thr Asn His Val
355 360 365

Leu Pro Thr Tyr Gly Tyr Thr Ala Thr Cys Ser Ser Leu Gly Leu Ala
370 375 380

Asp Phe Gln Lys Arg Met Thr Val Gln Glu Leu Ser Lys Glu Gly Phe
385 390 395 400

Ser Ala Val Ala Ser Thr Ile Glu Thr Leu Ala Ala Ala Glu Arg Leu
405 410 415

Thr Ala His Lys Asn Ala Val Thr Leu Arg Val Asn Ala Leu Lys Glu
420 425 430

Gln Ala

FIG. 18P

CGTTGTCAGAAGTAAGTTGGCCGCAGTGTTATCACTCATGGTTATGGCAGCACTGCATAATTCTCTTACTGTCATGCCAT
CCGTAAGATGCTTTTCTGTGACTGGTGAGTACTCAACCAAGTCATTCTGAGAATAGTGTATGCGGCGACCGAGTTGCTCT
TGCCCGGCGTCAACACGGGATAATACCGCGCCACATAGCAGAACTTTAAAAGTGCTCATCATTGGAAAACGTTCTTCGGG
GCGAAAACTCTCAAGGATCTTACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAAAAGGGAATAAGGGCGACACGG
AAATGTTGAATACTCATACTCTTCCTTTTTCAATATTATTGAAGCATTTATCAGGGTTATTGTCTCATGAGCGGATACAT
ATTTGAATGTATTTAGAAAAATAAACAAATAGGGGTTCCGCGCACATTTCCCCGAAAAGTGCCACCTGACGTCTAAGAAA
CCATTATTATCATGACATTAACCTA

EcoRI

TAAAAATAGGCGTATCACGAGGCCCTTTCGTCTTCAAGAATTCAGAGAGGTCTGGTGGAGCCTGCAAAAGTCCAGCTTTC
AAAGGAACACAGAAGTATGTGTATGGAATATTAGAAGATGTTGCTTTTACTCTTAAGTTGGTTCCTAGGAAAAATAGTTA
AATACTGTGACTTTAAAATGTGAGAGGGTTTTCAAGTACTCATTTTTTTAAATGTCCAAAATTTTTGTCAATCAATTTGA
GGTCTTGTTTGTGTAGAACTGACATTACTTAAAGTTTAACCGAGGAATGGGAGTGAGGCTCTCTCATACCCTATTCAGAA
CTGACTTTTAACAATAATAAATTAAGTTTAAAATATTTTTAAATGAATTGAGCAATGTTGAGTTGAGTCAAGATGGCCGA

PvuII

TCAGAACCGGAACACCTGCAGCAGCTGGCAGGAAGCAGGTCATGTGGCAAGGCTATTTGGGGAAGGAAAATAAAACCAC
TAGGTAAACTTGTAGCTGTGGTTTGAAGAAGTGGTTTTGAAACACTCTGTCCAGCCCCACCAAACCGAAAGTCCAGGCTG
AGCAAAACACCACCTGGGTAATTTGCATTTCTAAAATAAGTTGAGGATTCAGCCGAAACTGGAGAGGTCCTCTTTTAACT
TATTGAGTTCAACCTTTTAATTTTAGCTTGAGTAGTTCTAGTTTCCCCAAACTTAAGTTTATCGACTTCTAAAATGTATT

EcoRI

TAGAATTCCTTTGCCTAATATTAATGAGGACTTAACCTGTGGAAATATTTTGATGTGGGAAGCTGTTACTGTTAAAACTG
AGGTTATTGGGGTAACTGCTATGTTAAACTTGCATTCAGGGACACAAAAAACTCATGAAAATGGTGCTGGAAAACCCATT
CAAGGGTCAAATTTTCATTTTTTTGCTGTTGGTGGGGAACCTTTGGAGCTGCAGGGTGTGTTAGCAAACTACAGGACCAA
ATATCCTGCTCAAACTGTAACCCCAAAAAATGCTACAGTTGACAGTCAGCAGATGAACACTGACCACAAGGCTGTTTTGG
ATAAGGATAATGCTTATCCAGTGGAGTGCTGGGTTCCTGATCCAAGTAAAAATGAAAACACTAGATATTTTGGAACCTAC
ACAGGTGGGGAAAATGTGCCTCCTGTTTTGCACATTACTAACACAGCAACCACAGTGCTGCTTGATGAGCAGGGTGTTGG
GCCCTTGTGCAAAGCTGACAGCTTGTATGTTTCTGCTGTTGACATTTGTGGGCTGTTTACCAACACTTCTGGAACACAGC
AGTGGAAGGGACTTCCCAGATATTTTAAAATTACCCTTAGAAAGCGGTCTGTGAAAAACCCCTACCCAATTTCCTTTTTG
TTAAGTGACCTAATTAACAGGAGGACACAGAGGGTGGATGGGCAGCCTATGATTGGAATGTCCTCTCAAG

FIG. 19A

```
                                                 BamHI
TAGAGGAGGTTAGGGTTTATGAGGACACAGAGGAGCTTCCTGGGGATCCGATCCNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNATATAG
CACAAAGACATGCAA
                                            HindIII
ATAATATTTCCCTATGCTCATAAAAACAGCCCTGACCATGAAGCTTTGACAGACGCACAACCCTG
                                            EcoRV
GACTCCCAAGTCTTTCTCTTCAGTGACAAACACAGACATAGGATATCCACCATGGAATGGAGCTGGGTAATGCTCTTCCT
CCTGTCAGGAACTGCAGGTGTCCGCTCTGAGGTCCAGCTGCAACAGTCTGGACCTGAACTGGTGAAGCCTGGAGCTTCAA
TGAAGATTTCCTGCAAGGCTTCTGGTTACTCATTCACTGGCTACACCATGAACTGGGTGAAGCAGAGCCATGGAGAGAAC
CTTGAGTGGATTGGACGTATTAATCCTCACAATGGTGGTACTGACTACAACCAGAAGTTCAAGGACAAGGCCCCTTTAAC
TGTAGACAAGTCATCCAACACAGCCTACATGGAGCTCCTCAGTCTGACATCTGAGGACTCTGCAGTCTATTACTGTGCAA
GAGGCTACTATTACTATTCTTTGGACTACTGGGGTCAAGGAACCTCAGTCACCGT
```

FIG. 19B

```
       NheI
CTCCTCAGCTAGCACCAAGGGCCCATCCGTCTTCCCCCTGGCGCCCTGCTCCAGGAGGACCTCCGAGAGCACAGCCGCCC
TGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCTCCAGCAGCTTGGGCAC
GAAGACCTACACCTGCAACGTAGATCACAAGCCCAGCAACACCAAGGTGGACAAGAGAGTTGGTGAGAGGCCAGCACAGG
GAGGGAGGGTGTCTGCTGGAAGCCAGGCTCAGCCCTCCTGCCTGGACGCACCCCGGCTGTGCAGCCCCAGCCCAGGGCAG
CAAGGGCCCCATCTGTCTCCTCACCCGGAGGCCTCTGACCACCCCACTCATGCTCAGGGAGAGGGTCTTCTGGATTTTTC
CACCAGGCTCCCGGCACCACAGGCTGGATGCCCCTACCCCAGGCCCTGCGCATACAGGGCAGGTGCTGCGCTCAGACCTG
CCAAGAGCCATATCCGGGAGGACCCTGCCCCTGACCTAAGCCCACCCCAAAGGCCAAACTCTCCACTCCCTCAGCTCAGA
CACCTTCTCT
      BglII                       PstI
CCTCCCAGATCTGAGTAACTCCCAATCTTCTCTCTGCAGAGTCCAAATATGGTCCCCCATGCCCATCATGCCCAGGTAAG
CCAACCCAGGCCTCGCCCTCCAGCTCAAGGCGGGACAGGTGCCCTAGAGTAGCCTGCATCCAGGGACAGGCCCCAGCCGG
GTGCTGACGCATCCACCTCCATCTCTTCCTCAGCACCTGAGTTCCTGGGGGGACCATCAGTCTTCCTGTTCCCCCCAAAA
CCCAAGGACACTCTCATGATCTCCCGGACCCCTGAGGTCACGTGCGTGGTGGTGGACGTGAGCCAGGAAGACCCCGAGGT
CCAGT
                                                     SstII
TCAACTGGTACGTGGATGGCGTGGAGGTGCATAATGCCAAGACAAAGCCGCGGGAGGAGCAGTTCAACAGCACGTACCGT
GTGGTCAGCGTCCTCACCGTCCTGCACCAGGACTGGCTGAACGGCAAGGAGTACAAGTGCAAGGTCTCCAACAAAGGCCT
CCCGTCCTCCATCGAGAAAACCATCTCCAAAGCCA
           DraIII                   BglI
AAGGTGGGACCCACGGGGTGCGAGGGCCACACGGACAGAGGCCAGCTCGGCCCACCCTCTGCCCTGGGAGTGACCGCTGT
GCCAACCTCTGTCCCTACAGGGCAGCCCCGAGAGCCACAGGTGTACACCCTGCCCCCATCCCAGGAGGAGATGACCAAGA
ACCAGGTCAGCCTGACCTGCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTACAGCAGGCTAACCGTGGACAA
GAGCAGGTGGCAGGAGGGGAATGTCTTCTCATGCTCCGTGATGCATGAGGCTCTGCACAACCACTACACG
                                                               SmaI
CAGAAGAGCCTCTCCCTGTCTCCGGGTAAATGAGTGCCAGGGCCGGCAAGCCCCCGCTCCCCGGGCTCTCGGGGTCGCGC
GAGGATGCTTGGCACGTACCCCGTCTACATACTTCCCAGGCACCCAGCATGGAAATAAAGCACCCACCACTGCCCTGGGC
CCCTGTGAGACTGTGATGGTTCTTTCCACGGGTCAGGCCGAGTCTGAGGCCTGAGTGACATGAGGGAGGCAGAGCGGGTC
CCACTGTCCCCACACTGGNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNCAGCTGNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
```

FIG. 19C

NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNN

BamHI

NNNNNNNNNNNNNNNNNNNNNNNNNNNNNNNGGATCCAGACATGATAAGATACATTGATGAGTTTGGACAAACCACAACT
AGAATGCAGTGAAAAAAATGCTTTATTTGTGAAATTTGTGATGCTATTGC

HpaI

TTTATTTGTAACCATTATAAGCTGCAATAAACAAGTTAACAACAACAATTGCATTCATTTTATGTTTCAGGTTCAGGGGG
AGGTGTGGGAGGTTTTTTAAAGCAAGTAAAACCTCTACAAATGTGGTATGGCTGATTATGATCTCTAGTCAAGGCACTAT
ACATCAAATATTCCTTATTAACCCCTTTACAAATTAAAAAGCTAAAGGTACACAATTTTTGAGCATAGTTATTAATAGCA
GACACTCTATGCCTGTGTGGAGTAAGAAAAAACAGTATGTTATGATTATAACTGTTATGCCTACTTATAAAGGTTACAGA
ATATTTTTCCATAATTTTCTTGTATAGCAGTGCAGCTTTTTCCTTTGTGGTGTAAATAGCAAAGCAAGCAAGAGTTCTAT
TACTAAACACAGCATGACTCAAAAAACTTAGCAATTCTGAAGGAAAGTCCTTGGGGTCTTCTACCTTTCTCTTCTTTTTT
GGAGGAGTAGAATGTTGAGAGTCAGCAGTAGCCTCATCATCACTAGATGGCATTTCTTCTGAGCAAAACAGGTTTTCCTC
ATTAAAGGCATTCCACCACTGCTCCCATTCATCAGTTCCATAGGTTGGAATCTAAAATACACAAACAATTAGAATCAGTA
GTTTAACACATTATACACTTAAAAATTTATATTTACCTTATAGCTTTAAATCTCTGTAGGTAGTTTGTCCAATTATGTC
ACACCACAGAAGTAAGGTTCCTTCACAAAGATCCGGNNNNNNNNNNNNNNNNNNNNNNNN

HpaI

NTCATGCTTGCTCCTTGAGGGCGTTAACGCGCAAGGTAACGGCATTTTTATGGGCGGTCAGACGTTCGGCGGCGGCCAGT
GTTTCTATGGTTGAAGCCACCGCGGAGAACCCCTCTTTCGACAGTTCCTGTACGGTCATACGCTTCTGGAAATCTGCCAG
CCCGAGGCTGGAACAGGTGGCGGTGTAACCGTAAGTCGGTAGAACGTGGTTGGTTCCGGAGGCGTAATCACCTGCCGATT
CCGGTGACCAGTCACCAAGAAATACCGAACCGGCGCTGGTGATGCTATCGACCAGTTCACGGGCGTTGCGGGTCTGAATG
ATCAGGTGCTCCGGGCCGTACTGATTAGAGATCTCCACGCACTGCGCTGAATCTTTAGTCACGATCAGGCGGCTGGCGTT
CAGTGCCTGGCGGGCGGTTTCGGCACGCGGCAGTTCCGCCAGTTGGCGTTCGACGGCCTCGGCAACGCGACGCGCCATAT
CAGCAGCGGGCGTCAGTAAAATCACCTGTGAGTCCGGGCCGTGTTCAGCCTGAGAGAGCAAATCAGAAGCCACGAAATCC
GGCGTTGCGCCGCTGTCAGCAATCA

ClaI

CCAGCACTTCCGACGGGCCTGCGGGCATATCGATCTCCGCACCGTCCAGACGCTGGCTCACCTGACGTTTCGCTTCGGTG
ACAAAGGCGTTACCCGGCCCGAAGATTTGTCCACTTTTGGCACGGATTCCGTACCAAACGCCAGTGCGGCAATGGCCTG
TGCGCCGCCGACGTTGAACACGTCCTGCACACCGC

PvuII

ACAGCTGCGCCGCATAAAGGATCTCATCGGCAATCGGCGGCGGTGAGCACAGCACCACTTTTTTACAGCCCGCAATACGC
GCCGGAGTCGCCAGCATTAATACCGTTGAGAAGAGCGGGGCGGAGCCGCCAGGAATATACAACCCAACTGAAGCTACCGG
ACGCGTGACCTGCTGGCAACGCACGCCTGGCTGCGTTTCTACATCTACCGGCGGCAGTTTTTGCGCAGTGTGGAAGGTTT

FIG. 19D

```
CAATATTCTTTACTGCCACCGCCATCGCCTGTTTTAGCTCGTCGCTCAGGCGTTCGCTGGCGGCGGCGATCTCCTCTGCA
GACACCTTCAGCGCGGTAACCGTGGTTTTATCAAACTTCGCGCTGTATTCCCGCAGGGCCTCATCGCCGCGTGCTTTCAC
GTTATCGAGAATATCGTTAACAGTGCGGGTAATGCTTTCAGAGGCGGAAATCGCC
          PvuII
GGGCGCGTTAACAGCTGGCGTTGTTGCACCGCAGTACAGCTATTCCAGTCAATGATTGTGTTAAAGCTCATNNNNCCGGA
TCAGCTTTTTGCAAAAGCCTAGGCCTCCAAAAAAGCCTCCTCACTACTTCTGGAATAGCTCAGAGGCCGAGGCGCCTCGG
CCTCTGCATAAATAAAAAAAATTAGTCAGCCATGGGGCGGAGAATGGGCGGAACTGGGCGGAGTTAGGGGCGGGATGGGC
GGAGTTAGGGGCGGGACTATGGTTGCTGACTAATTGAGATGCATGCTTTGCATACTTCTGCCTGCTGGGGAGCCTGGGGA
CTTTCCACACCTGGTTGCTGACTAATTGAGATGCATGCTTTGCATACTTCTGCCTGCTGGGGAGCCTGGGGACTTTCCAC
ACCCTAACT
            PvuII
GACACACATTCCACAGCTGCCTCGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCGGGTGTTGGCGGGTGTCGGGGCGC
AGCCATGACCCAGTCACGTAGCGATAGCGGAGTGTATACTGGCTTAACTATGCGGCATCAGAGCAGATTGTACTGAGAGT
GCACCATATGCGGTGTGAAATACCGCACAGATGCGTAAGGAGAAAATACCGCATCAGGCGCTCTTCCGCTTCCTCGCTCA
CTGACTCGCTGCGCTCGGTCGTTCGGCTGCGGCGAGCGGTATCAGCTCACTCAAAGGCGGTAATACGGTTATCCACAGAA
TCAGGGGATAACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCAATGCTCACGCTGTAGGTATCTCAGTTCGGTGTAGGTCGTTCG
CTCCAAGCTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGGACAGTATTTGGTATCTGCGCTCTGCTGAAGCCAGT
TACCTTCGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAAGTTT
TAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGT
```

FIG. 19E

```
                                                                  PstI
TGCCGGGAAGCTAGAGTAAGTAGTTCGCCAGTTAATAGTTTGCGCAACGTTGTTGCCATTGCTGCAGGCATCGTGGTGTC
ACGCTCGTCGTTTGGTATGGCTTCATTCAGCTCCGGTTCCCAACGATCAA
                                                              PvuI
GGCGAGTTACATGATCCCCCATGTTGTGCAAAAAAGCGGTTAGCTCCTTCGGTCCTCCGAT
```

FIG. 19F

```
                                                                   ATG GAA TGG
                                                                   Met Glu Trp
                                                                     1

AGC TGG GTA ATG CTC TTC CTC CTG TCA GGA ACT GCA GGT GTC CGC TCT
Ser Trp Val Met Leu Phe Leu Leu Ser Gly Thr Ala Gly Val Arg Ser
     5                   10                  15

GAG GTC CAG CTG CAA CAG TCT GGA CCT GAA CTG GTG AAG CCT GGA GCT
Glu Val Gln Leu Gln Gln Ser Gly Pro Glu Leu Val Lys Pro Gly Ala
 20                  25                  30                  35

TCA ATG AAG ATT TCC TGC AAG GCT TCT GGT TAC TCA TTC ACT GGC TAC
Ser Met Lys Ile Ser Cys Lys Ala Ser Gly Tyr Ser Phe Thr Gly Tyr
                 40                  45                  50

ACC ATG AAC TGG GTG AAG CAG AGC CAT GGA GAG AAC CTT GAG TGG ATT
Thr Met Asn Trp Val Lys Gln Ser His Gly Glu Asn Leu Glu Trp Ile
             55                  60                  65

GGA CGT ATT AAT CCT CAC AAT GGT GGT ACT GAC TAC AAC CAG AAG TTC
Gly Arg Ile Asn Pro His Asn Gly Gly Thr Asp Tyr Asn Gln Lys Phe
         70                  75                  80

AAG GAC AAG GCC CCT TTA ACT GTA GAC AAG TCA TCC AAC ACA GCC TAC
Lys Asp Lys Ala Pro Leu Thr Val Asp Lys Ser Ser Asn Thr Ala Tyr
     85                  90                  95

ATG GAG CTC CTC AGT CTG ACA TCT GAG GAC TCT GCA GTC TAT TAC TGT
Met Glu Leu Leu Ser Leu Thr Ser Glu Asp Ser Ala Val Tyr Tyr Cys
100                 105                 110                 115

GCA AGA GGC TAC TAT TAC TAT TCT TTG GAC TAC TGG GGT CAA GGA ACC
Ala Arg Gly Tyr Tyr Tyr Tyr Ser Leu Asp Tyr Trp Gly Gln Gly Thr
                120                 125                 130

TCA GTC ACC GTC TCC TCA GCT AGC ACC AAG GGC CCA TCC GTC TTC CCC
Ser Val Thr Val Ser Ser Ala Ser Thr Lys Gly Pro Ser Val Phe Pro
            135                 140                 145

CTG GCG CCC TGC TCC AGG AGG ACC TCC GAG AGC ACA GCC GCC CTG GGC
Leu Ala Pro Cys Ser Arg Arg Thr Ser Glu Ser Thr Ala Ala Leu Gly
        150                 155                 160

TGC CTG GTC AAG GAC TAC TTC CCC GAA CCG GTG ACG GTG TCG TGG AAC
Cys Leu Val Lys Asp Tyr Phe Pro Glu Pro Val Thr Val Ser Trp Asn
    165                 170                 175
```

FIG. 19G

TCA GGC GCC CTG ACC AGC GGC GTG CAC ACC TTC CCG GCT GTC CTA CAG
Ser Gly Ala Leu Thr Ser Gly Val His Thr Phe Pro Ala Val Leu Gln
180 185 190 195

TCC TCA GGA CTC TAC TCC CTC AGC AGC GTG GTG ACC GTG CCC TCC AGC
Ser Ser Gly Leu Tyr Ser Leu Ser Ser Val Val Thr Val Pro Ser Ser
200 205 210

AGC TTG GGC ACG AAG ACC TAC ACC TGC AAC GTA GAT CAC AAG CCC AGC
Ser Leu Gly Thr Lys Thr Tyr Thr Cys Asn Val Asp His Lys Pro Ser
215 220 225

AAC ACC AAG GTG GAC AAG AGA GTT
Asn Thr Lys Val Asp Lys Arg Val
230 235

FIG. 19H

| | | | | | | | | | | | |
|---|---|---|---|---|---|---|---|---|---|---|---|
| GAG | TCC | AAA | TAT | GGT | CCC | CCA | TGC | CCA | TCA | TGC | CCA |
| Glu | Ser | Lys | Tyr | Gly | Pro | Pro | Cys | Pro | Ser | Cys | Pro |
| 1 | | | | 5 | | | | | 10 | | |

FIG. 19I

```
                                                                 GCA CCT GAG
                                                                 Ala Pro Glu
                                                                   1

TTC CTG GGG GGA CCA TCA GTC TTC CTG TTC CCC CCA AAA CCC AAG GAC
Phe Leu Gly Gly Pro Ser Val Phe Leu Phe Pro Pro Lys Pro Lys Asp
     5                   10                  15

ACT CTC ATG ATC TCC CGG ACC CCT GAG GTC ACG TGC GTG GTG GTG GAC
Thr Leu Met Ile Ser Arg Thr Pro Glu Val Thr Cys Val Val Val Asp
 20                  25                  30                  35

GTG AGC CAG GAA GAC CCC GAG GTC CAG TTC AAC TGG TAC GTG GAT GGC
Val Ser Gln Glu Asp Pro Glu Val Gln Phe Asn Trp Tyr Val Asp Gly
                 40                  45                  50

GTG GAG GTG CAT AAT GCC AAG ACA AAG CCG CGG GAG GAG CAG TTC AAC
Val Glu Val His Asn Ala Lys Thr Lys Pro Arg Glu Glu Gln Phe Asn
             55                  60                  65

AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp
         70                  75                  80

CTG AAC GGC AAG GAG TAC AAG TGC AAG GTC TCC AAC AAA GGC CTC CCG
Leu Asn Gly Lys Glu Tyr Lys Cys Lys Val Ser Asn Lys Gly Leu Pro
     85                  90                  95

TCC TCC ATC GAG AAA ACC ATC TCC AAA GCC AAA
Ser Ser Ile Glu Lys Thr Ile Ser Lys Ala Lys
100                 105                 110
```

FIG. 19J

GGG CAG CCC CGA GAG CCA CAG GTG TAC ACC CTG
Gly Gln Pro Arg Glu Pro Gln Val Tyr Thr Leu
1 5 10

CCC CCA TCC CAG GAG GAG ATG ACC AAG AAC CAG GTC AGC CTG ACC TGC
Pro Pro Ser Gln Glu Glu Met Thr Lys Asn Gln Val Ser Leu Thr Cys
15 20 25

CTG GTC AAA GGC TTC TAC CCC AGC GAC ATC GCC GTG GAG TGG GAG AGC
Leu Val Lys Gly Phe Tyr Pro Ser Asp Ile Ala Val Glu Trp Glu Ser
30 35 40

AAT GGG CAG CCG GAG AAC AAC TAC AAG ACC ACG CCT CCC GTG CTG GAC
Asn Gly Gln Pro Glu Asn Asn Tyr Lys Thr Thr Pro Pro Val Leu Asp
45 50 55

TCC GAC GGC TCC TTC TTC CTC TAC AGC AGG CTA ACC GTG GAC AAG AGC
Ser Asp Gly Ser Phe Phe Leu Tyr Ser Arg Leu Thr Val Asp Lys Ser
60 65 70 75

AGG TGG CAG GAG GGG AAT GTC TTC TCA TGC TCC GTG ATG CAT GAG GCT
Arg Trp Gln Glu Gly Asn Val Phe Ser Cys Ser Val Met His Glu Ala
80 85 90

CTG CAC AAC CAC TAC ACG CAG AAG AGC CTC TCC CTG TCT CCG GGT AAA
Leu His Asn His Tyr Thr Gln Lys Ser Leu Ser Leu Ser Pro Gly Lys
95 100 105

FIG. 19K

Met Ser Phe Asn Thr Ile Ile Asp Trp Asn Ser Cys Thr Ala Val Gln
1 5 10 15

Gln Arg Gln Leu Leu Thr Arg Pro Ala Ile Ser Ala Ser Glu Ser Ile
20 25 30

Thr Arg Thr Val Asn Asp Ile Leu Asp Asn Val Lys Ala Arg Gly Asp
35 40 45

Glu Ala Leu Arg Glu Tyr Ser Ala Lys Phe Asp Lys Thr Thr Val Thr
50 55 60

Ala Leu Lys Val Ser Ala Glu Glu Ile Ala Ala Ala Ser Glu Arg Leu
65 70 75 80

Ser Asp Glu Leu Lys Gln Ala Met Ala Val Ala Val Lys Asn Ile Glu
85 90 95

Thr Phe His Thr Ala Gln Lys Leu Pro Pro Val Asp Val Glu Thr Gln
100 105 110

Pro Gly Val Arg Cys Gln Gln Val Thr Arg Pro Val Ala Ser Val Gly
115 120 125

Leu Tyr Ile Pro Gly Gly Ser Ala Pro Leu Phe Ser Thr Val Leu Met
130 135 140

Leu Ala Thr Pro Ala Arg Ile Ala Gly Cys Lys Lys Val Val Leu Cys
145 150 155 160

Ser Pro Pro Pro Ile Ala Asp Glu Ile Leu Tyr Ala Ala Gln Leu Cys
165 170 175

Gly Val Gln Asp Val Phe Asn Val Gly Gly Ala Gln Ala Ile Ala Ala
180 185 190

Leu Ala Phe Gly Thr Glu Ser Val Pro Lys Val Asp Lys Ile Phe Gly
195 200 205

Pro Gly Asn Ala Phe Val Thr Glu Ala Lys Arg Gln Val Ser Gln Arg
210 215 220

Leu Asp Gly Ala Glu Ile Asp Met Pro Ala Gly Pro Ser Glu Val Leu
225 230 235 240

Val Ile Ala Asp Ser Gly Ala Thr Pro Asp Phe Val Ala Ser Asp Leu
245 250 255

Leu Ser Gln Ala Glu His Gly Pro Asp Ser Gln Val Ile Leu Leu Thr
260 265 270

FIG. 19L

```
Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```

FIG. 19M

```
                              SEQUENCE LISTING


(1) GENERAL INFORMATION:

   (iii) NUMBER OF SEQUENCES: 46


(2) INFORMATION FOR SEQ ID NO:1:

     (i) SEQUENCE CHARACTERISTICS:
          (A) LENGTH: 34 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (C) INDIVIDUAL ISOLATE: synthesized

    (ix) FEATURE:
          (A) NAME/KEY: misc_feature
          (B) LOCATION: 1..34
          (D) OTHER INFORMATION: /function= "Light Chain V Region"

    (xi) SEQUENCE DESCRIPTION: SEQ ID NO:1:

GCCGGAATTC TAGAAGCTTT TTTTTTTTTT TTTT                                   34


(2) INFORMATION FOR SEQ ID NO:2:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (C) INDIVIDUAL ISOLATE: synthesized

    (ix) FEATURE:
          (A) NAME/KEY: misc_feature
          (B) LOCATION: 1..39
          (D) OTHER INFORMATION: /function= "Heavy Chain V Region"

    (xi) SEQUENCE DESCRIPTION: SEQ ID NO:2:

AGGTCTAGAA YCTCCACACA CAGGRRCCAG TGGATAGAC                              39
```

-continued (2) INFORMATION FOR SEQ ID NO:3:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..39
(D) OTHER INFORMATION: /function= "Heavy Chain V Region"

(xi) SEQUENCE DESCRIPTION: SEQ ID NO:3:

GGGGATATCC ACCATGGRAT GSAGCTGKGT MATSCTCTT 39

(2) INFORMATION FOR SEQ ID NO:4:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..39
(D) OTHER INFORMATION: /function= "Heavy Chain V Region"

(xi) SEQUENCE DESCRIPTION: SEQ ID NO:4:

GGGGATATCC ACCATGRACT TCGGGYTGAG CTKGGTTTT 39

(2) INFORMATION FOR SEQ ID NO:5:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..38
(D) OTHER INFORMATION: /function= "Heavy Chain V Region"

(xi) SEQUENCE DESCRIPTION: SEQ ID NO:5:

-continued

GGGGATATCC ACCATGGCTG TCTTGGGGCT GCTCTTCT 38

(2) INFORMATION FOR SEQ ID NO:6:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(C) INDIVIDUAL ISOLATE: synthesized (ix) FEATURE:
(A) NAME/KEY: misc_feature
(B) LOCATION: 1..39
(D) OTHER INFORMATION: /function= "Heavy Chain C Region"

(xi) SEQUENCE DESCRIPTION: SEQ ID NO:6:

AGGTCTAGAA YCTCCACACA CAGGRRCCAG TGGATAGAC 39

(2) INFORMATION FOR SEQ ID NO:7:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..37
(D) OTHER INFORMATION: /function= "Light Chain V Region"

(xi) SEQUENCE DESCRIPTION: SEQ ID NO:7:

GGGGATATCC ACATGGAGAC AGACACACTC CTGCTAT 37

(2) INFORMATION FOR SEQ ID NO:8:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..39
(D) OTHER INFORMATION: /function= "Light Chain V Region"

-continued (xi) SEQUENCE DESCRIPTION: SEQ ID NO:8:

GGGGATATCC ACCATGGATT TTCAAGTGCA GATTTTCAG 39

(2) INFORMATION FOR SEQ ID NO:9:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: symthesized (ix) FEATURE:
(A) NAME/KEY: misc_feature
(B) LOCATION: 1..37
(D) OTHER INFORMATION: /function= "Light Chain V Region"

(xi) SEQUENCE DESCRIPTION: SEQ ID NO:9:

GGGGATATCC ACCATGGAGW CACAKWCTCA GGTCTTT 37

(2) INFORMATION FOR SEQ ID NO:10:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthesized (ix) FEATURE:
(A) NAME/KEY: misc_feature
(B) LOCATION: 1..36
(D) OTHER INFORMATION: /function= "Light Chain V Region"

(xi) SEQUENCE DESCRIPTION: SEQ ID NO:10:

GGGGATATCC ACCATGKCCC CWRCTCAGYT YCTKGT 36

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(C) INDIVIDUAL ISOLATE: synthesized (ix) FEATURE:
(A) NAME/KEY: misc_feature -continued (B) LOCATION: 1..30
(D) OTHER INFORMATION: /function= "Light Chain C Region"

(xi) SEQUENCE DESCRIPTION: SEQ ID NO:11:

GCGTCTAGAA CTGGATGGTG GGAAGATGGA 30

(2) INFORMATION FOR SEQ ID NO:12:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(C) INDIVIDUAL ISOLATE: synthesized (ix) FEATURE:
(A) NAME/KEY: misc_feature
(B) LOCATION: 1..39
(D) OTHER INFORMATION: /function= "Heavy Chain V-J Region"

(xi) SEQUENCE DESCRIPTION: SEQ ID NO:12:

TGGGTCGACA GATGGGGGTG TTGTGCTAGC TGAGGAGAC 39

(2) INFORMATION FOR SEQ ID NO:13:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(C) INDIVIDUAL ISOLATE: synthesized (ix) FEATURE:
(A) NAME/KEY: misc_feature
(B) LOCATION: 1..36
(D) OTHER INFORMATION: /function= "Light Chain V-J Region"

(xi) SEQUENCE DESCRIPTION: SEQ ID NO:13:

AGCGTCGACT TACGTCTGAT TTCCAGCCTG GTCCCT 36

(2) INFORMATION FOR SEQ ID NO:14:

(i) SEQUENCE CHARACTERISTICS:
(A) LENGTH: 384 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..384
(D) OTHER INFORMATION: /function= "Chimeric 128.1 Light Chain V Region"

-continued (xi) SEQUENCE DESCRIPTION: SEQ ID NO:14:

```
ATGGATTTTC AAGTGCAGAT TTTCAGCTTC CTGCTAATCA GTGCCTCAGT CATACTGTCC     60

AGAGGACAAA TTGTTCTCAC CCAGTCTCCA GCAATCATGT CTGTATCTCC AGGGGAGAAG    120

GTCACCATGA CCTGCAGTGC CAGCTCAAGT ATACGTTACA TTCACTGGTA CCAGCAGAGG    180

CCAGGCACCT CCCCCAAAAG ATGGATTTAT GACACATCCA ACCTGGCTTC TGGAGTCCCT    240

GCTCGCTTCA GTGGCAGTGG GTCTGGGACC TCTTATTCTC TCACAATCAG CAGCATGGAG    300

GCTGAAGATG CTGCCACTTA TTACTGCCAT CAGCGGAATA GTTACCCATG GACGTTCGGT    360

GGAGGCACCA GGCTGGAAAT CAGA                                           384
```

(2) INFORMATION FOR SEQ ID NO:15:

(i) SEQUENCE CHARACTERISTICS:
(A) LENGTH: 128 amino acids
(B) TYPE: amino acid
(D) TOPOLOGY: linear (ii) MOLECULE TYPE: peptide (v) FRAGMENT TYPE: N-terminal (ix) FEATURE:
(A) NAME/KEY: Peptide
(B) LOCATION: 1..128
(D) OTHER INFORMATION: /note= "Chimeric 128.1 Light Chain V Region"

(xi) SEQUENCE DESCRIPTION: SEQ ID NO:15:

```
Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Val Ser Pro Gly Glu Lys Val Thr Met Thr Cys Ser Ala Ser
        35                  40                  45

Ser Ser Ile Arg Tyr Ile His Trp Tyr Gln Gln Arg Pro Gly Thr Ser
    50                  55                  60

Pro Lys Arg Trp Ile Tyr Asp Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Arg
            100                 105                 110

Asn Ser Tyr Pro Trp Thr Phe Gly Gly Gly Thr Arg Leu Glu Ile Arg
        115                 120                 125
```

(2) INFORMATION FOR SEQ ID NO:16:

(i) SEQUENCE CHARACTERISTICS:
(A) LENGTH: 411 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..411
(D) OTHER INFORMATION: /function= "Chimeric 128.1 Heavy Chain V Region"

-continued (xi) SEQUENCE DESCRIPTION: SEQ ID NO:16:

```
ATGGAATGGA GCTGGGTAAT GCTCTTCCTC CTGTCAGGAA CTGCAGGTGT CCGCTCTGAG     60

GTCCAGCTGC AACAGTCTGG ACCTGAACTG GTGAAGCCTG GAGCTTCAAT GAAGATTTCC    120

TGCAAGGCTT CTGGTTACTC ATTCACTGGC TACACCATGA ACTGGGTGAA GCAGAGCCAT    180

GGAGAGAACC TTGAGTGGAT TGGACGTATT AATCCTCACA ATGGTGGTAC TGACTACAAC    240

CAGAAGTTCA AGGACAAGGC CCCTTTAACT GTAGACAAGT CATCCAACAC AGCCTACATG    300

GAGCTCCTCA GTCTGACATC TGGGGACTCT GCAGTCTATT ACTGTGCAAG AGGCTACTAT    360

TACTATTCTT TGGACTACTG GGGTCAAGGA ACCTCAGTCA CCGTCTCCTC A             411
```

(2) INFORMATION FOR SEQ ID NO:17:

(i) SEQUENCE CHARACTERISTICS:
(A) LENGTH: 137 amino acids
(B) TYPE: amino acid
(D) TOPOLOGY: linear (ii) MOLECULE TYPE: peptide (v) FRAGMENT TYPE: N-terminal (ix) FEATURE:
(A) NAME/KEY: Peptide
(B) LOCATION: 1..137
(D) OTHER INFORMATION: /note= "Chimeric 128.1 Heavy Chain V-Region"

(xi) SEQUENCE DESCRIPTION: SEQ ID NO:17:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Gly Asp Ser Ala Val
            100                 105                 110

Tyr Tyr Cys Ala Arg Gly Tyr Tyr Tyr Tyr Ser Leu Asp Tyr Trp Gly
        115                 120                 125

Gln Gly Thr Ser Val Thr Val Ser Ser
    130                 135
```

(2) INFORMATION FOR SEQ ID NO:18:

(i) SEQUENCE CHARACTERISTICS:
(A) LENGTH: 11528 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO

-continued (vii) IMMEDIATE SOURCE:
(B) CLONE: pAH4602

(ix) FEATURE:
(A) NAME/KEY: misc_feature
(B) LOCATION: 1..11528
(D) OTHER INFORMATION: /note= "Function="Expression Vector Coding Sequence""

(xi) SEQUENCE DESCRIPTION: SEQ ID NO:18:

```
CGTTGTCAGA AGTAAGTTGG CCGCAGTGTT ATCACTCATG GTTATGGCAG CACTGCATAA     60
TTCTCTTACT GTCATGCCAT CCGTAAGATG CTTTTCTGTG ACTGGTGAGT ACTCAACCAA    120
GTCATTCTGA GAATAGTGTA TGCGGCGACC GAGTTGCTCT TGCCCGGCGT CAACACGGGA    180
TAATACCGCG CCACATAGCA GAACTTTAAA AGTGCTCATC ATTGGAAAAC GTTCTTCGGG    240
GCGAAAACTC TCAAGGATCT TACCGCTGTT GAGATCCAGT TCGATGTAAC CCACTCGTGC    300
ACCCAACTGA TCTTCAGCAT CTTTTACTTT CACCAGCGTT TCTGGGTGAG CAAAAACAGG    360
AAGGCAAAAT GCCGCAAAAA AGGGAATAAG GGCGACACGG AAATGTTGAA TACTCATACT    420
CTTCCTTTTT CAATATTATT GAAGCATTTA TCAGGGTTAT TGTCTCATGA GCGGATACAT    480
ATTTGAATGT ATTTAGAAAA ATAAACAAAT AGGGGTTCCG CGCACATTTC CCCGAAAAGT    540
GCCACCTGAC GTCTAAGAAA CCATTATTAT CATGACATTA ACCTATAAAA ATAGGCGTAT    600
CACGAGGCCC TTTCGTCTTC AAGAATTCAG AGAGGTCTGG TGGAGCCTGC AAAAGTCCAG    660
CTTTCAAAGG AACACAGAAG TATGTGTATG GAATATTAGA AGATGTTGCT TTTACTCTTA    720
AGTTGGTTCC TAGGAAAAAT AGTTAAATAC TGTGACTTTA AAATGTGAGA GGGTTTTCAA    780
GTACTCATTT TTTTAAATGT CCAAAATTTT TGTCAATCAA TTTGAGGTCT TGTTTGTGTA    840
GAACTGACAT TACTTAAAGT TTAACCGAGG AATGGGAGTG AGGCTCTCTC ATACCCTATT    900
CAGAACTGAC TTTTAACAAT AATAAATTAA GTTTAAAATA TTTTTAAATG AATTGAGCAA    960
TGTTGAGTTG AGTCAAGATG GCCGATCAGA ACCGGAACAC CTGCAGCAGC TGGCAGGAAG   1020
CAGGTCATGT GGCAAGGCTA TTTGGGGAAG GGAAAATAAA ACCACTAGGT AAACTTGTAG   1080
CTGTGGTTTG AAGAAGTGGT TTTGAAACAC TCTGTCCAGC CCCACCAAAC CGAAAGTCCA   1140
GGCTGAGCAA AACACCACCT GGGTAATTTG CATTTCTAAA ATAAGTTGAG GATTCAGCCG   1200
AAACTGGAGA GGTCCTCTTT TAACTTATTG AGTTCAACCT TTTAATTTTA GCTTGAGTAG   1260
TTCTAGTTTC CCCAAACTTA AGTTTATCGA CTTCTAAAAT GTATTTAGAA TTCCTTTGCC   1320
TAATATTAAT GAGGACTTAA CCTGTGGAAA TATTTTGATG TGGGAAGCTG TTACTGTTAA   1380
AACTGAGGTT ATTGGGGTAA CTGCTATGTT AAACTTGCAT TCAGGGACAC AAAAAACTCA   1440
TGAAAATGGT GCTGGAAAAC CCATTCAAGG GTCAAATTTT CATTTTTTTG CTGTTGGTGG   1500
GGAACCTTTG GAGCTGCAGG GTGTGTTAGC AAACTACAGG ACCAAATATC CTGCTCAAAC   1560
TGTAACCCCA AAAAATGCTA CAGTTGACAG TCAGCAGATG AACACTGACC ACAAGGCTGT   1620
TTTGGATAAG GATAATGCTT ATCCAGTGGA GTGCTGGGTT CCTGATCCAA GTAAAAATGA   1680
AAACACTAGA TATTTTGGAA CCTACACAGG TGGGGAAAAT GTGCCTCCTG TTTTGCACAT   1740
TACTAACACA GCAACCACAG TGCTGCTTGA TGAGCAGGGT GTTGGGCCCT TGTGCAAAGC   1800
TGACAGCTTG TATGTTTCTG CTGTTGACAT TTGTGGGCTG TTTACCAACA CTTCTGGAAC   1860
ACAGCAGTGG AAGGGACTTC CCAGATATTT TAAAATTACC CTTAGAAAGC GGTCTGTGAA   1920
AAACCCCTAC CCAATTTCCT TTTTGTTAAG TGACCTAATT AACAGGAGGA CACAGAGGGT   1980
GGATGGGCAG CCTATGATTG GAATGTCCTC TCAAGTAGAG GAGGTTAGGG TTTATGAGGA   2040
```

-continued

```
CACAGAGGAG CTTCCTGGGG ATCCGATCCN NNNNNNNNNN NNNNNNNNNN NNNNNNNNNN   2100
NNNNNNNNNN NNNNNNNNNN NNNNNNNNNN NNNNNNNNNN NNNNNNNNNN NNNNNNNNNN   2160
NNNNNNNNNN NNNNNNNNNN NNNNNNNNNN NNNNNNNNNN NNNNNNNNNN NNNNNNNNNN   2220
NNNNNNNNNN NNNNNNNNNN NNNNNNNNNN NNNNNNNNNN NNNNNNNNNN NNNNNNNNNN   2280
NNNNNNNNNN NNNNNNNNNN NNNNNNNNNN NNNNNNNNNN NNNNNNNNNN NNNNNNNNNN   2340
NNNNNNNNNN NNNNNNNNNN NNNNNNNNNN NNNNNNNNNN NNNNNNNNNN NNNNNNNNNN   2400
NNNNNNNNNN NNNNNNNNNN NNNNNNNNNN NNNNNNNNNN NNNNNNNNNN NNNNNNNNNN   2460
NNNNNNNNNN NNNNNNNNNN NNNNNNNNNN NNNNNNNNNN NNNNNNNNNN NNNNNNNNNN   2520
NNNNNNNNNN NNNNNNNNNN NNNNNNNNNN NNNNNNNNNN NNNNNNNNNN NNNNNNNNNN   2580
NNNNNNNNNN NNNNNNNNNN NNNNNNNNNN NNNNNNNNNN NNNNNNNNNN NNNNNNNNNN   2640
NNNNNNNNNN NNNNNNNNNN NNNNNNNNNN NNNNNNNNNN NNNNNNNNNN NNNNNNNNNN   2700
NNNNNNNNNN NNNNNNNNNN NNNNNNNNNN NNNNNNNNNN NNNNNNNNNN NNNNNNNNNN   2760
NNNNNNNNNN NNNNNNNNNN NNNNNNNNNN NNNNNNNNNN NNNNNNNNNN NNNNNNNNNN   2820
NNNNNNNNNN NNNNNNNNNN NNNNNNNNNN NNNNNNNNNN NNNNNNNNNN NNNNNNNNNN   2880
NNNNNNNNNN NNNNNNNNNN NNNNNNNNNN NNNNNNNNNN NNNNNNNNNN NNNNNNNNNN   2940
NNNNNNNNNN NNNNNNNNNN NNNNNNNNNN NNNNNNNNNN NNNNNNNNNN NNNNNNNNNN   3000
NNNNNNNNNN NNNNNNNNNN NNNNNNNNNN NNNNNNNNNN NNNNNNNNNN NNNNNNNNNN   3060
NNNNNNNNNN NNNNNNNNNN NNNNNNNNNN NNNNNNNNNN NNNNNNNNNN NNNNNNNNNN   3120
NNNNNNNNNN NNNNNNNNNN NNNNNNNNNN NNNNNNNNNN NNNNNNNNNN NNNNNNNNNN   3180
NNNNNNNNNN NNNNNNNNNN NNNNNNNNNN NNNNNNNNNN NNNNNNNNNN NNNNNNNNNN   3240
NNNNNNNNNN NNNNNNNNNN NNNNNNNNNN NNNNNNNNNN NNNNNNNNNN NNNNNNNNNN   3300
NNNNNNNNNN NNNNNNNNNN NNNNNNNNNN NNNNNNNNNN NNNNNNNNNN NNNNNNNNNN   3360
NNNNNNNNNN NNNNNNNNNN NNNNNNNNNN NNNNNNNNNN NNNNNNNNNN NNNNNNNNNN   3420
NNNNNNNNNN NNNNNNNNNN NNNNNNNNNN NNNNNNNNNN NNNNNNNNNN NNNNNNNNNN   3480
NNNNNNNNNN NNNNNNNNNN NNNNNNNNNN NNNNNNNNNN NNNNNNNNNN NNNNNNNNNN   3540
NNNNNNNNNN NNNNNNNNNN NNNNNNNNNN NNNNNNNNNN NNNNNNNNNN NNNNNNNNNN   3600
NNNNNNNNNN NNNNNNNNNN NNNNNNNNNN NNNNNNNNNN NNNNNNNNNN NNNNNNNNNN   3660
NNNNNNNNNN NNNNNNNNNN NNNNNNNNNN NNNNNNNNNN NNNNNNNNNN NNNNNNNNNN   3720
NNNNNNNNNN NNNNNNNNNN NNNNNNNNNN NNNNNNNNNN NNNNNNNNNA TATAGCACAA   3780
AGACATGCAA ATAATATTTC CCTATGCTCA TAAAAACAGC CCTGACCATG AAGCTTTGAC   3840
AGACGCACAA CCCTGGACTC CCAAGTCTTT CTCTTCAGTG ACAAACACAG ACATAGGATA   3900
TCCACCATGG AATGGAGCTG GGTAATGCTC TTCCTCCTGT CAGGAACTGC AGGTGTCCGC   3960
TCTGAGGTCC AGCTGCAACA GTCTGGACCT GAACTGGTGA AGCCTGGAGC TTCAATGAAG   4020
ATTTCCTGCA AGGCTTCTGG TTACTCATTC ACTGGCTACA CCATGAACTG GGTGAAGCAG   4080
AGCCATGGAG AGAACCTTGA GTGGATTGGA CGTATTAATC CTCACAATGG TGGTACTGAC   4140
TACAACCAGA AGTTCAAGGA CAAGGCCCCT TTAACTGTAG ACAAGTCATC CAACACAGCC   4200
TACATGGAGC TCCTCAGTCT GACATCTGAG GACTCTGCAG TCTATTACTG TGCAAGAGGC   4260
TACTATTACT ATTCTTTGGA CTACTGGGGT CAAGGAACCT CAGTCACCGT CTCCTCAGCT   4320
AGCACCAAGG GCCCATCGGT CTTCCCCCTG GCACCCTCCT CCAAGAGCAC CTCTGGGGGC   4380
ACAGCGGCCC TGGGCTGCCT GGTCAAGGAC TACTTCCCCG AACCGGTGAC GGTGTCGTGG   4440
```

-continued

AACTCAGGCG CCCTGACCAG CGGCGTGCAC ACCTTCCCGG CTGTCCTACA GTCCTCAGGA 4500
CTCTACTCCC TCAGCAGCGT GGTGACCGTG CCCTCCAGCA GCTTGGGCAC CCAGACCTAC 4560
ATCTGCAACG TGAATCACAA GCCCAGCAAC ACCAAGGTGG ACAAGAAAGT TGGTGAGAGG 4620
CCAGCACAGG GAGGGAGGGT GTCTGCTGGA AGCAGGCTCA GCGCTCCTGC CTGGACGCAT 4680
CCCGGCTATG CAGCCCCAGT CCAGGGCAGC AAGGCAGGCC CCGTCTGCCT CTTCACCCGG 4740
AGCCTCTGCC CGCCCCACTC ATGCTCAGGG AGAGGGTCTT CTGGCTTTTT CCCAGGCTCT 4800
GGGCAGGCAC AGGCTAGGTG CCCCTAACCC AGGCCCTGCA CACAAAGGGG CAGGTGCTGG 4860
GCTCAGACCT GCCAAGAGCC ATATCCGGGA GGACCCTGCC CCTGACCTAA GCCCACCCCA 4920
AAGGCCAAAC TCTCCACTCC CTCAGCTCGG ACACCTTCTC TCCTCCCAGA TTCCAGTAAC 4980
TCCCAATCTT CTCTCTGCAG AGCCCAAATC TTGTGACAAA ACTCACACAT GCCCACCGTG 5040
CCCAGGTAAG CCAGCCCAGG CCTCGCCCTC CAGCTCAAGG CGGGACAGGT GCCCTAGAGT 5100
AGCCTGCATC CAGGGACAGG CCCCAGCCGG GTGCTGACAC GTCCACCTCC ATCTCTTCCT 5160
CAGCACCTGA ACTCCTGGGG GGACCGTCAG TCTTCCTCTT CCCCCCAAAA CCCAAGGACA 5220
CCCTCATGAT CTCCCGGACC CCTGAGGTCA CATGCGTGGT GGTGGACGTG AGCCACGAAG 5280
ACCCTGAGGT CAAGTTCAAC TGGTACGTGG ACGGCGTGGA GGTGCATAAT GCCAAGACAA 5340
AGCCGCGGGA GGAGCAGTAC AACAGCACGT ACCGGGTGGT CAGCGTCCTC ACCGTCCTGC 5400
ACCAGGACTG GCTGAATGGC AAGGAGTACA AGTGCAAGGT CTCCAACAAA GCCCTCCCAG 5460
CCCCCATCGA GAAAACCATC TCCAAAGCCA AAGGTGGGAC CCGTGGGGTG CGAGGGCCAC 5520
ATGGACAGAG GCCGGCTCGG CCCACCCTCT GCCCTGAGAG TGACCGCTGT ACCAACCTCT 5580
GTCCTACAGG GCAGCCCCGA GAACCACAGG TGTACACCCT GCCCCCATCC CGGGATGAGC 5640
TGACCAAGAA CCAGGTCAGC CTGACCTGCC TGGTCAAAGG CTTCTATCCC AGCGACATCG 5700
CCGTGGAGTG GGAGAGCAAT GGGCAGCCGG AGAACAACTA CAAGACCACG CCTCCCGTGC 5760
TGGACTCCGA CGGCTCCTTC TTCCTCTACA GCAAGCTCAC CGTGGACAAG AGCAGGTGGC 5820
AGCAGGGGAA CGTCTTCTCA TGCTCCGTGA TGCATGAGGC TCTGCACAAC CACTACACGC 5880
AGAAGAGCCT CTCCCTGTCT CCGGGTAAAT GAGTGCGACG GCCGGCAAGC CCCGCTCCCC 5940
GGGCTCTCGC GGTCGCACGA GGATGCTTGG CACGTACCCC CTGTACATAC TTCCCGGGCG 6000
CCCAGCATGG AAATAAAGCA CCCAGCGCTG CCCTGGGCCC CTGCGAGACT GTGATGGTTC 6060
TTTCCACGGG TCAGGCCGAG TCTGAGGCCT GAGTGGCATG AGGGAGGCAG AGCGGGTCNA 6120
ANNNNNNNNN NNNNNNNNNN NNNNNNNNNN NNNNNNNNNN NNNNNNNNNN NNNNNNNNNN 6180
NNNNNNNNNN NNNNNNNNNN NNNNNNNNNN NNNNNNNNNN NNNNNNNNNN NNNNNNNNNN 6240
NNNNNNNNNN NNNNNNNNNN NNNNNNNNNN NNNNNNNNNN NNNNNNNNNN NNNNNNNNNN 6300
NNNNNNNNNN NNNNNNNNNN NNNNNNNNNN NNNNNNNNNN NNNNNNNNNN NNNNNNNNNN 6360
NNNNNNNNNN NNNNNNNNNN NNNNNNNNNN NNNNNNNNNN NNNNNNNNNN NNNNNNNNNN 6420
NNNNNNNNNN NNNNNNNNNN NNNNNNNNNN NNNNNNNNNN NNNNNNNNNN NNNNNNNNNN 6480
NNNNNNNNNN NNNNNNNNNN NNNNNNNNNN NNNNNNNNNN NNNNNNNNNN NNNNNNNNNN 6540
NNNNNNNNNN NNNNNNNNNN NNNNNNNNNN NNNNNNNNNN NNNNNNNNNN NNNNNNNNNN 6600
NNNNNNNNNN NNNNNNNNNN NNNNNNNNNN NNNNNNNNNN NNNNNNNNNN NNNNNNNNNN 6660
NNNNNNNNNN NNNNNNNNNN NNNNNNNNNN NNNNNNNNNN NNNNNNNNNN NNNNNNNNNN 6720
NNNNNNNNNN NNNNNNNNNN NNNNNNNNNN NNNNNNNNNN NNNNNNNNNN NNNNNNNNNN 6780

-continued

NNNNNNNNNN NNNNNNNNNN NNNNNNNNNN NNNNNNNNNN NNNNNNNNNN NNNNNNNNNN 6840

NNNNNNNNNN NNNNNNNNNN NNNNNNNNNN NNNNNNNNNN NNNNNNNNNN NNNNNNNNNN 6900

NNNNNNNNNN NNNNNNNNNN NNNNNNNNNN NNNNNNNNNN NNNNNNNNNN NNNNNNNNNN 6960

NNNNNNNNNN NNNNNNNNNN NNNNNNNNNN NNNNNNNNNN NNNNNNNNNN NNNNNNNNNN 7020

NNNNNNNNNN NNNNNNNNNN NNNNNNNNNN NNNNNNNNNN NNNNNNNNNN NNNNNNNNNN 7080

NNNNNNNNNN NNNNNNNNNN NNNNNNNNNN NNNNNNNNNN NNNNNNNNNN NNNNNNNNNN 7140

NNNNNNNNNN NNNNNNNNNN NNNNNNNNNN NNNNNNNNNN NNNNNNNNNN NNNNNNNNNN 7200

NNNNNNNNNN NNNNNNNNNN NNNNNNNNNN NNNNNNNNNN NNNNNNNNNN NNNNNNNNNN 7260

NNNNNNNNNN NNNNNNNNNN NNNNNNNNNN NNNNNNNNNN NNNNNNNNNN NNNNNNNNNN 7320

NGGATCCAGA CATGATAAGA TACATTGATG AGTTTGGACA AACCACAACT AGAATGCAGT 7380

GAAAAAAATG CTTTATTTGT GAAATTTGTG ATGCTATTGC TTTATTTGTA ACCATTATAA 7440

GCTGCAATAA ACAAGTTAAC AACAACAATT GCATTCATTT TATGTTTCAG GTTCAGGGGG 7500

AGGTGTGGGA GGTTTTTTAA AGCAAGTAAA ACCTCTACAA ATGTGGTATG GCTGATTATG 7560

ATCTCTAGTC AAGGCACTAT ACATCAAATA TTCCTTATTA ACCCCTTTAC AAATTAAAAA 7620

GCTAAAGGTA CACAATTTTT GAGCATAGTT ATTAATAGCA GACACTCTAT GCCTGTGTGG 7680

AGTAAGAAAA AACAGTATGT TATGATTATA ACTGTTATGC CTACTTATAA AGGTTACAGA 7740

ATATTTTTCC ATAATTTTCT TGTATAGCAG TGCAGCTTTT TCCTTTGTGG TGTAAATAGC 7800

AAAGCAAGCA AGAGTTCTAT TACTAAACAC AGCATGACTC AAAAAACTTA GCAATTCTGA 7860

AGGAAAGTCC TTGGGGTCTT CTACCTTTCT CTTCTTTTTT GGAGGAGTAG AATGTTGAGA 7920

GTCAGCAGTA GCCTCATCAT CACTAGATGG CATTTCTTCT GAGCAAAACA GGTTTTCCTC 7980

ATTAAAGGCA TTCCACCACT GCTCCCATTC ATCAGTTCCA TAGGTTGGAA TCTAAAATAC 8040

ACAAACAATT AGAATCAGTA GTTTAACACA TTATACACTT AAAAATTTTA TATTTACCTT 8100

ATAGCTTTAA ATCTCTGTAG GTAGTTTGTC CAATTATGTC ACACCACAGA AGTAAGGTTC 8160

CTTCACAAAG ATCCGGNNNN NNNNNNNNNN NNNNNNNNNN NTCATGCTTG CTCCTTGAGG 8220

GCGTTAACGC GCAAGGTAAC GGCATTTTTA TGGGCGGTCA GACGTTCGGC GGCGGCCAGT 8280

GTTTCTATGG TTGAAGCCAC CGCGGAGAAC CCCTCTTTCG ACAGTTCCTG TACGGTCATA 8340

CGCTTCTGGA AATCTGCCAG CCCGAGGCTG GAACAGGTGG CGGTGTAACC GTAAGTCGGT 8400

AGAACGTGGT TGGTTCCGGA GGCGTAATCA CCTGCCGATT CCGGTGACCA GTCACCAAGA 8460

AATACCGAAC CGGCGCTGGT GATGCTATCG ACCAGTTCAC GGGCGTTGCG GGTCTGAATG 8520

ATCAGGTGCT CCGGGCCGTA CTGATTAGAG ATCTCCACGC ACTGCGCTGA ATCTTTAGTC 8580

ACGATCAGGC GGCTGGCGTT CAGTGCCTGG CGGGCGGTTT CGGCACGCGG CAGTTCCGCC 8640

AGTTGGCGTT CGACGGCCTC GGCAACGCGA CGCGCCATAT CAGCAGCGGG CGTCAGTAAA 8700

ATCACCTGTG AGTCCGGGCC GTGTTCAGCC TGAGAGAGCA AATCAGAAGC CACGAAATCC 8760

GGCGTTGCGC CGCTGTCAGC AATCACCAGC ACTTCCGACG GGCCTGCGGG CATATCGATC 8820

TCCGCACCGT CCAGACGCTG GCTCACCTGA CGTTTCGCTT CGGTGACAAA GGCGTTACCC 8880

GGCCCGAAGA TTTTGTCCAC TTTTGGCACG GATTCCGTAC CAAACGCCAG TGCGGCAATG 8940

GCCTGTGCGC CGCCGACGTT GAACACGTCC TGCACACCGC ACAGCTGCGC CGCATAAAGG 9000

ATCTCATCGG CAATCGGCGG CGGTGAGCAC AGCACCACTT TTTTACAGCC CGCAATACGC 9060

GCCGGAGTCG CCAGCATTAA TACCGTTGAG AAGAGCGGGG CGGAGCCGCC AGGAATATAC 9120

AACCCAACTG AAGCTACCGG ACGCGTGACC TGCTGGCAAC GCACGCCTGG CTGCGTTTCT 9180

-continued

```
ACATCTACCG GCGGCAGTTT TTGCGCAGTG TGGAAGGTTT CAATATTCTT TACTGCCACC   9240
GCCATCGCCT GTTTTAGCTC GTCGCTCAGG CGTTCGCTGG CGGCGGCGAT CTCCTCTGCA   9300
GACACCTTCA GCGCGGTAAC CGTGGTTTTA TCAAACTTCG CGCTGTATTC CCGCAGGGCC   9360
TCATCGCCGC GTGCTTTCAC GTTATCGAGA ATATCGTTAA CAGTGCGGGT AATGCTTTCA   9420
GAGGCGGAAA TCGCCGGGCG CGTTAACAGC TGGCGTTGTT GCACCGCAGT ACAGCTATTC   9480
CAGTCAATGA TTGTGTTAAA GCTCATNNNN CCGGATCAGC TTTTTGCAAA AGCCTAGGCC   9540
TCCAAAAAAG CCTCCTCACT ACTTCTGGAA TAGCTCAGAG GCCGAGGCGC CTCGGCCTCT   9600
GCATAAATAA AAAAAATTAG TCAGCCATGG GGCGGAGAAT GGGCGGAACT GGGCGGAGTT   9660
AGGGGCGGGA TGGGCGGAGT TAGGGGCGGG ACTATGGTTG CTGACTAATT GAGATGCATG   9720
CTTTGCATAC TTCTGCCTGC TGGGGAGCCT GGGGACTTTC CACACCTGGT TGCTGACTAA   9780
TTGAGATGCA TGCTTTGCAT ACTTCTGCCT GCTGGGGAGC CTGGGGACTT TCCACACCCT   9840
AACTGACACA CATTCCACAG CTGCCTCGCG CGTTTCGGTG ATGACGGTGA AAACCTCTGA   9900
CACATGCAGC TCCCGGAGAC GGTCACAGCT TGTCTGTAAG CGGATGCCGG GAGCAGACAA   9960
GCCCGTCAGG GCGCGTCAGC GGGTGTTGGC GGGTGTCGGG GCGCAGCCAT GACCCAGTCA  10020
CGTAGCGATA GCGGAGTGTA TACTGGCTTA ACTATGCGGC ATCAGAGCAG ATTGTACTGA  10080
GAGTGCACCA TATGCGGTGT GAAATACCGC ACAGATGCGT AAGGAGAAAA TACCGCATCA  10140
GGCGCTCTTC CGCTTCCTCG CTCACTGACT CGCTGCGCTC GGTCGTTCGG CTGCGGCGAG  10200
CGGTATCAGC TCACTCAAAG GCGGTAATAC GGTTATCCAC AGAATCAGGG GATAACGCAG  10260
GAAAGAACAT GTGAGCAAAA GGCCAGCAAA AGGCCAGGAA CCGTAAAAAG GCCGCGTTGC  10320
TGGCGTTTTT CCATAGGCTC CGCCCCCCTG ACGAGCATCA CAAAAATCGA CGCTCAAGTC  10380
AGAGGTGGCG AAACCCGACA GGACTATAAA GATACCAGGC GTTTCCCCCT GGAAGCTCCC  10440
TCGTGCGCTC TCCTGTTCCG ACCCTGCCGC TTACCGGATA CCTGTCCGCC TTTCTCCCTT  10500
CGGGAAGCGT GGCGCTTTCT CAATGCTCAC GCTGTAGGTA TCTCAGTTCG GTGTAGGTCG  10560
TTCGCTCCAA GCTGGGCTGT GTGCACGAAC CCCCCGTTCA GCCCGACCGC TGCGCCTTAT  10620
CCGGTAACTA TCGTCTTGAG TCCAACCCGG TAAGACACGA CTTATCGCCA CTGGCAGCAG  10680
CCACTGGTAA CAGGATTAGC AGAGCGAGGT ATGTAGGCGG TGCTACAGAG TTCTTGAAGT  10740
GGTGGCCTAA CTACGGCTAC ACTAGAAGGA CAGTATTTGG TATCTGCGCT CTGCTGAAGC  10800
CAGTTACCTT CGGAAAAAGA GTTGGTAGCT CTTGATCCGG CAAACAAACC ACCGCTGGTA  10860
GCGGTGGTTT TTTTGTTTGC AAGCAGCAGA TTACGCGCAG AAAAAAAGGA TCTCAAGAAG  10920
ATCCTTTGAT CTTTTCTACG GGGTCTGACG CTCAGTGGAA CGAAAACTCA CGTTAAGGGA  10980
TTTTGGTCAT GAGATTATCA AAAAGGATCT TCACCTAGAT CCTTTTAAAT TAAAAATGAA  11040
GTTTTAAATC AATCTAAAGT ATATATGAGT AAACTTGGTC TGACAGTTAC CAATGCTTAA  11100
TCAGTGAGGC ACCTATCTCA GCGATCTGTC TATTTCGTTC ATCCATAGTT GCCTGACTCC  11160
CCGTCGTGTA GATAACTACG ATACGGGAGG GCTTACCATC TGGCCCCAGT GCTGCAATGA  11220
TACCGCGAGA CCCACGCTCA CCGGCTCCAG ATTTATCAGC AATAAACCAG CCAGCCGGAA  11280
GGGCCGAGCG CAGAAGTGGT CCTGCAACTT TATCCGCCTC CATCCAGTCT ATTAATTGTT  11340
GCCGGGAAGC TAGAGTAAGT AGTTCGCCAG TTAATAGTTT GCGCAACGTT GTTGCCATTG  11400
CTGCAGGCAT CGTGGTGTCA CGCTCGTCGT TTGGTATGGC TTCATTCAGC TCCGGTTCCC  11460
AACGATCAAG GCGAGTTACA TGATCCCCCA TGTTGTGCAA AAAAGCGGTT AGCTCCTTCG  11520
```

-continued

GTCCTCCG 11528

(2) INFORMATION FOR SEQ ID NO:19:

(i) SEQUENCE CHARACTERISTICS:
(A) LENGTH: 235 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:19:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val
225                 230                 235
```

(2) INFORMATION FOR SEQ ID NO:20:

(i) SEQUENCE CHARACTERISTICS:
(A) LENGTH: 15 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:20:

-continued

```
Glu Pro Lys Ser Cys Asp Lys Thr His Thr Cys Pro Pro Cys Pro
1               5                   10                  15
```

(2) INFORMATION FOR SEQ ID NO:21:

(i) SEQUENCE CHARACTERISTICS:
(A) LENGTH: 110 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:21:

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

(2) INFORMATION FOR SEQ ID NO:22:

(i) SEQUENCE CHARACTERISTICS:
(A) LENGTH: 107 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:22:

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

(2) INFORMATION FOR SEQ ID NO:23:

(i) SEQUENCE CHARACTERISTICS:
(A) LENGTH: 434 amino acids
(B) TYPE: amino acid

-continued (D) TOPOLOGY: linear (ii) MOLECULE TYPE: protein (ix) FEATURE:
(A) NAME/KEY: Protein
(B) LOCATION: 1..434
(D) OTHER INFORMATION: /note= "Translation from complementary DNA."

(xi) SEQUENCE DESCRIPTION: SEQ ID NO:23:

```
Met Ser Phe Asn Thr Ile Ile Asp Trp Asn Ser Cys Thr Ala Val Gln
1               5                   10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
```

-continued

```
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```

(2) INFORMATION FOR SEQ ID NO:24:

(i) SEQUENCE CHARACTERISTICS:
(A) LENGTH: 13999 base pairs
(B) TYPE: nucleic acid
(C) STRANDEDNESS: double
(D) TOPOLOGY: circular (ii) MOLECULE TYPE: DNA (genomic)

(vii) IMMEDIATE SOURCE:
(B) CLONE: pAG4611

(ix) FEATURE:
(A) NAME/KEY: misc_feature
(B) LOCATION: 1..13999
(D) OTHER INFORMATION: /note= "Function = "Expression Vector Coding Sequence""

(xi) SEQUENCE DESCRIPTION: SEQ ID NO:24:

```
TTGCAAGCTT TTTGCAAAAG CCTAGGCCTC CAAAAAAGCC TCCTCACTAC TTCTGGAATA     60

GCTCAGAGGC CGAGGCGCCT CGGCCTCTGC ATAAATAAAA AAAATTAGTC AGCCATGGGG    120

CGGAGAATGG GCGGAACTGG GCGGAGTTAG GGGCGGGATG GGCGGAGTTA GGGGCGGGAC    180

TATGGTTGCT GACTAATTGA GATGCATGCT TTGCATACTT CTGCCTGCTG GGGAGCCTGG    240

GGACTTTCCA CACCTGGTTG CTGACTAATT GAGATGCATG CTTTGCATAC TTCTGCCTGC    300

TGGGGAGCCT GGGGACTTTC CACACCCTAA CTGACACACA TTCCACAGCT GCCTCGCGCG    360

TTTCGGTGAT GACGGTGAAA ACCTCTGACA CATGCAGCTC CCGGAGACGG TCACAGCTTG    420

TCTGTAAGCG GATGCCGGGA GCAGACAAGC CCGTCAGGGC GCGTCAGCGG GTGTTGGCGG    480

GTGTCGGGGC GCAGCCATGA CCCAGTCACG TAGCGATAGC GGAGTGTATA CTGGCTTAAC    540

TATGCGGCAT CAGAGCAGAT TGTACTGAGA GTGCACCATA TGCGGTGTGA AATACCGCAC    600

AGATGCGTAA GGAGAAAATA CCGCATCAGG CGCTCTTCCG CTTCCTCGCT CACTGACTCG    660

CTGCGCTCGG TCGTTCGGCT GCGGCGAGCG GTATCAGCTC ACTCAAAGGC GGTAATACGG    720

TTATCCACAG AATCAGGGGA TAACGCAGGA AAGAACATGT GAGCAAAAGG CCAGCAAAAG    780

GCCAGGAACC GTAAAAAGGC CGCGTTGCTG GCGTTTTTCC ATAGGCTCCG CCCCCCTGAC    840

GAGCATCACA AAAATCGACG CTCAAGTCAG AGGTGGCGAA ACCCGACAGG ACTATAAAGA    900

TACCAGGCGT TTCCCCCTGG AAGCTCCCTC GTGCGCTCTC CTGTTCCGAC CCTGCCGCTT    960

ACCGGATACC TGTCCGCCTT TCTCCCTTCG GGAAGCGTGG CGCTTTCTCA ATGCTCACGC   1020

TGTAGGTATC TCAGTTCGGT GTAGGTCGTT CGCTCCAAGC TGGGCTGTGT GCACGAACCC   1080

CCCGTTCAGC CCGACCGCTG CGCCTTATCC GGTAACTATC GTCTTGAGTC CAACCCGGTA   1140

AGACACGACT TATCGCCACT GGCAGCAGCC ACTGGTAACA GGATTAGCAG AGCGAGGTAT   1200

GTAGGCGGTG CTACAGAGTT CTTGAAGTGG TGGCCTAACT ACGGCTACAC TAGAAGGACA   1260
```

-continued

```
GTATTTGGTA TCTGCGCTCT GCTGAAGCCA GTTACCTTCG GAAAAAGAGT TGGTAGCTCT   1320
TGATCCGGCA AACAAACCAC CGCTGGTAGC GGTGGTTTTT TTGTTTGCAA GCAGCAGATT   1380
ACGCGCAGAA AAAAAGGATC TCAAGAAGAT CCTTTGATCT TTTCTACGGG GTCTGACGCT   1440
CAGTGGAACG AAAACTCACG TTAAGGGATT TTGGTCATGA GATTATCAAA AAGGATCTTC   1500
ACCTAGATCC TTTTAAATTA AAAATGAAGT TTTAAATCAA TCTAAAGTAT ATATGAGTAA   1560
ACTTGGTCTG ACAGTTACCA ATGCTTAATC AGTGAGGCAC CTATCTCAGC GATCTGTCTA   1620
TTTCGTTCAT CCATAGTTGC CTGACTCCCC GTCGTGTAGA TAACTACGAT ACGGGAGGGC   1680
TTACCATCTG GCCCCAGTGC TGCAATGATA CCGCGAGACC CACGCTCACC GGCTCCAGAT   1740
TTATCAGCAA TAAACCAGCC AGCCGGAAGG GCCGAGCGCA GAAGTGGTCC TGCAACTTTA   1800
TCCGCCTCCA TCCAGTCTAT TAATTGTTGC CGGGAAGCTA GAGTAAGTAG TTCGCCAGTT   1860
AATAGTTTGC GCAACGTTGT TGCCATTGCT GCAGGCATCG TGGTGTCACG CTCGTCGTTT   1920
GGTATGGCTT CATTCAGCTC CGGTTCCCAA CGATCAAGGC GAGTTACATG ATCCCCCATG   1980
TTGTGCAAAA AAGCGGTTAG CTCCTTCGGT CCTCGATCGT TGTCAGAAGT AAGTTGGCCG   2040
CAGTGTTATC ACTCATGGTT ATGGCAGCAC TGCATAATTC TCTTACTGTC ATGCCATCCG   2100
TAAGATGCTT TTCTGTGACT GGTGAGTACT CAACCAAGTC ATTCTGAGAA TAGTGTATGC   2160
GGCGACCGAG TTGCTCTTGC CCGGCGTCAA CACGGGATAA TACCGCGCCA CATAGCAGAA   2220
CTTTAAAAGT GCTCATCATT GGAAAACGTT CTTCGGGGCG AAAACTCTCA AGGATCTTAC   2280
CGCTGTTGAG ATCCAGTTCG ATGTAACCCA CTCGTGCACC CAACTGATCT TCAGCATCTT   2340
TTACTTTCAC CAGCGTTTCT GGGTGAGCAA AAACAGGAAG GCAAAATGCC GCAAAAAAGG   2400
GAATAAGGGC GACACGGAAA TGTTGAATAC TCATACTCTT CCTTTTTCAA TATTATTGAA   2460
GCATTTATCA GGGTTATTGT CTCATGAGCG GATACATATT TGAATGTATT TAGAAAAATA   2520
AACAAATAGG GGTTCCGCGC ACATTTCCCC GAAAAGTGCC ACCTGACGTC TAAGAAACCA   2580
TTATTATCAT GACATTAACC TATAAAAATA GGCGTATCAC GAGGCCCTTT CGTCTTCAAG   2640
AATTCCTTTG CCTAATATTA ATGAGGACTT AACCTGTGGA AATATTTTGA TGTGGGAAGC   2700
TGTTACTGTT AAAACTGAGG TTATTGGGGT AACTGCTATG TTAAACTTGC ATTCAGGGAC   2760
ACAAAAAACT CATGAAAATG GTGCTGGAAA ACCCATTCAA GGGTCAAATT TTCATTTTTT   2820
TGCTGTTGGT GGGGAACCTT TGGAGCTGCA GGGTGTGTTA GCAAACTACA GGACCAAATA   2880
TCCTGCTCAA ACTGTAACCC CAAAAAATGC TACAGTTGAC AGTCAGCAGA TGAACACTGA   2940
CCACAAGGCT GTTTTGGATA AGGATAATGC TTATCCAGTG GAGTGCTGGG TTCCTGATCC   3000
AAGTAAAAAT GAAAACACTA GATATTTTGG AACCTACACA GGTGGGGAAA ATGTGCCTCC   3060
TGTTTTGCAC ATTACTAACA CAGCAACCAC AGTGCTGCTT GATGAGCAGG GTGTTGGGCC   3120
CTTGTGCAAA GCTGACAGCT TGTATGTTTC TGCTGTTGAC ATTTGTGGGC TGTTTACCAA   3180
CACTTCTGGA ACACAGCAGT GGAAGGGACT TCCCAGATAT TTTAAAATTA CCCTTAGAAA   3240
GCGGTCTGTG AAAAACCCCT ACCCAATTTC CTTTTTGTTA AGTGACCTAA TTAACAGGAG   3300
GACACAGAGG GTGGATGGGC AGCCTATGAT TGGAATGTCC TCTCAAGTAG AGGAGGTTAG   3360
GGTTTATGAG GACACAGAGG AGCTTCCTGG GATCCNNNNN NNNNNNNNNN NNNNNNNNNN   3420
NNNNNNNNNN NNNNNNNNNN NNNNNNNNNN NNNNNNNNNN NNNNNNNNNN NNNNNNNNNN   3480
NNNNNNNNNN NNNNNNNNNN NNNNNNNNNN NNNNNNNNNN NNNNNNNNNN NNNNNNNNNN   3540
NNNNNNNNNN NNNNNNNNNN NNNNNNNNNN NNNNNNNNNN NNNNNNNNNN NNNNNNNNNN   3600
```

-continued

NNNNNNNNNN NNNNNNNNNN NNNNNNNNNN NNNNNNNNNN NNNNNNNNNN NNNNNNNNNN 3660

NNNNNNNNNN NNNNNNNNNN NNNNNNNNNN NNNNNNNNNN NNNNNNNNNN NNNNNNNNNN 3720

NNNNNNNNNN NNNNNNNNNN NNNNNNNNNN NNNNNNNNNN NNNNNNNNNN NNNNNNNNNN 3780

NNNNNNNNNN NNNNNNNNNN NNNNNNNNNN NNNNNNNNNN NNNNNNNNNN NNNNNNNNNN 3840

NNNNNNNNNN NNNNNNNNNN NNNNNNNNNN NNNNNNNNNN NNNNNNNNNN NNNNNNNNNN 3900

NNNNNNNNNN NNNNNNNNNN NNNNNNNNNN NNNNNNNNNN NNNNNNNNNN NNNNNNNNNN 3960

NNNNNNNNNN NNNNNNNNNN NNNNNNNNNN NNNNNNNNNN NNNNNNNNNN NNNNNNNNNN 4020

NNNNNNNNNN NNNNNNNNNN NNNNNNNNNN NNNNNNNNNN NNNNNNNNNN NNNNNNNNNN 4080

NNNNNNNNNN NNNNNNNNNN NNNNNNNNNN NNNNNNNNNN NNNNNNNNNN NNNNNNNNNN 4140

NNNNNNNNNN NNNNNNNNNN NNNNNNNNNN NNNNNNNNNN NNNNNNNNNN NNNNNNNNNN 4200

NNNNNNNNNN NNNNNNNNNN NNNNNNNNNN NNNNNNNNNN NNNNNNNNNN NNNNNNNNNN 4260

NNNNNNNNNN NNNNNNNNNN NNNNNNNNNN NNNNNNNNNN NNNNNNNNNN NNNNNNNNNN 4320

NNNNNNNNNN NNNNNNNNNN NNNNNNNNNN NNNNNNNNNN NNNNNNNNNN NNNNNNNNNN 4380

NNNNNNNNNN NNNNNNNNNN NNNNNNNNNN NNNNNNNNNN NNNNNNNNNN NNNNNNNNNN 4440

NNNNNNNNNN NNNNNNNNNN NNNNNNNNNN NNNNNNNNNN NNNNNNNNNN NNNNNNNNNN 4500

NNNNNNNNNN NNNNNNNNNN NNNNNNNNNN NNNNNNNNNN NNNNNNNNNN NNNNNNNNNN 4560

NNNNNNNNNN NNNNNNNNNN NNNNNNNNNN NNNNNNNNNN NNNNNNNNNN NNNNNNNNNN 4620

NNNNNNNNNN NNNNNNNNNN NNNNNNNNNN NNNNNNNNNN NNNNNNNNNN NNNNNNNNNN 4680

NNNNNNNNNN NNNNNNNNNN NNNNNNNNNN NNNNNNNNNN NNNNNNNNNN NNNNNNNNNN 4740

NNNNNNNNNN NNNNNNNNNN NNNNNNNNNN NNNNNNNNNN NNNNNNNNNN NNNNNNNNNN 4800

NNNNNNNNNN NNNNNNNNNN NNNNNNNNNN NNNNNNNNNN NNNNNNNNNN NNNNNNNNNN 4860

NNNNNNNNNN NNNNNNNNNN NNNNNNNNNN NNNNNNNNNN NNNNNNNNNN NNNNNNNNNN 4920

NNNNNNNNNN NNNNNNNNNN NNNNNNNNNN NNNNNNNNNN NNNNNNNNNN NNNNNNNNNN 4980

NNNNNNNNNN NNNNNNNNNN NNNNNNNNNN NNNNNNNNNN NNNNNNNNNN NNNNNNNNNN 5040

NNNNNNNNNN NNNNNNNNNN NNNNNNNNNN NNNNNNNNNN NNNNNNNNNN NNNNNATATA 5100

GCACAAAGAC ATGCAAATAA TATTTCCCTA TGCTCATAAA AACAGCCCTG ACCATGAAGC 5160

TTTGACAGAC GCACAACCCT GGACTCCCAA GTCTTTCTCT TCAGTGACAA ACACAGACAT 5220

AGGATATCCA CCATGGATTT TCAAGTGCAG ATTTTCAGCT TCCTGCTAAT CAGTGCCTCA 5280

GTCATACTGT CCAGAGGACA AATTGTTCTC ACCCAGTCTC CAGCAATCAT GTCTGCATCT 5340

CCAGGGGAGA AGGTCACCAT GACCTGCAGT GCCAGCTCAA GTATAGATTA CATTCACTGG 5400

TACCAGCAGA AGTCAGGCAC CTCCCCCAAA AGATGGATTT ATGACACATC CAAACTGGCT 5460

TCTGGAGTCC CTGCTCGCTT CAGTGGCAGT GGGTCTGGGA CCTCTTATTC TCTCACAATC 5520

AGCAGCATGG AGCCTGAAGA TGCTGCCACT TATTACTGCC ATCAGCGGAA TAGTTACCCA 5580

TGGACGTTCG GTGGAGGGAC CAGGCTGGAA ATCAGACGTA AGTCGACTTT CTCATCTTTT 5640

TTTATGTGTA AGACACAGGT TTTCATGTTA GGAGTTAAAG TCAGTTCAGA AAATCTTGAG 5700

AAAATGGAGA GGGCTCATTA TCAGTTGACG TGGCATACAG TGTCAGATTT TCTGTTTATC 5760

AAGCTAGTGA GATTAGGGGC AAAAAGAGGC TTTAGTTGAG AGGAAAGTAA TTAATACTAT 5820

GGTCACCATC CAAGAGATTG GATCGGAGAA TAAGCATGAG TAGTTATTGA GATCTGGGTC 5880

TGACTGCAGG TAGCGTGGTC TTCTAGACGT TTAAGTGGGA GATTTGGAGG GGATGAGGAA 5940

TGAAGGAACT TCAGGATAGA AAAGGGCTGA AGTCAAGTTC AGCTCCTAAA ATGGATGTGG 6000

-continued

GAGCAAACTT TGAAGATAAA CTGAATGACC CAGAGGATGA AACAGCGCAG ATCAAAGAGG 6060

GGCCTAGAGC TCTGAGAAGA GAAGGAGACT CATCCGTGTT GAGTTTCCAC AAGTACTGTC 6120

TTGAGTTTTG CAATAAAAGT GGGATAGCAG AGTTGAGTGT NAGCCGTANA GTATACTCTC 6180

TTTTGTCTCC TAAGATTTTT ATGACTACAA AAATCAGTAG TATGTCCTGA AATAATCATT 6240

AAGCTGTTTG AAAGTATGAC TGCTTGCCAT GTAGATACCA TGGCTTGCTG AATGATCAGA 6300

AGAGGTGTGA CTCTTATTCT AAAATTTGTC ACAAAATGTC AAAATGAGAG ACTCTGTAGG 6360

AACGAGTCCC TTGACAGACA GCTGCAAGGG GTTTTTTTCC TTTGTCTCAT TTCTACATGA 6420

AAGTAAATTT GAAATGATCN TTTTTTATTA TAAGAGTAGA AATACAGTTG GGTTTGAACT 6480

ATATGTTTTA ATNGGCCNCA CGGTTTTGTA AGACATTTGG TCCTTTGTTT TCCCAGTTAT 6540

TACTCGATTG TAATTTTATA TCGCCAGCAN TGGTCTGAAA CGGTNNNNNN CGCAACCTCT 6600

TCGTTTACTA ACTGGGTGAC CTTCGGCTGT GCCAGCCATT TGGCGTTCAC CCTGCCGCNG 6660

GCCNATGAGA ACCCCCGCGG TAGNNCCCTT GCTCCGCGTG GACCACTTTC CTGAGGACAC 6720

AGTGATAGGA ACAGAGCCAC TAATCTGAAG AGAACAGAGA TGTGACAGAC TACACTAATG 6780

TGAGAAAAAC AAGGAAAGGG TGACTTATTG GAGATTTCAG AAATAAAATG CATTTATTAT 6840

TATATTCCCT TATTTTAATT TTCTATTAGG GAATTAGAAA GGGCATAAAC TGCTTTATCC 6900

AGTGTTATAT TAAAAGCTTN NNNNNNNNNN NNNNNNNNNN NNNNNNNNNN NNNNNNNNNN 6960

NNNNNNNNNN NNNNNNNNNN NNNNNNNNNN NNNNNNNNNN NNNNNNNNNN NNNNNNNNNN 7020

NNNNNNNNNN NNNNNNNNNN NNNNNNNNNN NNNNNNNNNN NNNNNNNNNN NNNNNNNNNN 7080

NNNNNNNNNN NNNNNNNNNN NNNNNNNNNN NNNNNNNNNN NNNNNNNNNN NNNNNNNNNN 7140

NNNNNNNNNN NNNNNNNNNN NNNNNNNNNN NNNNNNNNNN NNNNNNNNNN NNNNNNNNNN 7200

NNNNNNNNNN NNNNNNNNAA TCATTTCAAA ATGATTTTAG AGAGCCTTTT GAAAACTCTT 7260

TTAAACACTT TTTAAACTCT ATTAAAACTA ATAAGATAAC TTGAAATAAT TTTCATGTCA 7320

AATACATTAA CTGTTTAATG TTTAAATGCC AGATGAAAAA TGTAAAGCTA TCAAGAATTC 7380

ACCCAGATAG GAGTATCTTC ATAGCATGTT TTTCCCTGCT TATTTTCCAG TGATCACATT 7440

ATTTTGCTAC CATGGTTATT TTATACAATT ATCTGAAAAA AATTAGTTAT GAAGATTAAA 7500

AGAGAAGAAA ATATTAAACA TAAGAGATTC AGTCTTTCAT GTTGAACTGC TTGGTTAACA 7560

GTGAAGTTAG TTTTAAAAAA AAAAAAAACT ATTTCTGTTA TCAGCTGACT TCTCCCTATC 7620

TGTTGACTTC TCCCAGCAAA AGATTCTTAC TTATTTTACA TTTTAACCTA CTGCTCTCCC 7680

ACCCAACGGG TGGAATCCCC CAGAGGGGGA TTTCCAAGAG GCCACCTGGC AGTTGCTGAG 7740

GGTCAGAAGT GAAGCTAGCC ACTTCCTCTT AGGCAGGTGG CCAAGATTAC AGTTGACCTC 7800

TCCTGGTATG GCTGAAAATT GCTGCATATG GTTACAGGCC TTGAGGCTTT GGGAGGGCTT 7860

AGAGAGAGTT GCTGGAACAG TCAGAAGGTG GAGGGGCTGA CACCACCCAG GCGCAGAGGC 7920

AGGGCTCAGG GCCTGCTCTG CAGGGAGGTT TTAGCCCAGC CCAGCCAAAG TAACCCCCGG 7980

GAGCCTGTTA TCCCAGCACA GTCCTGGAAG AGGCACAGGG GAAATAAAAG CGGACGGAGG 8040

CTTTCCTTGA CTCAGCCGCT GCCTGGTCTT CTTCAGACCT GTTCTGAATT CTAAACTCTG 8100

AGGGGGTCGG ATGACGTGGC CATTCTTTGC CTAAAGCATT GAGTTTACTG CAAGGTCAGA 8160

AAAGCATGCA AAGCCCTCAG AATGGCTGCA AAGAGCTCCA ACAAAACAAT TTAGAACTTT 8220

ATTAAGGAAT AGGGGGAAGC TAGGAAGAAA CTCAAAACAT CAAGATTTTA AATACGCTTC 8280

TTGGTCTCCT TGCTATAATT ATCTGGGATA AGCATGCTGT TTCTGTCTG TCCCTAACAT 8340

-continued

```
GCCCTGTGAT TATCCGCAAA CAACACACCC AAGGGCAGAA CTTTGTTACT TAAACACCAT   8400
CCTGTTTGCT TCTTTCCTCA GGAACTGTGG CTGCACCATC TGTCTTCATC TTCCCGCCAT   8460
CTGATGAGCA GTTGAAATCT GGAACTGCCT CTGTTGTGTG CCTGCTGAAT AACTTCTATC   8520
CCAGAGAGGC CAAAGTACAG TGGAAGGTGG ATAACGCCCT CCAATCGGGT AACTCCCAGG   8580
AGAGTGTCAC AGAGCAGGAC AGCAAGGACA GCACCTACAG CCTCAGCAGC ACCCTGACGC   8640
TGAGCAAAGC AGACTACGAG AAACACAAAG TCTACGCCTG CGAAGTCACC CATCAGGGCC   8700
TGAGCTCGCC CGTCACAAAG AGCTTCAACA GGGGAGAGTG TTAGAGGGAG AAGTGCCCCC   8760
ACCTGCTCCT CAGTTCCAGC CTGACCCCCT CCCATCCTTT GGCCTCTGAC CCTTTTTCCA   8820
CAGGGGACCT ACCCCTATTG CGGTCCTCCA GCTCATCTTT CACCTCACCC CCCTCCTCCT   8880
CCTTGGCTTT AATTATGCTA ATGTTGGAGG AGAATGAATA AATAAAGTGA ATCTTTGCAC   8940
CTGTGGTTTC TCTCTTTCCT CAATTTAATA ATTATTATCT GTTGTTTACC AACTACTCAA   9000
TTTCTCTTAT AAGGGACTAA ATATGTAGTC ATCCTAAGGC GCATAACCAT TTATAAAAAT   9060
CATCCTTCAT TCTATTTTAC CCTATCATCC TCTGCAAGAC AGTCCTCCCT CAAACCCACA   9120
AGCCTTCTGT CCTCACAGTC CCCTGGGCCG TGGTAGGAGA GACTTGCTTC CTTGTTTTCC   9180
CCTCCTCAGC AAGCCCTCAT AGTCCTTTTT AAGGGTGACA GGTCTTACGG TCATATATCC   9240
TTTGATTCAA TTCCCTGGGA ATCAACCAAG GCAAATTTTT CAAAAGAAGA AACCTGCNAN   9300
NNNNNNNNNN NNNNNNNNNN NNNNNNNNNN NNNNNNNNNN NNNNNNNNNN NNNNNNNNNN   9360
NNNNNNNNNN NNNNNNNNNN NNNNNNNNNN NNNNNNNNNN NNNNNNNNNN NNNNNNNNNN   9420
NNNNNNNNNN NNNNNNNNNN NNNNNNNNNN NNNNNNNNNN NNNNNNNNNN NNNNNNNNNN   9480
NNNNNNNNNN NNNNNNNNNN NNNNNNNNNN NNNNNNNNNN NNNNNNNNNN NNNNNNNNNN   9540
NNNNNNNNNN NNNNNNNNNN NNNNNNNNNN NNNNNNNNNN NNNNNNNNNN NNNNNNNNNN   9600
NNNNNNNNNN NNNNNNNNNN NNNNNNNNNN NNNNNNNNNN NNNNNNNNNN NNNNNNNNNN   9660
NNNNNNNNNN NNNNNNNNNN NNNNNNNNNN NNNNNNNNNN NNNNNNNNNN NNNNNNNNNN   9720
NNNNNNNNNN NNNNNNNNNN NNNNNNNNNN NNNNNNNNNN NNNNNNNNNN NNNNNNNNNN   9780
NNNNNNNNNN NNNNNNNNNN NNNNNNNNNN NNNNNNNNNN NNNNNNNNNN NNNNNNNNNN   9840
NNNNNNNNNN NNNNNNNNNN NNNNNNNNNN NNNNNNNNNN NNNNNNNNNN NNNNNNNNNN   9900
NNNNNNNNNN NNNNNNNNNN NNNNNNNNNN NNNNNNNNNN NNNNNNNNNN NNNNNNNNNN   9960
NNNNNNNNNN NNNNNNNNNN NNNNNNNNNN NNNNNNNNNN NNNNNNNNNN NNNNNNNNNN  10020
NNNNNNNNNN NNNNNNNNNN NNNNNNNNNN NNNNNNNNNN NNNNNNNNNN NNNNNNNNNN  10080
NNNNNNNNNN NNNNNNNNNN NNNNNNNNNN NNNNNNNNNN NNNNNNNNNN NNNNNNNNNN  10140
NNNNNNNNNN NNNNNNNNNN NNNNNNNNNN NNNNNNNNNN NNNNNNNNNN NNNNNNNNNN  10200
NNNNNNNNNN NNNNNNNNNN NNNNNNNNNN NNNNNNNNNN NNNNNNNNNN NNNNNNNNNN  10260
NNNNNNNNNN NNNNNNNNNN NNNNNNNNNN NNNNNNNNNN NNNNNNNNNN NNNNNNNNNN  10320
NNNNNNNNNN NNNNNNNNNN NNNNNNNNNN NNNNNNNNNN NNNNNNNNNN NNNNNNNNNN  10380
NNNNNNNNNN NNNNNNNNNN NNNNNNNNNN NNNNNNNNNN NNNNNNNNNN NNNNNNNNNN  10440
NNNNNNNNNN NNNNNNNNNN NNNNNNNNNN NNNNNNNNNN NNNNNNNNNN NNNNNNNNNN  10500
NNNNNNNNNN NNNNNNNNNN NNNNNNNNNN NNNNNNNNNN NNNNNNNNNN NNNNNNNNNN  10560
NNNNNNNNNN NNNNNNNNNN NNNNNNNNNN NNNNNNNNNN NNNNNNNNNN NNNNNNNNNN  10620
NNNNNNNNNN NNNNNNNNNN NNNNNNNNNN NNNNNNNNNN NNNNNNNNNN NNNNNNNNNN  10680
NNNNNNNNNN NNNNNNNNNN NNNNNNNNNN NNNNNNNNNN NNNNNNNNNN NNNNNNNNNN  10740
```

-continued

NNNNNNNNNN NNNNNNNNNN NNNNNNNNNN NNNNNNNNNN NNNNNNNNNN NNNNNNNNNN 10800

NNNNNNNNNN NNNNNNNNNN NNNNNNNNNN NNNNNNNNNN NNNNNNNNNN NNNNNNNNNN 10860

NNNNNNNNNN NNNNNNNNNN NNNNNNNNNN NNNNNNNNNN NNNNNNNNNN NNNNNNNNNN 10920

NNNNNNNNNN NNNNNNNNNN NNNNNNNNNN NNNNNNNNNN NNNNNNNNNN NNNNNNNNNN 10980

NNNNNNNNNN NNNNNNNNNN NNNNNNNNNN NNNNNNNNNN NNNNNNNNNN NNNNNNNNNN 11040

NNNNNNNNNN NNNNNNNNNN NNNNNNNNNN NNNNNNNNNN NNNNNNNNNN NNNNNNNNNN 11100

NNNNNNNNNN NNNNNNNNNN NNNNNNNNNN NNNNNNNNNN NNNNNNNNNN NNNNNNNNNN 11160

NNNNNNNNNN NNNNNNNNNN NNNNNNNNNN NNNNNNNNNN NNNNNNNNNN NNNNNNNNNN 11220

NNNNNNNNNN NNNNNNNNNN NNNNNNNNNN NNNNNNNNNN NNNNNNNNNN NNNNNNNNNN 11280

NNNNNNNNNN NNNNNNNNNN NNNNNNNNNN NNNNNNNNNN NNNNNNNNNN NNNNNNNNNN 11340

NNNNNNNNNN NNNNNNNNNN NNNNNNNNNN NNNNNNNNNN NNNNNNNNNN NNNNNNNNNN 11400

NNNNNNNNNN NNNNNNNNNN NNNNNNNNNN NNNNNNNNNN NNNNNNNNNN NNNNNNNGAT 11460

TCNNNNNNNN NNNNNNNNNN NNNNNNNNNN NNNNNNNNNN NNNNNNNNNN NNNNNNNNNN 11520

NNNNNNNNNN NNNNNNNNNN NNNNNNNNNN NNNNNNNNNN NNNNNNNNNN NNNNNNNNNN 11580

NNNNNNNNNN NNNNNNNNNN NNNNNNNNNN NNNNNNNNNN NNNNNNNNNN NNNNNNNNNN 11640

NNNNNNNNNN NNNNNNNNNN NNNNNNNNNN NNNNNNNNNN NNNNNNNNNN NNNNNNNNNN 11700

NNNNNNNNNN NNNNNNNNNN NNNNNNNNNN NNNNNNNNNN NNNNNNNNNN NNNNNNNNNN 11760

NNNNNNNNNN NNNNNNNNNN NNNNNNNNNN NNNNNNNNNN NNNNNNNNNN NNNNNNNNNN 11820

NNNNNNNNNN NNNNNNNNNN NNNNNNNNNN NNNNNNNNNN NNNNNNNNNN NNNNNNNNNN 11880

NNNNNNNNNN NNNNNNNNNN NNNNNNNNNN NNNNNNNNNN NNNNNNNNNN NNNNNNNNNN 11940

NNNNNNNNNN NNNNNNNNNN NNNNNNNNNN NNNNNNNNNN NNNNNNNNNN NNNNNNNNNN 12000

NNNNNNNNNN NNNNNNNNNN NNNNNNNNNN NNNNNNNNNN NNNNNNNNNN NNNNNNNNNN 12060

NNNNNNNNNN NNNNNNNNNN NNNNNNNNNN NNGGATCCAG ACATGATAAG ATACATTGAT 12120

GAGTTTGGAC AAACCACAAC TAGAATGCAG TGAAAAAAAT GCTTTATTTG TGAAATTTGT 12180

GATGCTATTG CTTTATTTGT AACCATTATA AGCTGCAATA AACAAGTTAA CAACAACAAT 12240

TGCATTCATT TTATGTTTCA GGTTCAGGGG GAGGTGTGGG AGGTTTTTTA AAGCAAGTAA 12300

AACCTCTACA AATGTGGTAT GGCTGATTAT GATCTCTAGT CAAGGCACTA TACATCAAAT 12360

ATTCCTTATT AACCCCTTTA CAAATTAAAA AGCTAAAGGT ACACAATTTT TGAGCATAGT 12420

TATTAATAGC AGACACTCTA TGCCTGTGTG GAGTAAGAAA AAACAGTATG TTATGATTAT 12480

AACTGTTATG CCTACTTATA AAGGTTACAG AATATTTTTC CATAATTTTC TTGTATAGCA 12540

GTGCAGCTTT TTCCTTTGTG GTGTAAATAG CAAAGCAAGC AAGAGTTCTA TTACTAAACA 12600

CAGCATGACT CAAAAAACTT AGCAATTCTG AAGGAAAGTC CTTGGGGTCT TCTACCTTTC 12660

TCTTCTTTTT TGGAGGAGTA GAATGTTGAG AGTCAGCAGT AGCCTCATCA TCACTAGATG 12720

GCATTTCTTC TGAGCAAAAC AGGTTTTCCT CATTAAAGGC ATTCCACCAC TGCTCCCATT 12780

CATCAGTTCC ATAGGTTGGA ATCTAAAATA CACAAACAAT TAGAATCAGT AGTTTAACAC 12840

ATTATACACT TAAAAATTTT ATATTTACCT TATAGCTTTA AATCTCTGTA GGTAGTTTGT 12900

CCAATTATGT CACACCACAG AAGTAAGGTT CCTTCACAAA GATCGATCCG GGGCCCACTC 12960

ATAAATCCAG TTGCCGCCAC GGTAGCCAAT CACCGTATCG TATAAATCAT CGCGGTACGT 13020

TCGGCATCGC TCATCACAAT ACGTGCCTGG ACGTCGAGGA TTTCGCGTGG GTCAATGCCG 13080

-continued

```
CGCCAGATCC ACATCAGACG GTTAATCATG CGATACCAGT GAGGGATGGT TTTACCATCA  13140

AGGGCCGACT GCACAGGCGG TTGTGCGCCG TGATTAAAGC GGCGGACTAG CGTCGAGGTT  13200

TCAGGATGTT TAAAGCGGGG TTTGAACAGG GTTTCGCTCA GGTTTGCCTG TGTCATGGAT  13260

GCAGCCTCCA GAATACTTAC TGGAAACTAT TGTAACCCGC CTGAAGTTAA AAAGAACAAC  13320

GCCCGGCAGT GCCAGGCGTT GAAAAGATTA GCGACCGGAG ATTGGCGGGA CGAATACGAC  13380

GCCCATATCC CACGGCTGTT CAATCCAGGT ATCTTGCGGG ATATCAACAA CATAGTCATC  13440

AACCAGCGGA CGACCAGCCG GTTTTGCGAA GATGGTGACA AAGTGCGCTT TTGGATACAT  13500

TTCACGAATC GCAACCGCAG TACCACCGGT ATCCACCAGG TCATCAATAA CGATGAAGCC  13560

TTCGCCATCG CCTTCTGCGC GTTTCAGCAC TTTAAGCTCG CGCTGGTTGT CGTGATCGTA  13620

GCTGGAAATA CAAACGGTAT CGACATGACG AATACCCAGT TCACGCGCCA GTAACGCACC  13680

CGGTACCAGA CCGCCACGGC TTACGGCAAT AATGCCTTTC CATTGTTCAG AAGGCATCAG  13740

TCGGCTTGCG AGTTTACGTG CATGGATCTG CAACATGTCC CAGGTGACGA TGTATTTTTC  13800

GCTCATGTGA AGTGTCCCAG CCTGTTTATC TACGGCTTAA AAAGTGTTCG AGGGGAAAAT  13860

AGGTTGCGCG AGATTATAGA GATCTGGCGC ACTAAAAACC AGTATTTCAC ATGAGTCCGC  13920

GTCTTTTTAC GCACTGCCTC TCCCTGACGC GGGATAAAGT GGTATTCTCA AACATATCTC  13980

GCAAGCCTGT CTTGTGTCC                                               13999
```

(2) INFORMATION FOR SEQ ID NO:25:

(i) SEQUENCE CHARACTERISTICS:
(A) LENGTH: 128 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:25:

```
Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Ile Asp Tyr Ile His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Pro Glu Asp Ala Ala Thr Tyr Tyr Cys His Gln Arg
            100                 105                 110

Asn Ser Tyr Pro Trp Thr Phe Gly Gly Gly Thr Arg Leu Glu Ile Arg
        115                 120                 125
```

(2) INFORMATION FOR SEQ ID NO:26:

(i) SEQUENCE CHARACTERISTICS:
(A) LENGTH: 106 amino acids
(B) TYPE: amino acid
(D) TOPOLOGY: linear (ii) MOLECULE TYPE: protein -continued (v) FRAGMENT TYPE: internal (xi) SEQUENCE DESCRIPTION: SEQ ID NO:26:

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

(2) INFORMATION FOR SEQ ID NO:27:

(i) SEQUENCE CHARACTERISTICS:
(A) LENGTH: 10785 base pairs
(B) TYPE: nucleic acid
(C) STRANDEDNESS: double
(D) TOPOLOGY: circular (ii) MOLECULE TYPE: DNA (genomic)

(vii) IMMEDIATE SOURCE:
(B) CLONE: pAH4625

(ix) FEATURE:
(A) NAME/KEY: misc_feature
(B) LOCATION: 1..10785
(D) OTHER INFORMATION: /note= “Function = ”Expression Vector Coding Sequence“”

(xi) SEQUENCE DESCRIPTION: SEQ ID NO:27:

```
GATCCGATCC NNNNNNNNNN NNNNNNNNNN NNNNNNNNNN NNNNNNNNNN NNNNNNNNNN     60

NNNNNNNNNN NNNNNNNNNN NNNNNNNNNN NNNNNNNNNN NNNNNNNNNN NNNNNNNNNN    120

NNNNNNNNNN NNNNNNNNNN NNNNNNNNNN NNNNNNNNNN NNNNNNNNNN NNNNNNNNNN    180

NNNNNNNNNN NNNNNNNNNN NNNNNNNNNN NNNNNNNNNN NNNNNNNNNN NNNNNNNNNN    240

NNNNNNNNNN NNNNNNNNNN NNNNNNNNNN NNNNNNNNNN NNNNNNNNNN NNNNNNNNNN    300

NNNNNNNNNN NNNNNNNNNN NNNNNNNNNN NNNNNNNNNN NNNNNNNNNN NNNNNNNNNN    360

NNNNNNNNNN NNNNNNNNNN NNNNNNNNNN NNNNNNNNNN NNNNNNNNNN NNNNNNNNNN    420

NNNNNNNNNN NNNNNNNNNN NNNNNNNNNN NNNNNNNNNN NNNNNNNNNN NNNNNNNNNN    480

NNNNNNNNNN NNNNNNNNNN NNNNNNNNNN NNNNNNNNNN NNNNNNNNNN NNNNNNNNNN    540

NNNNNNNNNN NNNNNNNNNN NNNNNNNNNN NNNNNNNNNN NNNNNNNNNN NNNNNNNNNN    600

NNNNNNNNNN NNNNNNNNNN NNNNNNNNNN NNNNNNNNNN NNNNNNNNNN NNNNNNNNNN    660

NNNNNNNNNN NNNNNNNNNN NNNNNNNNNN NNNNNNNNNN NNNNNNNNNN NNNNNNNNNN    720

NNNNNNNNNN NNNNNNNNNN NNNNNNNNNN NNNNNNNNNN NNNNNNNNNN NNNNNNNNNN    780

NNNNNNNNNN NNNNNNNNNN NNNNNNNNNN NNNNNNNNNN NNNNNNNNNN NNNNNNNNNN    840

NNNNNNNNNN NNNNNNNNNN NNNNNNNNNN NNNNNNNNNN NNNNNNNNNN NNNNNNNNNN    900

NNNNNNNNNN NNNNNNNNNN NNNNNNNNNN NNNNNNNNNN NNNNNNNNNN NNNNNNNNNN    960
```

-continued

```
NNNNNNNNNN NNNNNNNNNN NNNNNNNNNN NNNNNNNNNN NNNNNNNNNN NNNNNNNNNN   1020
NNNNNNNNNN NNNNNNNNNN NNNNNNNNNN NNNNNNNNNN NNNNNNNNNN NNNNNNNNNN   1080
NNNNNNNNNN NNNNNNNNNN NNNNNNNNNN NNNNNNNNNN NNNNNNNNNN NNNNNNNNNN   1140
NNNNNNNNNN NNNNNNNNNN NNNNNNNNNN NNNNNNNNNN NNNNNNNNNN NNNNNNNNNN   1200
NNNNNNNNNN NNNNNNNNNN NNNNNNNNNN NNNNNNNNNN NNNNNNNNNN NNNNNNNNNN   1260
NNNNNNNNNN NNNNNNNNNN NNNNNNNNNN NNNNNNNNNN NNNNNNNNNN NNNNNNNNNN   1320
NNNNNNNNNN NNNNNNNNNN NNNNNNNNNN NNNNNNNNNN NNNNNNNNNN NNNNNNNNNN   1380
NNNNNNNNNN NNNNNNNNNN NNNNNNNNNN NNNNNNNNNN NNNNNNNNNN NNNNNNNNNN   1440
NNNNNNNNNN NNNNNNNNNN NNNNNNNNNN NNNNNNNNNN NNNNNNNNNN NNNNNNNNNN   1500
NNNNNNNNNN NNNNNNNNNN NNNNNNNNNN NNNNNNNNNN NNNNNNNNNN NNNNNNNNNN   1560
NNNNNNNNNN NNNNNNNNNN NNNNNNNNNN NNNNNNNNNN NNNNNNNNNN NNNNNNNNNN   1620
NNNNNNNNNN NNNNNNNNNN NNNNNNNNNN NNNNNNNNNN NNNNNNNNNN NNNNNNNNNN   1680
NNNNNNNNNN NNNNNNNNNN NNNNNNNNNN ATATAGCACA AAGACATGCA AATAATATTT   1740
CCCTATGCTC ATAAAAACAG CCCTGACCAT GAAGCTTTGA CAGACGCACA ACCCTGGACT   1800
CCCAAGTCTT TCTCTTCAGT GACAAACACA GACATAGGAT ATCCACCATG GAATGGAGCT   1860
GGGTAATGCT CTTCCTCCTG TCAGGAACTG CAGGTGTCCG CTCTGAGGTC CAGCTGCAAC   1920
AGTCTGGACC TGAACTGGTG AAGCCTGGAG CTTCAATGAA GATTTCCTGC AAGGCTTCTG   1980
GTTACTCATT CACTGGCTAC ACCATGAACT GGGTGAAGCA GAGCCATGGA GAGAACCTTG   2040
AGTGGATTGG ACGTATTAAT CCTCACAATG GTGGTACTGA CTACAACCAG AAGTTCAAGG   2100
ACAAGGCCCC TTTAACTGTA GACAAGTCAT CCAACACAGC CTACATGGAG CTCCTCAGTC   2160
TGACATCTGA GGACTCTGCA GTCTATTACT GTGCAAGAGG CTACTATTAC TATTCTTTGG   2220
ACTACTGGGG TCAAGGAACC TCAGTCACCG TCTCCTCAGC TAGCACCAAG GGCCCATCGG   2280
TCTTCCCCCT GGCGCCCTGC TCCAGGAGCA CCTCCGAGAG CACAGCGGCC CTGGGCTGCC   2340
TGGTCAAGGA CTACTTCCCC GAACCGGTGA CGGTGTCGTG GAACTCAGGC GCTCTGACCA   2400
GCGGCGTGCA CACCTTCCCA GCTGTCCTAC AGTCCTCAGG ACTCTACTCC CTCAGCAGCG   2460
TGGTGACCGT GCCCTCCAGC AACTTCGGCA CCCAGACCTA CACCTGCAAC GTAGATCACA   2520
AGCCCAGCAA CACCAAGGTG GACAAGACAG TTGGTGAGAG GCCAGCTCAG GGAGGGAGGG   2580
TGTCTGCTGG AAGCCAGGCT CAGCCCTCCT GCCTGGACGC ACCCCGGCTG TGCAGCCCCA   2640
GCCCAGGGCA GCAAGGCAGG CCCCATCTGT CTCCTCACCC GGAGGCCTCT GCCCGCCCCA   2700
CTCATGCTCA GGGAGAGGGT CTTCTGGCTT TTTCCACCAG GCTCCAGGCA GGCACAGGCT   2760
GGGTGCCCCT ACCCCAGGCC CTTCACACAC AGGGGCAGGT GCTTGGCTCA GACCTGCCAA   2820
AAGCCATATC CGGGAGGACC CTGCCCCTGA CCTAAGCCGA CCCCAAAGGC CAAACTGTCC   2880
ACTCCCTCAG CTCGGACACC TTCTCTCCTC CCAGATCCGA GTAACTCCCA ATCTTCTCTC   2940
TGCAGAGCGC AAATGTTGTG TCGAGTGCCC ACCGTGCCCA GGTAAGCCAG CCCAGGCCTC   3000
GCCCTCCAGC TCAAGGCGGG ACAGGTGCCC TAGAGTAGCC TGCATCCAGG GACAGGCCCC   3060
AGCTGGGTGC TGACACGTCC ACCTCCATCT CTTCCTCAGC ACCACCTGTG GCAGGACCGT   3120
CAGTCTTCCT CTTCCCCCCA AAACCCAAGG ACACCCTCAT GATCTCCCGG ACCCCTGAGG   3180
TCACGTGCGT GGTGGTGGAC GTGAGCCACG AAGACCCCGA GGTCCAGTTC AACTGGTACG   3240
TGGACGGCGT GGAGGTGCAT AATGCCAAGA CAAAGCCACG GGAGGAGCAG TTCAACAGCA   3300
```

-continued

```
CGTTCCGTGT GGTCAGCGTC CTCACCGTTG TGCACCAGGA CTGGCTGAAC GGCAAGGAGT   3360
ACAAGTGCAA GGTCTCCAAC AAAGGCCTCC CAGCCCCCAT CGAGAAAACC ATCTCCAAAA   3420
CCAAAGGTGG GACCCGCGGG GTATGAGGGC CACATGGACA GAGGCCGGCT CGGCCCACCC   3480
TCTGCCCTGG GAGTGACCGC TGTGCCAACC TCTGTCCCTA CAGGGAGGAG ATGACCAAGA   3540
ACCAGGTCAG CCTGACCTGC CTGGTCAAAG GCTTCTACCC CAGCGACATC GCCGTGGAGT   3600
GGGAGAGCAA TGGGCAGCCG GAGAACAACT ACAAGACCAC ACCTCCCATG CTGGACTCCG   3660
ACGGCTCCTT CTTCCTCTAC AGCAAGCTCA CCGTGGACAA GAGCAGGTGG CAGCAGGGGA   3720
ACGTCTTCTC ATGCTCCGTG ATGCATGAGG CTCTGCACAA CCACTACACG CAGAAGAGCC   3780
TCTCCCTGTC TCCGGGTAAA TGAGTGCCAC GGCCGGCAAG CCCCCGCTCC CCAGGCTCTC   3840
GGGGTCGCGT GAGGATGCTT GGCACGTACC CCGTGTACAT ACTTCCCAGG CACCCAGCAT   3900
GGAAATAAAG CACCCAGCGC TGCCCTGGGC CCCTGCGAGA CTGTGATGGT TCTTTCCGTG   3960
GGTCAGGCCG AGTCTGAGGC CTGAGTGGCA TGAGGGAGGC AGAGTGGGTC ANNNNNNNNN   4020
NNNNNNNNNN NNNNNNNNNN NNNNNNNNNN NNNNNNNNNN NNNNNNNNNN NNNNNNNNNN   4080
NNNNNNNNNN NNNNNNNNNN NNNNNNNNNN NNNNNNNNNN NNNNNNNNNN NNNNNNNNNN   4140
NNNNNNNNNN NNNNNNNNNN NNNNNNNNNN NNNNNNNNNN NNNNNNNNNN NNNNNNNNNN   4200
NNNNNNNNNN NNNNNNNNNN NNNNNNNNNN NNNNNNNNNN NNNNNNNNNN NNNNNNNNNN   4260
NNNNNNNNNN NNNNNNNNNN NNNNNNNNNN NNNNNNNNNN NNNNNNNNNN NCAGCTGNNN   4320
NNNNNNNNNN NNNNNNNNNN NNNNNNNNNN NNNNNNNNNN NNNNNNNNNN NNNNNNNNNN   4380
NNNNNNNNNN NNNNNNNNNN NNNNNNNNNN NNNNNNNNNN NNNNNNNNNN NNNNNNNNNN   4440
NNNNNNNNNN NNNNNNNNNN NNNNNNNNNN NNNNNNNNNN NNNNNNNNNN NNNNNNNNNN   4500
NNNNNNNNNN NNNNNNNGGA TCCAGACATG ATAAGATACA TTGATGAGTT TGGACAAACC   4560
ACAACTAGAA TGCAGTGAAA AAAATGCTTT ATTTGTGAAA TTTGTGATGC TATTGCTTTA   4620
TTTGTAACCA TTATAAGCTG CAATAAACAA GTTAACAACA ACAATTGCAT TCATTTTATG   4680
TTTCAGGTTC AGGGGGAGGT GTGGGAGGTT TTTTAAAGCA AGTAAAACCT CTACAAATGT   4740
GGTATGGCTG ATTATGATCT CTAGTCAAGG CACTATACAT CAAATATTCC TTATTAACCC   4800
CTTTACAAAT TAAAAAGCTA AAGGTACACA ATTTTTGAGC ATAGTTATTA ATAGCAGACA   4860
CTCTATGCCT GTGTGGAGTA AGAAAAAACA GTATGTTATG ATTATAACTG TTATGCCTAC   4920
TTATAAAGGT TACAGAATAT TTTTCCATAA TTTTCTTGTA TAGCAGTGCA GCTTTTTCCT   4980
TTGTGGTGTA AATAGCAAAG CAAGCAAGAG TTCTATTACT AAACACAGCA TGACTCAAAA   5040
AACTTAGCAA TTCTGAAGGA AAGTCCTTGG GGTCTTCTAC CTTTCTCTTC TTTTTTGGAG   5100
GAGTAGAATG TTGAGAGTCA GCAGTAGCCT CATCATCACT AGATGGCATT TCTTCTGAGC   5160
AAAACAGGTT TTCCTCATTA AAGGCATTCC ACCACTGCTC CCATTCATCA GTTCCATAGG   5220
TTGGAATCTA AAATACACAA ACAATTAGAA TCAGTAGTTT AACACATTAT ACACTTAAAA   5280
ATTTTATATT TACCTTATAG CTTTAAATCT CTGTAGGTAG TTTGTCCAAT TATGTCACAC   5340
CACAGAAGTA AGGTTCCTTC ACAAAGATCC GGNNNNNNNN NNNNNNNNNN NNNNNNNTCA   5400
TGCTTGCTCC TTGAGGGCGT TAACGCGCAA GGTAACGGCA TTTTTATGGG CGGTCAGACG   5460
TTCGGCGGCG GCCAGTGTTT CTATGGTTGA AGCCACCGCG GAGAACCCCT CTTTCGACAG   5520
TTCCTGTACG GTCATACGCT TCTGGAAATC TGCCAGCCCG AGGCTGGAAC AGGTGGCGGT   5580
GTAACCGTAA GTCGGTAGAA CGTGGTTGGT TCCGGAGGCG TAATCACCTG CCGATTCCGG   5640
TGACCAGTCA CCAAGAAATA CCGAACCGGC GCTGGTGATG CTATCGACCA GTTCACGGGC   5700
```

-continued

```
GTTGCGGGTC TGAATGATCA GGTGCTCCGG GCCGTACTGA TTAGAGATCT CCACGCACTG   5760
CGCTGAATCT TTAGTCACGA TCAGGCGGCT GGCGTTCAGT GCCTGGCGGG CGGTTTCGGC   5820
ACGCGGCAGT TCCGCCAGTT GGCGTTCGAC GGCCTCGGCA ACGCGACGCG CCATATCAGC   5880
AGCGGGCGTC AGTAAAATCA CCTGTGAGTC CGGGCCGTGT TCAGCCTGAG AGAGCAAATC   5940
AGAAGCCACG AAATCCGGCG TTGCGCCGCT GTCAGCAATC ACCAGCACTT CCGACGGGCC   6000
TGCGGGCATA TCGATCTCCG CACCGTCCAG ACGCTGGCTC ACCTGACGTT TCGCTTCGGT   6060
GACAAAGGCG TTACCCGGCC CGAAGATTTT GTCCACTTTT GGCACGGATT CCGTACCAAA   6120
CGCCAGTGCG GCAATGGCCT GTGCGCCGCC GACGTTGAAC ACGTCCTGCA CACCGCACAG   6180
CTGCGCCGCA TAAAGGATCT CATCGGCAAT CGGCGGCGGT GAGCACAGCA CCACTTTTTT   6240
ACAGCCCGCA ATACGCGCCG GAGTCGCCAG CATTAATACC GTTGAGAAGA GCGGGGCGGA   6300
GCCGCCAGGA ATATACAACC CAACTGAAGC TACCGGACGC GTGACCTGCT GGCAACGCAC   6360
GCCTGGCTGC GTTTCTACAT CTACCGGCGG CAGTTTTTGC GCAGTGTGGA AGGTTTCAAT   6420
ATTCTTTACT GCCACCGCCA TCGCCTGTTT TAGCTCGTCG CTCAGGCGTT CGCTGGCGGC   6480
GGCGATCTCC TCTGCAGACA CCTTCAGCGC GGTAACCGTG GTTTTATCAA ACTTCGCGCT   6540
GTATTCCCGC AGGGCCTCAT CGCCGCGTGC TTTCACGTTA TCGAGAATAT CGTTAACAGT   6600
GCGGGTAATG CTTTCAGAGG CGGAAATCGC CGGGCGCGTT AACAGCTGGC GTTGTTGCAC   6660
CGCAGTACAG CTATTCCAGT CAATGATTGT GTTAAAGCTC ATNNNNCCGG ATCAGCTTTT   6720
TGCAAAAGCC TAGGCCTCCA AAAAAGCCTC CTCACTACTT CTGGAATAGC TCAGAGGCCG   6780
AGGCGCCTCG GCCTCTGCAT AAATAAAAAA AATTAGTCAG CCATGGGGCG GAGAATGGGC   6840
GGAACTGGGC GGAGTTAGGG GCGGGATGGG CGGAGTTAGG GGCGGGACTA TGGTTGCTGA   6900
CTAATTGAGA TGCATGCTTT GCATACTTCT GCCTGCTGGG GAGCCTGGGG ACTTTCCACA   6960
CCTGGTTGCT GACTAATTGA GATGCATGCT TTGCATACTT CTGCCTGCTG GGGAGCCTGG   7020
GGACTTTCCA CACCCTAACT GACACACATT CCACAGCTGC CTCGCGCGTT TCGGTGATGA   7080
CGGTGAAAAC CTCTGACACA TGCAGCTCCC GGAGACGGTC ACAGCTTGTC TGTAAGCGGA   7140
TGCCGGGAGC AGACAAGCCC GTCAGGGCGC GTCAGCGGGT GTTGGCGGGT GTCGGGGCGC   7200
AGCCATGACC CAGTCACGTA GCGATAGCGG AGTGTATACT GGCTTAACTA TGCGGCATCA   7260
GAGCAGATTG TACTGAGAGT GCACCATATG CGGTGTGAAA TACCGCACAG ATGCGTAAGG   7320
AGAAAATACC GCATCAGGCG CTCTTCCGCT TCCTCGCTCA CTGACTCGCT GCGCTCGGTC   7380
GTTCGGCTGC GGCGAGCGGT ATCAGCTCAC TCAAAGGCGG TAATACGGTT ATCCACAGAA   7440
TCAGGGGATA ACGCAGGAAA GAACATGTGA GCAAAAGGCC AGCAAAAGGC CAGGAACCGT   7500
AAAAAGGCCG CGTTGCTGGC GTTTTTCCAT AGGCTCCGCC CCCCTGACGA GCATCACAAA   7560
AATCGACGCT CAAGTCAGAG GTGGCGAAAC CCGACAGGAC TATAAAGATA CCAGGCGTTT   7620
CCCCCTGGAA GCTCCCTCGT GCGCTCTCCT GTTCCGACCC TGCCGCTTAC CGGATACCTG   7680
TCCGCCTTTC TCCCTTCGGG AAGCGTGGCG CTTTCTCAAT GCTCACGCTG TAGGTATCTC   7740
AGTTCGGTGT AGGTCGTTCG CTCCAAGCTG GGCTGTGTGC ACGAACCCCC CGTTCAGCCC   7800
GACCGCTGCG CCTTATCCGG TAACTATCGT CTTGAGTCCA ACCCGGTAAG ACACGACTTA   7860
TCGCCACTGG CAGCAGCCAC TGGTAACAGG ATTAGCAGAG CGAGGTATGT AGGCGGTGCT   7920
ACAGAGTTCT TGAAGTGGTG GCCTAACTAC GGCTACACTA GAAGGACAGT ATTTGGTATC   7980
TGCGCTCTGC TGAAGCCAGT TACCTTCGGA AAAAGAGTTG GTAGCTCTTG ATCCGGCAAA   8040
```

-continued

```
CAAACCACCG CTGGTAGCGG TGGTTTTTTT GTTTGCAAGC AGCAGATTAC GCGCAGAAAA   8100
AAAGGATCTC AAGAAGATCC TTTGATCTTT TCTACGGGGT CTGACGCTCA GTGGAACGAA   8160
AACTCACGTT AAGGGATTTT GGTCATGAGA TTATCAAAAA GGATCTTCAC CTAGATCCTT   8220
TTAAATTAAA AATGAAGTTT TAAATCAATC TAAAGTATAT ATGAGTAAAC TTGGTCTGAC   8280
AGTTACCAAT GCTTAATCAG TGAGGCACCT ATCTCAGCGA TCTGTCTATT TCGTTCATCC   8340
ATAGTTGCCT GACTCCCCGT CGTGTAGATA ACTACGATAC GGGAGGGCTT ACCATCTGGC   8400
CCCAGTGCTG CAATGATACC GCGAGACCCA CGCTCACCGG CTCCAGATTT ATCAGCAATA   8460
AACCAGCCAG CCGGAAGGGC CGAGCGCAGA AGTGGTCCTG CAACTTTATC CGCCTCCATC   8520
CAGTCTATTA ATTGTTGCCG GGAAGCTAGA GTAAGTAGTT CGCCAGTTAA TAGTTTGCGC   8580
AACGTTGTTG CCATTGCTGC AGGCATCGTG GTGTCACGCT CGTCGTTTGG TATGGCTTCA   8640
TTCAGCTCCG GTTCCCAACG ATCAAGGCGA GTTACATGAT CCCCCATGTT GTGCAAAAAA   8700
GCGGTTAGCT CCTTCGGTCC TCCGATCGTT GTCAGAAGTA AGTTGGCCGC AGTGTTATCA   8760
CTCATGGTTA TGGCAGCACT GCATAATTCT CTTACTGTCA TGCCATCCGT AAGATGCTTT   8820
TCTGTGACTG GTGAGTACTC AACCAAGTCA TTCTGAGAAT AGTGTATGCG GCGACCGAGT   8880
TGCTCTTGCC CGGCGTCAAC ACGGGATAAT ACCGCGCCAC ATAGCAGAAC TTTAAAAGTG   8940
CTCATCATTG GAAAACGTTC TTCGGGGCGA AAACTCTCAA GGATCTTACC GCTGTTGAGA   9000
TCCAGTTCGA TGTAACCCAC TCGTGCACCC AACTGATCTT CAGCATCTTT TACTTTCACC   9060
AGCGTTTCTG GGTGAGCAAA AACAGGAAGG CAAAATGCCG CAAAAAAGGG AATAAGGGCG   9120
ACACGGAAAT GTTGAATACT CATACTCTTC CTTTTTCAAT ATTATTGAAG CATTTATCAG   9180
GGTTATTGTC TCATGAGCGG ATACATATTT GAATGTATTT AGAAAAATAA ACAAATAGGG   9240
GTTCCGCGCA CATTTCCCCG AAAAGTGCCA CCTGACGTCT AAGAAACCAT TATTATCATG   9300
ACATTAACCT ATAAAAATAG GCGTATCACG AGGCCCTTTC GTCTTCAAGA ATTCAGAGAG   9360
GTCTGGTGGA GCCTGCAAAA GTCCAGCTTT CAAAGGAACA CAGAAGTATG TGTATGGAAT   9420
ATTAGAAGAT GTTGCTTTTA CTCTTAAGTT GGTTCCTAGG AAAAATAGTT AAATACTGTG   9480
ACTTTAAAAT GTGAGAGGGT TTTCAAGTAC TCATTTTTTT AAATGTCCAA AATTTTTGTC   9540
AATCAATTTG AGGTCTTGTT TGTGTAGAAC TGACATTACT TAAAGTTTAA CCGAGGAATG   9600
GGAGTGAGGC TCTCTCATAC CCTATTCAGA ACTGACTTTT AACAATAATA AATTAAGTTT   9660
AAAATATTTT TAAATGAATT GAGCAATGTT GAGTTGAGTC AAGATGGCCG ATCAGAACCG   9720
GAACACCTGC AGCAGCTGGC AGGAAGCAGG TCATGTGGCA AGGCTATTTG GGGAAGGGAA   9780
AATAAAACCA CTAGGTAAAC TTGTAGCTGT GGTTTGAAGA AGTGGTTTTG AAACACTCTG   9840
TCCAGCCCCA CCAAACCGAA AGTCCAGGCT GAGCAAAACA CCACCTGGGT AATTTGCATT   9900
TCTAAAATAA GTTGAGGATT CAGCCGAAAC TGGAGAGGTC CTCTTTTAAC TTATTGAGTT   9960
CAACCTTTTA ATTTTAGCTT GAGTAGTTCT AGTTTCCCCA AACTTAAGTT TATCGACTTC  10020
TAAAATGTAT TTAGAATTCC TTTGCCTAAT ATTAATGAGG ACTTAACCTG TGGAAATATT  10080
TTGATGTGGG AAGCTGTTAC TGTTAAAACT GAGGTTATTG GGGTAACTGC TATGTTAAAC  10140
TTGCATTCAG GGACACAAAA AACTCATGAA AATGGTGCTG GAAAACCCAT TCAAGGGTCA  10200
AATTTTCATT TTTTTGCTGT TGGTGGGGAA CCTTTGGAGC TGCAGGGTGT GTTAGCAAAC  10260
TACAGGACCA AATATCCTGC TCAAACTGTA ACCCCAAAAA ATGCTACAGT TGACAGTCAG  10320
CAGATGAACA CTGACCACAA GGCTGTTTTG GATAAGGATA ATGCTTATCC AGTGGAGTGC  10380
TGGGTTCCTG ATCCAAGTAA AAATGAAAAC ACTAGATATT TTGGAACCTA CACAGGTGGG  10440
```

-continued

```
GAAAATGTGC CTCCTGTTTT GCACATTACT AACACAGCAA CCACAGTGCT GCTTGATGAG  10500

CAGGGTGTTG GGCCCTTGTG CAAAGCTGAC AGCTTGTATG TTTCTGCTGT TGACATTTGT  10560

GGGCTGTTTA CCAACACTTC TGGAACACAG CAGTGGAAGG GACTTCCCAG ATATTTTAAA  10620

ATTACCCTTA GAAAGCGGTC TGTGAAAAAC CCCTACCCAA TTTCCTTTTT GTTAAGTGAC  10680

CTAATTAACA GGAGGACACA GAGGGTGGAT GGGCAGCCTA TGATTGGAAT GTCCTCTCAA  10740

GTAGAGGAGG TTAGGGTTTA TGAGGACACA GAGGAGCTTC CTGGG                  10785
```

(2) INFORMATION FOR SEQ ID NO:28:

(i) SEQUENCE CHARACTERISTICS:
(A) LENGTH: 235 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO:28:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val
225                 230                 235
```

(2) INFORMATION FOR SEQ ID NO:29:

(i) SEQUENCE CHARACTERISTICS:
(A) LENGTH: 12 amino acids
(B) TYPE: amino acid
(D) TOPOLOGY: linear -continued (ii) MOLECULE TYPE: protein (v) FRAGMENT TYPE: internal (xi) SEQUENCE DESCRIPTION: SEQ ID NO:29:

```
Glu Arg Lys Cys Cys Val Glu Cys Pro Pro Cys Pro
1               5                   10
```

(2) INFORMATION FOR SEQ ID NO:30:

(i) SEQUENCE CHARACTERISTICS:
(A) LENGTH: 109 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:30:

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105
```

(2) INFORMATION FOR SEQ ID NO:31:

(i) SEQUENCE CHARACTERISTICS:
(A) LENGTH: 434 amino acids
(B) TYPE: amino acid
(D) TOPOLOGY: linear (ii) MOLECULE TYPE: protein (ix) FEATURE:
(A) NAME/KEY: Protein
(B) LOCATION: 1..434
(D) OTHER INFORMATION: /note= “Translation from complementary DNA.”

(xi) SEQUENCE DESCRIPTION: SEQ ID NO:31:

```
Met Ser Phe Asn Thr Ile Ile Asp Trp Asn Ser Cys Thr Ala Val Gln
1               5                   10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
```

-continued

```
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```

(2) INFORMATION FOR SEQ ID NO:32:

(i) SEQUENCE CHARACTERISTICS:
(A) LENGTH: 12127 base pairs
(B) TYPE: nucleic acid
(C) STRANDEDNESS: double
(D) TOPOLOGY: circular (ii) MOLECULE TYPE: DNA (genomic)

(vii) IMMEDIATE SOURCE:

-continued (B) CLONE: pAH4807

(ix) FEATURE:
(A) NAME/KEY: misc_feature
(B) LOCATION: 1..12127
(D) OTHER INFORMATION: /note= "Function = "Expression Vector Coding Sequence""

(xi) SEQUENCE DESCRIPTION: SEQ ID NO:32:

```
GATCCGATCC NNNNNNNNNN NNNNNNNNNN NNNNNNNNNN NNNNNNNNNN NNNNNNNNNN     60
NNNNNNNNNN NNNNNNNNNN NNNNNNNNNN NNNNNNNNNN NNNNNNNNNN NNNNNNNNNN    120
NNNNNNNNNN NNNNNNNNNN NNNNNNNNNN NNNNNNNNNN NNNNNNNNNN NNNNNNNNNN    180
NNNNNNNNNN NNNNNNNNNN NNNNNNNNNN NNNNNNNNNN NNNNNNNNNN NNNNNNNNNN    240
NNNNNNNNNN NNNNNNNNNN NNNNNNNNNN NNNNNNNNNN NNNNNNNNNN NNNNNNNNNN    300
NNNNNNNNNN NNNNNNNNNN NNNNNNNNNN NNNNNNNNNN NNNNNNNNNN NNNNNNNNNN    360
NNNNNNNNNN NNNNNNNNNN NNNNNNNNNN NNNNNNNNNN NNNNNNNNNN NNNNNNNNNN    420
NNNNNNNNNN NNNNNNNNNN NNNNNNNNNN NNNNNNNNNN NNNNNNNNNN NNNNNNNNNN    480
NNNNNNNNNN NNNNNNNNNN NNNNNNNNNN NNNNNNNNNN NNNNNNNNNN NNNNNNNNNN    540
NNNNNNNNNN NNNNNNNNNN NNNNNNNNNN NNNNNNNNNN NNNNNNNNNN NNNNNNNNNN    600
NNNNNNNNNN NNNNNNNNNN NNNNNNNNNN NNNNNNNNNN NNNNNNNNNN NNNNNNNNNN    660
NNNNNNNNNN NNNNNNNNNN NNNNNNNNNN NNNNNNNNNN NNNNNNNNNN NNNNNNNNNN    720
NNNNNNNNNN NNNNNNNNNN NNNNNNNNNN NNNNNNNNNN NNNNNNNNNN NNNNNNNNNN    780
NNNNNNNNNN NNNNNNNNNN NNNNNNNNNN NNNNNNNNNN NNNNNNNNNN NNNNNNNNNN    840
NNNNNNNNNN NNNNNNNNNN NNNNNNNNNN NNNNNNNNNN NNNNNNNNNN NNNNNNNNNN    900
NNNNNNNNNN NNNNNNNNNN NNNNNNNNNN NNNNNNNNNN NNNNNNNNNN NNNNNNNNNN    960
NNNNNNNNNN NNNNNNNNNN NNNNNNNNNN NNNNNNNNNN NNNNNNNNNN NNNNNNNNNN   1020
NNNNNNNNNN NNNNNNNNNN NNNNNNNNNN NNNNNNNNNN NNNNNNNNNN NNNNNNNNNN   1080
NNNNNNNNNN NNNNNNNNNN NNNNNNNNNN NNNNNNNNNN NNNNNNNNNN NNNNNNNNNN   1140
NNNNNNNNNN NNNNNNNNNN NNNNNNNNNN NNNNNNNNNN NNNNNNNNNN NNNNNNNNNN   1200
NNNNNNNNNN NNNNNNNNNN NNNNNNNNNN NNNNNNNNNN NNNNNNNNNN NNNNNNNNNN   1260
NNNNNNNNNN NNNNNNNNNN NNNNNNNNNN NNNNNNNNNN NNNNNNNNNN NNNNNNNNNN   1320
NNNNNNNNNN NNNNNNNNNN NNNNNNNNNN NNNNNNNNNN NNNNNNNNNN NNNNNNNNNN   1380
NNNNNNNNNN NNNNNNNNNN NNNNNNNNNN NNNNNNNNNN NNNNNNNNNN NNNNNNNNNN   1440
NNNNNNNNNN NNNNNNNNNN NNNNNNNNNN NNNNNNNNNN NNNNNNNNNN NNNNNNNNNN   1500
NNNNNNNNNN NNNNNNNNNN NNNNNNNNNN NNNNNNNNNN NNNNNNNNNN NNNNNNNNNN   1560
NNNNNNNNNN NNNNNNNNNN NNNNNNNNNN NNNNNNNNNN NNNNNNNNNN NNNNNNNNNN   1620
NNNNNNNNNN NNNNNNNNNN NNNNNNNNNN NNNNNNNNNN NNNNNNNNNN NNNNNNNNNN   1680
NNNNNNNNNN NNNNNNNNNN NNNNNNNNNN ATATAGCACA AAGACATGCA AATAATATTT   1740
CCCTATGCTC ATAAAAACAG CCCTGACCAT GAAGCTTTGA CAGACGCACA ACCCTGGACT   1800
CCCAAGTCTT TCTCTTCAGT GACAAACACA GACATAGGAT ATCCACCATG GAATGGAGCT   1860
GGGTAATGCT CTTCCTCCTG TCAGGAACTG CAGGTGTCCG CTCTGAGGTC CAGCTGCAAC   1920
AGTCTGGACC TGAACTGGTG AAGCCTGGAG CTTCAATGAA GATTTCCTGC AAGGCTTCTG   1980
GTTACTCATT CACTGGCTAC ACCATGAACT GGGTGAAGCA GAGCCATGGA GAGAACCTTG   2040
AGTGGATTGG ACGTATTAAT CCTCACAATG GTGGTACTGA CTACAACCAG AAGTTCAAGG   2100
```

-continued

```
ACAAGGCCCC TTTAACTGTA GACAAGTCAT CCAACACAGC CTACATGGAG CTCCTCAGTC   2160
TGACATCTGA GGACTCTGCA GTCTATTACT GTGCAAGAGG CTACTATTAC TATTCTTTGG   2220
ACTACTGGGG TCAAGGAACC TCAGTCACCG TCTCCTCAAC CAAGGGCCCA TCGGTCTTCC   2280
CCCTGGCGCC CTGCTCCAGG AGCACCTCTG GGGGCACAGC GGCCCTGGGC TGCCTGGTCA   2340
AGGACTACTT CCCCGAACCG GTGACGGTGT CGTGGAACTC AGGCGCCCTG ACCAGCGGCG   2400
TGCACACCTT CCCGGCTGTC CTACAGTCCT CAGGACTCTA CTCCCTCAGC AGCGTGGTGA   2460
CCGTGCCCTC CAGCAGCTTG GGCACCCAGA CCTACACCTG CAACGTGAAT CACAAGCCCA   2520
GCAACACCAA GGTGGACAAG AGAGTTGGTG AGAGGCCAGC GCAGGGAGGG AGGGTGTCTG   2580
CTGGAAGCCA GGCTCAGCCC TCCTGCCTGG ACGCATCCCG GCTGTGCAGT CCCAGCCCAG   2640
GGCACCAAGG CAGGCCCCGT CTGACTCCTC ACCCGGAGGC CTCTGCCCGC CCCACTCATG   2700
CTCAGGGAGA GGGTCTTCTG GCTTTTTCCA CCAGGCTCCG GGCAGGCACA GGCTGGATGC   2760
CCCTACCCCA GGCCCTTCAC ACACAGGGGC AGGTGCTGCG CTCAGAGCTG CCAAGAGCCA   2820
TATCCAGGAG GACCCTGCCC CTGACCTAAG CCCACCCCAA AGGCCAAACT CTCTACTCAC   2880
TCAGCTCAGA CACCTTCTCT CTTCCCAGAT CTGAGTAACT CCCAATCTTC TCTCTGCAGA   2940
GCTCAAAACC CCACTTGGTG ACACAACTCA CACATGCCCA CGGTGCCCAG GTAAGCCAGC   3000
CCAGGCCTCG CCCTCCAGCT CAAGGCGGGA CAAGAGCCCT AGAGTGGCCT GAGTCCAGGG   3060
ACAGGCCCCA GCAGGGTGCT GACGCATCCA CCTCCATCCC AGATCCCCGT AACTCCCAAT   3120
CTTCTCTCTG CAGAGCCCAA ATCTTGTGAC ACACCTCCCC CGTGCCCAAG GTGCCCAGGT   3180
AAGCCAGCCC AGGCCTCGCC CTCCAGCTCA AGGCAGGACA GGTGCCCTAG AGTGGCCTGA   3240
GTCCAGGGAC AGGCCCCAGC AGGGTGCTGA CGCATCCACC TCCATCCCAG ATCCCCGTAA   3300
CTCCCAATCT TCTCTCTGCA GAGCCCAAAT CTTGTGACAC ACCTCCCCCG TGCCCAAGGT   3360
GCCCAGGTAA GCCAGCCCAG GCCTCGCCCT CCAGCTCAAG GCAGGACAGG TGCCCTAGAG   3420
TGGCCTGAGT CCAGGGACAG GCCCCAGCAG GGTGCTGACG CATCCACCTC CATCCCAGAT   3480
CCCCGTAACT CCCAATCTTC TCTCTGCAGA GCCCAAATCT TGTGACACAC CTCCCCCGTG   3540
CCCAAGGTGC CCAGGTAAGC CAGCCCAGGC CTCGCCCTCC AGCTCAAGGC AGGACAGGTG   3600
CCCTAGAGTG GCCTGCATCC AGGGACAGGT CCCAGTCGGG TGCTGACACA TCTGCCTCCA   3660
TCTCTTCCTC AGCACCTGAA CTCCTGGGAG GACCGTCAGT CTTCCTCTTC CCCCCAAAAC   3720
CCAAGGATAC CCTTATGATT TCCCGGACCC CTGAGGTCAC GTGCGTGGTG GTGGACGTGA   3780
GCCACGAAGA CCCCGAGGTC CAGTTCAAGT GGTACGTGGA CGGCGTGGAG GTGCATAATG   3840
CCAAGACAAA GCTGCGGGAG GAGCAGTACA ACAGCACGTT CCGTGTGGTC AGCGTCCTCA   3900
CCGTCCTGCA CCAGGACTGG CTGAACGGCA AGGAGTACAA GTGCAAGGTC TCCAACAAAG   3960
CCCTCCCAGC CCCCATCGAG AAAACCATCT CCAAAGCCAA AGGTGGGACC CGCGGGGTAT   4020
GAGGGCCACG TGGACAGAGG CCAGCTTGAC CCACCCTCTG CCCTGGGAGT GACCGCTGTG   4080
CCAACCTCTG TCCCTACAGG ACAGCCCCGA GAACCACAGG TGTACACCCT GCCCCCATCC   4140
CGGGAGGAGA TGACCAAGAA CCAGGTCAGC CTGACCTGCC TGGTCAAAGG CTTCTACCCC   4200
AGCGACATCG CCGTGGAGTG GGAGAGCAAT GGGCAGCCGG AGAACAACTA CAACACCACG   4260
CCTCCCATGC TGGACTCCGA CGGCTCCTTC TTCCTCTACA GCAAGCTCAC CGTGGACAAG   4320
AGCAGGTGGC AGCAGGGGAA CATCTTCTCA TGCTCCGTGA TGCATGAGGC TCTGCACAAC   4380
CGCTACACCC AGAAGAGCCT CTCCCTGTCT CCGGGTAAAT GAGTGCGACA GCCGGCAAGC   4440
```

-continued

```
CCCCGCTCCC CGGGCTCTCG GGGTCGCGCG AGGATGCTTG GCACGTACCC CGTGTACATA   4500
CTTCCCGGGC ACCCAGCATG GAAATAAAGC ACCCAGCGCT GCCCTGGGCC CCTGTGAGAC   4560
TGTGATGGTT CTTTCCACGG GTCAGGCCGA GTCTGAGGCC TGAGTGACAT GAGGGAGGCA   4620
GAGCGGGTCN NNNNNNNNNN NNNNNNNNNN NNNNNNNNNN NNNNNNNNNN NNNNNNNNNN   4680
NNNNNNNNNN NNNNNNNNNN NNNNNNNNNN NNNNNNNNNN NNNNNNNNNN NNNNNNNNNN   4740
NNNNNNNNNN NNNNNNNNNN NNNNNNNNNN NNNNNNNNNN NNNNNNNNNN NNNNNNNNNN   4800
NNNNNNNNNN NNNNNNNNNN NNNNNNNNNN NNNNNNNNNN NNNNNNNNNN NNNNNNNNNN   4860
NNNNNNNNNN NNNNNNNNNN NNNNNNNNNN NNNNNNNNNN NNNNNNNNNN NNNNNNNNNN   4920
NNNNNNNNNN NNNNNNNNNN NNNNNNNNNN NNNNNNNNNN NNNNNNNNNN NNNNNNNNNN   4980
NNNNNNNNNN NNNNNNNNNN NNNNNNNNNN NNNNNNNNNN NNNNNNNNNN NNNNNNNNNN   5040
NNNNNNNNNN NNNNNNNNNN NNNNNNNNNN NNNNNNNNNN NNNNNNNNNN NNNNNNNNNN   5100
NNNNNNNNNN NNNNNNNNNN NNNNNNNNNN NNNNNNNNNN NNNNNNNNNN NNNNNNNNNN   5160
NNNNNNNNNN NNNNNNNNNN NNNNNNNNNN NNNNNNNNNN NNNNNNNNNN NNNNNNNNNN   5220
NNNNNNNNNN NNNNNNNNNN NNNNNNNNNN NNNNNNNNNN NNNNNNNNNN NNNNNNNNNN   5280
NNNNNNNNNN NNNNNNNNNN NNNNNNNNNN NNNNNNNNNN NNNNNNNNNN NNNNNNNNNN   5340
NNNNNNNNNN NNNNNNNNNN NNNNNNNNNN NNNNNNNNNN NNNNNNNNNN NNNNNNNNNN   5400
NNNNNNNNNN NNNNNNNNNN NNNNNNNNNN NNNNNNNNNN NNNNNNNNNN NNNNNNNNNN   5460
NNNNNNNNNN NNNNNNNNNN NNNNNNNNNN NNNNNNNNNN NNNNNNNNNN NNNNNNNNNN   5520
NNNNNNNNNN NNNNNNNNNN NNNNNNNNNN NNNNCAGCTG NNNNNNNNNN NNNNNNNNNN   5580
NNNNNNNNNN NNNNNNNNNN NNNNNNNNNN NNNNNNNNNN NNNNNNNNNN NNNNNNNNNN   5640
NNNNNNNNNN NNNNNNNNNN NNNNNNNNNN NNNNNNNNNN NNNNNNNNNN NNNNNNNNNN   5700
NNNNNNNNNN NNNNNNNNNN NNNNNNNNNN NNNNNNNNNN NNNNNNNNNN NNNNNNNNNN   5760
NNNNNNNNNN NNNNNNNNNN NNNNNNNNNN NNNNNNNNNN NNNNNNNNNN NNNNNNNNNN   5820
NNNNNNNNNN NNNNNNNNNN NNNNNNNNNN NNNNNNNNNG GATCCAGACA TGATAAGATA   5880
CATTGATGAG TTTGGACAAA CCACAACTAG AATGCAGTGA AAAAAATGCT TTATTTGTGA   5940
AATTTGTGAT GCTATTGCTT TATTTGTAAC CATTATAAGC TGCAATAAAC AAGTTAACAA   6000
CAACAATTGC ATTCATTTTA TGTTTCAGGT TCAGGGGGAG GTGTGGGAGG TTTTTTAAAG   6060
CAAGTAAAAC CTCTACAAAT GTGGTATGGC TGATTATGAT CTCTAGTCAA GGCACTATAC   6120
ATCAAATATT CCTTATTAAC CCCTTTACAA ATTAAAAAGC TAAAGGTACA CAATTTTTGA   6180
GCATAGTTAT TAATAGCAGA CACTCTATGC CTGTGTGGAG TAAGAAAAAA CAGTATGTTA   6240
TGATTATAAC TGTTATGCCT ACTTATAAAG GTTACAGAAT ATTTTTCCAT AATTTTCTTG   6300
TATAGCAGTG CAGCTTTTTC CTTTGTGGTG TAAATAGCAA AGCAAGCAAG AGTTCTATTA   6360
CTAAACACAG CATGACTCAA AAAACTTAGC AATTCTGAAG GAAAGTCCTT GGGGTCTTCT   6420
ACCTTTCTCT TCTTTTTTGG AGGAGTAGAA TGTTGAGAGT CAGCAGTAGC CTCATCATCA   6480
CTAGATGGCA TTTCTTCTGA GCAAAACAGG TTTTCCTCAT TAAAGGCATT CCACCACTGC   6540
TCCCATTCAT CAGTTCCATA GGTTGGAATC TAAAATACAC AAACAATTAG AATCAGTAGT   6600
TTAACACATT ATACACTTAA AAATTTTATA TTTACCTTAT AGCTTTAAAT CTCTGTAGGT   6660
AGTTTGTCCA ATTATGTCAC ACCACAGAAG TAAGGTTCCT TCACAAAGAT CCGGNNNNNN   6720
NNNNNNNNNN NNNNNNNNNT CATGCTTGCT CCTTGAGGGC GTTAACGCGC AAGGTAACGG   6780
CATTTTTATG GGCGGTCAGA CGTTCGGCGG CGGCCAGTGT TTCTATGGTT GAAGCCACCG   6840
```

-continued

CGGAGAACCC CTCTTTCGAC AGTTCCTGTA CGGTCATACG CTTCTGGAAA TCTGCCAGCC 6900

CGAGGCTGGA ACAGGTGGCG GTGTAACCGT AAGTCGGTAG AACGTGGTTG GTTCCGGAGG 6960

CGTAATCACC TGCCGATTCC GGTGACCAGT CACCAAGAAA TACCGAACCG GCGCTGGTGA 7020

TGCTATCGAC CAGTTCACGG GCGTTGCGGG TCTGAATGAT CAGGTGCTCC GGGCCGTACT 7080

GATTAGAGAT CTCCACGCAC TGCGCTGAAT CTTTAGTCAC GATCAGGCGG CTGGCGTTCA 7140

GTGCCTGGCG GGCGGTTTCG GCACGCGGCA GTTCCGCCAG TTGGCGTTCG ACGGCCTCGG 7200

CAACGCGACG CGCCATATCA GCAGCGGGCG TCAGTAAAAT CACCTGTGAG TCCGGGCCGT 7260

GTTCAGCCTG AGAGAGCAAA TCAGAAGCCA CGAAATCCGG CGTTGCGCCG CTGTCAGCAA 7320

TCACCAGCAC TTCCGACGGG CCTGCGGGCA TATCGATCTC CGCACCGTCC AGACGCTGGC 7380

TCACCTGACG TTTCGCTTCG GTGACAAAGG CGTTACCCGG CCCGAAGATT TTGTCCACTT 7440

TTGGCACGGA TTCCGTACCA AACGCCAGTG CGGCAATGGC CTGTGCGCCG CCGACGTTGA 7500

ACACGTCCTG CACACCGCAC AGCTGCGCCG CATAAAGGAT CTCATCGGCA ATCGGCGGCG 7560

GTGAGCACAG CACCACTTTT TTACAGCCCG CAATACGCGC CGGAGTCGCC AGCATTAATA 7620

CCGTTGAGAA GAGCGGGGCG GAGCCGCCAG GAATATACAA CCCAACTGAA GCTACCGGAC 7680

GCGTGACCTG CTGGCAACGC ACGCCTGGCT GCGTTTCTAC ATCTACCGGC GGCAGTTTTT 7740

GCGCAGTGTG GAAGGTTTCA ATATTCTTTA CTGCCACCGC CATCGCCTGT TTTAGCTCGT 7800

CGCTCAGGCG TTCGCTGGCG GCGGCGATCT CCTCTGCAGA CACCTTCAGC GCGGTAACCG 7860

TGGTTTTATC AAACTTCGCG CTGTATTCCC GCAGGGCCTC ATCGCCGCGT GCTTTCACGT 7920

TATCGAGAAT ATCGTTAACA GTGCGGGTAA TGCTTTCAGA GGCGGAAATC GCCGGGCGCG 7980

TTAACAGCTG GCGTTGTTGC ACCGCAGTAC AGCTATTCCA GTCAATGATT GTGTTAAAGC 8040

TCATNNNNCC GGATCAGCTT TTTGCAAAAG CCTAGGCCTC CAAAAAAGCC TCCTCACTAC 8100

TTCTGGAATA GCTCAGAGGC CGAGGCGCCT CGGCCTCTGC ATAAATAAAA AAAATTAGTC 8160

AGCCATGGGG CGGAGAATGG GCGGAACTGG GCGGAGTTAG GGGCGGGATG GGCGGAGTTA 8220

GGGGCGGGAC TATGGTTGCT GACTAATTGA GATGCATGCT TTGCATACTT CTGCCTGCTG 8280

GGGAGCCTGG GGACTTTCCA CACCTGGTTG CTGACTAATT GAGATGCATG CTTTGCATAC 8340

TTCTGCCTGC TGGGGAGCCT GGGGACTTTC CACACCCTAA CTGACACACA TTCCACAGCT 8400

GCCTCGCGCG TTTCGGTGAT GACGGTGAAA ACCTCTGACA CATGCAGCTC CCGGAGACGG 8460

TCACAGCTTG TCTGTAAGCG GATGCCGGGA GCAGACAAGC CCGTCAGGGC GCGTCAGCGG 8520

GTGTTGGCGG GTGTCGGGGC GCAGCCATGA CCCAGTCACG TAGCGATAGC GGAGTGTATA 8580

CTGGCTTAAC TATGCGGCAT CAGAGCAGAT TGTACTGAGA GTGCACCATA TGCGGTGTGA 8640

AATACCGCAC AGATGCGTAA GGAGAAAATA CCGCATCAGG CGCTCTTCCG CTTCCTCGCT 8700

CACTGACTCG CTGCGCTCGG TCGTTCGGCT GCGGCGAGCG GTATCAGCTC ACTCAAAGGC 8760

GGTAATACGG TTATCCACAG AATCAGGGGA TAACGCAGGA AAGAACATGT GAGCAAAAGG 8820

CCAGCAAAAG GCCAGGAACC GTAAAAAGGC CGCGTTGCTG GCGTTTTTCC ATAGGCTCCG 8880

CCCCCCTGAC GAGCATCACA AAAATCGACG CTCAAGTCAG AGGTGGCGAA ACCCGACAGG 8940

ACTATAAAGA TACCAGGCGT TTCCCCCTGG AAGCTCCCTC GTGCGCTCTC CTGTTCCGAC 9000

CCTGCCGCTT ACCGGATACC TGTCCGCCTT TCTCCCTTCG GGAAGCGTGG CGCTTTCTCA 9060

ATGCTCACGC TGTAGGTATC TCAGTTCGGT GTAGGTCGTT CGCTCCAAGC TGGGCTGTGT 9120

GCACGAACCC CCCGTTCAGC CCGACCGCTG CGCCTTATCC GGTAACTATC GTCTTGAGTC 9180

-continued

```
CAACCCGGTA AGACACGACT TATCGCCACT GGCAGCAGCC ACTGGTAACA GGATTAGCAG   9240
AGCGAGGTAT GTAGGCGGTG CTACAGAGTT CTTGAAGTGG TGGCCTAACT ACGGCTACAC   9300
TAGAAGGACA GTATTTGGTA TCTGCGCTCT GCTGAAGCCA GTTACCTTCG GAAAAAGAGT   9360
TGGTAGCTCT TGATCCGGCA AACAAACCAC CGCTGGTAGC GGTGGTTTTT TTGTTTGCAA   9420
GCAGCAGATT ACGCGCAGAA AAAAAGGATC TCAAGAAGAT CCTTTGATCT TTTCTACGGG   9480
GTCTGACGCT CAGTGGAACG AAAACTCACG TTAAGGGATT TTGGTCATGA GATTATCAAA   9540
AAGGATCTTC ACCTAGATCC TTTTAAATTA AAAATGAAGT TTTAAATCAA TCTAAAGTAT   9600
ATATGAGTAA ACTTGGTCTG ACAGTTACCA ATGCTTAATC AGTGAGGCAC CTATCTCAGC   9660
GATCTGTCTA TTTCGTTCAT CCATAGTTGC CTGACTCCCC GTCGTGTAGA TAACTACGAT   9720
ACGGGAGGGC TTACCATCTG GCCCCAGTGC TGCAATGATA CCGCGAGACC CACGCTCACC   9780
GGCTCCAGAT TTATCAGCAA TAAACCAGCC AGCCGGAAGG GCCGAGCGCA GAAGTGGTCC   9840
TGCAACTTTA TCCGCCTCCA TCCAGTCTAT TAATTGTTGC CGGGAAGCTA GAGTAAGTAG   9900
TTCGCCAGTT AATAGTTTGC GCAACGTTGT TGCCATTGCT GCAGGCATCG TGGTGTCACG   9960
CTCGTCGTTT GGTATGGCTT CATTCAGCTC CGGTTCCCAA CGATCAAGGC GAGTTACATG  10020
ATCCCCCATG TTGTGCAAAA AAGCGGTTAG CTCCTTCGGT CCTCCGATCG TTGTCAGAAG  10080
TAAGTTGGCC GCAGTGTTAT CACTCATGGT TATGGCAGCA CTGCATAATT CTCTTACTGT  10140
CATGCCATCC GTAAGATGCT TTTCTGTGAC TGGTGAGTAC TCAACCAAGT CATTCTGAGA  10200
ATAGTGTATG CGGCGACCGA GTTGCTCTTG CCCGGCGTCA ACACGGGATA ATACCGCGCC  10260
ACATAGCAGA ACTTTAAAAG TGCTCATCAT TGGAAAACGT TCTTCGGGGC GAAAACTCTC  10320
AAGGATCTTA CCGCTGTTGA GATCCAGTTC GATGTAACCC ACTCGTGCAC CCAACTGATC  10380
TTCAGCATCT TTTACTTTCA CCAGCGTTTC TGGGTGAGCA AAAACAGGAA GGCAAAATGC  10440
CGCAAAAAAG GGAATAAGGG CGACACGGAA ATGTTGAATA CTCATACTCT TCCTTTTTCA  10500
ATATTATTGA AGCATTTATC AGGGTTATTG TCTCATGAGC GGATACATAT TTGAATGTAT  10560
TTAGAAAAAT AAACAAATAG GGGTTCCGCG CACATTTCCC CGAAAAGTGC CACCTGACGT  10620
CTAAGAAACC ATTATTATCA TGACATTAAC CTATAAAAAT AGGCGTATCA CGAGGCCCTT  10680
TCGTCTTCAA GAATTCAGAG AGGTCTGGTG GAGCCTGCAA AAGTCCAGCT TTCAAAGGAA  10740
CACAGAAGTA TGTGTATGGA ATATTAGAAG ATGTTGCTTT TACTCTTAAG TTGGTTCCTA  10800
GGAAAAATAG TTAAATACTG TGACTTTAAA ATGTGAGAGG GTTTTCAAGT ACTCATTTTT  10860
TTAAATGTCC AAAATTTTTG TCAATCAATT TGAGGTCTTG TTTGTGTAGA ACTGACATTA  10920
CTTAAAGTTT AACCGAGGAA TGGGAGTGAG GCTCTCTCAT ACCCTATTCA GAACTGACTT  10980
TTAACAATAA TAAATTAAGT TTAAAATATT TTTAAATGAA TTGAGCAATG TTGAGTTGAG  11040
TCAAGATGGC CGATCAGAAC CGGAACACCT GCAGCAGCTG GCAGGAAGCA GGTCATGTGG  11100
CAAGGCTATT TGGGGAAGGG AAAATAAAAC CACTAGGTAA ACTTGTAGCT GTGGTTTGAA  11160
GAAGTGGTTT TGAAACACTC TGTCCAGCCC CACCAAACCG AAAGTCCAGG CTGAGCAAAA  11220
CACCACCTGG GTAATTTGCA TTTCTAAAAT AAGTTGAGGA TTCAGCCGAA ACTGGAGAGG  11280
TCCTCTTTTA ACTTATTGAG TTCAACCTTT TAATTTTAGC TTGAGTAGTT CTAGTTTCCC  11340
CAAACTTAAG TTTATCGACT TCTAAAATGT ATTTAGAATT CCTTTGCCTA ATATTAATGA  11400
GGACTTAACC TGTGGAAATA TTTTGATGTG GGAAGCTGTT ACTGTTAAAA CTGAGGTTAT  11460
TGGGGTAACT GCTATGTTAA ACTTGCATTC AGGGACACAA AAAACTCATG AAAATGGTGC  11520
TGGAAAACCC ATTCAAGGGT CAAATTTTCA TTTTTTTGCT GTTGGTGGGG AACCTTTGGA  11580
```

-continued

```
GCTGCAGGGT GTGTTAGCAA ACTACAGGAC CAAATATCCT GCTCAAACTG TAACCCCAAA  11640
AAATGCTACA GTTGACAGTC AGCAGATGAA CACTGACCAC AAGGCTGTTT TGGATAAGGA  11700
TAATGCTTAT CCAGTGGAGT GCTGGGTTCC TGATCCAAGT AAAAATGAAA ACACTAGATA  11760
TTTTGGAACC TACACAGGTG GGGAAAATGT GCCTCCTGTT TTGCACATTA CTAACACAGC  11820
AACCACAGTG CTGCTTGATG AGCAGGGTGT TGGGCCCTTG TGCAAAGCTG ACAGCTTGTA  11880
TGTTTCTGCT GTTGACATTT GTGGGCTGTT TACCAACACT TCTGGAACAC AGCAGTGGAA  11940
GGGACTTCCC AGATATTTTA AAATTACCCT TAGAAAGCGG TCTGTGAAAA ACCCCTACCC  12000
AATTTCCTTT TTGTTAAGTG ACCTAATTAA CAGGAGGACA CAGAGGGTGG ATGGGCAGCC  12060
TATGATTGGA ATGTCCTCTC AAGTAGAGGA GGTTAGGGTT TATGAGGACA CAGAGGAGCT  12120
TCCTGGG                                                            12127
```

(2) INFORMATION FOR SEQ ID NO:33:

(i) SEQUENCE CHARACTERISTICS:
(A) LENGTH: 233 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO:33:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Tyr Ser Leu Asp Tyr Trp Gly
        115                 120                 125

Gln Gly Thr Ser Val Thr Val Ser Ser Thr Lys Gly Pro Ser Val Phe
    130                 135                 140

Pro Leu Ala Pro Cys Ser Arg Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Thr Cys Asn Val Asn His Lys Pro
    210                 215                 220

Ser Asn Thr Lys Val Asp Lys Arg Val
225                 230
```

-continued (2) INFORMATION FOR SEQ ID NO:34:

(i) SEQUENCE CHARACTERISTICS:
(A) LENGTH: 17 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:34:

```
Glu Leu Lys Thr Pro Leu Gly Asp Thr Thr His Thr Cys Pro Arg Cys
1               5                   10                  15

Pro
```

(2) INFORMATION FOR SEQ ID NO:35:

(i) SEQUENCE CHARACTERISTICS:
(A) LENGTH: 15 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:35:

```
Glu Pro Lys Ser Cys Asp Thr Pro Pro Pro Cys Pro Arg Cys Pro
1               5                   10                  15
```

(2) INFORMATION FOR SEQ ID NO:36:

(i) SEQUENCE CHARACTERISTICS:
(A) LENGTH: 15 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:36:

```
Glu Pro Lys Ser Cys Asp Thr Pro Pro Pro Cys Pro Arg Cys Pro
1               5                   10                  15
```

(2) INFORMATION FOR SEQ ID NO:37:

(i) SEQUENCE CHARACTERISTICS:
(A) LENGTH: 15 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:37:

```
Glu Pro Lys Ser Cys Asp Thr Pro Pro Pro Cys Pro Arg Cys Pro
1               5                   10                  15
```

(2) INFORMATION FOR SEQ ID NO:38:

(i) SEQUENCE CHARACTERISTICS:
(A) LENGTH: 110 amino acids
(B) TYPE: amino acid
(D) TOPOLOGY: linear -continued (ii) MOLECULE TYPE: protein (v) FRAGMENT TYPE: internal (xi) SEQUENCE DESCRIPTION: SEQ ID NO:38:

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Leu Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

(2) INFORMATION FOR SEQ ID NO:39:

(i) SEQUENCE CHARACTERISTICS:
(A) LENGTH: 107 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:39:

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Tyr
                85                  90                  95

Thr Gln Lys Ser Leu Ser Leu Ser Pro Gly Lys
            100                 105
```

(2) INFORMATION FOR SEQ ID NO:40:

(i) SEQUENCE CHARACTERISTICS:
(A) LENGTH: 434 amino acids
(B) TYPE: amino acid
(D) TOPOLOGY: linear (ii) MOLECULE TYPE: protein (ix) FEATURE:
(A) NAME/KEY: Protein
(B) LOCATION: 1..434
(D) OTHER INFORMATION: /note= "Translation from complementary DNA."

(xi) SEQUENCE DESCRIPTION: SEQ ID NO:40:

-continued

```
Met Ser Phe Asn Thr Ile Ile Asp Trp Asn Ser Cys Thr Ala Val Gln
1               5                   10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415
```

-continued

Thr Ala His Lys Asn Ala Val Thr Leu Arg Val Asn Ala Leu Lys Glu
420 425 430

Gln Ala (2) INFORMATION FOR SEQ ID NO:41:

(i) SEQUENCE CHARACTERISTICS:
(A) LENGTH: 10844 base pairs
(B) TYPE: nucleic acid
(C) STRANDEDNESS: double
(D) TOPOLOGY: circular (ii) MOLECULE TYPE: DNA (genomic)

(v) FRAGMENT TYPE: N-terminal (vii) IMMEDIATE SOURCE:
(B) CLONE: pAH4808

(ix) FEATURE:
(A) NAME/KEY: misc_feature
(B) LOCATION: 1..10844
(D) OTHER INFORMATION: /note= "Function = "Expression Vector Coding Sequence""

(xi) SEQUENCE DESCRIPTION: SEQ ID NO:41:

CGTTGTCAGA AGTAAGTTGG CCGCAGTGTT ATCACTCATG GTTATGGCAG CACTGCATAA 60

TTCTCTTACT GTCATGCCAT CCGTAAGATG CTTTTCTGTG ACTGGTGAGT ACTCAACCAA 120

GTCATTCTGA GAATAGTGTA TGCGGCGACC GAGTTGCTCT TGCCCGGCGT CAACACGGGA 180

TAATACCGCG CCACATAGCA GAACTTTAAA AGTGCTCATC ATTGGAAAAC GTTCTTCGGG 240

GCGAAAACTC TCAAGGATCT TACCGCTGTT GAGATCCAGT TCGATGTAAC CCACTCGTGC 300

ACCCAACTGA TCTTCAGCAT CTTTTACTTT CACCAGCGTT TCTGGGTGAG CAAAAACAGG 360

AAGGCAAAAT GCCGCAAAAA AGGGAATAAG GGCGACACGG AAATGTTGAA TACTCATACT 420

CTTCCTTTTT CAATATTATT GAAGCATTTA TCAGGGTTAT TGTCTCATGA GCGGATACAT 480

ATTTGAATGT ATTTAGAAAA ATAAACAAAT AGGGGTTCCG CGCACATTTC CCCGAAAAGT 540

GCCACCTGAC GTCTAAGAAA CCATTATTAT CATGACATTA ACCTATAAAA ATAGGCGTAT 600

CACGAGGCCC TTTCGTCTTC AAGAATTCAG AGAGGTCTGG TGGAGCCTGC AAAAGTCCAG 660

CTTTCAAAGG AACACAGAAG TATGTGTATG GAATATTAGA AGATGTTGCT TTTACTCTTA 720

AGTTGGTTCC TAGGAAAAAT AGTTAAATAC TGTGACTTTA AAATGTGAGA GGGTTTTCAA 780

GTACTCATTT TTTTAAATGT CCAAAATTTT TGTCAATCAA TTTGAGGTCT TGTTTGTGTA 840

GAACTGACAT TACTTAAAGT TTAACCGAGG AATGGGAGTG AGGCTCTCTC ATACCCTATT 900

CAGAACTGAC TTTTAACAAT AATAAATTAA GTTTAAAATA TTTTTAAATG AATTGAGCAA 960

TGTTGAGTTG AGTCAAGATG GCCGATCAGA ACCGGAACAC CTGCAGCAGC TGGCAGGAAG 1020

CAGGTCATGT GGCAAGGCTA TTTGGGGAAG GGAAAATAAA ACCACTAGGT AAACTTGTAG 1080

CTGTGGTTTG AAGAAGTGGT TTTGAAACAC TCTGTCCAGC CCCACCAAAC CGAAAGTCCA 1140

GGCTGAGCAA AACACCACCT GGGTAATTTG CATTTCTAAA ATAAGTTGAG GATTCAGCCG 1200

AAACTGGAGA GGTCCTCTTT TAACTTATTG AGTTCAACCT TTTAATTTTA GCTTGAGTAG 1260

TTCTAGTTTC CCCAAACTTA AGTTTATCGA CTTCTAAAAT GTATTTAGAA TTCCTTTGCC 1320

TAATATTAAT GAGGACTTAA CCTGTGGAAA TATTTTGATG TGGGAAGCTG TTACTGTTAA 1380

AACTGAGGTT ATTGGGGTAA CTGCTATGTT AAACTTGCAT TCAGGGACAC AAAAAACTCA 1440

TGAAAATGGT GCTGGAAAAC CCATTCAAGG GTCAAATTTT CATTTTTTTG CTGTTGGTGG 1500

-continued

```
GGAACCTTTG GAGCTGCAGG GTGTGTTAGC AAACTACAGG ACCAAATATC CTGCTCAAAC   1560
TGTAACCCCA AAAAATGCTA CAGTTGACAG TCAGCAGATG AACACTGACC ACAAGGCTGT   1620
TTTGGATAAG GATAATGCTT ATCCAGTGGA GTGCTGGGTT CCTGATCCAA GTAAAAATGA   1680
AAACACTAGA TATTTTGGAA CCTACACAGG TGGGGAAAAT GTGCCTCCTG TTTTGCACAT   1740
TACTAACACA GCAACCACAG TGCTGCTTGA TGAGCAGGGT GTTGGGCCCT TGTGCAAAGC   1800
TGACAGCTTG TATGTTTCTG CTGTTGACAT TTGTGGGCTG TTTACCAACA CTTCTGGAAC   1860
ACAGCAGTGG AAGGGACTTC CCAGATATTT TAAAATTACC CTTAGAAAGC GGTCTGTGAA   1920
AAACCCCTAC CCAATTTCCT TTTTGTTAAG TGACCTAATT AACAGGAGGA CACAGAGGGT   1980
GGATGGGCAG CCTATGATTG GAATGTCCTC TCAAGTAGAG GAGGTTAGGG TTTATGAGGA   2040
CACAGAGGAG CTTCCTGGGG ATCCGATCCN NNNNNNNNNN NNNNNNNNNN NNNNNNNNNN   2100
NNNNNNNNNN NNNNNNNNNN NNNNNNNNNN NNNNNNNNNN NNNNNNNNNN NNNNNNNNNN   2160
NNNNNNNNNN NNNNNNNNNN NNNNNNNNNN NNNNNNNNNN NNNNNNNNNN NNNNNNNNNN   2220
NNNNNNNNNN NNNNNNNNNN NNNNNNNNNN NNNNNNNNNN NNNNNNNNNN NNNNNNNNNN   2280
NNNNNNNNNN NNNNNNNNNN NNNNNNNNNN NNNNNNNNNN NNNNNNNNNN NNNNNNNNNN   2340
NNNNNNNNNN NNNNNNNNNN NNNNNNNNNN NNNNNNNNNN NNNNNNNNNN NNNNNNNNNN   2400
NNNNNNNNNN NNNNNNNNNN NNNNNNNNNN NNNNNNNNNN NNNNNNNNNN NNNNNNNNNN   2460
NNNNNNNNNN NNNNNNNNNN NNNNNNNNNN NNNNNNNNNN NNNNNNNNNN NNNNNNNNNN   2520
NNNNNNNNNN NNNNNNNNNN NNNNNNNNNN NNNNNNNNNN NNNNNNNNNN NNNNNNNNNN   2580
NNNNNNNNNN NNNNNNNNNN NNNNNNNNNN NNNNNNNNNN NNNNNNNNNN NNNNNNNNNN   2640
NNNNNNNNNN NNNNNNNNNN NNNNNNNNNN NNNNNNNNNN NNNNNNNNNN NNNNNNNNNN   2700
NNNNNNNNNN NNNNNNNNNN NNNNNNNNNN NNNNNNNNNN NNNNNNNNNN NNNNNNNNNN   2760
NNNNNNNNNN NNNNNNNNNN NNNNNNNNNN NNNNNNNNNN NNNNNNNNNN NNNNNNNNNN   2820
NNNNNNNNNN NNNNNNNNNN NNNNNNNNNN NNNNNNNNNN NNNNNNNNNN NNNNNNNNNN   2880
NNNNNNNNNN NNNNNNNNNN NNNNNNNNNN NNNNNNNNNN NNNNNNNNNN NNNNNNNNNN   2940
NNNNNNNNNN NNNNNNNNNN NNNNNNNNNN NNNNNNNNNN NNNNNNNNNN NNNNNNNNNN   3000
NNNNNNNNNN NNNNNNNNNN NNNNNNNNNN NNNNNNNNNN NNNNNNNNNN NNNNNNNNNN   3060
NNNNNNNNNN NNNNNNNNNN NNNNNNNNNN NNNNNNNNNN NNNNNNNNNN NNNNNNNNNN   3120
NNNNNNNNNN NNNNNNNNNN NNNNNNNNNN NNNNNNNNNN NNNNNNNNNN NNNNNNNNNN   3180
NNNNNNNNNN NNNNNNNNNN NNNNNNNNNN NNNNNNNNNN NNNNNNNNNN NNNNNNNNNN   3240
NNNNNNNNNN NNNNNNNNNN NNNNNNNNNN NNNNNNNNNN NNNNNNNNNN NNNNNNNNNN   3300
NNNNNNNNNN NNNNNNNNNN NNNNNNNNNN NNNNNNNNNN NNNNNNNNNN NNNNNNNNNN   3360
NNNNNNNNNN NNNNNNNNNN NNNNNNNNNN NNNNNNNNNN NNNNNNNNNN NNNNNNNNNN   3420
NNNNNNNNNN NNNNNNNNNN NNNNNNNNNN NNNNNNNNNN NNNNNNNNNN NNNNNNNNNN   3480
NNNNNNNNNN NNNNNNNNNN NNNNNNNNNN NNNNNNNNNN NNNNNNNNNN NNNNNNNNNN   3540
NNNNNNNNNN NNNNNNNNNN NNNNNNNNNN NNNNNNNNNN NNNNNNNNNN NNNNNNNNNN   3600
NNNNNNNNNN NNNNNNNNNN NNNNNNNNNN NNNNNNNNNN NNNNNNNNNN NNNNNNNNNN   3660
NNNNNNNNNN NNNNNNNNNN NNNNNNNNNN NNNNNNNNNN NNNNNNNNNN NNNNNNNNNN   3720
NNNNNNNNNN NNNNNNNNNN NNNNNNNNNN NNNNNNNNNN NNNNNNNNNA TATAGCACAA   3780
AGACATGCAA ATAATATTTC CCTATGCTCA TAAAAACAGC CCTGACCATG AAGCTTTGAC   3840
AGACGCACAA CCCTGGACTC CCAAGTCTTT CTCTTCAGTG ACAAACACAG ACATAGGATA   3900
```

-continued

```
TCCACCATGG AATGGAGCTG GGTAATGCTC TTCCTCCTGT CAGGAACTGC AGGTGTCCGC   3960
TCTGAGGTCC AGCTGCAACA GTCTGGACCT GAACTGGTGA AGCCTGGAGC TTCAATGAAG   4020
ATTTCCTGCA AGGCTTCTGG TTACTCATTC ACTGGCTACA CCATGAACTG GGTGAAGCAG   4080
AGCCATGGAG AGAACCTTGA GTGGATTGGA CGTATTAATC CTCACAATGG TGGTACTGAC   4140
TACAACCAGA AGTTCAAGGA CAAGGCCCCT TTAACTGTAG ACAAGTCATC CAACACAGCC   4200
TACATGGAGC TCCTCAGTCT GACATCTGAG GACTCTGCAG TCTATTACTG TGCAAGAGGC   4260
TACTATTACT ATTCTTTGGA CTACTGGGGT CAAGGAACCT CAGTCACCGT CTCCTCAGCT   4320
AGCACCAAGG GCCCATCCGT CTTCCCCCTG GCGCCCTGCT CCAGGAGGAC CTCCGAGAGC   4380
ACAGCCGCCC TGGGCTGCCT GGTCAAGGAC TACTTCCCCG AACCGGTGAC GGTGTCGTGG   4440
AACTCAGGCG CCCTGACCAG CGGCGTGCAC ACCTTCCCGG CTGTCCTACA GTCCTCAGGA   4500
CTCTACTCCC TCAGCAGCGT GGTGACCGTG CCCTCCAGCA GCTTGGGCAC GAAGACCTAC   4560
ACCTGCAACG TAGATCACAA GCCCAGCAAC ACCAAGGTGG ACAAGAGAGT TGGTGAGAGG   4620
CCAGCACAGG GAGGGAGGGT GTCTGCTGGA AGCCAGGCTC AGCCCTCCTG CCTGGACGCA   4680
CCCCGGCTGT GCAGCCCCAG CCCAGGGCAG CAAGGGCCCC ATCTGTCTCC TCACCCGGAG   4740
GCCTCTGACC ACCCCACTCA TGCTCAGGGA GAGGGTCTTC TGGATTTTTC CACCAGGCTC   4800
CCGGCACCAC AGGCTGGATG CCCCTACCCC AGGCCCTGCG CATACAGGGC AGGTGCTGCG   4860
CTCAGACCTG CCAAGAGCCA TATCCGGGAG GACCCTGCCC CTGACCTAAG CCCACCCCAA   4920
AGGCCAAACT CTCCACTCCC TCAGCTCAGA CACCTTCTCT CCTCCCAGAT CTGAGTAACT   4980
CCCAATCTTC TCTCTGCAGA GTCCAAATAT GGTCCCCCAT GCCCATCATG CCCAGGTAAG   5040
CCAACCCAGG CCTCGCCCTC CAGCTCAAGG CGGGACAGGT GCCCTAGAGT AGCCTGCATC   5100
CAGGGACAGG CCCCAGCCGG GTGCTGACGC ATCCACCTCC ATCTCTTCCT CAGCACCTGA   5160
GTTCCTGGGG GGACCATCAG TCTTCCTGTT CCCCCCAAAA CCCAAGGACA CTCTCATGAT   5220
CTCCCGGACC CCTGAGGTCA CGTGCGTGGT GGTGGACGTG AGCCAGGAAG ACCCCGAGGT   5280
CCAGTTCAAC TGGTACGTGG ATGGCGTGGA GGTGCATAAT GCCAAGACAA AGCCGCGGGA   5340
GGAGCAGTTC AACAGCACGT ACCGTGTGGT CAGCGTCCTC ACCGTCCTGC ACCAGGACTG   5400
GCTGAACGGC AAGGAGTACA AGTGCAAGGT CTCCAACAAA GGCCTCCCGT CCTCCATCGA   5460
GAAAACCATC TCCAAAGCCA AAGGTGGGAC CCACGGGGTG CGAGGGCCAC ACGGACAGAG   5520
GCCAGCTCGG CCCACCCTCT GCCCTGGGAG TGACCGCTGT GCCAACCTCT GTCCCTACAG   5580
GGCAGCCCCG AGAGCCACAG GTGTACACCC TGCCCCCATC CCAGGAGGAG ATGACCAAGA   5640
ACCAGGTCAG CCTGACCTGC CTGGTCAAAG GCTTCTACCC CAGCGACATC GCCGTGGAGT   5700
GGGAGAGCAA TGGGCAGCCG GAGAACAACT ACAAGACCAC GCCTCCCGTG CTGGACTCCG   5760
ACGGCTCCTT CTTCCTCTAC AGCAGGCTAA CCGTGGACAA GAGCAGGTGG CAGGAGGGGA   5820
ATGTCTTCTC ATGCTCCGTG ATGCATGAGG CTCTGCACAA CCACTACACG CAGAAGAGCC   5880
TCTCCCTGTC TCCGGGTAAA TGAGTGCCAG GGCCGGCAAG CCCCCGCTCC CCGGGCTCTC   5940
GGGGTCGCGC GAGGATGCTT GGCACGTACC CCGTCTACAT ACTTCCCAGG CACCCAGCAT   6000
GGAAATAAAG CACCCACCAC TGCCCTGGGC CCCTGTGAGA CTGTGATGGT TCTTTCCACG   6060
GGTCAGGCCG AGTCTGAGGC CTGAGTGACA TGAGGGAGGC AGAGCGGGTC CCACTGTCCC   6120
CACACTGGNN NNNNNNNNNN NNNNNNNNNN NNNNNNNNNN NNNNNNNNNN NNNNNNNNNN   6180
NNNNNNNNNN NNNNNNNNNN NNNNNNNNNN NNNNNNNNNN NNNNNNNNNN NNNNNNNNNN   6240
```

-continued

```
NNNNNNNNNN NNNNNNNNNN NNNNNNNNNN NNNNNNNNNN NNNNNNNNNN NNNNNNNNNN   6300
NNNNNNNNNN NNNNNNNNNN NNNNNNNNNC AGCTGNNNNN NNNNNNNNNN NNNNNNNNNN   6360
NNNNNNNNNN NNNNNNNNNN NNNNNNNNNN NNNNNNNNNN NNNNNNNNNN NNNNNNNNNN   6420
NNNNNNNNNN NNNNNNNNNN NNNNNNNNNN NNNNNNNNNN NNNNNNNNNN NNNNNNNNNN   6480
NNNNNNNNNN NNNNNNNNNN NNNNNNNNNN NNNNNNNNNN NNNNNNNNNN NNNNNNNNNN   6540
NNNNNNNNNN NNNNNNNNNN NNNNNNNNNN NNNNNNNNNN NNNNNNNNNN NNNNNNNNNN   6600
NNNNNNNNNN NNNNNNNNNN NNNNNNNNNN NNNNNGGATC CAGACATGAT AAGATACATT   6660
GATGAGTTTG GACAAACCAC AACTAGAATG CAGTGAAAAA AATGCTTTAT TTGTGAAATT   6720
TGTGATGCTA TTGCTTTATT TGTAACCATT ATAAGCTGCA ATAAACAAGT TAACAACAAC   6780
AATTGCATTC ATTTTATGTT TCAGGTTCAG GGGGAGGTGT GGGAGGTTTT TTAAAGCAAG   6840
TAAAACCTCT ACAAATGTGG TATGGCTGAT TATGATCTCT AGTCAAGGCA CTATACATCA   6900
AATATTCCTT ATTAACCCCT TTACAAATTA AAAAGCTAAA GGTACACAAT TTTTGAGCAT   6960
AGTTATTAAT AGCAGACACT CTATGCCTGT GTGGAGTAAG AAAAAACAGT ATGTTATGAT   7020
TATAACTGTT ATGCCTACTT ATAAAGGTTA CAGAATATTT TTCCATAATT TTCTTGTATA   7080
GCAGTGCAGC TTTTTCCTTT GTGGTGTAAA TAGCAAAGCA AGCAAGAGTT CTATTACTAA   7140
ACACAGCATG ACTCAAAAAA CTTAGCAATT CTGAAGGAAA GTCCTTGGGG TCTTCTACCT   7200
TTCTCTTCTT TTTTGGAGGA GTAGAATGTT GAGAGTCAGC AGTAGCCTCA TCATCACTAG   7260
ATGGCATTTC TTCTGAGCAA AACAGGTTTT CCTCATTAAA GGCATTCCAC CACTGCTCCC   7320
ATTCATCAGT TCCATAGGTT GGAATCTAAA ATACACAAAC AATTAGAATC AGTAGTTTAA   7380
CACATTATAC ACTTAAAAAT TTTATATTTA CCTTATAGCT TTAAATCTCT GTAGGTAGTT   7440
TGTCCAATTA TGTCACACCA CAGAAGTAAG GTTCCTTCAC AAAGATCCGG NNNNNNNNNN   7500
NNNNNNNNNN NNNNNTCATG CTTGCTCCTT GAGGGCGTTA ACGCGCAAGG TAACGGCATT   7560
TTTATGGGCG GTCAGACGTT CGGCGGCGGC CAGTGTTTCT ATGGTTGAAG CCACCGCGGA   7620
GAACCCCTCT TTCGACAGTT CCTGTACGGT CATACGCTTC TGGAAATCTG CCAGCCCGAG   7680
GCTGGAACAG GTGGCGGTGT AACCGTAAGT CGGTAGAACG TGGTTGGTTC CGGAGGCGTA   7740
ATCACCTGCC GATTCCGGTG ACCAGTCACC AAGAAATACC GAACCGGCGC TGGTGATGCT   7800
ATCGACCAGT TCACGGGCGT TGCGGGTCTG AATGATCAGG TGCTCCGGGC CGTACTGATT   7860
AGAGATCTCC ACGCACTGCG CTGAATCTTT AGTCACGATC AGGCGGCTGG CGTTCAGTGC   7920
CTGGCGGGCG GTTTCGGCAC GCGGCAGTTC CGCCAGTTGG CGTTCGACGG CCTCGGCAAC   7980
GCGACGCGCC ATATCAGCAG CGGGCGTCAG TAAAATCACC TGTGAGTCCG GGCCGTGTTC   8040
AGCCTGAGAG AGCAAATCAG AAGCCACGAA ATCCGGCGTT GCGCCGCTGT CAGCAATCAC   8100
CAGCACTTCC GACGGGCCTG CGGGCATATC GATCTCCGCA CCGTCCAGAC GCTGGCTCAC   8160
CTGACGTTTC GCTTCGGTGA CAAAGGCGTT ACCCGGCCCG AAGATTTTGT CCACTTTTGG   8220
CACGGATTCC GTACCAAACG CCAGTGCGGC AATGGCCTGT GCGCCGCCGA CGTTGAACAC   8280
GTCCTGCACA CCGCACAGCT GCGCCGCATA AAGGATCTCA TCGGCAATCG GCGGCGGTGA   8340
GCACAGCACC ACTTTTTTAC AGCCCGCAAT ACGCGCCGGA GTCGCCAGCA TTAATACCGT   8400
TGAGAAGAGC GGGGCGGAGC CGCCAGGAAT ATACAACCCA ACTGAAGCTA CCGGACGCGT   8460
GACCTGCTGG CAACGCACGC CTGGCTGCGT TTCTACATCT ACCGGCGGCA GTTTTTGCGC   8520
AGTGTGGAAG GTTTCAATAT TCTTTACTGC CACCGCCATC GCCTGTTTTA GCTCGTCGCT   8580
CAGGCGTTCG CTGGCGGCGG CGATCTCCTC TGCAGACACC TTCAGCGCGG TAACCGTGGT   8640
```

-continued

```
TTTATCAAAC TTCGCGCTGT ATTCCCGCAG GGCCTCATCG CCGCGTGCTT TCACGTTATC   8700
GAGAATATCG TTAACAGTGC GGGTAATGCT TTCAGAGGCG GAAATCGCCG GGCGCGTTAA   8760
CAGCTGGCGT TGTTGCACCG CAGTACAGCT ATTCCAGTCA ATGATTGTGT TAAAGCTCAT   8820
NNNNCCGGAT CAGCTTTTTG CAAAAGCCTA GGCCTCCAAA AAGCCTCCT CACTACTTCT   8880
GGAATAGCTC AGAGGCCGAG GCGCCTCGGC CTCTGCATAA ATAAAAAAAA TTAGTCAGCC   8940
ATGGGGCGGA GAATGGGCGG AACTGGGCGG AGTTAGGGGC GGGATGGGCG GAGTTAGGGG   9000
CGGGACTATG GTTGCTGACT AATTGAGATG CATGCTTTGC ATACTTCTGC CTGCTGGGGA   9060
GCCTGGGGAC TTTCCACACC TGGTTGCTGA CTAATTGAGA TGCATGCTTT GCATACTTCT   9120
GCCTGCTGGG GAGCCTGGGG ACTTTCCACA CCCTAACTGA CACACATTCC ACAGCTGCCT   9180
CGCGCGTTTC GGTGATGACG GTGAAAACCT CTGACACATG CAGCTCCCGG AGACGGTCAC   9240
AGCTTGTCTG TAAGCGGATG CCGGGAGCAG ACAAGCCCGT CAGGGCGCGT CAGCGGGTGT   9300
TGGCGGGTGT CGGGGCGCAG CCATGACCCA GTCACGTAGC GATAGCGGAG TGTATACTGG   9360
CTTAACTATG CGGCATCAGA GCAGATTGTA CTGAGAGTGC ACCATATGCG GTGTGAAATA   9420
CCGCACAGAT GCGTAAGGAG AAAATACCGC ATCAGGCGCT CTTCCGCTTC CTCGCTCACT   9480
GACTCGCTGC GCTCGGTCGT TCGGCTGCGG CGAGCGGTAT CAGCTCACTC AAAGGCGGTA   9540
ATACGGTTAT CCACAGAATC AGGGGATAAC GCAGGAAAGA ACATGTGAGC AAAAGGCCAG   9600
CAAAAGGCCA GGAACCGTAA AAAGGCCGCG TTGCTGGCGT TTTTCCATAG GCTCCGCCCC   9660
CCTGACGAGC ATCACAAAAA TCGACGCTCA AGTCAGAGGT GGCGAAACCC GACAGGACTA   9720
TAAAGATACC AGGCGTTTCC CCCTGGAAGC TCCCTCGTGC GCTCTCCTGT TCCGACCCTG   9780
CCGCTTACCG GATACCTGTC CGCCTTTCTC CCTTCGGGAA GCGTGGCGCT TTCTCAATGC   9840
TCACGCTGTA GGTATCTCAG TTCGGTGTAG GTCGTTCGCT CCAAGCTGGG CTGTGTGCAC   9900
GAACCCCCCG TTCAGCCCGA CCGCTGCGCC TTATCCGGTA ACTATCGTCT TGAGTCCAAC   9960
CCGGTAAGAC ACGACTTATC GCCACTGGCA GCAGCCACTG GTAACAGGAT TAGCAGAGCG  10020
AGGTATGTAG GCGGTGCTAC AGAGTTCTTG AAGTGGTGGC CTAACTACGG CTACACTAGA  10080
AGGACAGTAT TTGGTATCTG CGCTCTGCTG AAGCCAGTTA CCTTCGGAAA AAGAGTTGGT  10140
AGCTCTTGAT CCGGCAAACA AACCACCGCT GGTAGCGGTG GTTTTTTTGT TTGCAAGCAG  10200
CAGATTACGC GCAGAAAAAA AGGATCTCAA GAAGATCCTT TGATCTTTTC TACGGGGTCT  10260
GACGCTCAGT GGAACGAAAA CTCACGTTAA GGGATTTTGG TCATGAGATT ATCAAAAAGG  10320
ATCTTCACCT AGATCCTTTT AAATTAAAAA TGAAGTTTTA AATCAATCTA AAGTATATAT  10380
GAGTAAACTT GGTCTGACAG TTACCAATGC TTAATCAGTG AGGCACCTAT CTCAGCGATC  10440
TGTCTATTTC GTTCATCCAT AGTTGCCTGA CTCCCCGTCG TGTAGATAAC TACGATACGG  10500
GAGGGCTTAC CATCTGGCCC CAGTGCTGCA ATGATACCGC GAGACCCACG CTCACCGGCT  10560
CCAGATTTAT CAGCAATAAA CCAGCCAGCC GGAAGGGCCG AGCGCAGAAG TGGTCCTGCA  10620
ACTTTATCCG CCTCCATCCA GTCTATTAAT TGTTGCCGGG AAGCTAGAGT AAGTAGTTCG  10680
CCAGTTAATA GTTTGCGCAA CGTTGTTGCC ATTGCTGCAG GCATCGTGGT GTCACGCTCG  10740
TCGTTTGGTA TGGCTTCATT CAGCTCCGGT TCCCAACGAT CAAGGCGAGT TACATGATCC  10800
CCCATGTTGT GCAAAAAAGC GGTTAGCTCC TTCGGTCCTC CGAT                   10844
```

(2) INFORMATION FOR SEQ ID NO:42:

(i) SEQUENCE CHARACTERISTICS:

-continued (A) LENGTH: 235 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO:42:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Arg Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val
225                 230                 235
```

(2) INFORMATION FOR SEQ ID NO:43:

(i) SEQUENCE CHARACTERISTICS:
(A) LENGTH: 12 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:43:

```
Glu Ser Lys Tyr Gly Pro Pro Cys Pro Ser Cys Pro
1               5                   10
```

(2) INFORMATION FOR SEQ ID NO:44:

(i) SEQUENCE CHARACTERISTICS:
(A) LENGTH: 110 amino acids
(B) TYPE: amino acid
(D) TOPOLOGY: linear -continued (ii) MOLECULE TYPE: protein (v) FRAGMENT TYPE: internal (xi) SEQUENCE DESCRIPTION: SEQ ID NO:44:

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

(2) INFORMATION FOR SEQ ID NO:45:

(i) SEQUENCE CHARACTERISTICS:
(A) LENGTH: 107 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:45:

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

(2) INFORMATION FOR SEQ ID NO:46:

(i) SEQUENCE CHARACTERISTICS:
(A) LENGTH: 434 amino acids
(B) TYPE: amino acid
(D) TOPOLOGY: linear (ii) MOLECULE TYPE: protein (ix) FEATURE:
(A) NAME/KEY: Protein
(B) LOCATION: 1..434
(D) OTHER INFORMATION: /note= "Translation from complementary DNA."

-continued (xi) SEQUENCE DESCRIPTION: SEQ ID NO:46:

```
Met Ser Phe Asn Thr Ile Ile Asp Trp Asn Ser Cys Thr Ala Val Gln
1               5                   10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415
```

-continued

```
Thr Ala His Lys Asn Ala Val Thr Leu Arg Val Asn Ala Leu Lys Glu
            420                 425                 430

Gln Ala
```

TRANSFERRIN RECEPTOR REACTIVE CHIMERIC ANTIBODIES

RELATED APPLICATIONS

This Application is the U.S. National Stage of PCT U.S. Ser. No. 92/10206 which is a Continuation-in-Part of U.S. application Ser. No. 07/800,458, filed Nov. 26, 1991, now abandoned, which is a Continuation-in-Part of PCT/U.S. Ser. No. 90/05077, filed Sep. 7, 1990 designating the United States, which, in turn, is a Continuation-in-Part of U.S. application Ser. No. 07/404,089, filed Sep. 7, 1989, now U.S. Pat. No. 5,154,924, issued Oct. 13, 1992, all of which are incorporated in their entirety herein by reference.

BACKGROUND

The capillaries that supply blood to the tissues of the brain constitute the blood brain barrier (Goldstein et al. (1986) *Scientific American* 255:74–83; Pardridge, W. M. (1986) *Endocrin. Rev.* 7:314–330). The endothelial cells which form the brain capillaries are different from those found in other tissues in the body. Brain capillary endothelial cells are joined together by tight intercellular junctions which form a continuous wall against the passive movement of substances from the blood to the brain. These cells are also different in that they have few pinocytic vesicles which in other tissues allow somewhat unselective transport across the capillary wall. Also lacking are continuous gaps or channels running through the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al, cited supra). If the brain were not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated receptors which, upon binding of their respective ligand, are internalized by the cell (Pardridge, W. M., cited supra). Vesicles containing the receptor-ligand complex then migrate to the abluminal surface of the endothelial cell where the ligand is released.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al, cited supra; Pardridge, W. M., cited supra). Some drugs can be modified to make them more lipophilic and thereby increase their ability to cross the blood brain barrier. However, each modification has to be tested individually on each drug and the modification can alter the activity of the drug. The modification can also have a very general effect in that it will increase the ability of the compound to cross all cellular membranes, not only those of brain capillary endothelial cells.

SUMMARY OF THE INVENTION

The present invention pertains to a method for delivering a neuropharmaceutical or diagnostic agent across the blood brain barrier to the brain of a host. The method comprises administering to the host a therapeutically effective amount of an antibody-neuropharmaceutical or diagnostic agent conjugate wherein the antibody is reactive with a transferrin receptor and the antibody is a chimera between the variable region from one animal source and the constant region from a different animal source. The conjugate is administered under conditions whereby binding of the antibody to a transferrin receptor on a brain capillary endothelial cell occurs and the neuropharmaceutical agent is transferred across the blood brain barrier in a pharmaceutically active form. Other aspects of this invention include a delivery system comprising an antibody reactive with a transferrin receptor linked to a neuropharmaceutical agent and methods for treating hosts afflicted with a disease associated with a neurological disorder.

In embodiments of the present invention, the antibody that is reactive with a transferrin receptor is a chimeric antibody. This antibody is composed of a variable region, immunologically reactive with the transferrin receptor, that is derived from one animal source and a constant region that is derived from an animal source other than the one which provided the variable region. The chimeric antibodies of this invention can exist either as isolated entities or as conjugates with a neuropharmaceutical agent for transferal across the blood brain barrier. In the latter mode, the chimeric antibody-neuropharmaceutical agent conjugate forms a delivery system for delivering the neuropharmaceutical agent across the blood brain barrier.

Presently available means for delivering therapeutic agents to the brain are limited in that they are invasive. The delivery system of the present invention is non-invasive and can utilize readily available antibodies reactive with a transferrin receptor as carriers for neuropharmaceutical agents. The delivery system is advantageous in that the antibodies are capable of transporting neuropharmaceutical agents across the blood brain barrier without being susceptible to premature release of the neuropharmaceutical agent prior to reaching the brain-side of the blood brain barrier. Further, if the therapeutic activity of the agent to be delivered to the brain is not altered by the addition of a linker, a noncleavable linker can be used to link the neuropharmaceutical agent to the antibody.

DESCRIPTION OF THE DRAWINGS

FIGS. 11A–11C (SEQ ID NO:18) is the antibody coding sequence of heavy chain expression vector pAH4602 containing the γ-1 isotype constant region.

FIGS. 11H–11I (SEQ ID NO: 19),

FIG. 11J (SEQ ID NO: 20),

FIG. 11K (SEQ ID NO: 21),

FIG. 11L (SEQ ID NO: 22), and

FIGS. 11M–11N (SEQ ID NO: 23) are amino acid sequences of polypeptides which are encoded within the pAH4602 coding sequence (the polypeptide of FIGS. 11M–11N is encoded within the complementary polynucleotide sequence).

FIGS. 13A–13F (SEQ ID NO:24) is the antibody coding sequence of light chain expression vector pAG4611.

FIG. 13G (SEQ ID NO: 25) and

FIG. 13H (SEQ ID NO: 26) are amino acid sequences of polypeptides which are encoded within the pAG4611 coding sequence.

FIGS. 17A–17F (SEQ ID NO:27) is the antibody coding sequence of heavy chain expression vector pAH4625 containing the γ-2 isotype constant region.

FIGS. 17G–17H (SEQ ID NO: 28),

FIG. 17I (SEQ ID NO: 29),

FIG. 17J (SEQ ID NO: 30), and

FIGS. 17K–17L (SEQ ID NO: 31) are amino acid sequences of polypeptides which are encoded within the pAH4625 coding sequence (the polypeptide of FIGS. 17K–17L is encoded within the complementary polynucleotide sequence).

FIGS. 18A–18F (SEQ ID NO:32) is the antibody coding sequence of heavy chain expression vector pAH4807 containing the γ-3 isotype constant region.

FIGS. 18G–18H (SEQ ID NO: 33),

FIG. 18I (SEQ ID NO: 34),

FIG. 18J (SEQ ID NO: 35),

FIG. 18K (SEQ ID NO: 36),

FIG. 18L (SEQ ID NO: 37),

FIG. 18M (SEQ ID NO: 38),

FIG. 18N (SEQ ID NO: 39), and

FIG. 18O–18P (SEQ ID NO: 40) are amino acid sequences of polypeptides which are encoded within the pAH4807 coding sequence (the polypeptide of FIGS. 18O–18P is encoded within the complementary polynucleotide sequence).

FIGS. 19A–19F (SEQ ID NO:41) is the antibody coding sequence of heavy chain expression vector pAH4808 containing the γ-4 isotype constant region.

FIGS. 19G–19H, (SEQ ID NO: 42),

FIG. 19I (SEQ ID NO: 43),

FIG. 19J (SEQ ID NO: 44),

FIG. 19K (SEQ ID NO: 45), and

FIGS. 19L–19M (SEQ ID NO: 46) are amino acid sequences of polypeptides which are encoded within the pAH4808 coding sequence (the polypeptide of FIGS. 19L–19M is encoded within the complementary polynucleotide sequence).

DETAILED DESCRIPTION

Figure 1:
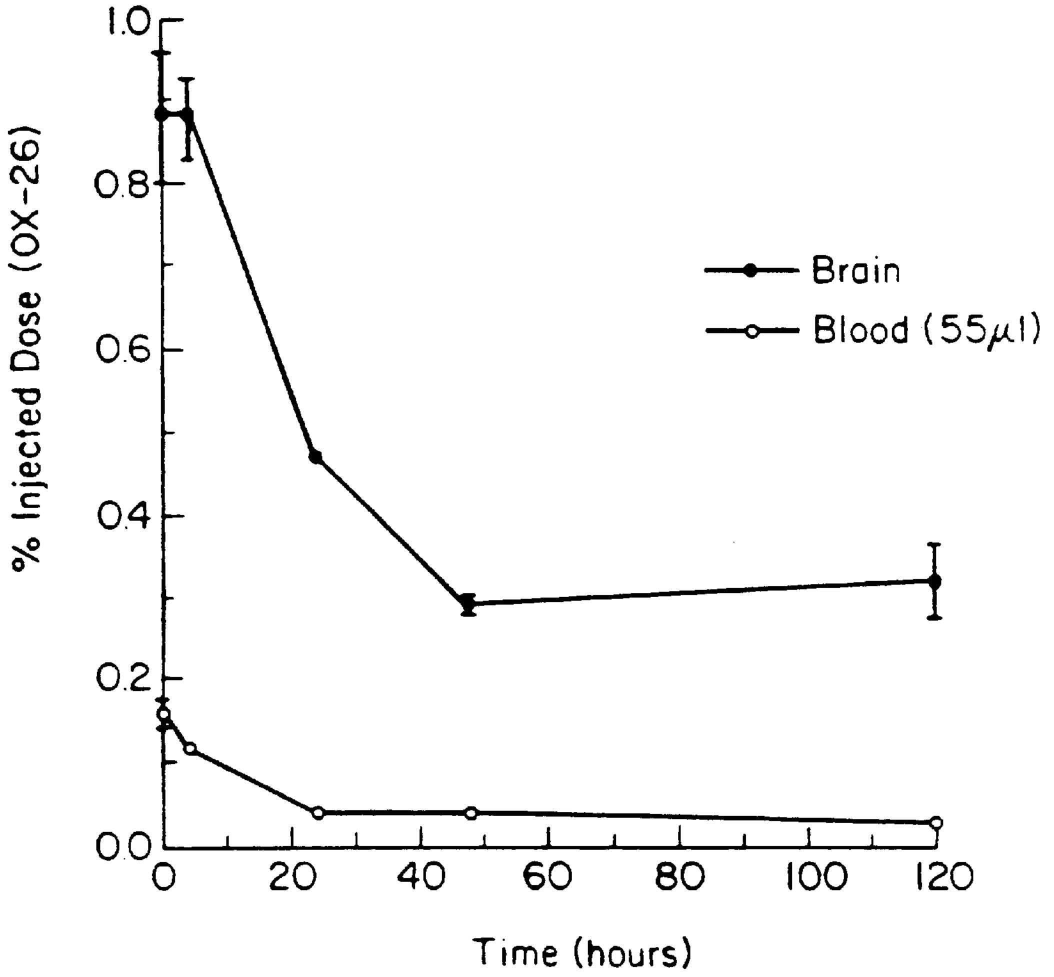
FIG. 1 is a graphic representation of rat brain uptake of $^{14}C$-labelled murine monoclonal antibody (OX-26) to rat transferrin receptor in rats where the percent injected dose of radiolabelled antibody per brain and per 55 $\mu l$ of blood is plotted versus time post-injection.

The method for delivering a neuropharmaceutical agent across the blood brain barrier to the brain of a host comprises administering to the host a therapeutically effective amount of an antibody-neuropharmaceutical agent conjugate wherein the antibody is reactive with a transferrin receptor present on a brain capillary endothelial cell. The method is conducted under conditions whereby the antibody binds to the transferrin receptor on the brain capillary endothelial cell and the neuropharmaceutical agent is transferred across the blood brain barrier in a pharmaceutically active form.

The host can be an animal susceptible to a neurological disorder (i.e., an animal having a brain). Examples of hosts include mammals such as humans, domestic animals (e.g., dog, cat, cow or horse), mice and rats.

The neuropharmaceutical agent can be an agent having a therapeutic or prophylactic effect on a neurological disorder or any condition which affects biological functioning of the central nervous system. Examples of neurological disorders include cancer (e.g. brain tumors), Autoimmune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents which can be used in this invention include proteins, antibiotics, adrenergic agents, anticonvulsants, small molecules, nucleotide analogs, chemotherapeutic agents, anti-trauma agents, peptides and other classes of agents used to treat or prevent a neurological disorder. Examples of proteins include CD4 (including soluble portions thereof), growth factors (e.g. nerve growth factor and interferon), dopamine decarboxylase and tricosanthin. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides would be somatostatin analogues and enkephalinase inhibitors. Nucleotide analogs which can be used include azido thymidine (hereinafter AZT), dideoxy Inosine (ddI) and dideoxy cytodine (ddc).

The antibody, which is reactive with a transferrin receptor present on a brain capillary endothelial cell, may also be conjugated to a diagnostic agent. In this method and delivery system, the neuropharmaceutical agent of the neuropharmaceutical agent-anti-transferrin receptor conjugate has been replaced with a diagnostic agent. The diagnostic agent is then delivered across the blood brain barrier to the brain of the host. The diagnostic agent is then detected as indicative of the presence of a physiological condition for which the diagnostic agent is intended. For example, the diagnostic agent may be an antibody to amyloid plaques. When conjugated to an antibody reactive with a transferrin receptor present on a brain capillary endothelial cell, this diagnostic agent antibody can be transferred across the blood brain barrier and can then subsequently immunoreact with amyloid plaques. Such an immunoreaction is indicative of Alzheimer's Disease.

Serum transferrin is a monomeric glycoprotein with a molecular weight of 80,000 daltons that binds iron in the circulation and transports it to the various tissues(Aisen et al. (1980) *Ann. Rev. Biochem.* 49:357–393; MacGillivray et al. (1981) *J. Biol. Chem.* 258:3543–3553). The uptake of iron by individual cells is mediated by the transferrin receptor, an integral membrane glycoprotein consisting of two identical 95,000 dalton subunits that are linked by a disulfide bond. The number of receptors on the surface of a cell appears to correlate with cellular proliferation, with the highest number being on actively growing cells and the lowest being on resting and terminally differentiated cells. Jeffries et al (*Nature* Vol. 312 (November 1984) pp. 167–168) used monoclonal antibodies to show that brain capillary endothelial cells have a high density of transferrin receptors on their cell surface.

Antibodies which can be used within this invention are reactive with a transferrin receptor. The term antibody is intended to encompass both polyclonal and monoclonal antibodies. The preferred antibody is a monoclonal antibody reactive with a transferrin receptor. The term antibody is also intended to encompass mixtures of more than one antibody reactive with a transferrin receptor (e.g., a cocktail of different types of monoclonal antibodies reactive with a transferrin receptor). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to the transferrin receptor to occur.

The antibodies, chimeric or otherwise, are not to be considered as being restricted to a specific isotype. Any of the antibody isotypes are within the present invention. For example, antibodies with identical light chains but different heavy chains are intended. In addition, mutations of certain regions of the antibodies, e.g., in the $\gamma$ chains, are also intended. These mutations, particularly point mutations, may occur anywhere provided functionality of the antibodies as reactive with a transferrin receptor is still maintained.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

One genetic engineering approach that can be used to produce or clone chimeric antibodies reactive with a transferrin receptor is to prime the DNAs encoding the variable region of functional antibodies for amplification by PCR using specific oligonucleotides. The variable region of functional antibodies is that portion of the antibody that immunologically reacts with the transferrin receptor antigen. Both the heavy chain and light chain of antibodies contribute to the variable region. Thus, the DNA encoding the variable region has two portions: a polynucleotide sequence encoding the variable region heavy chain and a polynucleotide sequence encoding the variable region light chain. The primed variable regions can then be cloned into vectors which contain the DNA encoding the constant region of antibodies. A particularly useful vector is one which contains DNA encoding the constant region of human antibodies that has been designed to also express immunoglobulin variable regions from other sources. The DNA encoding the constant region is usually from a separate source than the one whose DNA encodes the variable region. Although different animals from the same species may be the sources of the DNA encoding the variable region and the constant region, the usual situation is where the animal species are different (e.g., human constant region and murine variable region). Following the cloning of the primed variable regions into vectors containing the constant region, chimeric antibodies can be expressed from such vectors.

A general strategy that can be used to amplify immunoglobulin variable regions has been previously described (Orlandi et al., *Proc. Natl. Acad. Sci.*, 86: 3833–3837 (1989); Larrick et al., *Bio/technology*, 7: 934–938 (1989); Gavilondo et al., *Hybridoma*, 9(5): 407–417 (1990)). Two approaches have been used in the general strategy. In one approach, 5' primers are designed to prime the first framework region of the variable region. The 3' primers are designed to prime either the J region or the constant region. Priming in the frameworks (Orlandi) takes advantage of the conserved nature of these sequences. This makes it feasible to use relatively few degenerate primers to clone the majority of the variable regions. The disadvantage of this approach is that it may introduce amino acid substitutions into the framework regions which affect antibody affinity.

In the second approach (Larrick, Gavilondo), 5' primers are designed to prime some portion of the leader sequence. The 3' primers are designed to prime either the J region or the constant region, as in the first approach. The second approach takes advantage of the relatively conserved nature of the leader sequences and uses a set of redundant oligonucleotides to prime this site. Priming in the leader sequences is generally the more powerful approach since this (leader) peptide is removed from the mature antibody molecule and variations in its sequence will have no effect on antibody affinity. Many different leader peptide sequences are effective in targeting the immature antibody molecule to the endoplasmic reticulum. This second approach is the preferred embodiment in this disclosure.

The term transferrin receptor is intended to encompass the entire receptor or portions thereof. Portions of the transferrin receptor include those portions sufficient for binding of the receptor to an anti-transferrin receptor antibody to occur.

Monoclonal antibodies reactive with at least a portion of the transferrin receptor can be obtained (e.g., OX-26, B3/25 (Omary et al. (1980) *Nature* 286,888–891), T56/14 (Gatter et al. (1983) *J. Clin. Path.* 36 539–545; Jefferies et al. *Immunology* (1985) 54:333–341), OKT-9 (Sutherland et al. (1981) *Proc. Natl. Acad. Sci. USA* 78:4515–4519), L5.1 (Rovera, C. (1982) *Blood* 59:671–678), 5E-9 (Haynes et al. (1981) *J. Immunol.* 127:347–351), RI7 217 (Trowbridge et al. *Proc. Natl. Acad. Sci. USA* 78:3039 (1981) and T58/30 (Omary et al. cited supra)or can be produced using conventional somatic cell hybridization techniques (Kohler and Milstein (1975) *Nature* 256, 495–497). A crude or purified protein or peptide comprising at least a portion of the transferrin receptor can be used as the immunogen. An animal is vaccinated with the immunogen to obtain an anti-transferrin receptor antibody-producing spleen cells. The species of animal immunized will vary depending on the species of monoclonal antibody desired. The antibody producing cell is fused with an immortalizing cell (e.g. myeloma cell) to create a hybridoma capable of secreting anti-transferrin receptor antibodies. The unfused residual antibody-producing cells and immortalizing cells are eliminated. Hybridomas producing the anti-transferrin receptor antibodies are selected using conventional techniques and the selected anti-tranferrin receptor antibody producing hybridomas are cloned and cultured.

Polyclonal antibodies can be prepared by immunizing an animal with a crude or purified protein or peptide comprising at least a portion of a transferrin receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgG, IgM).

The neuropharmaceutical agent can be linked to the antibody using standard chemical conjugation techniques. Generally, the link is made via an amine or a sulfhydryl group. The link can be a cleavable link or non-cleavable link depending upon whether the neuropharmaceutical agent is more effective when released in its native form or whether the pharmaceutical activity of the agent can be maintained while linked to the antibody. The determination of whether to use a cleavable or non-cleavable linker can be made without undue experimentation by measuring the activity of the drug in both native and linked forms or for some drugs can be determined based on known activities of the drug in both the native and linked form.

For some cases involving the delivery of proteins or peptides to the brain, release of the free protein or peptide may not be necessary if the biologically active portion of the protein or peptide is uneffected by the link. As a result, antibody-protein or antibody peptide conjugates can be constructed using noncleavable linkers. Examples of such proteins or peptides include CD4, superoxide dismutase, interferon, nerve growth factor, tricosanthin, dopamine decarboxylase, somatostatin analogues and enkephalinase inhibitors. Terms such as “CD4” are used herein to include modified versions of the natural molecule, such as soluble CD4, truncated CD4, etc. Examples of non-cleavable linker systems which can be used in this invention include the carbodiimide (EDC), the sulfhydryl-maleimide, the N-succinimidyl-3-(2-pyridyldithio) propionate (SPDP; Pharmacia), and the periodate systems. In the carbodiimide system, a water soluble carbodiimide reacts with carboxylic acid groups on proteins and activates the carboxyl group. The carboxyl group is coupled to an amino group of the second protein. The result of this reaction is a noncleavable amide bond between two proteins.

In the sulfhydryl-maleimide system, a sulfhydryl group is introduced onto an amine group of one of the proteins using a compound such as Traut’s reagent. The other protein is reacted with an NHS ester (such as gamma-maleimidobutyric acid NHS ester (GMBS)) to form a maleimide derivative that is reactive with sulfhydryl groups. The two modified proteins are then reacted to form a covalent linkage that is noncleavable.

SPDP is a heterobifunctional crosslinking reagent that introduces thiol-reactive groups into either the monoclonal antibody or the neuropharmaceutical agent. The thiol-reactive group reacts with a free sulfhydryl group forming a disulfide bond.

Periodate coupling requires the presence of oligosaccharide groups on either the carrier or the protein to be delivered. If these groups are available on the protein to be delivered (as in the case of horseradish peroxidase (HRP)), an active aldehyde is formed on the protein to be delivered which can react with an amino group on the carrier. It is also possible to form active aldehyde groups from the carbohydrate groups present on antibody molecules. These groups can then be reacted with amino groups on the protein to be delivered generating a stable conjugate. Alternatively, the periodate oxidized antibody can be reacted with a hydrazide derivative of a protein to be delivered which will also yield a stable conjugate.

Cleavable linkers can be used to link neuropharmaceutical agents which are to be deposited in the brain or when a non-cleavable linker alters the activity of a neuropharmaceutical agent. Examples of cleavable linkers include the acid labile linkers described in copending patent application Ser. No. 07/308,960 filed Feb. 6, 1989, and issued as U.S. Pat. No. 5,144,011 on Sep. 1, 1992, the contents of which are hereby incorporated by reference. Acid labile linkers include cis-aconitic acid, cis-carboxylic alkadienes, cis-carboxylic alkatrienes, and poly-maleic anhydrides. Other cleavable linkers are linkers capable of attaching to primary alcohol groups. Examples of neuropharmaceutical agents which can be linked via a cleavable link include AZT, ddI, ddc, adriamycin, amphotericin B, pyrimethamine, valproate, methotrexate, cyclophosphamide, carboplatin and superoxide dimutase. The noncleavable linkers used generally to link proteins to the antibody can also be used to link other neuropharmaceutical agents to the antibody.

The antibody-neuropharmaceutical agent conjugates can be administered orally, by subcutaneous or other injection, intravenously, intramuscularly, parenternally, transdermally, nasally or rectally. The form in which the conjugate is administered (e.g., capsule, tablet, solution, emulsion) will depend at least in part on the route by which it is administered.

A therapeutically effective amount of an antibody-neuropharmaceutical agent conjugate is that amount necessary to significantly reduce or eliminate symptoms associated with a particular neurological disorder. The therapeutically effective amount will be determined on an individual basis and will be based, at least in part, on consideration of the individuals’s size, the severity of symptoms to be treated, the result sought, the specific antibody, etc. Thus, the therapeutically effective amount can be determined by one of ordinary skill in the art employing such factors and using no more than routine experimentation.

Although the description above focuses on antibodies, any protein which interacts with the extracellular domain of the transferrin receptor, including the ligand binding site, could potentially serve as a vehicle for the delivery of drugs across the blood-brain barrier. In addition to anti-transferrin receptor antibodies, this would include transferrin, the ligand which binds to the receptor, and any transferrin derivatives which retain receptor-binding activity. In fact, any ligand which binds to the transferrin receptors could potentially be employed.

Figure 8:
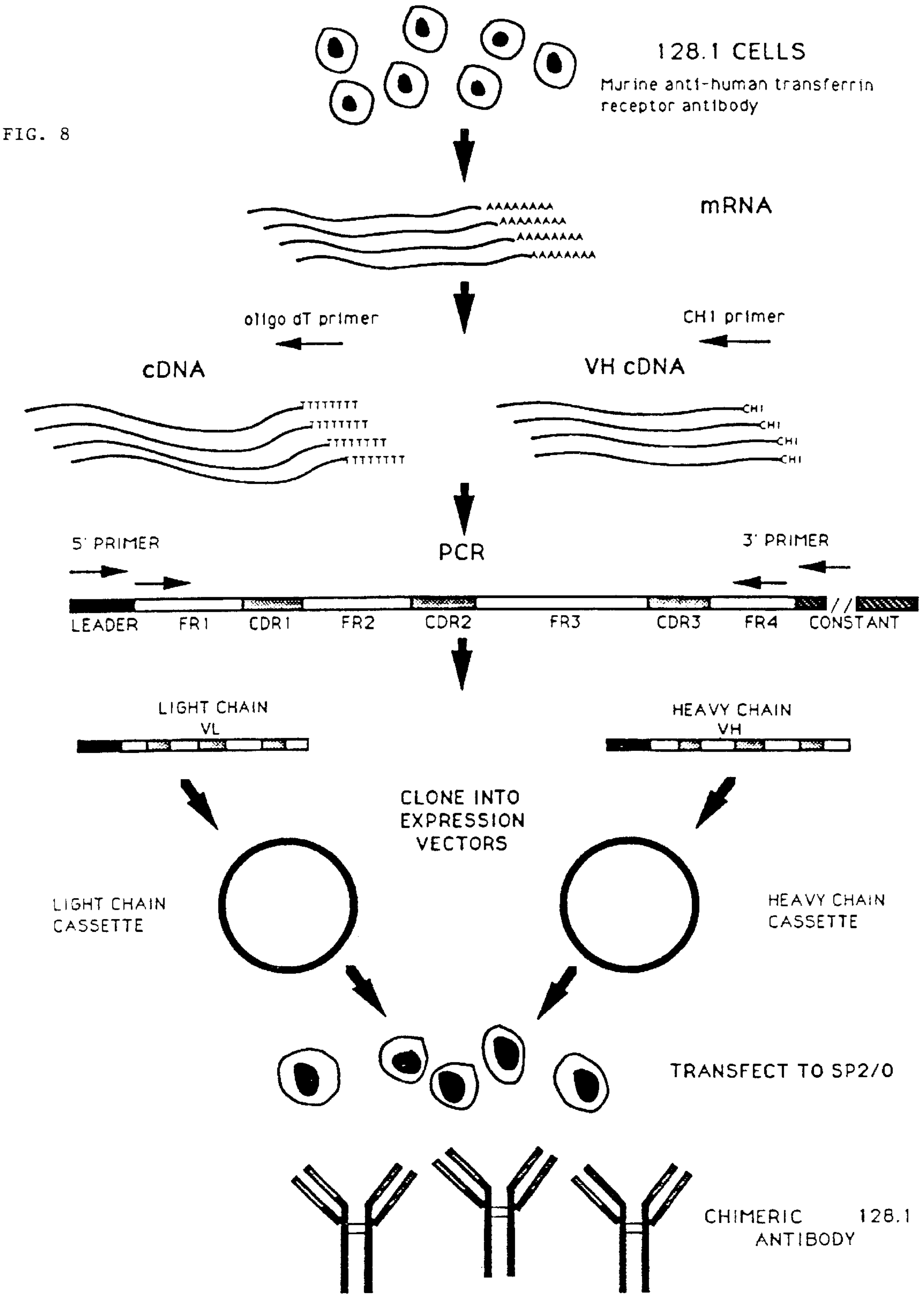
FIG. 8 is a flow diagram of the general strategy for the expression of immunoglobulin variable region genes obtained by PCR.

A procedure for producing chimeric antibodies reactive with a transferrin receptor may be performed as follows: cDNA is synthesized from mRNA purified from a small number of cells producing the antibody of interest. A PCR reaction is performed in order to obtain the antibody heavy and light chain variable regions which are then cloned and sequenced. After a second PCR reaction to modify the ends of these regions to make them compatible with the expression cassettes, they are cloned into novel expression vectors which contain human constant regions, immunoglobulin promoter and enhancers, and selection markers. In these vectors, a murine heavy chain promoter has been provided with restriction sites so that the leader sequences primed and expanded can be directly cloned into a functional promoter. Restriction sites have also been provided for the direct cloning of the 3' end of the variable region into a constant region. In the heavy chain vector, a novel restriction site has been engineered into the CH1 domain of the human γ1 heavy chain gene. VH can then be joined at this site to provide a complete heavy chain protein. For VL, a restriction site has been engineered just 3' of the splice site so that the cloned VL will then splice the kappa to produce a complete κ light chain protein. The final constructs are then transfected into non-producer hybridoma cell lines as SP2/0 or P3.X63.Ag8653 and the supernatants tested for antibody production (FIG. 8).

Further procedures and materials, such as expression cassettes, for producing chimeric antibodies reactive with a transferrin receptor can be found in the patent application Ser. No. 07/798,696, filed on the same date as the present application. Such teachings of this co-filed application are herein incorporated by reference.

The present invention will be illustrated by the following examples.

EXAMPLE 1

In Vitro Binding of Murine Monoclonal Antibodies to Human Brain Endothelial Cells Two murine monoclonal antibodies, B3/25 and T58/30, described by Trowbridge (U.S. Pat. No. 4,434,156 issued Feb. 28, 1984, and *Nature* Vol. 294, pp. 171–173 (1981)), the contents of both are hereby incorporated by reference, which recognize the human transferrin receptor were tested for their ability to bind to human brain capillary endothelial cells. Hybridoma cell lines which produce B3/25 and T58/30 antibodies were obtained from the American Type Culture Collection (ATTC) in Rockville, Md., and grown in DMEM medium supplemented with 2.0 mM glutamine, 10.0 mM HEPES (pH 7.2), 100 μM non-essential amino acids and 10% heat-inactivated fetal calf serum. The hybridoma cultures were scaled-up in 225 $cm^2$ T-flasks for the production of milligram quantities of IgG antibody. The hybridoma supernatants were concentrated 50× using vacuum dialysis and applied to a protein-A sepharose column using the BioRad MAPS buffer system. Purified antibody was eluted from the column, dialyzed against 0.1 M sodium phosphate (pH 8.0), concentrated and stored in aliquots at −20° C.

Primary cultures of human brain endothelial cells were grown in flat-bottom 96-well plates until five days post-confluency. The cells were then fixed using 3.0% buffered formalin and the plate blocked with 1.0% bovine serum albumin (BSA) in Dulbecco's phosphate buffered saline (DPBS). Aliquots (100 μl) of the B3/25 or T58/30 antibodies, either in the form of culture supernatants or purified protein, were then added to the wells (antibody concentrations were in the range of 1–50 μg/ml). Antibody which had specifically bound to the fixed cells was detected using a biotin-labeled polyclonal goat-anti-mouse IgG antisera followed by a biotinylated horseradish peroxidase (HRP)/avidin mixture (Avidin Biotin Complex technique). Positive wells were determined using a Titertek Multiscan Enzyme Linked Immunosorbent Assay (ELISA) plate reader. The results showed that both antibodies bind to human brain capillary endothelial cells with the T58/30 antibody exhibiting a higher level of binding.

These same antibodies were also tested for binding to human brain capillaries using sections of human brain tissue that were fresh frozen (without fixation), sectioned on a cryostat (section thickness was 5–20 μm), placed on glass slides and fixed in acetone (10 minutes at room temperature). These sections were then stored at −20° C. prior to use.

The slides containing the human brain sections were allowed to come to room temperature prior to use. The sections were then rehydrated in DPBS and incubated in methanol containing 0.3% $H_2O_2$ to block endogenous peroxidate activity. The sections were blocked for fifteen minutes in a solution containing 0.2% non-fat dry milk and 0.2% methylmannopyranoside. B3/25 and T58/30 antibodies, purified as discussed above, were applied to the sections at a concentration of 5–50 μg/ml and incubated at room temperature for one to two hours. Antibody that specifically bound to the tissue was detected using the Avidin-Biotin Complex (ABC) technique as described above for the ELISA assay. Staining of capillaries in the human brain sections was observed with both the B3/25 and T58/30 antibodies. The T58/30 antibody also displayed some binding to the white matter of the brain cortex.

EXAMPLE 2

In-Vitro Binding of Murine Monoclonal Antibody OX-26 to Rat Transferrin Receptor The OX-26 murine antibody, which recognizes the rat transferrin receptor, has been shown in vivo to bind to brain capillary endothelial cells (Jeffries et al., cited supra). The murine hybridoma line which produces the OX-26 murine antibody was obtained and the hybridoma cell line was grown in RPMI 1640 medium supplemented with 2.0 mM glutamine and 10% heat-inactivated fetal calf serum. The OX-26 antibody was purified using the affinity chromatography technique described in Example 1.

The purified antibody was tested in vitro as described for the anti-human transferrin receptor antibodies in Example 1 to determine whether it would bind to brain capillaries in fresh frozen, acetone-fixed rat brain sections. The results showed that the OX-26 anti-transferrin receptor antibody did bind to capillaries in rat brain sections in vitro.

EXAMPLE 3

In-Vivo Binding of OX-26 Murine Monoclonal Antibody to Rat Transferrin Receptor Dose Range The rat anti-transferrin receptor antibody OX-26 was tested in vivo by injecting purified antibody (purification as described in Example 1) into female Sprague-Dawley rats (100–150 gm) via the tail vein. Prior to injection, the rats were anesthetized with halothane. The samples, ranging from 2.0 mg to 0.05 mg of antibody/rat were injected into the tail vein in 400 μl aliquots. All doses were tested in duplicate animals. One hour post-injection, the animals were sacrificed and perfused through the heart with DPBS to clear the blood from the organs. Immediately after the perfusion was completed, the brain was removed and quick frozen in liquid nitrogen. The frozen brain was then sectioned (30–50

$\mu$) on a cryostat and the sections placed on glass microscope slides. The brain sections were air dried at room temperature one to two hours before fixation in acetone (10 minutes at room temperature). After this treatment the sections could be stored at −20° C.

The OX-26 antibody was localized in the brain sections using immunohistochemistry as described above for the in vitro experiments in Example 1. The addition of the primary antibody was unnecessary in that it is present in the brain sections. The results indicated that the OX-26 antibody binds to rat brain capillary endothelial cells and that doses of as little as 50 $\mu$g result in detectable levels of antibody in the brain using the methods described herein. Doses above 0.5 mg did not appear to show significantly more antibody binding to the endothelial cells, suggesting that the sites for antibody binding may be saturated. No specific binding to capillary endothelium was detected in the liver, kidney, heart, spleen or lung.

A non-specific antibody of the same subclass as OX-26 (IgG 2a) was also tested in vivo to show that the binding of OX-26 to rat brain endothelial cells that has been observed is specific to the OX-26 antibody. 0.5 mg of the control antibody was injected per rat as described above. The results indicate that the staining pattern observed with the OX-26 antibody is specific to that antibody.

Time Course

After establishing that the OX-26 antibody is detectable in the rat brain capillaries after in vivo administration, the time frame in which this binding occurred was determined. Using 0.5 mg of purified OX-26 antibody as the standard dose, brain sections taken from animals sacrificed 5 minutes, 15 minutes, 1 hour, 2 hours, 4 hours, 8 hours and 24 hours post-injection were examined for the presence of OX-26 antibody. All doses were administered in 400 $\mu$l aliquots and each time point was tested in duplicate animals. Samples were injected and the rats were processed at the various times post-injection as described above in the dose range section.

The results showed that the OX-26 antibody can be detected in or on the rat brain capillary endothelial cells as early as five minutes and as late as 24 hours post-injection. At 4 and 8 hours post-injection, the staining pattern of the antibody is very punctate suggesting that the antibody has accumulated in vesicular compartments either in endothelial or perivascular cells.

EXAMPLE 4

The Use of a Conjugate of OX-26 Murine Monoclonal Antibody for Tranferring Horseradish Peroxidase Across the Blood Brain Barrier Horseradish Peroxidase (HRP; 40 kD) was chosen as a compound to be delivered to the brain because it is similar in size to several therapeutic agents and it can be easily detected in the brain using an enzymatic assay. HRP was conjugated to the OX-26 antibody using a non-cleavable periodate linkage and the ability of the antibody to function as a carrier of compounds to the brain was examined. The antibody conjugate was tested in vivo to determine if the antibody could deliver HRP to the brain.

The antibody (10 mg) was first dialyzed overnight against 0.01 M sodium bicarbonate (pH 9.0). The HRP (10 mg) was dissolved in 2.5 ml deionized water, 0.1 M sodium periodate (160 $\mu$l) was added and the mixture was incubated for five minutes at room temperature. Ethylene glycol (250 $\mu$l) was added to the HRP solution followed by an additional five minute incubation. This solution was then dialyzed overnight against 1.0 mM sodium acetate buffer (pH 4.4). To the dialyzed OX-26 antibody (2.0 ml, 5.08 mg/ml) was added 200 $\mu$l of 1.0 M sodium bicarbonate buffer, pH 9.5 and 1.25 ml of the dialyzed HRP solution. This mixture was incubated in the dark for two hours followed by the addition of 100 $\mu$l of 10 mg/ml sodium borohydride. The resulting mixture was incubated two additional hours in the dark at 4° C. The protein was precipitated from the solution by the addition of an equal volume of saturated ammonium sulfate and resuspended in a minimal volume of water. Free antibody was removed from the mixture by chromatography on a concanavalin A-sepharose column (a column which binds HRP and the HRP-antibody conjugate and allows the free antibody to pass through). The free HRP was removed by chromatography on a protein A-sepharose column which retains the antibody-HRP conjugate. The final product had an HRP/antibody ratio of 4/1.

A time course experiment identical to that described in Example 3 was performed using the antibody-HRP conjugate. The antibody-HRP conjugate (0.5 mg) was injected in a 400 $\mu$l aliquot/rat. The animals were sacrificed at the various times post-injection and the brains processed as described above in Example 3. The antibody HRP conjugate was localized in the brain either by staining for antibody immunohistochemically as described in Example 1 or by directly staining the brain sections for the presence of HRP. To detect HRP, the slides were first allowed to come to room temperature before incubating in methanol for thirty minutes. The brain sections were then washed in DPBS and reacted with 3,3'-diamino benzidine (DAB), the substrate for HRP. The results showed that the OX-26 antibody HRP conjugate binds to rat brain capillary endothelial cells in a manner identical to that of the unconjugated antibody. The punctate staining 4–8 hours after injection which was seen with the antibody alone is also seen with the antibody conjugate, suggesting that the conjugate can also be going into the pericytes on the abluminal side of the blood brain barrier. Taken together, these results indicate that the OX-26 antibody can deliver a protein molecule of at least 40 KD to the brain.

EXAMPLE 5

The In-Vivo Delivery of Adriamycin to the Brain by Murine Monoclonal Antibody OX-26

A non-cleavable linker system similar to that used in Example 4, was used to couple the chemotherapeutic drug adriamycin to the OX-26 antibody. The availability of antibodies that can detect adriamycin as well as the system previously described in Example 1 for detecting the antibody carrier allowed the use of immunohistochemical techniques for monitoring the localization of the antibody carrier as well as the delivery of adriamycin to the brain.

To conjugate adriamycin to the antibody, the drug (10 mg in 0.5 ml DPBS) was oxidized by the addition of 200 $\mu$l of 0.1 M sodium periodate. This mixture was incubated for one hour at room temperature in the dark. The reaction was quenched by the addition of 200 $\mu$l of ethylene glycol followed by a five minute incubation. The OX-26 antibody (5.0 mg in 0.5 ml of carbonate buffer (pH 9.5)) was added to the oxidized adriamycin and incubated at room temperature for one hour. Sodium borohydride (100 $\mu$l of 10 mg/ml) was added and the mixture was incubated for an additional two hours at room temperature. The free adriamycin was separated from the OX-26 antibody-adriamycin conjugate by chromatography on a PD-10 column. The adriamycin/OX-26 antibody ratio within the conjugate was 2/1. for this particular batch of conjugate.

The effectiveness of the OX-26 antibody as a carrier for delivering adriamycin to the brain was determined by administering 0.5 mg of the antibody-adriamycin conjugate in a 400 μl aliquot per rat by injection via the tail vein. One hour post-injection, the rat was sacrificed and the brain processed as described in Example 1. All injections were performed in duplicate. As a control, 400 μg of free adriamycin in a 400 μl aliquot was also injected into a rat. Immunohistochemistry was used to detect both the carrier OX-26 antibody and the adriamycin in the rat brain sections. In the case of adriamycin, polyclonal rabbit anti-adriamycin antisera was applied to the sections followed by a biotinylated goat anti-rabbit IgG antisera. This was then followed by the addition of a biotinylated HRP/avidin mixture and enzymatic detection of HRP.

The results indicate that both the OX-26 antibody and the conjugated adriamycin localized to the rat brain capillary endothelial cells after in vivo administration. There is no evidence that free adriamycin binds to brain capillary endothelial cells or enters the brain.

An adriamycin-Ox-26 conjugate coupled via a carbodiimide linkage was also synthesized (drug/antibody ratio of 10/1) and tested in vivo. The results of this experiment were essentially identical to that obtained with the periodate-linked antibody-drug conjugate. In both cases, staining for the antibody carrier was quite strong and was visualized in the capillaries in all areas of the brain. This staining was evenly distributed along the capillaries. Staining for adriamycin was less intense but again was seen in capillaries throughout the brain. Some punctate staining was observed which suggests accumulation in pericytes which lie on the brain side of the blood-brain barrier.

EXAMPLE 6

In Vivo Delivery of Methotrexate to the Brain by Murine Monoclonal Antibody OX-26.

A noncleavable carbodiimide linkage was used to couple methotrexate to the OX-26 murine monoclonal antibody. A system analogous to that described in Example 5 was used to monitor the delivery of both the methotrexate and the carrier antibody to the brain capillary endothelial cells.

Methotrexate was coupled to murine monoclonal antibody OX-26 via its active ester. Briefly, 81 mg (0.178 mM) of methotrexate (Aldrich) was stirred with 21 mg (0.182 mM) of N-hydroxysuccinimide (Aldrich) in 3 ml of dimethylformamide (DMF) at 4° C. Ethyl-3-dimethylaminopropyl-carbodiimide (180 mg; EDC; 0.52 mM) was added to this solution and the reaction mixture was stirred overnight. The crude ester was purified from the reaction by-products by flash chromatography over silica gel 60 (Merck) using a solution of 10% methanol in chloroform as an eluant. The purified active ester fractions were pooled and concentrated to dryness. The ester was dissolved in 1 ml of DMF and stored at −20 ° C. until use. 50 mg (50%) of active ester was recovered as determined by $A_{372}(\epsilon_{372}=7200)$.

A solution of OX-26 containing 2.1 mg (14 nmoles) of antibody in 0.9 ml of 0.1 M phosphate (pH 8.0) was thawed to 4° C. To this stirred antibody solution was added 1.4 μL (140 nmoles) of the active ester prepared as described above. After 16 hours at 4° C., the mixture was chromatographed over Sephadex PD-10 column (Pharmacia) using phosphate buffered saline (PBS) to separate conjugate from free drug. The fractions containing the antibody-methotrexate conjugate were pooled. Antibody and drug concentration were determined spectrophotometrically as described by Endo et al. (*Cancer Research* (1988) 48:3330–3335). The final conjugate contained 7 methotrexates/antibody.

The ability of the OX-26 monoclonal antibody to deliver methotrexate to the rat brain capillary endothelial cells was tested in vivo by injecting 0.2 mg of conjugate (in 400 μl) into each of two rats via the tail vein. The animals were sacrificed one hour post-injection and the brains processed for immunohistochemistry as described in Example 1. To detect methotrexate in the brain, a rabbit antisera raised against methotrexate was used as the primary antibody. A biotinylated goat-anti-rabbit antisera in conjunction with a mixture of biotinylated HRP and avidin was then used to visualize methotrexate in the rat brain. The carrier antibody was detected as described previously.

The results of these experiments indicate that methotrexate in the form of a conjugate with OX-26 does accumulate along or in the capillary endothelial cells of the brain. The staining observed for methotrexate is comparable in intensity to that seen for the carrier. The staining appears to be in all areas of the brain and is evenly distributed along the capillaries.

EXAMPLE 7

Antibody Derivatives

The Fc portion of the OX-26 murine monoclonal antibody was removed to determine whether this would alter its localization to or uptake by the rat brain capillary endothelial cells. $F(ab)_2$ fragments of OX-26 were produced from intact IgG's via digestion with pepsin. A kit available from Pierce Chemical Co. contains the reagents and protocols for cleaving the antibody to obtain the fragments . The $F(ab')_2$ fragment (0.2 mg doses) in 400 μl aliquots were injected into rats via the tail vein. A time course experiment identical to that done with the intact antibody (Example 2) was then performed. $F(ab')_2$ fragment was detected immunohistochemically using a goat anti-mouse $F(ab')_2$ antisera followed by a biotinylated rabbit anti-goat IgG antisera. A biotinylated HRP/avidin mixture was added and the antibody complex was visualized using an HRP enzymatic assay. The results indicate that the $F(ab)_2$ fragment of the OX-26 antibody binds to the capillary endothelial cells of the rat brain.

EXAMPLE 8

Measurement of OX-26 in Brain Tissue

To quantitate the amount of OX-26 which accumulates in the brain, radioactively-labelled antibody was injected into rats via the tail vein. Antibodies were labelled with either $^{14}C$-acetic anhydride or $^{3}H$-succinimidyl proprionate essentially as described in Kummer, U., *Methods in Enzymology*, 121: 670–678 (1986), Mondelaro, R. C., and Rueckert, R. R., *J. of Biological Chemistry*, 250: 1413–1421 (1975), hereby incorporated by reference. For all experiments, the radiolabelled compounds were injected as a 400 μl bolus into the tail vein of female Sprague-Dawley rats (100–125 gms) under Halothane anesthesia and the animals were sacrificed at the appropriate time post-injection using a lethal dose of anesthetic. A $^{3}H$-labelled IgC2a control antibody was co-injected with the $^{14}C$-labelled OX-26 to serve as a control for non-specific radioactivity in the brain due to residual blood. At the appropriate time post-injection, animals were sacrificed and the brains were removed immediately and homogenized in 5 ml of 0.5% sodium dodecysulfate using an Omni-mixer. An aliquot of the homogenate was incubated overnight with 2 ml of Soluene 350 tissue solubilizer prior to liquid scintillation counting. All data were collected as disintegrations per minute (dpm). Blood samples were centrifuged to pellet red blood cells (which do not display significant binding of radiolabelled materials) and the radioactivity in an aliquot of serum determined using liquid scintillation counting.

The amount of antibody associated with the brain was determined at various times post-injection to examine the pharmacokinetics of brain uptake. In addition, the amount of labelled antibody in the blood was measured so that the rate of clearance from the bloodstream could be determined. This information was also used to calculate the amount of radioactivity in the brain due to blood contamination, which was then subtracted from the total to give the amount of antibody that is specifically associated with the brain.

A peak level of $^{14}C$-labelled OX-26 corresponding to approximately 0.9% of the injected dose was reached in the brain between 1 and 4 hours post-injection as illustrated in FIG. 1 (with the values shown as means plus or minus standard error of measurement (SEM) and N=3 rats per time point). The amount of radioactivity associated with the brain decreased steadily from 4 to 48 hours post-injection, at which point it leveled off at approximately 0.3% of the injected dose. The accumulation of OX-26 in the brain was significantly reduced by the addition of unlabelled monoclonal antibody (0.5 or 2.0 mg in the bolus injection). As an additional control, a $^{3}H$-IgG2a control antibody was co-injected with the $^{14}C$-OX-26. The control antibody did not accumulate in the brain and represented the blood contamination of the brain.

In contrast to the levels in the brain, the blood level of OX-26 dropped quite dramatically immediately after injection such that by 1 hour post-injection, the percent of injected dose in 55 $\mu$l of blood (the volume of blood associated with the brain) was approximately 0.16% as illustrated in FIG. 1. This corresponds to a value of approximately 20% of the injected dose in the total blood volume of the rat. Extraction of total IgG from serum followed by polyacrylamide gel electrophoresis (PAGE) and autoradiography did not reveal detectable levels of OX-26 degradation indicating that the antibody remains intact in the blood as long as 48 hours after injection.

EXAMPLE 9

Distribution of OX-26 in Brain Parenchyma and Capillaries

To demonstrate that anti-transferrin receptor antibody accumulates in the brain parenchyma, homogenates of brains taken from animals injected with labelled OX-26 were depleted of capillaries by centrifugation through dextran to yield a brain tissue supernatant and a capillary pellet. Capillary depletion experiments followed the procedure of Triguero, et al., *J. of Neurochemistry*, 54: 1882–1888 (1990), hereby incorporated by reference. As for the brain uptake experiments of Example 8, the radiolabelled compounds were injected as a 400 $\mu$l bolus into the tail vein of femals Sprague-Dawley rats (100–125 gm) under Halothane anesthesia and the animals were sacrificed at the appropriate time post-injection using a lethal dose of anesthetic. A $^{3}H$-labelled IgG 2a control antibody was co-injected with the $^{14}C$-labelled OX-26 to serve as a control for non-specific radioactivity in the brain due to residual blood. After sacrifice, the brains were removed and kept on ice. After an initial mincing, the brains were homogenized by hand (8–10 strokes) in 3.5 ml of ice cold physiologic buffer (100 mM NaCl, 4.7 mM KCl, 2.5 mM $CaCl_2$, 1.2 mM $KH_2PO_4$, 1.2 mM $MgSO_4$, 14.5 mM HEPES, 10 mM D-glucose, pH 7.4). Four ml of 26% dextran solution in buffer was added and homogenization was continued (3 strokes). After removing an aliquot of the homogenate, the remainder was spun at 7200 rpm in a swinging bucket rotor. The resulting supernatant was carefully removed from the capillary pellet. The entire capillary pellet and aliquots of the homogenate and supernatant were incubated overnight with 2 ml of Soluene 350 prior to liquid scintillation counting. This method removes greater than 90% of the vasculature from the brain homogenate (Triguero et al., cited supra).

Figure 2:
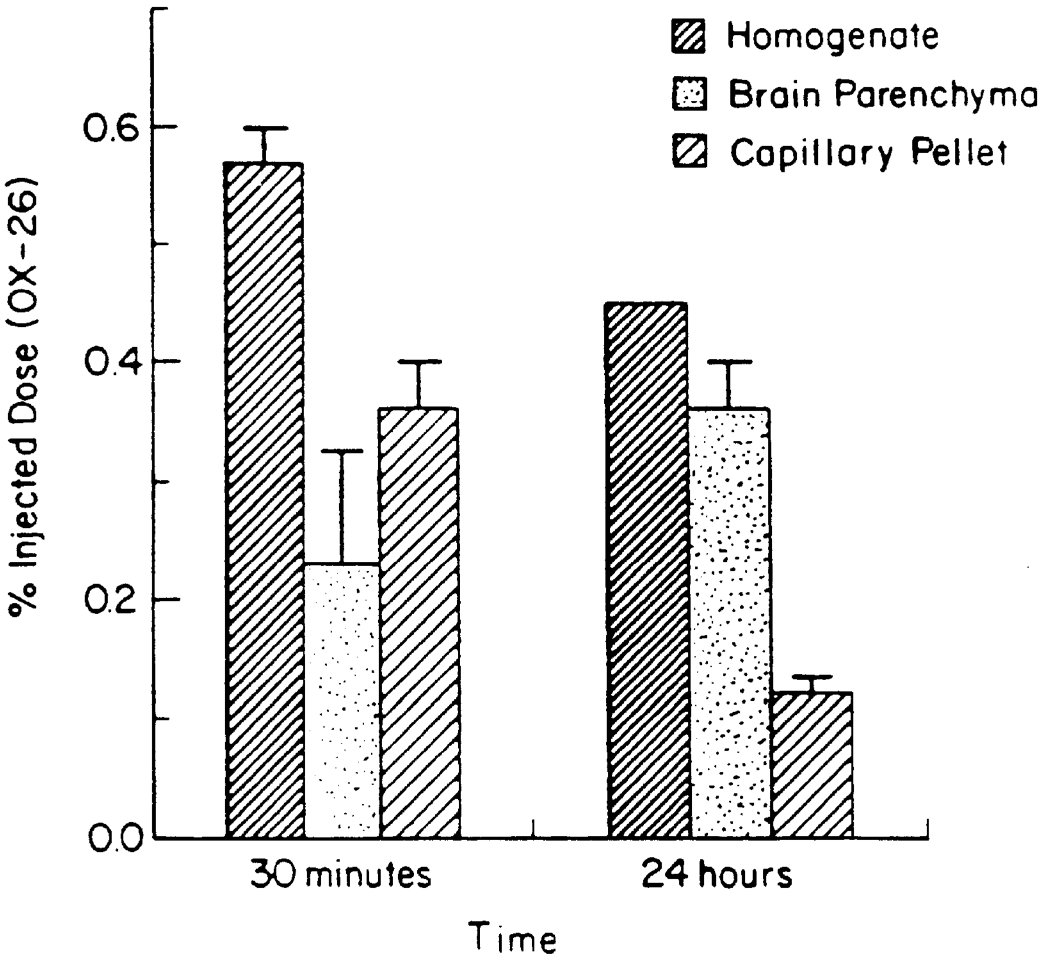
FIG. 2 is a histogram illustrating time dependent changes in the disposition of radiolabelled OX-26 between brain parenchyma and vasculature.

A comparison of the relative amounts of radioactivity in the different brain fractions as a function of time indicates whether transcytosis of the labelled antibody has occurred. The amount of OX-26 in total brain homogenate, the brain parenchyma fraction and the brain capillary fraction at an early time (30 minutes) and a later time (24 hours) post-injection is illustrated in FIG. 2. The values in FIG. 2 are shown as means+SEM with N=3 rats per time point. At the 30 minute time point, more of the radiolabelled antibody is associated with the capillary fraction than with the brain parenchyma fraction (0.36% of the injected dose (%ID) and 0.23% ID, respectively). By 24 hours post-injection, the distribution is reversed and the majority of the radioactivity (0.36% ID) is in the parenchymal fraction as compared to the capillary fraction (0.12% ID). The redistribution of the radiolabelled OX-26 from the capillary fraction to the parenchyma fraction is consistent with the time dependent migration of the anti-transferrin receptor antibody across the blood-brain barrier.

EXAMPLE 10

Figure 3:
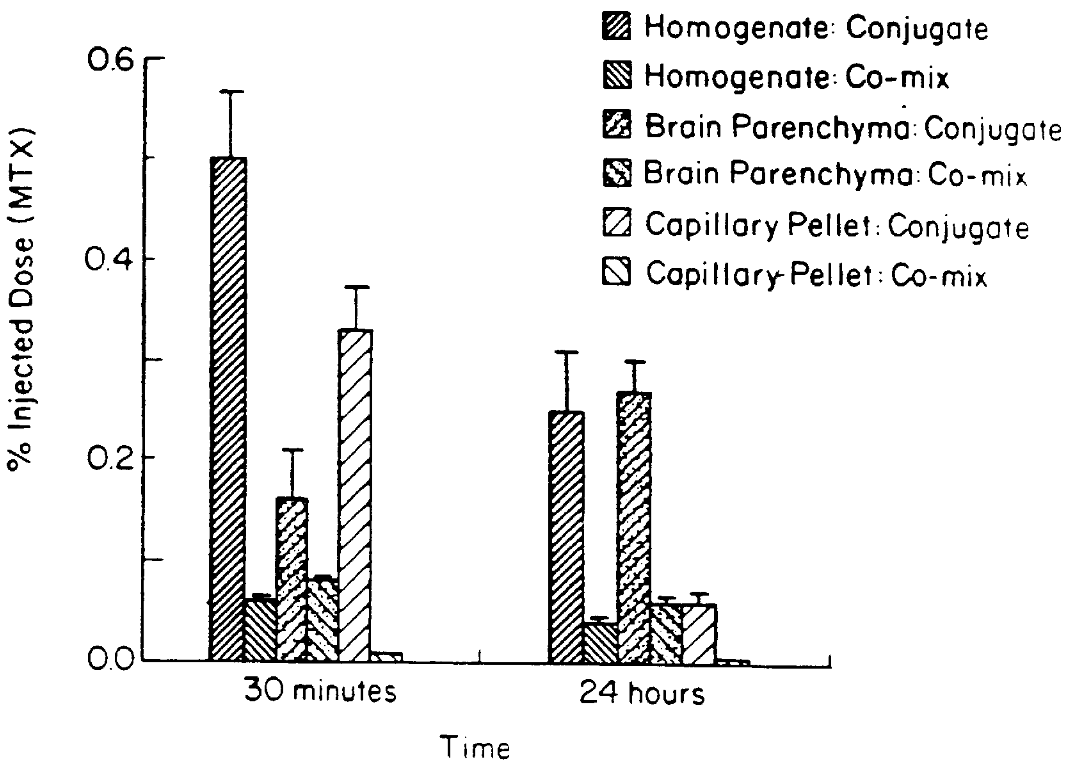
FIG. 3 is a histogram illustrating the enhanced delivery of methotrexate across the blood-brain barrier when administered as a conjugate with OX-26.

Distribution of an OX-26-methotrexate Conjugate in Brain Parenchyma and Capillaries Capillary depletion studies following the procedures described in Example 9 were performed with an OX-26-methotrexate (MTX) conjugate linked via a gamma-hydrazid as described in Kralovec, et al., *J. of Medicinal Chem.*, 32: 2426–2431 (1989), hereby incorporated by reference, in which the MTX moiety was labelled with $^{3}H$. As with unconjugated antibody, the amount of label in the capillary fraction at 30 minutes post-injection is greater than the parenchyma fraction (approximately 2-fold as illustrated in FIG. 3, with the data expressed as means±SEM and N=3 rats per time point). This distribution changes over time such that by 24 hours post-injection, approximately 4.5-fold more of the labelled MTX is in the brain parenchyma than in the capillaries. These results are consistent to those obtained with unconjugated antibody and, again, suggest that these compounds cross the blood-brain barrier.

To ensure that these results were not due to contaminating amounts of free $^{3}H$-MTX or $^{3}H$-MTX that had been cleaved from the conjugate after injection, a co-mix of labelled drug and antibody was injected into rats and a capillary depletion experiment performed. The amount of $^{3}H$-MTX in the different brain fraction is significantly lower for the co-mix as compared to the conjugate (as much as 47 fold in the case of the capillary fraction at 30 minutes post-injection as illustrated in FIG. 3). The $^{3}H$-MTX and the co-mix also does not show the change in distribution of the label between the different brain fractions over time as was seen with the antibody-MTX conjugate or antibody alone. These results demonstrate that delivery of $^{3}H$-MTX across the blood-brain barrier to the brain parenchyma is greatly enhanced by the conjugation of the drug to the anti-transferrin receptor antibody OX-26.

EXAMPLE 11

Distribution of OX-26-AZT in Brain Parenchyma and Capillaries

Capillary depletion studies following the procedures of Example 9 were performed with an OX-26-AZT conjugate using a pH-sensitive succinate linker. These studies employed a dual-labelled conjugate in which the AZT was $^{14}$C-labelled and the antibody carrier was $^{3}$H-labelled. The use of such a conjugate allowed independent monitoring of the disposition of both the antibody and AZT within the brain.

The linker was synthesized as follows. Succinic anhydride was used to acylate the AZT by reacting equimolar amounts of these two compounds for 3 hours at room temperature under argon in the presence of dimethylaminopyridine and sodium bisulfate in freshly distilled pyridine. The product was isolated by chromatography on a DEAE sephadex A50 column run with a triethylammonium bicarbonate buffer. The succinate derivative of AZT was activated at the carboxyl group as the NHS ester by reaction with equimolar amounts of N-hydroxysuccinimide and dicyclohexylcarbodiimide (DCC) in freshly distilled THF at 4° C. for 2 hours. The product was purified by flash charomatography on silica gel. The resulting NHS-ester of AZT-succinate was used to acylate amine groups on OX-26, resulting in an AZT-OX-26 conjugate. A 15-fold molar excess of AZT-NHS ester was reacted with OX-26 in HEPES buffer overnight at 4° C. The antibody-drug conjugate was isolated from free drug on a PD-10 column. The molar ratio of drug to antibody was 7:1. These studies employed a dual-labelled conjugate in which the AZT was $^{14}$C-labelled and the antibody carrier was $^{3}$H-labelled.

Figure 4A:
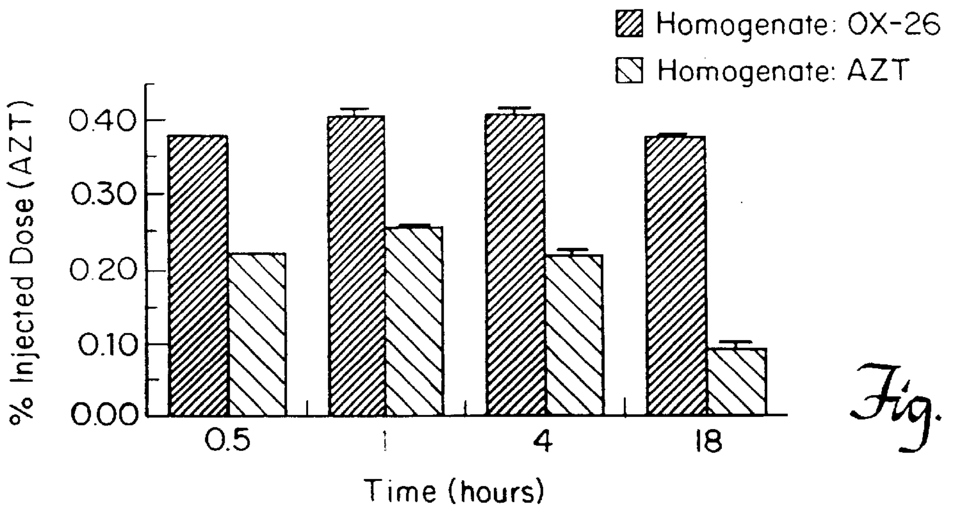
FIG. 4 is a set of histograms illustrating the distribution in the brain of both the antibody and AZT components of an OX-26-AZT conjugate. Panel A shows the distribution of components in the brain homogenate; panel B shows the distribution of components in the brain parenchyma fraction; and panel C shows the distribution of components in the capillary pellet.
Figure 4B:
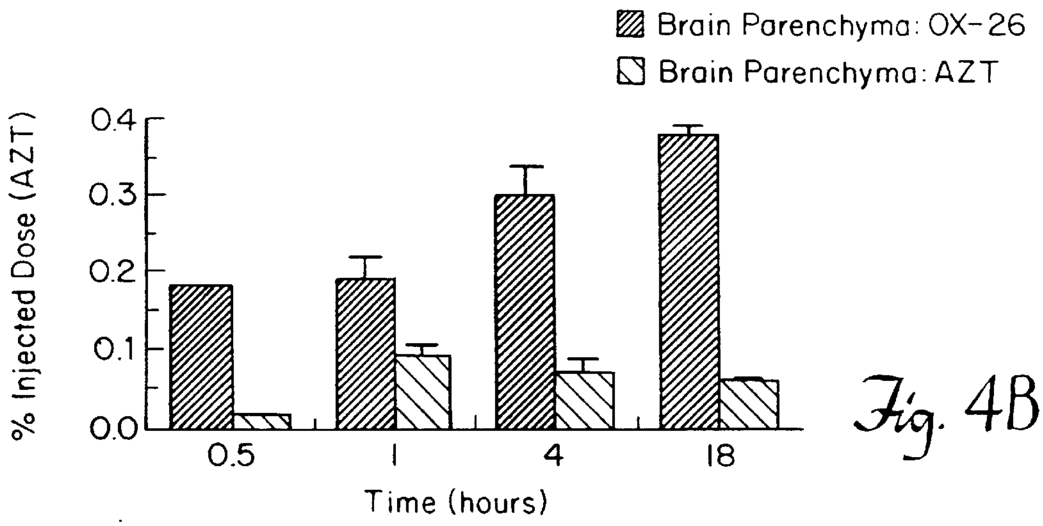
Figure 4C:
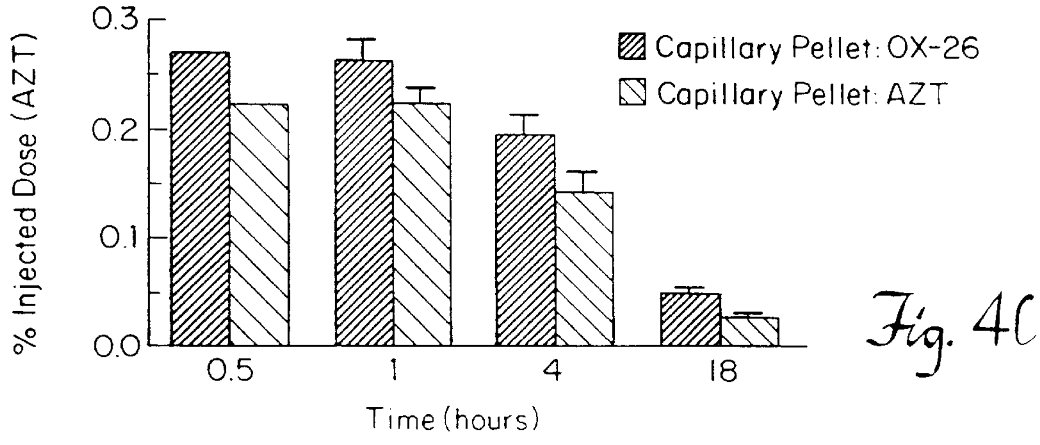

Similar levels of OX-26 and AZT are seen in the capillary fraction of the brain and these levels decrease with time, suggesting that the materials are not being retained by the capillary endothelial cells as illustrated in FIG. 4*c*. As the levels of OX-26 in the capillary fraction decrease, the levels in the parenchyma fraction increase, indicating that the antibody is migrating from the capillaries to the parenchyma in a time-dependent manner as illustrated in FIG. 4*b*. In contrast, the levels of AZT in the brain parenchyma do not rise significantly, suggesting that the majority of the drug is released in the endothelial cells and is not transported across the blood-brain barrier. The levels of OX-26 and AZT remained similar in unfractionated homogenates over time as illustrated in FIG. 4*a*. The data in FIG. 4 are expressed as means±SEM with N=3 rats per time point. These results indicate that the linker is cleaved within the endothelial cells and may represent a method for delivering compounds to those cells.

EXAMPLE 12

Figure 5:
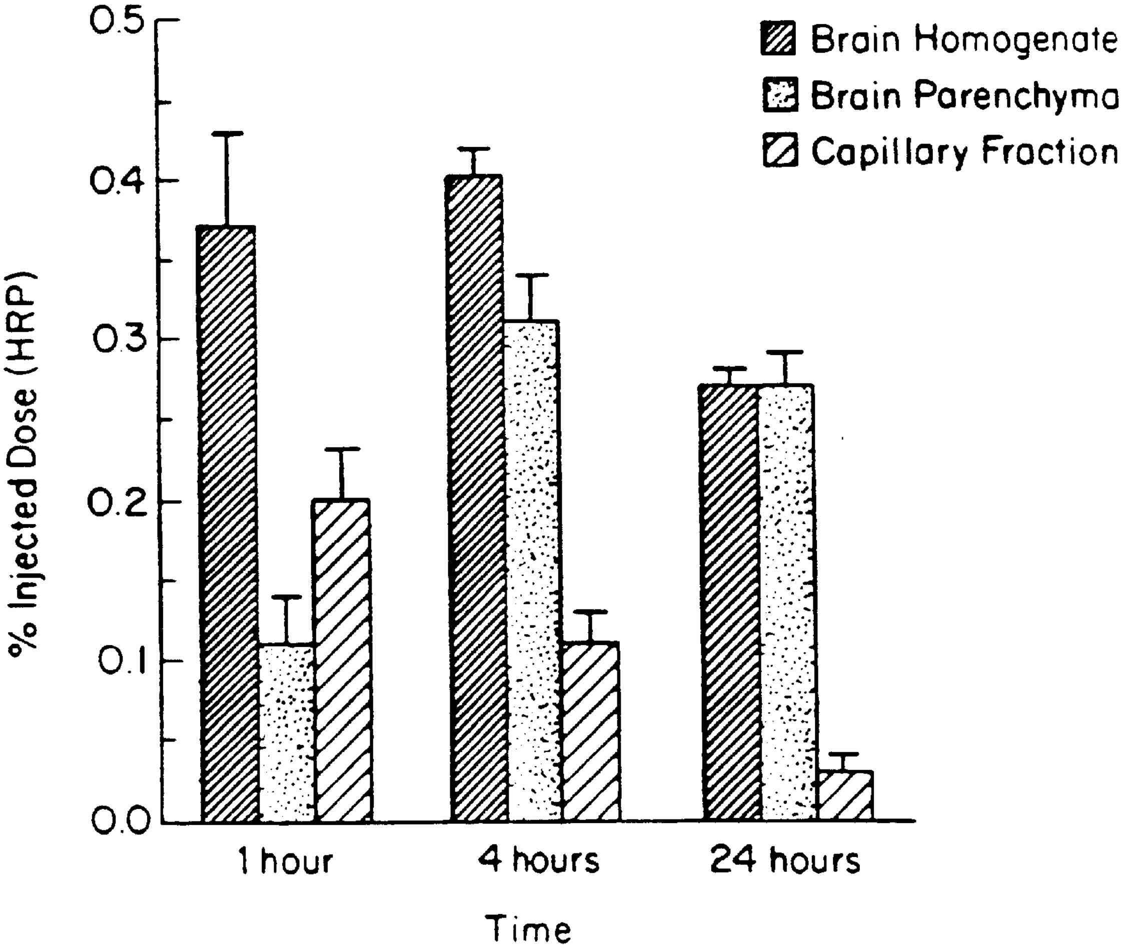
FIG. 5 is a histogram illustrating the experimental results of delivery of a protein, horseradish peroxidase, across the blood-brain barrier in rat brains in the form of a conjugate with OX-26.

Distribution of OX-26-Horseradish Peroxidase (HRP) in Brain Perenchyma and Capillaries Capillary depletion studies following the procedures described for OX-26 in Example 9 were performed with a $^{3}$H-labelled OX-26-HRP conjugate that was prepared using a non-cleavable periodate linkage as described in Example 4. The tritium label was distributed between the antibody and the HRP portion of the conjugate. At 1 hour post-injection, the majority of the radioactivity associated with the brain is in the capillary fraction as illustrated in FIG. 5. The data in FIG. 5 are expressed as means±SEM with N=3 rats per time point. By 4 hours post-injection, the distribution of radioactivity associated with the brain changed such that the majority is in the fraction which represents the brain parenchyma. At 24 hours post-injection, essentially all of the $^{3}$H-labelled OX-26-HRP conjugate is in the parenchyma fraction of the brain indicating that the material has crossed the blood-brain barrier. Similar results were obtained in experiments in which only the HRP portion of the conjugate was radiolabelled.

The percent of injected dose of the OX-26-HRP conjugate that reaches the brain is somewhat lower than that for antibody alone or the OX-26-HRP conjugate. This is most likely due to the presence of 2 to 3 40 kD HRP molecules attached to each carrier and that these "passenger" molecules are randomly attached to the carrier. Due to this, many of the HRP passengers may be attached to the antibody in such a way as to interfere with antigen recognition. This problem can be alleviated by directing the attachment of the passenger to regions of the carrier removed from critical functional domains.

EXAMPLE 13

Distribution of OX-26-CD4 in Brain Parenchyma and Capillaries

A soluble form of CD4, consisting of amino acids 1–368, was conjugated to OX-26 using a linkage that directed the attachment of the CD4 to the carbohydrate groups located in the Fc portion of the antibody. By directing the site of attachment in this way, the chance that the passenger molecules will interfere with antibody-antigen recognition is lessened. The linkage between the proteins was achieved by first introducing a sulfhydryl group onto CD4 using SATA (N-Succinimidyl S-acetylthioacetate), a commerically available compound. A hydrizid derivative of SDPD, another commercial cross-linking agent, was attached to OX-26 via carbohydrate groups on the antibody. Reaction of the two modified proteins gives rise to a disulfide-linked conjugate.

More specifically the linkage between the proteins was achieved by first introducing a sulfhydryl group onto CD4 using N-succinimidyl S-acetylthioacetate (SATA), a commercially available compound. A 4-fold molar excess of SATA was added to 5 mg of CD4 in 0.1 M sodium phosphate buffer containing 3 mM EDTA (pH 7.5). This mixture was reacted at room temperature in the dark for 30 minutes. Unreacted starting materials were removed by passage over a PD-10 column. A hydrizid derivative of SPDP, another commercially available cross-linking agent, was attached to OX-26 via carbohydrate groups on the antibody. Ten milligrams of OX-26 in 2.0 ml of 0.1 M sodium acetate, 0.15 M sodium chloride (pH 5.0) was reacted with a 1000-fold molar excess of sodium periodate for 1 hour at 4° C. in the dark. Unreacted starting materials were removed by passage over a PD-10 column. The oxidized antibody was reacted with a 30-fold molar excess of hydrazido-SPDP overnight at 4° C. with stirring. Reaction of the two modified proteins gives rise to a disulfide-linked conjugate. One tenth volume of 0.5 M hydroxylamine was added to the thioacetylated CD4 (CD4-DATA) and derivatized antibody was then added such that the ratio of CD4 to antibody was 7.5:1. This mixture was reacted at room temperature in the dark for 2 hours. Conjugate was purified by running the reaction mixture over a protein A column followed by a CD4 affinity column.

Figure 6:
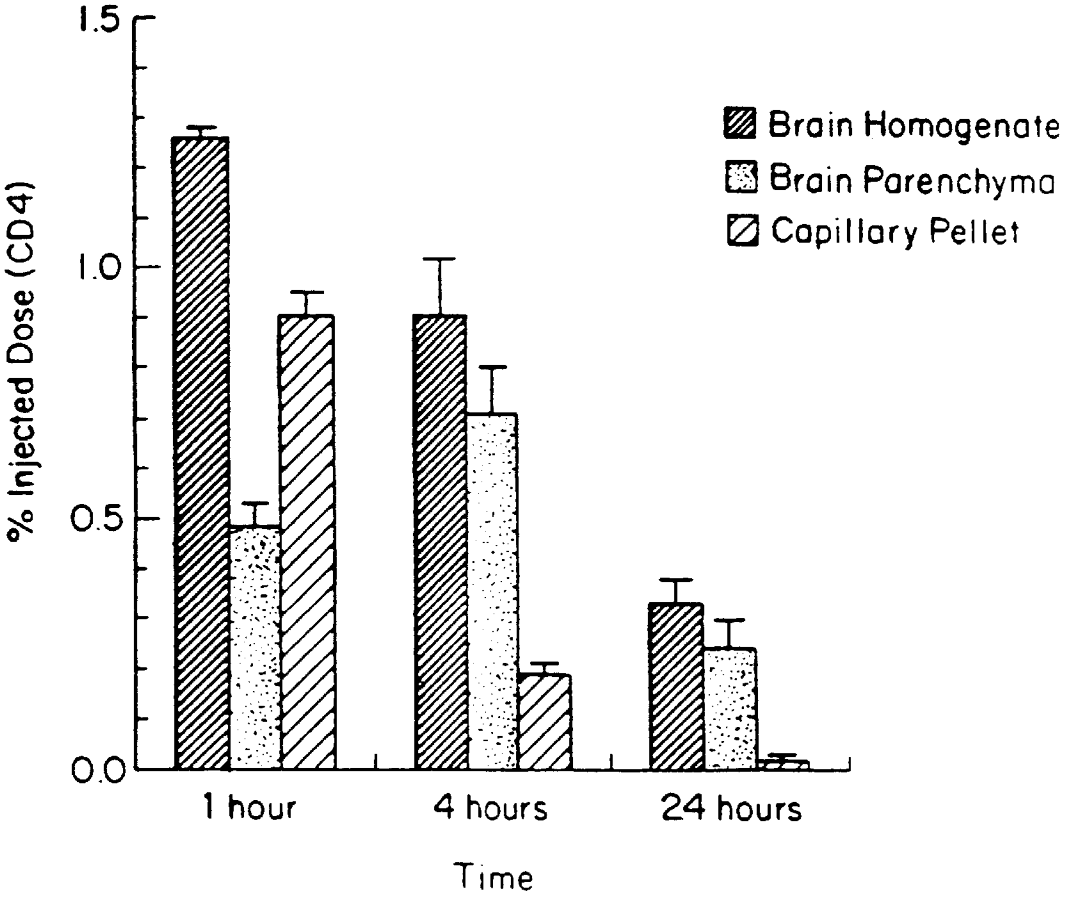
FIG. 6 is a histogram illustrating the experimental results of delivering soluble CD4 to rat brain parenchyma using CD4 in the form of a conjugate with OX-26.

Capillary depletion experiments following the procedures described in Example 9 with OX-26 were performed with an OX-26-CD4 conjugate in which only the CD4 portion was $^3H$-labelled. Time dependent changes in the distribution of the labelled conjugate between the capillary and parenchyma fractions of the brain which are consistent with transcytosis across the blood-brain barrier were observed as illustrated in FIG. 6. The data in FIG. 6 are expressed as means±SEM with N=3 rats per time point.

EXAMPLE 14

Biodistribution and Brain Uptake of Anti-Human Transferrin Receptor Antibodies in Cynomolgous Monkeys A collection of 32 murine monoclonal antibodies which recognize various epitopes on the human transferrin receptor were examined for reactivity with brain capillary endothelial cells in sections from human, monkey (cynomolgous), rat and rabbit brain samples by the immunohistochemical methods described in Example 1. These antibodies were obtained from Dr. Ian Trowbridge of the Salk Institute, LaJolla, Calif. All 32 antibodies displayed some reactivity with human brain endothelial cells. Two antibodies reacted very weakly with rabbit brain capillaries and none reacted with rat. While 21 of the antibodies reacted with monkey brain capillaries, only 2 displayed strong reactivity comparable to that seen with human brain capillaries. These 2 antibodies are herewithin referred to as 128.1 and Z35.2.

Figure 7:
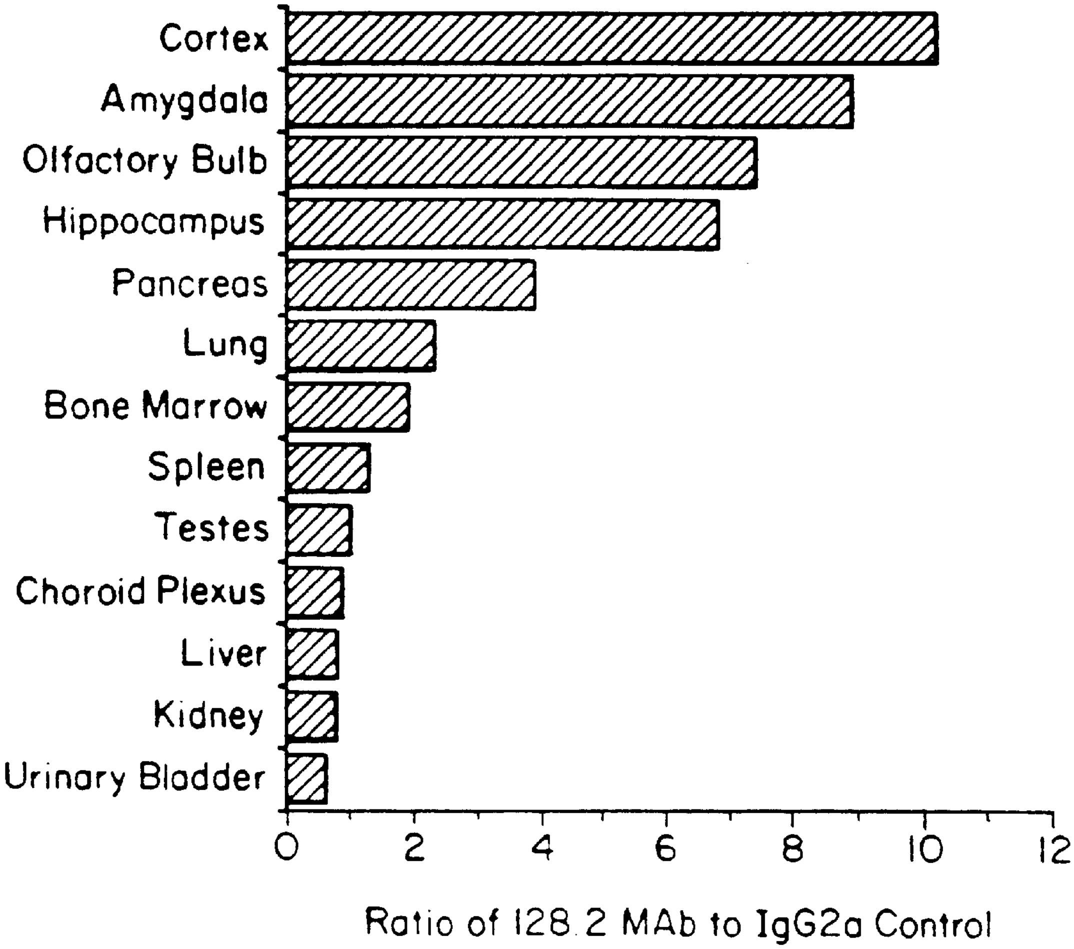
FIG. 7 is a histogram illustrating the biodistribution of antibody 128.1 and control IgG in a cynomolgous monkey.

These antibodies were used to determine the tissue distribution and blood clearance of the $^{14}C$-labelled anti-human transferrin receptor antibodies 128.1 and Z35.2 in 2 male cynomolgous monkeys. 128.1 or Z35.2 was administered concurrently with a $^3H$-labelled control IgG to one of the monkeys with an intravenous catheter. During the course of the study, blood samples were collected to determine the clearance of the antibodies from the circulation. At 24 hours post-injection, the animals were euthanized and selected organs and representative tissues were collected for the determination of isotope distribution and clearance by combustion. In addition, samples from different regions of the brain were processed as described for the capillary depletion experiments in Example 9 to determine whether the antibodies had crossed the blood-brain barrier. The results of the capillary depletion experiments were performed on samples from the cortex, frontal cortex, cerebellum and striatum. All samples had greater than 90% of the 128.1 or Z35.2 in the brain parenchyma, suggesting that the antibodies crossed the blood-brain barrier. The levels of the control antibody in the same samples were from 5 to 10-fold lower. Using the average brain homogenate value for dpm/G tissue, the percent injected dose of 128.1 in the whole brain is approximately 0.2–0.3%. This compares to a value of 0.3–0.5% for OX-26 in the rat at 24 hours post-injection. A comparison of the ratios of 128.1 to the control antibody for various organs is illustrated in FIG. 7. Similar results were obtained for Z35.2. These results suggest that 128.1 is preferentially taken up by the brain as compared to control antibody. For the majority of organs and tissues tested, the ratio of 128.1 to control is less than 2.

EXAMPLE 15

Cloning and Expressing of ALK 128.1: An Anti-Human Transferrin Receptor Chimeric Antibody

RNA EXTRACTION:

RNA was extracted following the single step guanidinium/phenol method (P.Chomczynski and S. Sacchi. 1987, Anal. Bioch. 162:156–259). All the instruments and containers used were previously autoclaved and rinsed with diethyl pyrocarbonate (depc) treated water to avoid degradation due to RNAases. Several samples each containing $5\times10^5$ cells from the 128.1 hybridoma which secretes a murine anti human transferrin receptor monoclonal antibody, were washed twice with PBS. The pellets were quick frozen in liquid nitrogen and either kept at −70° C. for later use or extracted immediately.

For the extraction, in a RNase free microfuge tube, ½ ml of solution D (Solution D:36 $\mu$l 2-mercaptoethanol per 5 ml of 1×GITC [1×GITC: 250 g guanidinium thiocyanate, 17.6 ml 0.75 M Na citrate pH7, 26.4 ml 10% sarcosyl, 293 ml dH2O]), 50 $\mu$l of 2M Na acetate pH 4, 0.5 ml phenol (dH2O equilibrated) and 100 ρl of chloroform:isoamylalcohol (49:1) were added to the cell pellet mixing by inversion after each addition. The extraction was left on ice for 15 minutes and centrifuged at 13000 g for 20 min at 4° C.

The upper aqueous phase containing the RNA was removed to a new tube and precipitated with 2 volumes of cold absolute ethanol for 2 hr. at −70° C. After two 70% depc-ethanol washes the RNA pellet was dried briefly and resuspended in dH20 0.5% SDS.

FIRST STRAND cDNA SYNTHESIS

Total RNA from $5\times10^5$ cells was resuspended in 18 $\mu$l of 0.5% SDS. 9 $\mu$l of RNA were annealed with 2 $\mu$l of 3' primer (1 mg/ml) at 60° C. for 10 minutes. For light chain V region amplifications, an oligo dT primer was used, whereas for the amplification of heavy chain V regions a γ CH1 antisense primer, containing an XbaI site (underlined in Table 1), with degeneracies introduced so that it will prime all isotypes of murine heavy chains except γ3 was used (Table 1).

After annealing, the samples were cooled on ice, 4 $\mu$l of first strand cDNA buffer (50 mM Tris pH 8.3, 50 mM KCl, 10 mM $MgCl_2$, 1 mM DTT, 1 mM EDTA, 0.5 mM spermidine), 1 $\mu$l of RNAse inhibitor (Promega), 2 $\mu$l of 10 mM dNTP's and 2 $\mu$l of prediluted 1:10 Promega AMV Reverse Transcriptase were added and the reaction incubated for 1 hour at 42° C. The cDNA was kept at −20° C. until used for PCR.

TABLE 1

| PRIMERS FOR cDNA SYNTHESIS | |
|---|---|
| PRIMER FOR SYNTHESIS OF LIGHT CHAIN V REGION cDNA | |
| OLIGO dT.R1.XBA.H3 | |
| 5' GCCGGAATTCTAGAAGC$(T)_{17}$ | (SEQ ID NO:1) |
| PRIMER FOR SYNTHESIS OF HEAVY CHAIN V REGION cDNA MγC.CHI AS | |

TABLE 1-continued

| PRIMERS FOR cDNA SYNTHESIS |
|---|
| (Degeneracies at a single position are shown in parenthesis.) |
| 5' AGG **<u>TCTAGA</u>** **A**(CT)C TCC ACA CAC AGG (AG)(AG)C CAG TGG ATA GAC (SEQ ID NO:2) |

PRIMERS AND PCR REACTION:

A first PCR reaction was performed in order to amplify the variable regions and determine their sequence. To achieve this the PCR primers were designed to hybridize to the leader sequence (5' primer) and to the constant region immediately downstream of the V-J region (3' primer).

The oligonucleotides were synthesized in an Applied Biosystem 391 DNA Synthesizer, eluted without purification, diluted to 20 $\mu$M and kept at 4° C.

All primers were designed with a restriction site with three additional bases upstream to protect the site and facilitate enzyme digestion. The sites were chosen to make possible the cloning of the PCR product into a subcloning vector and into the final expression cassett vectors.

For the leader region, the primers contain a ribosome recognition site (Kozak's sequence CACC; Kozak M. 1981, Nucl. Acid. Res., 9:20, 5233–5252) 5' of the start codon, and an EcoR V site (underlined in Tables 2 and 3) protected by three 5' G's. A set of 4 universal 5' sense primers was used simultaneously in the light variable region amplification, and a set of 3 universal 5' sense primers in the case of heavy variable regions (Coloma et al. 1991, Biotechniques 11,2, 152–156). An equimolar amount of each primer was used in the PCR reaction. These primers contain degeneracies in order to hybridize with all the families of murine leader sequences reported in Kabat's database. (Kabat E. 1987, Sequences of Proteins of Immunological Interest, NIH). The 3' primers were designed in the constant region 20 bases downstream of the V-J region and contain an XbaI site (underlined in Tables 2 and 3) for subcloning purposes (Tables 2 and 3).

TABLE 2

| PRIMERS FOR MURINE HEAVY CHAIN VARIABLE REGION AMPLIFICATION. (Degeneracies at a single position are shown in parenthesis.) | | |
|---|---|---|
| <u>LEADER REGION PRIMERS (5'SENSE)</u> | | |
| MHALT1.RV | #085 | |
| Leader Murine Heavy IgV | | |
| 5' GGG **<u>GATATC</u>** **CACC** ATG G(AG)A TG(CG) AGC TG(TG) GT(CA) AT(CG) CTC TT | | (SEQ ID NO:3) |
| MHALT2.RV | #086 | |
| Leader Murine Heavy IgV | | |
| 5' GGG **<u>GATATC</u>** **CACC** ATG (AG)AC TTC GGG (TC)TG AGC T(TG)G GTT TT | | (SEQ ID NO:4) |
| MHALT3.RV | #087 | |
| Leader Murine Heavy IgV | | |
| 5' GGG **<u>GATATC</u>** **CACC** ATG GCT GTC TTG GGG CTG CTC TTC T | | (SEQ ID NO:5) |
| <u>CONSTANT REGION PRIMER (3'ANTISENSE)</u> | | |
| Primer designed to hybridize at aminoacids 130–120 in CH1 of Igγ. This primer is identical to the primer used for heavy chain first strand cDNA synthesis. | | |
| MCγ CH1AS.XBA | #097 | |
| CH1 anitsense primer for murine Igγ, except Igγ3 | | |
| 5' AGG **<u>TCTAGA</u>** **A**(CT)C TCC ACA CAC AGG (AG) (AG)C CAG TGG ATA GAC | | (SEQ ID NO:6) |

TABLE 3

| PRIMERS FOR MURINE LIGHT CHAIN VARIABLE REGION AMPLIFICATION. (Degeneracies at a single position are shown in parenthessis.) | | |
|---|---|---|
| <u>LEADER REGION PRIMERS (5'SENSE)</u> | | |
| MLALT1.RV | #088 | |
| Leader Murine Light IgV | | |
| 5' GGG **<u>GATATC</u>** **CACC** ATG GAG ACA GAC ACA CTC CTG CTA T | | (SEQ ID NO:7) |
| MLALT2.RV | #089 | |
| Leader Murine Light IgV | | |
| 5' GGG **<u>GATATC</u>** **CACC** ATG GAT TTT CAA GTG CAG ATT TTC AG | | (SEQ ID NO:8) |
| MLALT3.RV | #090 | |
| Leader Murine Light IgV | | |
| 5' GGG **<u>GATATC</u>** **CACC** ATG GAG (TA)CA CA(GT) (TA)CT CAG GTC TTT (GA)TA | | (SEQ ID NO:9) |
| MLALT4.RV | #091 | |

TABLE 3-continued

| PRIMERS FOR MURINE LIGHT CHAIN VARIABLE REGION AMPLIFICATION. (Degeneracies at a single position are shown in parenthessis.) | |
|---|---|
| Leader Murine Light IgV | |
| 5' GGG **GATATC CACC** ATG (GT)CC CC(AT) (GA)CT CAG (CT)T(CT) CT(TG) GT | (SEQ ID NO:10) |
| CONSTANT REGION PRIMER (3'ANTISENSE) | |
| Primer designed to hybridize to amino acids 122–116 of kappa constant region. | |
| MCκ AS.XBA #096 | |
| Constant Murine Light | |
| 5'GCG **TCTAGA** ACT GGA TGG TGG GAA GAT GGA | (SEQ ID NO:11) |

Figure 9:
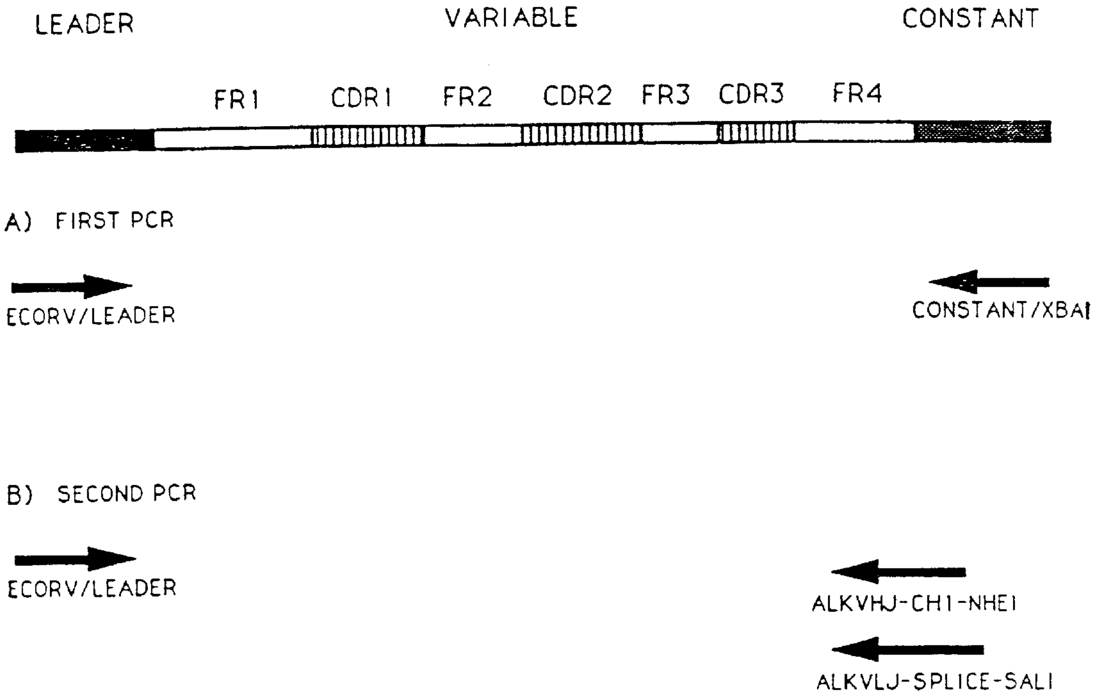
FIG. 9 illustrates the primers used for variable region amplification, both for first cloning and sequencing the V region and then for cloning into the final expression vector.

The primers for the second PCR reaction (Table 4) have the actual sequence of the V-J regions, determined by sequencing of the subcloned products (FIG. 9). These primers have a Nhe I site in the case of the VH primer and Sal I for the VL primer, which permits the cloning into the expression vectors. (The restriction enzyme sites are underlined in Table 4). The Nhe I site in the 3' primer for the VH allows the direct ligation of the VH-J region to the first two amino acids of the CH1 of the γ1 constant region. The VL 3' primer has a donor splice sequence before its Sal I site which is necessary to splice the VL to C κ in the expression vector.

TABLE 4

| PRIMERS FOR 128.1 V–J REGION MODIFICATION BY SECOND PCR PRIOR TO THE CLONING INTO EXPRESSION VECTORS | |
|---|---|
| HEAVY CHAIN PRIMER (3'ANTISENSE): | |
| Primer designed to hybridize to amino acids 111–113 in J4 region of 128.1 heavy chain V region. It includes a Nhe I site for cloning into the expression vector (links J4 to CHI) and Sal I for subcloning (upstream Nhe I). | |
| ALKJ4 AS.NHE.SAL1 #098 | |
| Antisense of VHJ4 + γ1 CH1 | |
| 5' TGG **GTCGAC** AGA TGG GGG TGT TGT **GCTAGC** TGA GGA GAC | (SEQ ID NO:12) |
| LIGHT CHAIN PRIMER (3'ANTISENSE): | |
| Primer designed to hybridize to amino acids 101–107 in J4 region of 128.1 light chain V region. It includes a donor splicing sequence which is highlighted. | |
| ALKκ-J4AS.SAL1 #101 | |
| Antisense of VL J4 + splicing donor | |
| 5' AGC **GTCGAC** **TTACG** TCT GAT TTC CAG CCT GGT CCCT | (SEQ ID NO:13) |

PCR reactions were performed in a volume of 100 μl with the following final conditions: 2 μl of cDNA, 0.5 μl Taq polymerase (Cetus Corporation), 1×buffer (10 mM Tris pH8, 1.5 mM $MgCl_2$, 50 mM KCl, 100 μg BSA), 200 μM each dNTP, 1 μM of each primer and 50 μl of mineral oil. PCR was carried out for 30 cycles in a PTC 100 Thermal Controller (M. J. Research Inc.) with 1 min. denaturing (94° C.), 1 min. annealing (55° C.), 1.5 min. extension (72° C.), and a final extension of 10 min.

The size of the PCR products was verified by agarose gel electrophoresis in a 2% TAE gel stained with ethidium bromide. The correct products were approximately 380 base pairs for the light chain and 420 base pairs for the heavy chain variable region.

SUBCLONING AND SEQUENCING:

After the PCR reaction the oil was removed by chloroform extraction and the samples kept at 4° C. For subcloning, the products were either directly cloned into Bluescript KS T-A (blunt ended by digestion at EcoR V site and tailed with dideoxythymidine triphosphate using terminal transferase) prepared following the procedure by Holton (T. A. Holton and M. W. Graham. 1990 Nucl. Acid. Res., 19:5, 1156), or gel isolated, cut with the appropriate restriction enzymes (EcoR V and Sal I) and cloned into Bluescript KS previously cut with the same enzymes.

For TA cloning 3 μl of the PCR product was directly ligated with 50 ng of T-A vector in a 15 μl reaction for 4–12 hours at 16° C. For sticky end ligations 200 ng of cut Bluescript was ligated with 200–400 ng of cut product in 20 μl ligation reactions. 5 μl of the ligation was used for transformation of *E. Coli.* XL1-blue (Stratagene) competent cells prepared by calcium chloride treatment. White colonies, containing inserts were picked above a blue colony background. Miniprep DNA was restriction digested, analyzed and the apparently correct clones sequenced.

Dideoxynucleotide chain termination sequencing was carried out using T7 DNA polymerase (Pharmacia, Uppsala, Sweden or Sequenase, US Biochemical Corp., Cleveland, Ohio) according to the manufacturer's protocol. Four independent clones from different PCR reactions were sequenced in both directions, to obtain the concensus sequence.

The obtained sequences were compared against other murine sequences in Genbank and aligned with reported V regions in Kabat's database to identify their family and conserved amino acids. (See Tables 5 and 6.)

TABLE 5

COMPLETE SEQUENCE OF CHIMERIC 128.1 (Anti-Human Transferrin Receptor) LIGHT CHAIN VARIABLE REGION, MOUSE KAPPA SUBGROUP VI -22 LEADER (SEQ ID NO 14)
ATG GAT TTT CAA GTG CAG ATT (SEQ ID NO 15)
Met Asp Phe Gln Val Gln Ile TTC AGC TTC CTG CTA ATC AGT GCC TCA GTC ATA CTG TCC AGA
Phe Ser Phe Leu Leu Ile Ser Ala Ser Val Ile Leu Ser Arg -1 1 FR1
GGA --- CAA ATT GTT CTC ACC CAG TCT CCA GCA ATC ATG TCT
Gly --- Gln Ile VAL LEU Thr GLN SER PRO ALA ILE Met Ser FR1 24 CDR1
GTA TCT CCA GGG GAG AAG AAG GTC ACC ATG ACC TGC
AGT GCC AGC
ALA SER Pro GLY Glu LYS VAL THR Met THR CYS Ser ALA SER 27—29 * CDR1 35 FR2
TCA AGT ATA CGT TAC ATT CAC TGG TAC CAG CAG AAG TCA GGC
SER SER Ile ARG TYR Ile His TRP Tyr GLN GLN ARG PRO Gly FR2 50 CDR2
ACC TCC CCC AAA AGA TGG ATT TAT GAC ACA TCC AAC CTG GCT
Thr SER PRO LYS Arg Trp ILE TYR Asp Thr SER Asn LEU Ala 57 FR3
TCT GGA GTC CCT GCT CGC TTC AGT GGC AGT GGG TCT GGG ACC
SER GLY VAL PRO Ala ARG PHE SER GLY SER GLY SER GLY Thr FR3
TCT TAT TCT CTC ACA ATC AGC AGC ATG GAG GCT GAA GAT GCT
Ser Tyr Ser LEU Thr ILE Ser Ser Met GLU Ala GLU ASP Ala 89 CDR3 97
GCC ACT TAT TAC TGC CAT CAG CGG AAT AGT TAC CCA TGG ACG
ALA THR TYR TYR CYS His GLN Arg Asn Ser Tyr Pro Trp THR 98 FR4 * 107 CONST.
TTC GGT GGA GGC ACC AGG CTG GAA ATC AGA --> CGG GCT
PHE GLY GLY GLY THR Arg LEU GLU Ile ARG --> ARG ALA
J4

Conserved amino acids are capitalized and bold.
* NOTE: Amino acid #30 is a conserved Val and amino acid #103 and #107 a conserved Lys in 98% of the sequences reported in Kabat's database for this family.

TABLE 6

COMPLETE SEQUENCE OF CHIMERIC 128.1 (Anti-Human Transferrin Receptor) HEAVY CHAIN VARIABLE REGION. MOUSE GAMMA SUBGROUP IIB.

-19 LEADER
ATG GAA TGG AGC TGG GTA (SEQ ID NO:16)
Met Glu Trp Ser Trp Val (SEQ ID NO:17)

LEADER -1
ATG CTC TTC CTC CTG TCA GGA ACT GCA GGT GTC CGC TCT ---
Met Leu Phe LEU Leu Ser Gly Thr Ala Gly Val Arg Ser ---

1 FR1
GAG GTC CAG CTG CAA CAG TCT GGA CCT GAA CTG GTG AAG CCT
Glu VAL GLN LEU Gln GLN Ser GLY Pro Glu LEU VAL Lys PRO

*18 FR1
GGA GCT TCA ATG AAG ATT TCC TGC AAG GCT TCT GGT TAC TCA
GLY Ala SER Met LYS Ile SER CYS LYS ALA SER GLY TYR Ser

31 CDR1 36 FR2
TTC ACT GGC TAC ACC ATG AAC TGG GTG AAG CAG AGC CAT GGA
Phe Thr Gly Tyr Thr Met Asn TRP VAL Lys GLN Ser His Gly

FR2 50 52--a- 53 CDR2

TABLE 6-continued

COMPLETE SEQUENCE OF CHIMERIC 128.1 (Anti-Human Transferrin Receptor) HEAVY CHAIN VARIABLE REGION. MOUSE GAMMA SUBGROUP IIB.

GAG AAC CTT GAG TGG ATT GGA CGT ATT AAT CCT CAC AAT GGT
Glu Asn Leu Glu Trp Ile Gly Arg Ile Asn PRO His Asn Gly

CDR2 66 *68
GGT ACT GAC TAC AAC CAG AAG TTC AAG GAC AAG GCC CCT TTA
Gly Thr Asp TYR Asn Gln LYS PHE Lys Asp LYS Ala Pro LEU

FR3 82--a-
ACT GTA GAC AAG TCA TCC AAC ACA GCC TAC ATG GAG CTC CTC
THR Val Asp Lys SER Ser Asn THR Ala TYR Met Glu LEU Leu 82b-c- 83 FR3
AGT CTG ACA TCT GGG GAC TCT GCA GTC TAT TAC TGT GCA AGA
Ser Leu THR SER GLU ASP Ser ALA Val TYR Tyr CYS Ala Arg

95 CDR3 100--a- 103 FR4
GGC TAC TAT TAC TAT TCT TTG GAC TAC TGG GGT CAA GGA ACC
Gly Tyr Tyr Tyr Tyr Ser Leu Asp Tyr TRP GLY Gln GLY THR

FR4 113 CH1
TCA GTC ACC GTC TCC TCA --> GCC AAA
Ser Val THR VAL SER Ser --> Ala Lys
J4

Conserved amino acids are capitalized and bold. Amino acid #18 is a conserved Val and amino acid #68 a conserved Thr in 98% of the sequences reported in Kabat's database for this family.

The final clones were named pBKS4600 for the VH region and pBKS4601 for the VL region.

CLONING INTO EXPRESSION VECTORS:

Plasmid pAH4274 is the vector for expression of heavy chain variable regions obtained by PCR with leader/J region priming. V region cloning into this cassette is performed by a complete digestion of vector and product with EcoR V and Nhe I. This vector has a human γ1 constant region whose CHI is directly linked with the 3' end of the VH-J region by means of a Nhe I site. This 11 kb vector contains an ampicillin resistance gene for procaryotic selection, a heavy chain immunoglobulin enhancer and a histidine (histidinol) selection marker for selection of transfectants (Hartman, S., R. Mulligan, Proc. Natl. Acad. Sci. 85, 8047–8051); transcription is from the VH promoter of the murine 27.44 gene.

Figure 10:
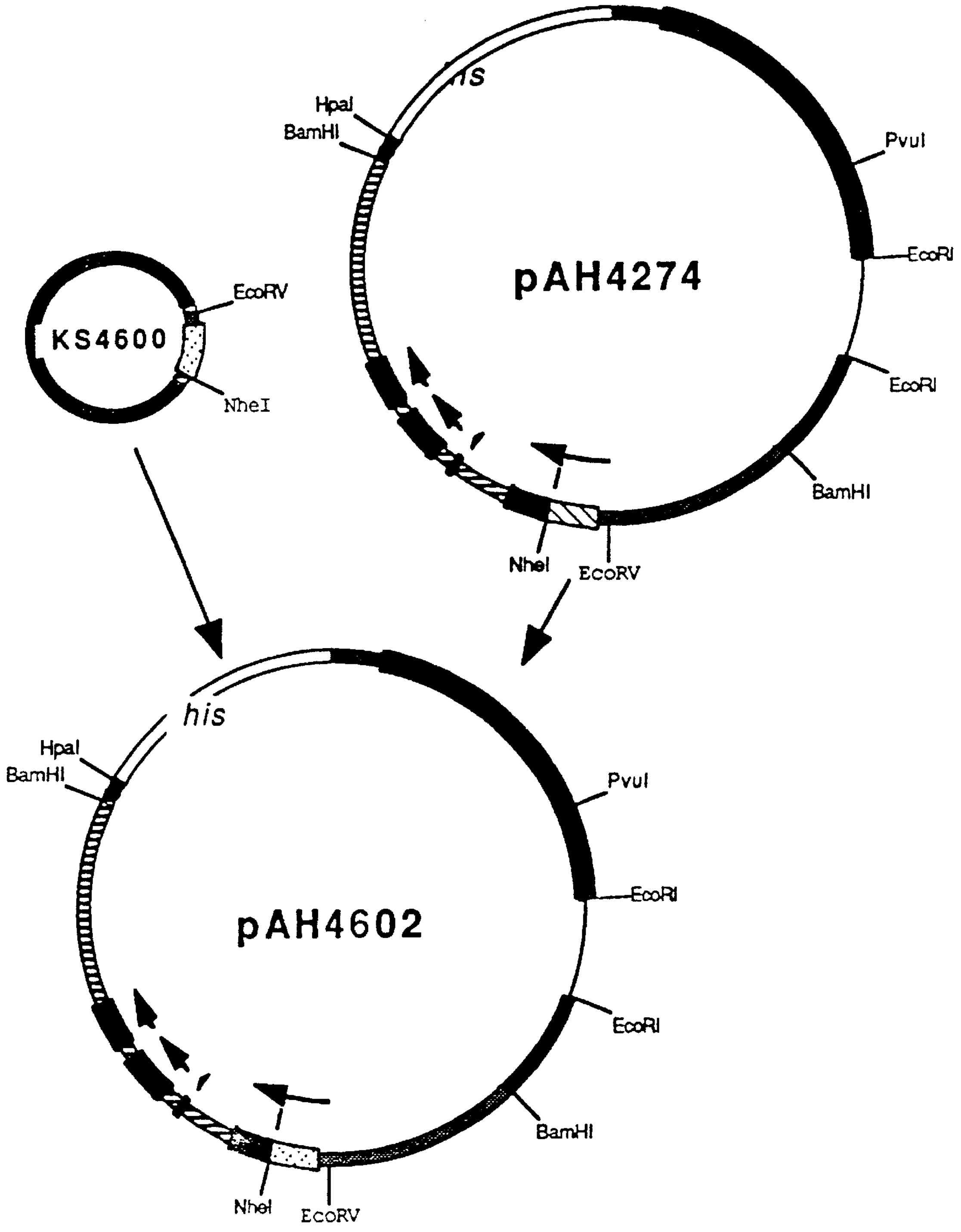
FIG. 10 illustrates the cloning of the 128.1 heavy chain variable region.

The 400 bp. EcoR V-Nhe I fragment (VH of 128.1) from pBKS4600 was used to replace the EcoR V-Nhe I fragment in plasmid pAH 4274. HB101 competent cells were transformed and plated on LB plates with 50 μg/ml of ampicillin. Colonies were screened by colony hybridization with a $^{32}P$ end labelled leader region oligonucleotide. Positive clones were restriction mapped and maxi plasmid preps prepared using the QIAGEN maxi prep kit (QIAGEN Inc., Studio City, Calif.). The final expression vector with the VH of 128.1 joined to human γ1 constant region was named pAH4602 (FIG. 10). The coding sequence for this expression vector is given in FIGS. 11A–11G (SEQ ID NO: 18), (SEQ ID NO: 19), (SEQ ID NO: 20), (SEQ ID NO: 21), (SEQ ID NO: 22), and (SEQ ID NO: 23).

Plasmid pAG4270 is the expression vector for light chain variable regions obtained by PCR with leader/J region priming. The 14 kb vector has an ampicillin resistance gene, a gpt (mycophenolic acid resistance) selected marker, an immunoglobulin H enhancer and an introl for V-Constant region splicing; transcription is from the murine VH promoter from the 27.44 gene.

Figure 12:
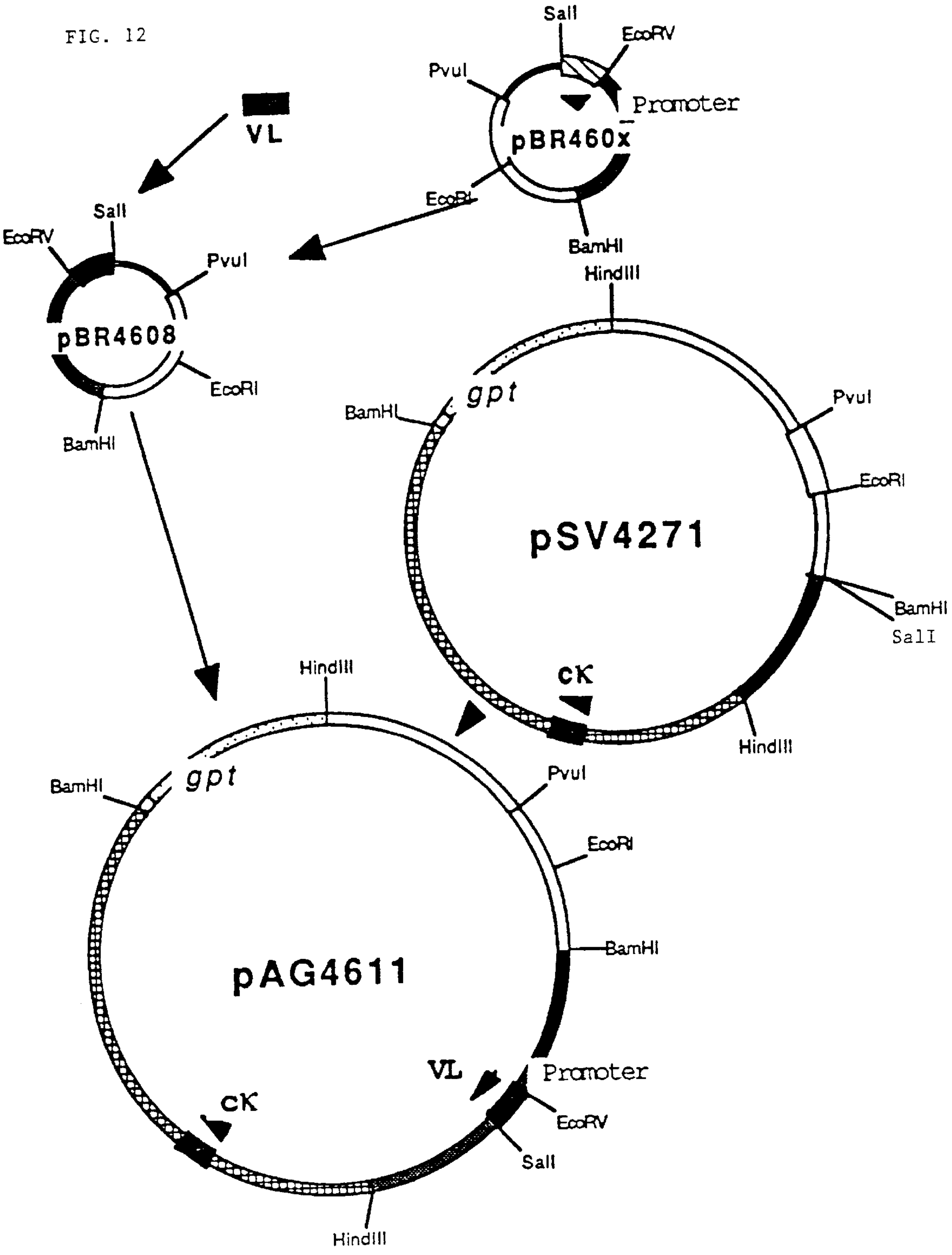
FIG. 12 illustrates the cloning of the 128.1 light chain variable region.

Due to the presence of an EcoR V within the gpt gene in the vector, the cloning of the anti-transferrin receptor VL was performed in two steps to avoid inefficient partial digestions. The 380 bp EcoR V-Sal I fragment (VL) from pBKS4601 was cloned into pBR460x (6.9 kb), a subcloning vector with the VH promoter, previously cut with the same enzymes. The resulting construct (pBR4608) was then cut with Pvu I-Sal I and the 4 kb fragment containing the promoter, the V region and part of the ampicillin resistance gene was ligated to the 9.7 kb Pvu I-Sal I fragment of pSV4271 an intermediate vector which lacks the promoter. HB101 competent cells were transformed and positives screened by colony hybridization and restriction digestion. Maxipreps were prepared as described above. The final expression vector was named pAG4611 (FIG. 12). The coding sequence of this expression vector is shown in FIGS. 13A–13F (SEQ ID NO: 24), (SEQ ID NO: 25), and (SEQ ID NO: 26).

TRANSFECTION AND SELECTION:

Ten μg of maxiprep DNA from each final expression vector was linearized by BSPCl (Stratagene, Pvu I isochizomer) digestion and $1\times10^7$ SP2/0 cells were cotransfected by electroporation. Prior to transfection the cells were washed with cold PBS, then resuspended in 0.9 ml of the same cold buffer and placed in a 0.4 cm electrode gap electroporation cuvette (Bio-Rad) with the DNA. For the electrical pulse, the Gene Pulser from Bio-Rad (Bio-Rad, Richmond, Calif.) was set at a capacitance of 960 μF and 200 V. After the pulse the cells were incubated on ice for 10 minutes then washed once in IMDM with 10% calf serum and resuspended in IMDM with 10% calf serum at a concentration of $10^5$ cells/ml.

The transfected cells were plated into five 96 well plates at a concentration of $10^4$ cells/well. Selection was started after 48 hours. Two plates were selected with 5 mM histidinol (heavy chain selection), 2 plates were selected with 1 μl/ml mycophenolic acid (light chain selection) and 1 plate was selected with histidinol and mycophenolic acid (heavy and light chain selection).

Twelve days post selection supernatants were screened by ELISA to test for the secretion of both chains. Immulon II 96 well plates were coated with 5 μg/ml of goat anti human γ1 in carbonate buffer at pH9.6, and blocked with 3% BSA. Supernatants from the transfectants were added and the plates were incubated overnight at 4° C. After washing, plates were developed with goat anti-human κ conjugated with alkaline phosphatase and wells secreting H and L chains identified (Table 7).

Table 7: RESULTS OF TRANSFECTIONS

Results of cotransfection with vectors pAH4602 and pAG4611 in SP2/0 cells. 2 plates were selected with 5 mM histidinol (HIS), 2 plates with 1 μg/ml mycophenolic acid (HXM) and 1 plate selected with both (HIS+HXM). Wells containing clones were analyzed by ELISA to determine those containing secreted antibody (# positive wells).

| | SELECTION | | |
|---|---|---|---|
| | HIS | HXM | HIS + HXM |
| #WELLS WITH | 78/96 | 76/96 | 13/96 |
| CLONES | 83/96 | 64/96 | |
| #POSITIVE | 20/78 | 28/76 | 10/13 |
| WELLS | 25/83 | 20/64 | |

High producers were expanded for further analysis; selected transfectants were subcloned.

ANTIBODY ANALYSIS:

To determine the nature of the protein being produced, transfectants were biosynthetically labelled with $^{35}S$ methionine, cytoplasmic and secreted antibodies immunoprecipitated with rabbit anti-human Ig and protein-A and the immunoprecipitates fractioned on SDS polyacrylamide gels.

Clones with the highest production identified by ELISA were expanded to 5 ml petri dishes and removed from selection. $1\times10^6$ cells were pelleted at 220×g for 5 minutes at 4° C. and washed twice with labelling medium (high glucose DME deficient in methionine: GIBCO). Cells were finally resuspended in 1 ml labeling medium containing 25 μCi $^{35}S$-Methionine (Amersham Corp.) and allowed to incorporate label for 3 hours at 37° C. under tissue culture atmospheric conditions.

Cells were pelleted and supernatants drawn off for immunoprecipitation of secreted IgG. Cell pellets were lysed in NDET (1% NP-40, 0.4% deoxycholate, 66 mM EDTA, 10 mM Tris, pH 7.4), centrifuged, and the supernatants removed and incubated 1 hour at 4° C. with rabbit anti-human IgG Fc polyclonal antiserum (5 μl/ml). To the labelled supernatants, 100 μl/ml of protein A (10% in NDET, IgG Sorb) was added and mixed by rotation at 4° C. for 15 minutes. Protein-A bound IgG was washed by centrifuging through 1 ml 30% sucrose in 100 μl NDET+0.3% SDS. The protein A pellet was then resuspended in 100 μl NDET/3% SDS, transferred to a 1.5 ml polypropylene tube with 100 μl of the same buffer, and the previous tube rinsed with 100 μl . The 300 μl suspension was centrifuged and washed with deionized water. Finally, the protein A pellet was resuspended in 50 μl of loading buffer (25 mMTris pH 6.7, 0.2% SDS, 10% glycerol, 8% μg/100 ml bromophenol blue) and boiled for two minutes prior to gel loading. Antibodies were analyzed by SDS-PAGE (5% acrylamide gels, 0.1% sodium phosphate buffered) to confirm proper assembly of H and L chains. In addition, a portion of the labelled sample was reduced by treatment with 0.15 M 2-mercaptoethanol, 37° C. for 1 hour and analyzed on 12% acrylamide gels to confirm the size of the unassembled H and L chains. The gels were stained, dried and exposed for autoradiograms.

The resultant autoradiograms revealed the expected patterns for fully functional antibodies. The secreted antibodies that were in the cell supernatant exhibited the expected molecular weight pattern of free light chain, light chain dimer and the tetramer formed from two light chains and two heavy chains for fully expressed and assembled functional antibodies. The pattern for antibody parts in the cell cytoplasm was also as expected for fully expressed antibody constitutents.

EXAMPLE 16

Further Mouse/Human Chimeras of the Anti-Human Transferrin Receptor Antibody 128.1.

Figure 14:
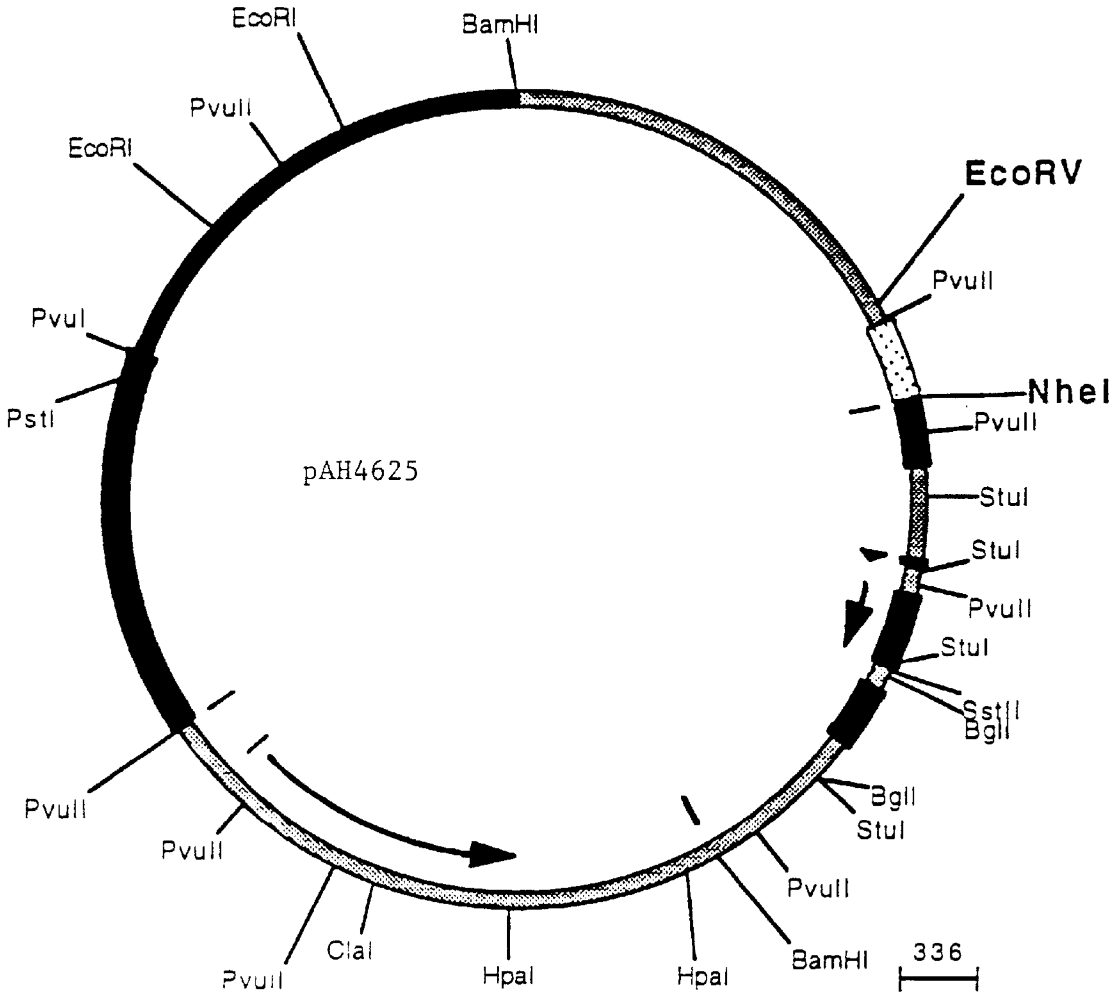
FIG. 14 illustrates the plasmid map of the heavy chain expression vector pAH4625 containing the γ-2 isotype.
Figure 15:
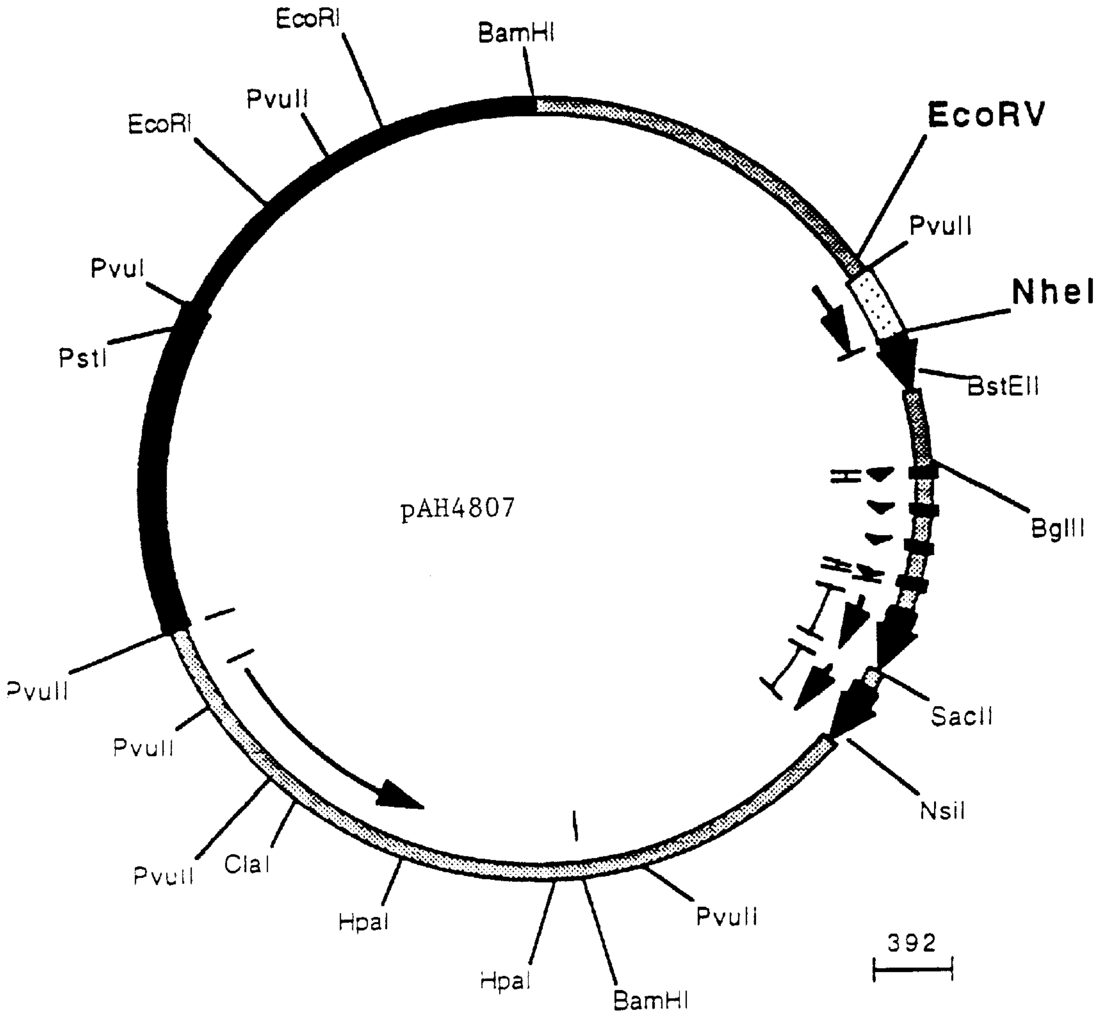
FIG. 15 illustrates the plasmid map of the heavy chain expression vector pAH4807 containing the γ-3 isotype.
Figure 16:
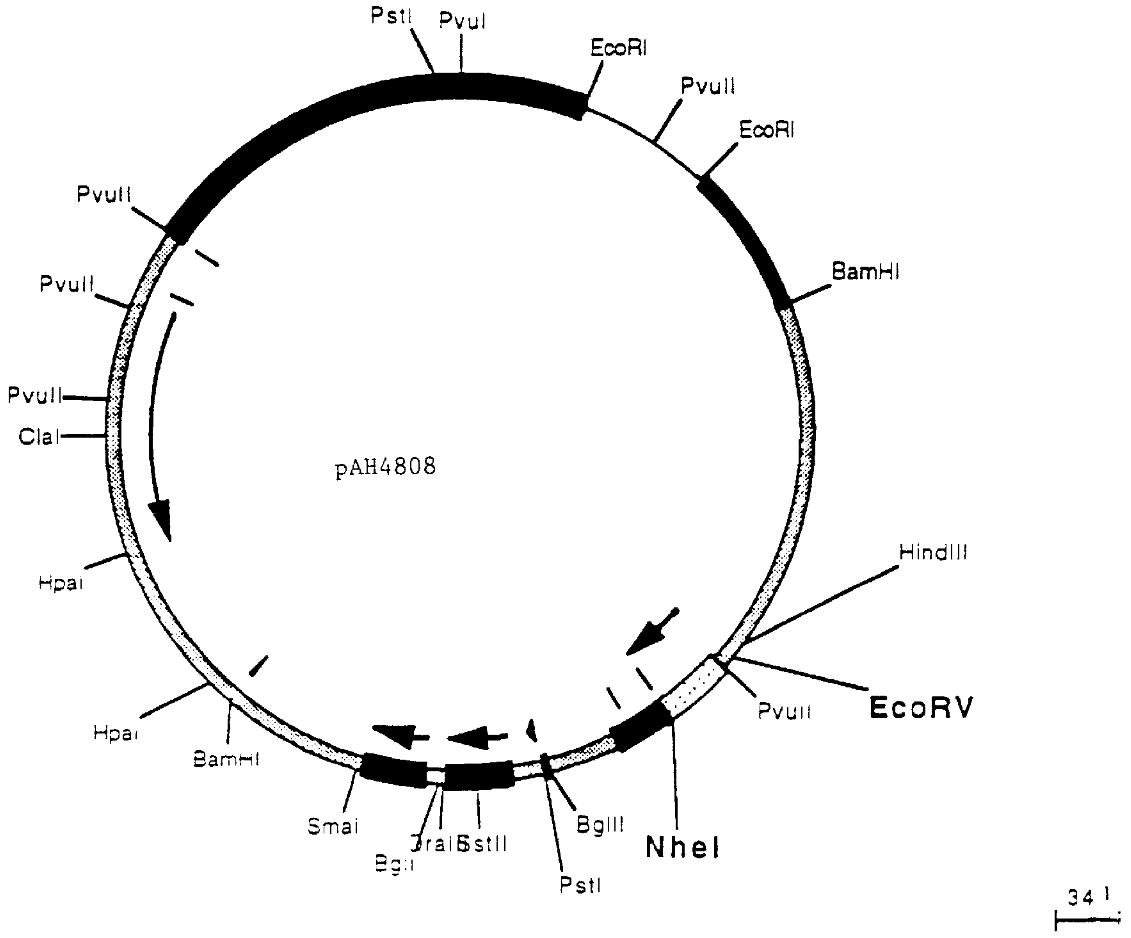
FIG. 16 illustrates the plasmid map of the heavy chain expression vector pAH4808 containing the γ-4 isotype.
Figure 18K:
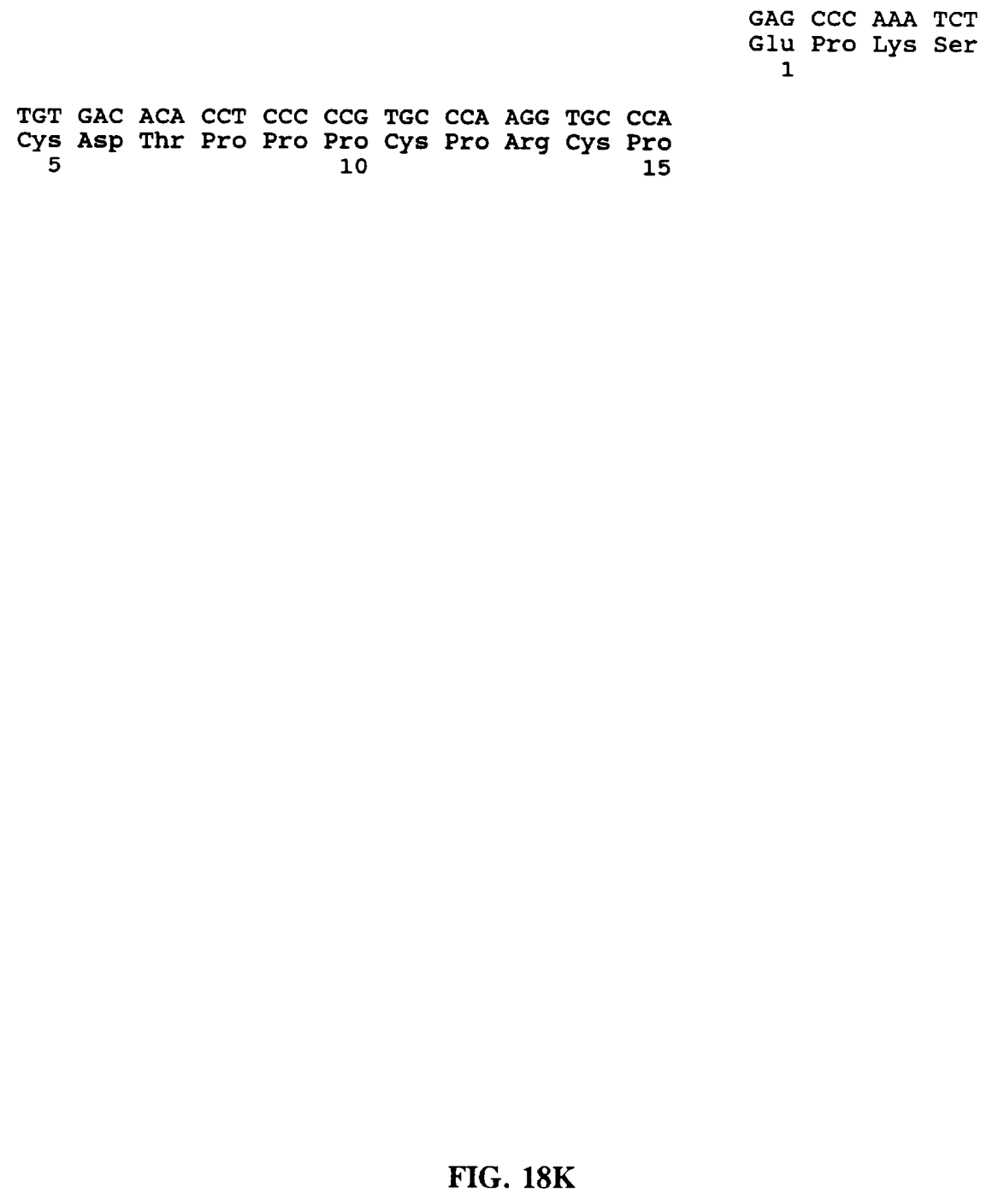

As described in Example 15, the initial cloning of the gene encoding the heavy chain of the murine monoclonal antibody 128.1, which binds the human transferrin receptor, involved placing the sequences encoding the variable region of the heavy chain into an expression vector containing the human γ1 constant region framework. This created a mouse/human chimera in which the sequences encoding the variable region of the antibody heavy chain (VH) were derived from a murine source and the sequences encoding $CH_1$, $CH_2$ and $CH_3$ were derived from a human source. Because the different human gamma isotypes (γ-1, -2, -3 and -4) have different biological properties, it was necessary to create chimeric antibodies with constant region sequences from each isotype in order to obtain mouse/human chimeras for each of these isotypes. The production of these chimeras was accomplished by cloning the 400 bp Eco RV-Nhe 1 fragment containing the VH region of antibody 128.1 from plasmid pBSK4600 into expression vectors containing the γ-2, γ-3 and γ-4 constant regions in a fashion similar to that previously described in Example 15 for the cloning of the VH region of antibody 128.1 into the expression vector containing the γ-1 constant region. These clonings with the γ-2, γ-3 and γ-4 constant regions resulted in respective plasmids pAH4625, pAH4807 and pAH4808 whose plasmid maps are shown in FIG. 14, FIG. 15 and FIG. 16, respectively. The antibody coding sequences of the heavy chain expression vectors pAH4625, pAH4807 and pAH4808 are shown in FIGS. 17A–17F (SEQ ID NO: 27), (SEQ ID NO: 28), (SEQ ID NO: 29), (SEQ ID NO: 30), and (SEQ ID NO: 31), FIGS. 18A–18F (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), and (SEQ ID NO: 40) and FIGS. 19A–19F (SEQ ID NO: 41), (SEQ ID NO: 42), (SEQ ID NO: 43), (SEQ ID NO: 44), (SEQ ID NO: 45) and (SEQ ID NO: 46), respectively.

These vectors, in combination with the chimeric light chain vector pAG4611, were transfected into SP2/0 cells and clones selected as described in Example 15. Initial antibody analysis using biosynthetically labeled proteins, immunoprecipitation and SDS-PAGE as previously described gave rise to the appropriate bands for the heavy and light chains as well as the assembled antibody for the γ-3 and γ-4 chimeras. No detectable protein was made by the γ-2 transfectants.

EXAMPLE 17

Antibody Production by Transfectants

Antibody production by selected transfectants was assessed by ELISA. Cells were diluted in fresh medium to a density of $10^6$ cells/ml and 1 ml was aliquoted into each of 3 wells on a 24-well culture plate. The plates were then incubated for 24 hours at 37° C. with 5% $CO_2$. The media was then collected from the wells and the cells and debris were spun down to give a clarified supernatant. For the ELISA, a 96-well microtiter dish was coated with a goat antisera against human IgG. After blocking with 3% BSA, the plate was washed and a series of dilutions of both the cell supernatants and human IgG standard of known concentration were applied to the plate and incubated for 1 hour at room temperature. The plate was then washed and biotinylated goat antisera against human IgG was added, followed by a mixture of avidin and biotinylated horseradish peroxidase (HRP). The amount of antibody present in the samples was then determined, based on the amount of substrate converted by the HRP.

Three clones resulting from the γ-1 chimera transfection were tested for antibody production. The average values from three experiments were 39, 21 and 24 μg/ml IgG/$10^6$ cells/24 hours, respectively, for the different clones. One γ-3 clone has been tested and it was found to produce approximately 1 μg/ml IgG/$10^6$ cells/24 hours. Two different clones of the γ-4 chimera have been tested and were found to produce 2.8 and 0.2 ng/ml IgG/$10^6$ cells/24 hours, respectively.

Equivalents

Those skilled in the art will know, or be able to ascertain using no more than routine experimentation, many equivalents to the specific embodiments expressly described herein. These are intended to be within the scope of the invention as described by the claims herein.

What is claimed is:

1. A chimeric antibody comprising a variable region which binds with a transferrin receptor present on brain capillary endothelial cells and a constant region of a separate antibody.

2. A chimeric antibody of claim 1 wherein the variable region is of murine origin.

3. A chimeric antibody of claim 2 wherein the constant region is of an animal source other than murine.

4. A chimeric antibody of claim 3 wherein the constant region is of a human source.

* * * * *